(12) United States Patent
Wurden

(10) Patent No.: US 12,193,429 B2
(45) Date of Patent: *Jan. 14, 2025

(54) COLLABORATIVE ROBOT NETWORK WITH HYBRID ELECTRO-MECHANICAL PLANT MANAGEMENT METHODS

(71) Applicant: AIGEN INC., San Francisco, CA (US)

(72) Inventor: Richard Theodore Wurden, Seattle, WA (US)

(73) Assignee: AIGEN INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,015

(22) Filed: Jul. 14, 2023

(65) Prior Publication Data

US 2024/0180142 A1 Jun. 6, 2024

Related U.S. Application Data

(63) Continuation of application No. 17/451,278, filed on Oct. 18, 2021, now Pat. No. 11,744,240.
(Continued)

(51) Int. Cl.
*B25J 15/00* (2006.01)
*A01M 21/04* (2006.01)
(Continued)

(52) U.S. Cl.
CPC .......... *A01M 21/046* (2013.01); *B25J 9/1679* (2013.01); *B25J 15/0019* (2013.01);
(Continued)

(58) Field of Classification Search
CPC .. G05D 1/0088; G05D 1/0231; G05D 1/0246; G05D 1/0094; G05D 1/0212;
(Continued)

(56) References Cited

U.S. PATENT DOCUMENTS 9,965,850 B2 5/2018 Fryshman
9,984,455 B1 5/2018 Fox
(Continued)

FOREIGN PATENT DOCUMENTS

AU 2015295035 2/2019
EP 3 174 388 9/2019
(Continued)

OTHER PUBLICATIONS

Vedula et al., Computer Vision Assisted Autonomous Intra-Row Weeder, 2018, IEEE, p. 79-84 (Year: 2018).*
(Continued)

*Primary Examiner* — Mcdieunel Marc
(74) *Attorney, Agent, or Firm* — Perkins Coie LLP

(57) ABSTRACT

An autonomous ground vehicle for agricultural plant and soil management operations. According to some embodiments, autonomous ground vehicle includes: a camera unit configured to generate images of agricultural ground soil and plant organisms, a first mechanical arm having an end effector comprising a hoe portion and an electrode portion, a second mechanical arm having an end effector comprising an electrode portion, a high voltage booster electrically connected to the electrode portions, an electronic memory storage medium comprising computer-executable instructions; one or more processors in electronic communication with the electronic memory storage medium, configured to execute the computer-executable instructions stored in an electronic memory storage medium for implementing a plant species control management operation comprising electrical control and mechanical control options.

20 Claims, 71 Drawing Sheets

Related U.S. Application Data

(60) Provisional application No. 63/128,627, filed on Dec. 21, 2020, provisional application No. 63/093,694, filed on Oct. 19, 2020.

(51) Int. Cl.
| | |
|---|---|
| *B25J 9/16* | (2006.01) |
| *G01N 33/00* | (2006.01) |
| *G01N 33/24* | (2006.01) |
| *G05D 1/00* | (2006.01) |
| *H02S 10/40* | (2014.01) |
| *H02S 40/38* | (2014.01) |

(52) U.S. Cl.
CPC ......... *G01N 33/0098* (2013.01); *G01N 33/24* (2013.01); *G05D 1/0088* (2013.01); *G05D 1/0094* (2013.01); *G05D 1/0212* (2013.01); *G05D 1/0231* (2013.01); *H02S 10/40* (2014.12); *H02S 40/38* (2014.12); *G01N 33/245* (2024.05)

(58) Field of Classification Search
CPC . G05D 1/101; G05D 2201/0201; B25J 9/026; B25J 15/0019; B25J 9/1679; B25J 5/007; B25J 9/0084; G01N 33/24; G01N 33/0098; G01N 2033/245; H02S 20/30; H02S 10/40; H02S 40/38; A01M 21/046; A01B 79/005; Y02E 10/50; Y02E 70/30; Y02P 60/12
See application file for complete search history.

(56) References Cited

U.S. PATENT DOCUMENTS

| | | | | |
|---|---|---|---|---|
| 10,627,386 | B2 * | 4/2020 | Saez | ............ G01N 33/24 |
| 10,936,871 | B2 | 3/2021 | Tran | |
| 11,074,447 | B1 | 7/2021 | Fox | |
| 11,308,323 | B2 | 4/2022 | Sibley | |
| 11,406,052 | B2 * | 8/2022 | Sibley | ............ G05D 1/0274 |
| 11,449,976 | B2 | 9/2022 | Sibley | |
| 11,465,162 | B2 | 10/2022 | Sibley | |
| 11,521,381 | B2 * | 12/2022 | Tran | ............ B64C 39/024 |
| 11,526,997 | B2 | 12/2022 | Sibley | |
| 11,744,240 | B2 * | 9/2023 | Wurden | ............ A01B 76/00 |
| | | | | 700/253 |
| 2015/0051779 | A1 | 2/2015 | Camacho-Cook et al. | |
| 2018/0132473 | A1 | 5/2018 | Diprose | |
| 2018/0156770 | A1 * | 6/2018 | Saez | ............ B64C 39/02 |
| 2018/0325091 | A1 | 11/2018 | Kroeger et al. | |
| 2019/0124855 | A1 | 5/2019 | Rowan et al. | |
| 2019/0274241 | A1 | 9/2019 | Tippery et al. | |
| 2020/0249669 | A1 | 8/2020 | Kosa et al. | |
| 2020/0264154 | A1 * | 8/2020 | Saez | ............ B64C 39/02 |
| 2021/0185886 | A1 | 6/2021 | Sibley | |
| 2022/0117217 | A1 * | 4/2022 | Wurden | ............ H02S 20/30 |
| 2024/0053748 | A1 * | 2/2024 | Wurden | ............ G05D 1/689 |

FOREIGN PATENT DOCUMENTS

| | | |
|---|---|---|
| KR | 10-2020-0103823 | 9/2020 |
| WO | WO 2016/016627 | 2/2016 |
| WO | WO 2016/162667 | 10/2016 |
| WO | WO 2018/050137 | 3/2018 |
| WO | WO 2018/095450 | 5/2018 |
| WO | WO 2019/102243 | 5/2019 |

OTHER PUBLICATIONS

Barosa et al., Smart Aquaponics with Disease Detection, 2019, IEEE, p. 1-6 (Year: 2019).*

Santhosh et al., IoT Based Agriculture Using AGRIBOT, 2019, IEEE, p. 1520-1526 (Year: 2019).*

Khamis et al., LED lighting with remote monitoring and controlling system for indoor greenhouse, 2018, IEEE, p. 81-84 (Year: 2018).*

Reed et al., "Desk Study: Electrical weed control in Field Vegetables", Jan. 7, 2009, in 18 pages.

International Search Report and Written Opinion issued in PCT Application No. PCT/US2021/055466, dated Jan. 28, 2022, in 6 pages. [AIGEN.002WO].

Nichele et al., Towards a plant bio-machine, 2017, IEEE, p. 1-8 (Year: 2017).

Mondini et al., A preliminary study of a robotic probe for soil exploration inspired by plant root apexes, 2009, IEEE, p. 115-120 (Year: 2009).

Finegan et al., Development of an Autonomous Agricultural Vehicle to Measure Soil Respiration, 2019, IEEE, p. 1-6 (Year: 2019).

* cited by examiner

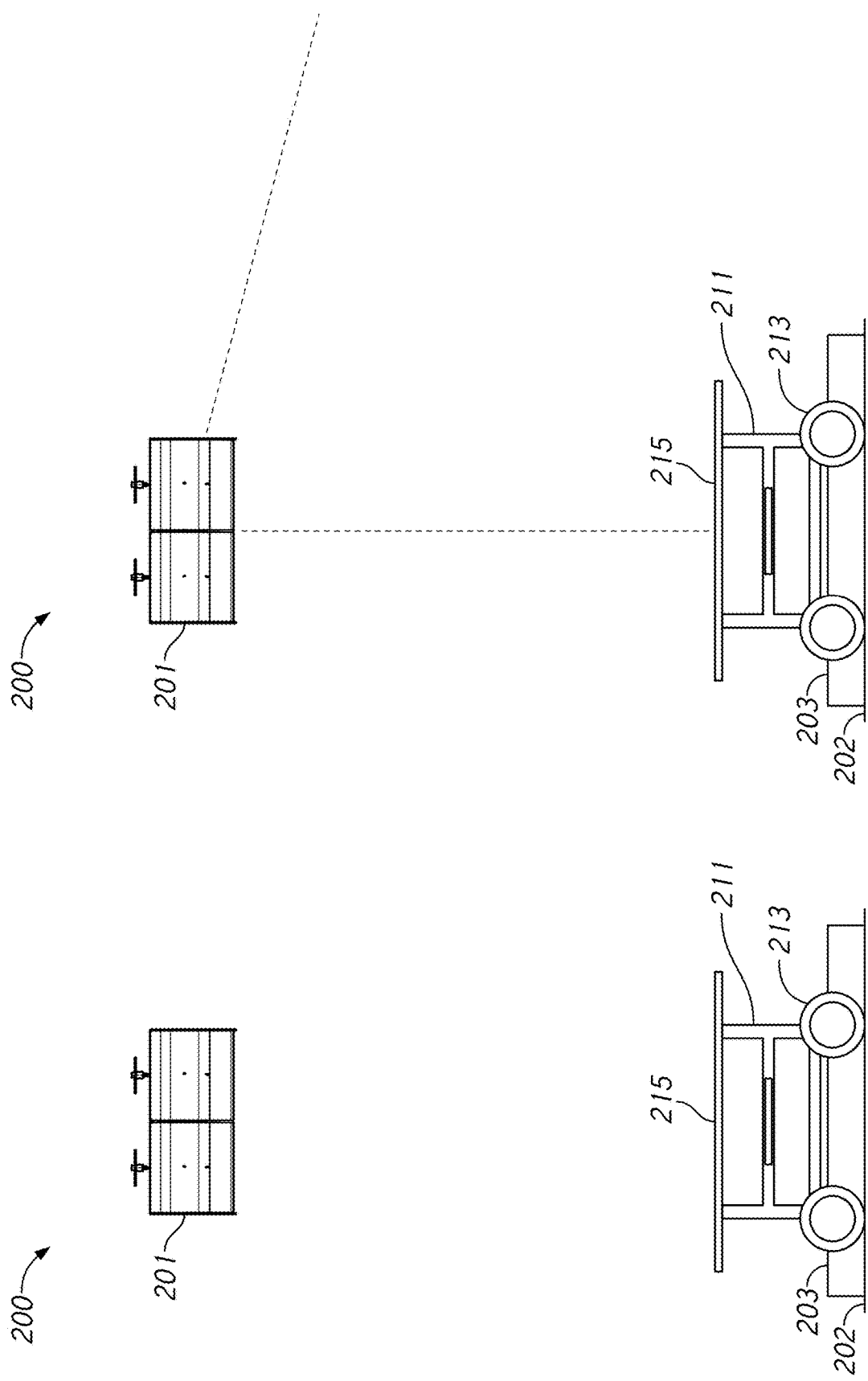

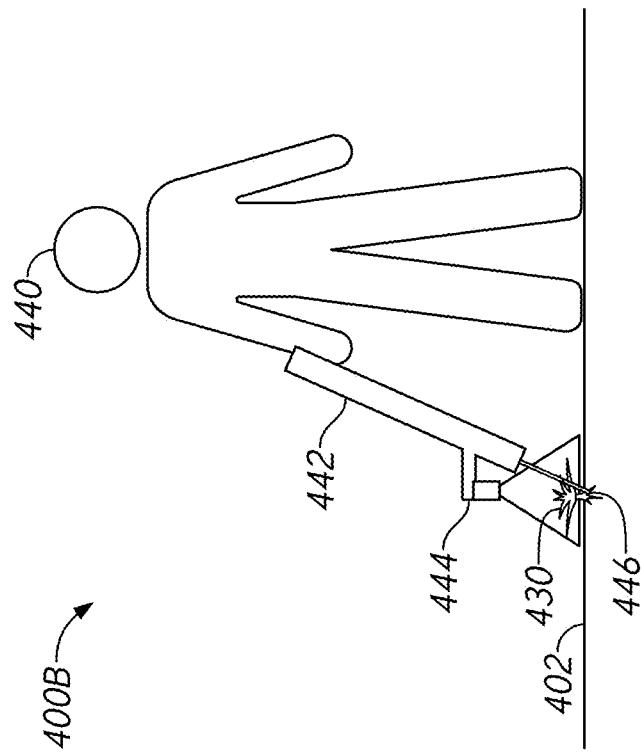
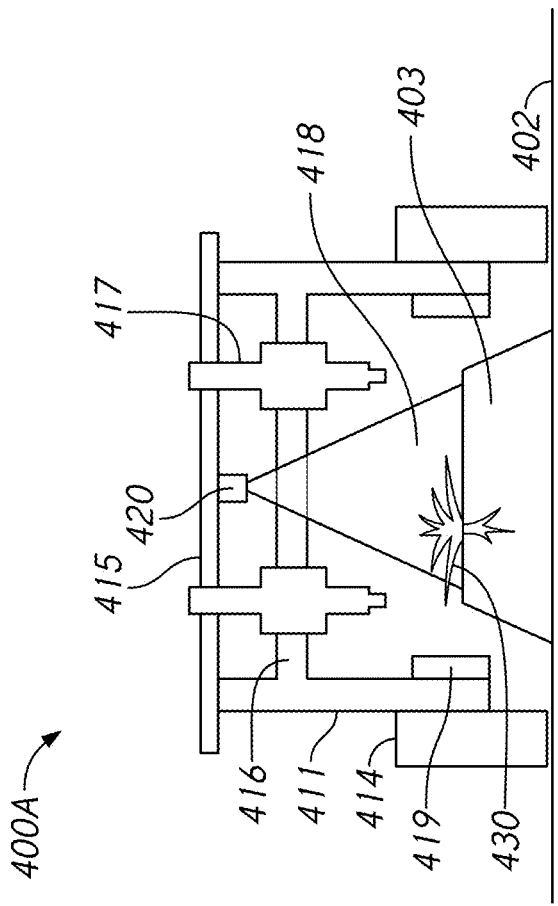
FIG. 4B
FIG. 4A

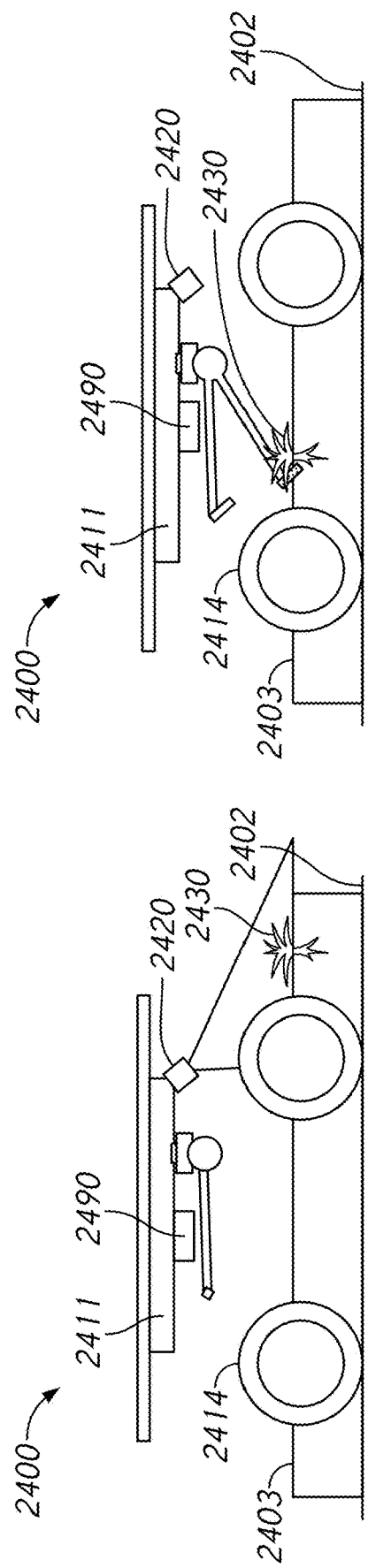

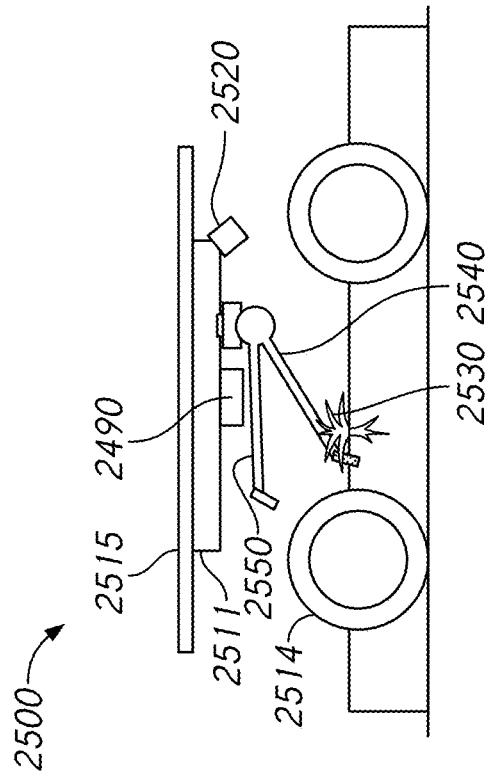
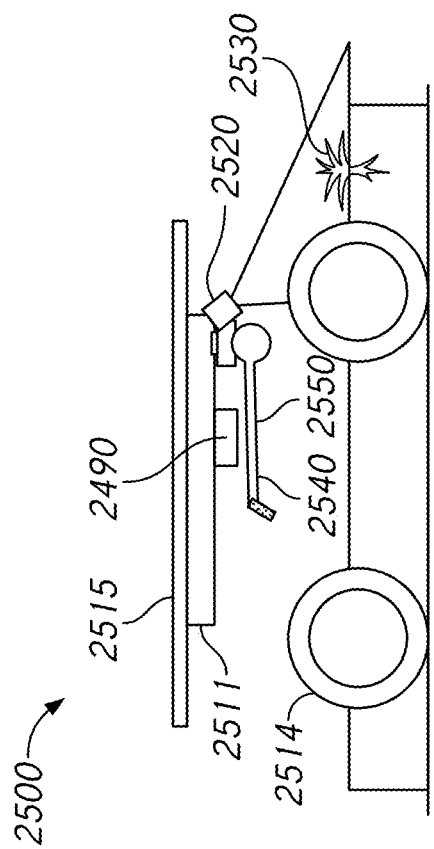
FIG. 25B
FIG. 25A

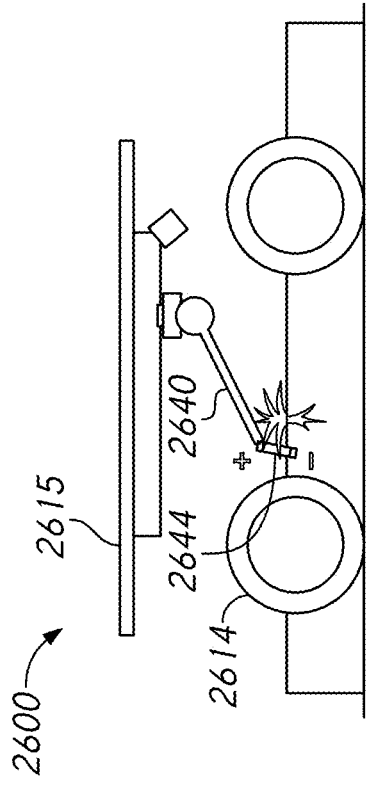
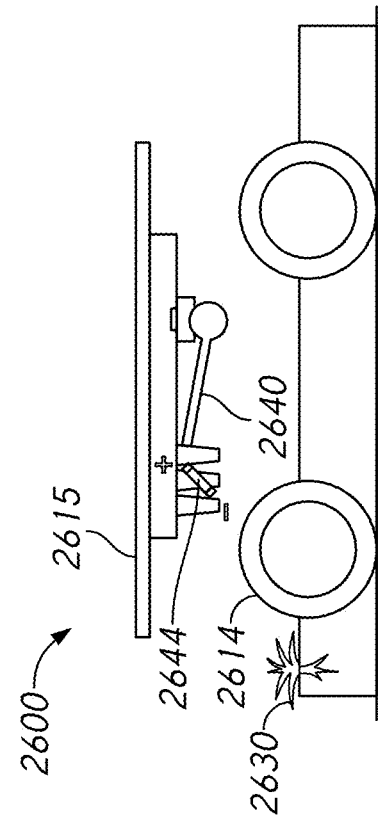
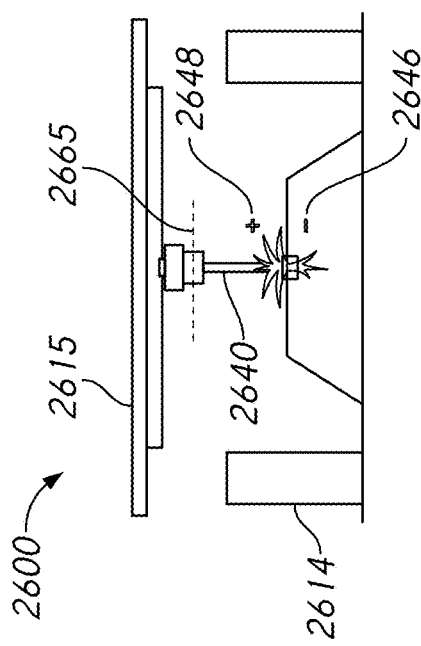
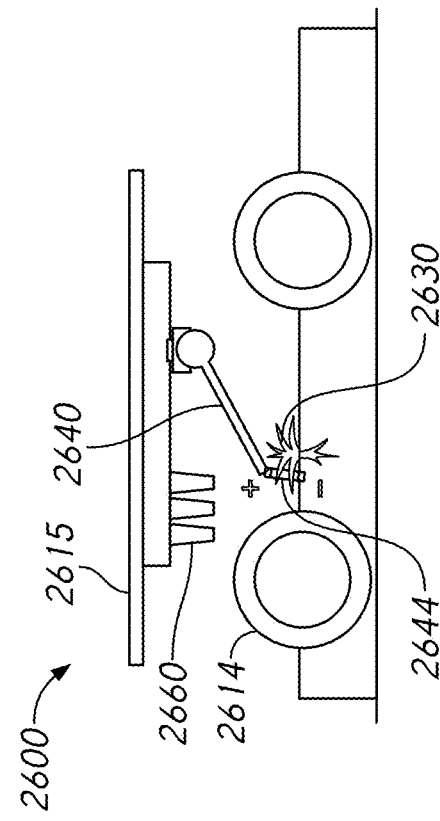

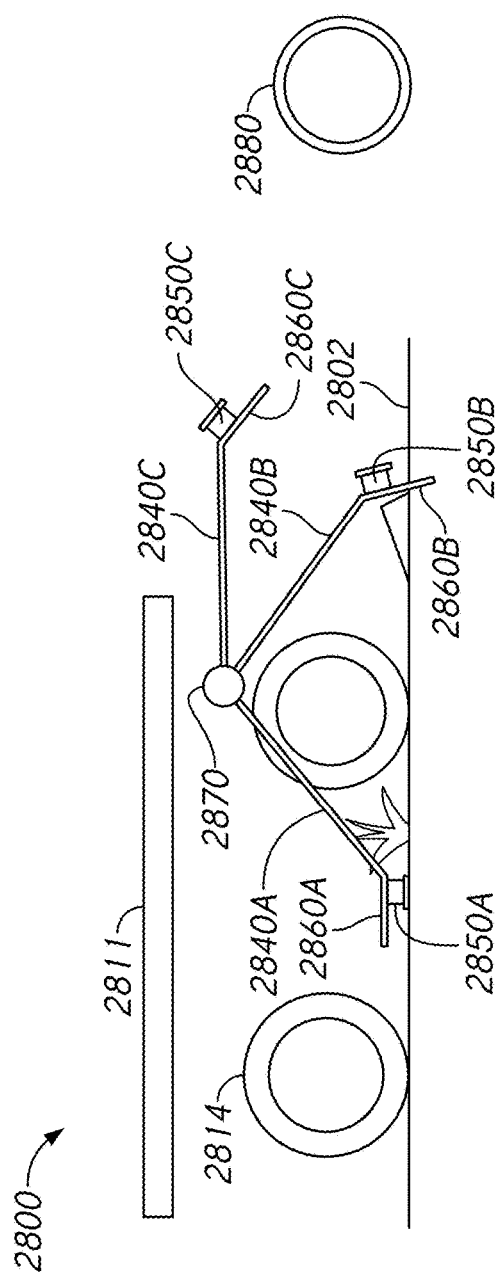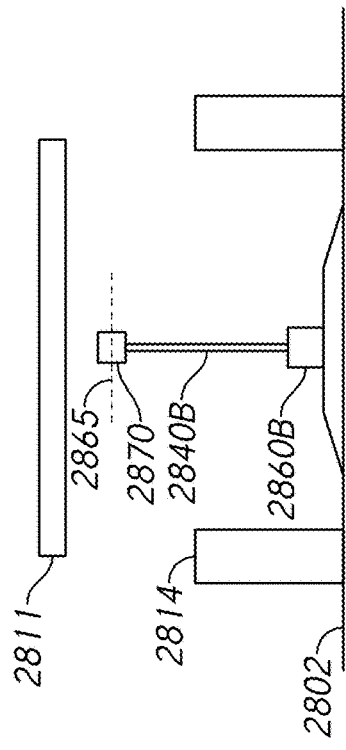
FIG. 28A
FIG. 28B

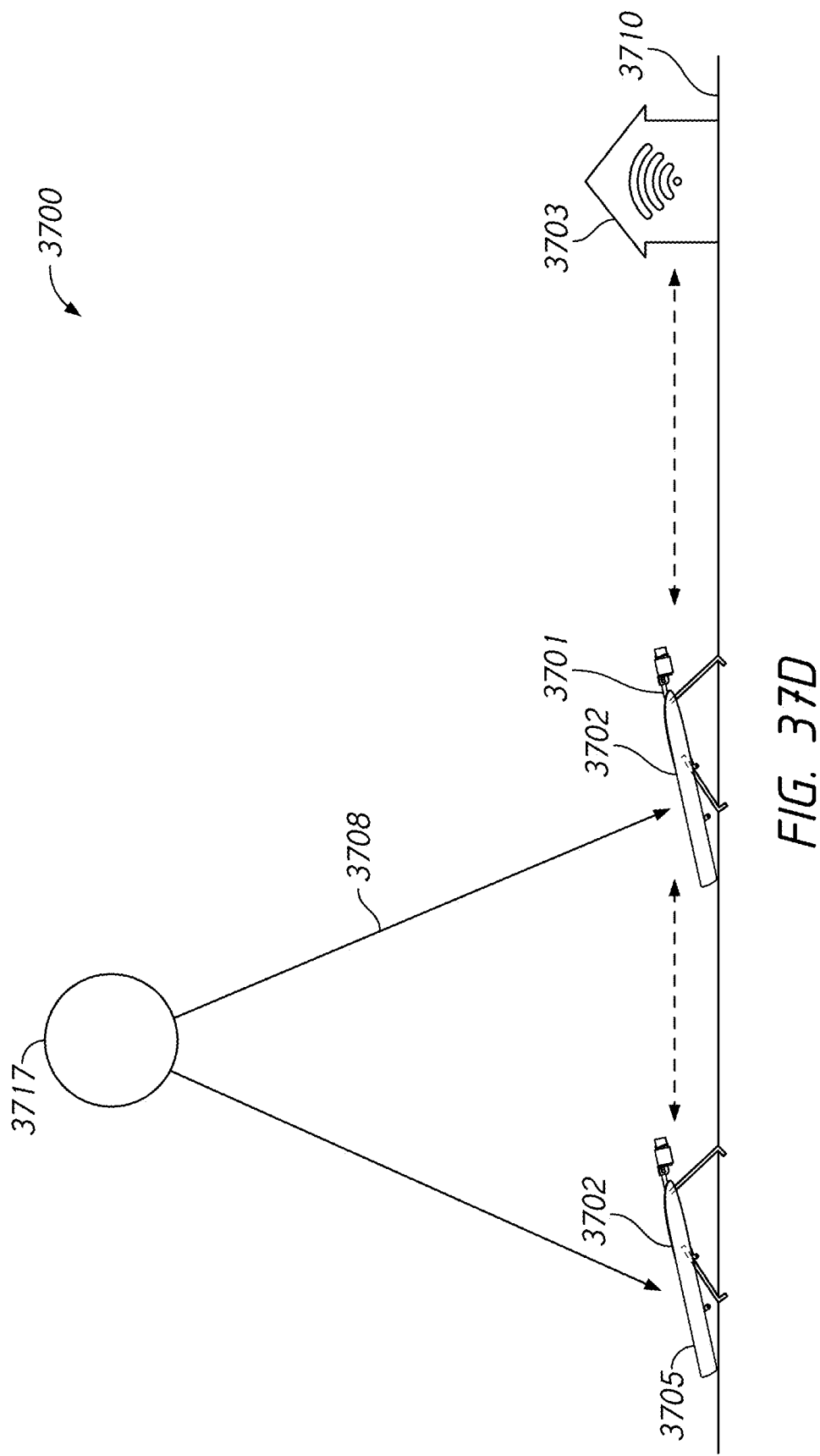

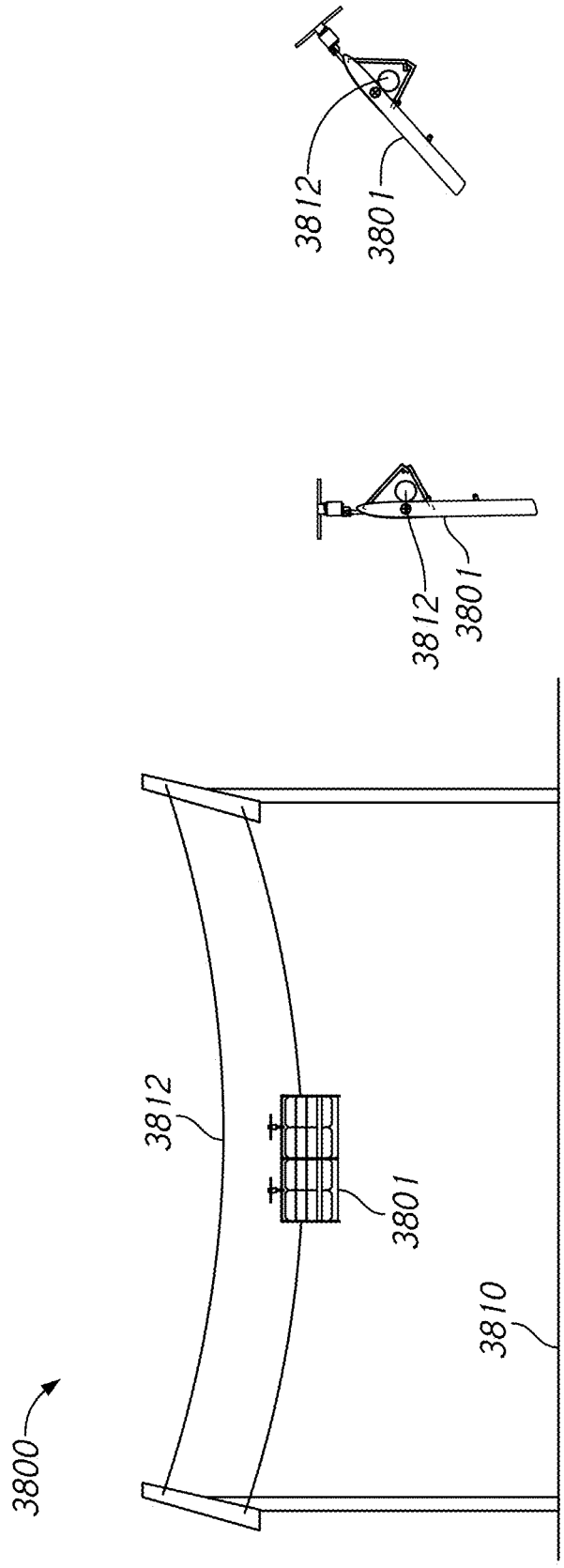

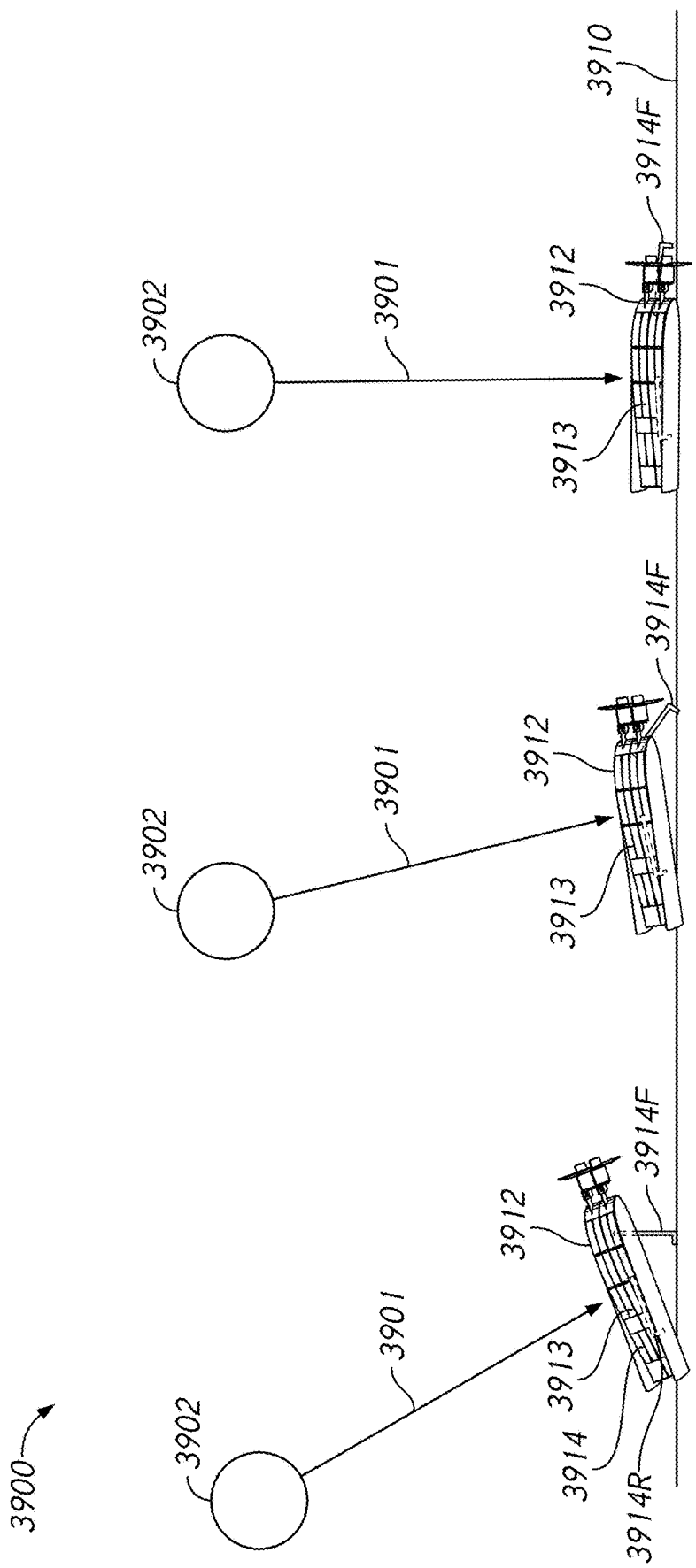

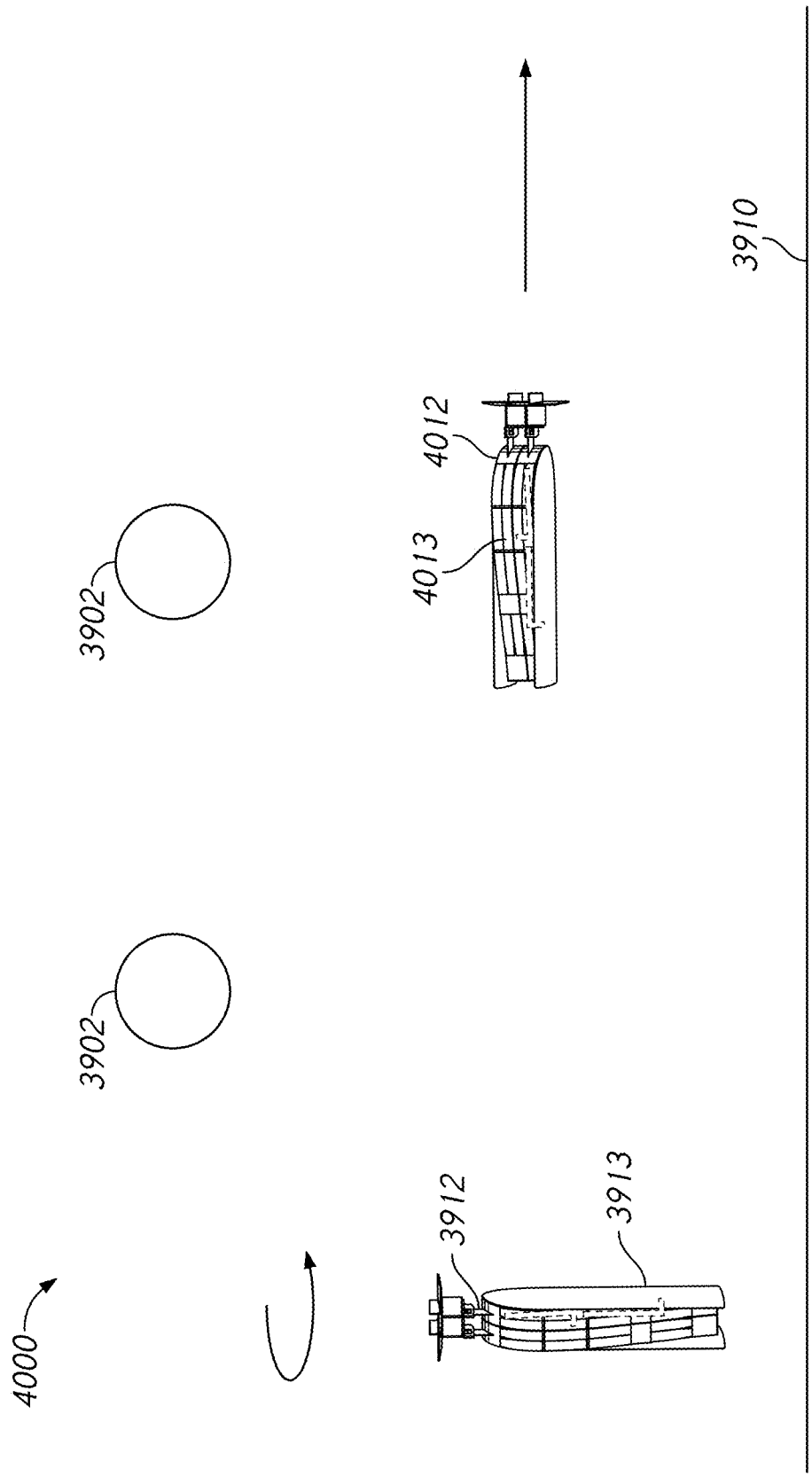

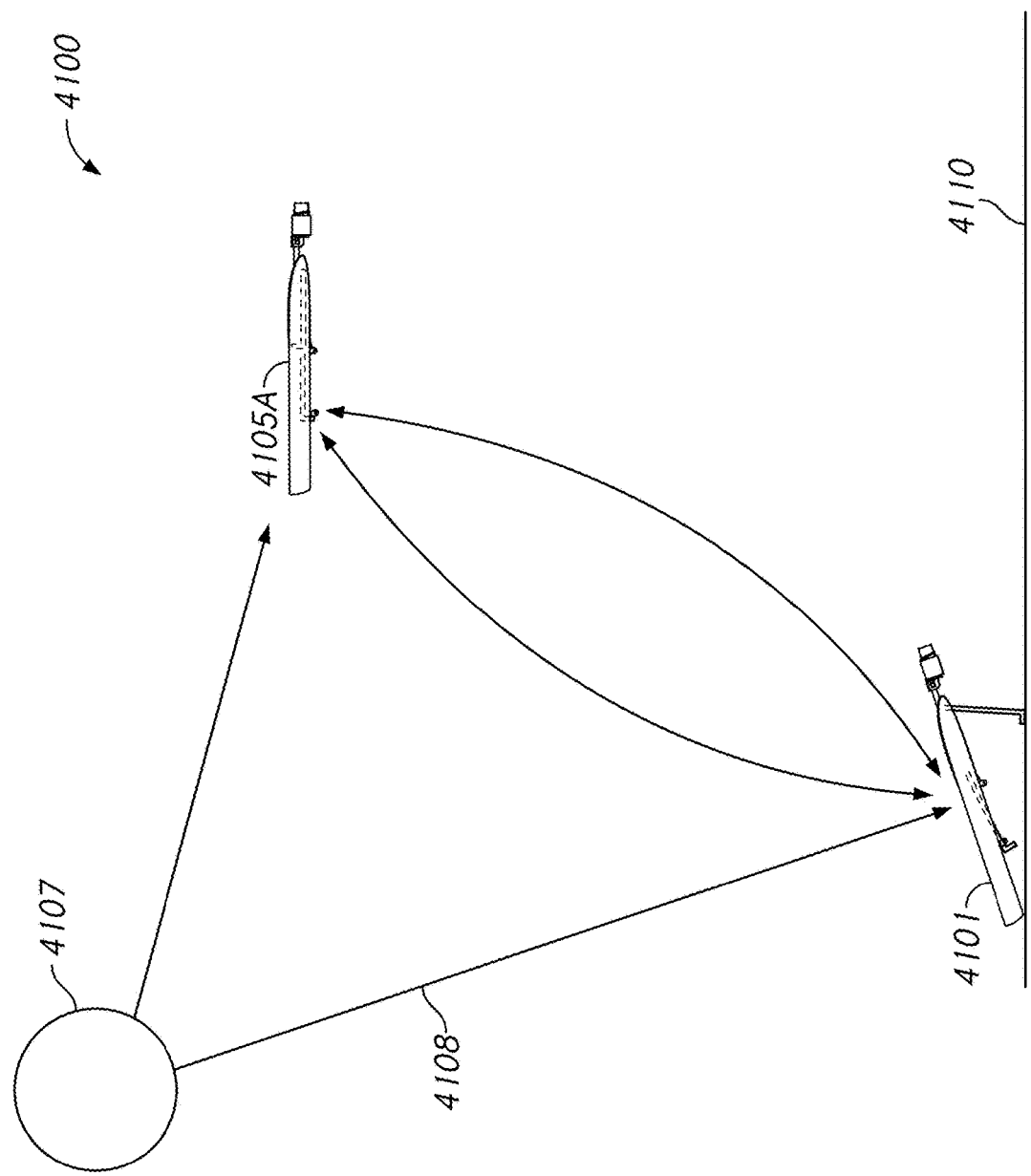

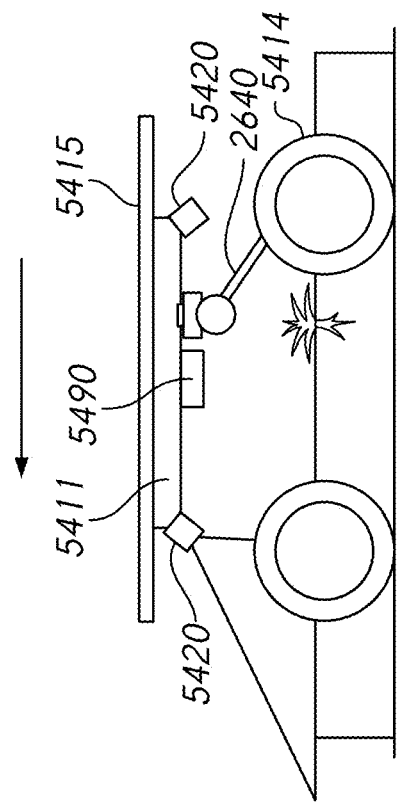
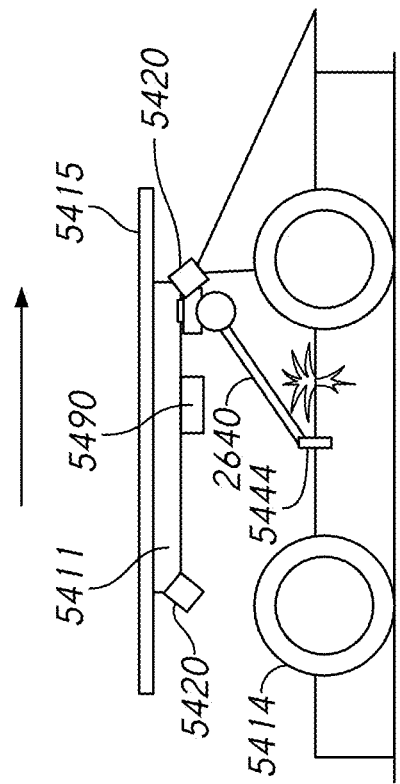
FIG. 54B
FIG. 54A

COLLABORATIVE ROBOT NETWORK WITH HYBRID ELECTRO-MECHANICAL PLANT MANAGEMENT METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57. This application is a continuation of U.S. application Ser. No. 17/451,278, entitled "Collaborative Robot Network With Hybrid ElectroMechanical Plant Management Methods," filed Oct. 18, 2021 which claims the benefit under 35 U.S.C. 119(c) to U.S. Provisional Application No. 63/128,627, entitled "Collaborative Robot Network with Optimized Weed Control Methods," filed on Dec. 21, 2020, and to U.S. Provisional Application No. 63/093,694, entitled "Multi-Modal, Weather Resistant, Robot Network and Methods of Data Transfer," filed on Oct. 19, 2020, and the entirety of both provisional applications are hereby incorporated by reference herein.

BACKGROUND

Field

The present disclosure generally relates to the fields of drones, robotics, remote network connectivity, and precision agriculture.

Description

By 2050, the global population will increase from 7.8 billion to 9.7 billion people, and food demand will increase by 70%. During this time, the amount of farmland will be relatively unchanged. As a result, farmers will be challenged to find more efficient, sustainable methods of farming.

SUMMARY

The present disclosure generally relates to the fields of drones, robotics, remote network connectivity, and precision agriculture. More specifically, embodiments of the disclosure relate to ground robots performing plant management without chemical use. In some embodiments, autonomous ground vehicles perform various weed control operations using mechanical, electrical, and/or both mechanical and electrical means to eliminate weeds. In some embodiments, autonomous ground vehicles perform ground terraforming operations and livestock herd management.

Some embodiments comprise an autonomous network of robots and drones wherein at least one drone inspects an area for a specific agriculture asset and at least one ground robot performs an action based on the drone inspection. In some embodiments, drones perform an inspection of an area of farmland, the inspection data is analyzed via AI to identify areas with high concentrations of weeds, and ground robots travel to identified areas and perform weed control.

Some embodiments relate to an autonomous network of drones that transfer data between each other and are linked to the other networks through a link drone capable of ground and aerial mobility, and in some embodiments, the drones are powered by solar charging and align themselves to the sun. In some embodiments, the drones can affix to the ground at night and during extreme weather.

According to some embodiments, a Multi-modal VTOL Robot is capable of attaching itself to the ground and/or an object, moving on the ground and/or the object, and/or conducting aerial movement, and may be referred to as a weather resistant VTOL robotic system, aircraft, drone, or an aircraft in various embodiments through the disclosure.

According to some embodiments, an autonomous ground vehicle for agricultural plant and soil management operations, the autonomous ground vehicle comprising: a ground vehicle unit having two or more wheels or mechanical propulsion mechanisms coupled to the ground vehicle unit; a camera unit coupled to the ground vehicle unit, the camera unit configured to generate one or more images of agricultural ground soil and plant organisms in a forward path of the ground vehicle unit; a first mechanical arm coupled to a first undercarriage portion of the ground vehicle unit, the first mechanical arm having a first end effector comprising a first hoe portion and a first electrode portion; a second mechanical arm coupled to a second undercarriage portion of the ground vehicle unit, the second mechanical arm having a second end effector comprising a second electrode portion; a high voltage booster unit housed in the ground vehicle unit, the high voltage booster unit is electrically connected to the first electrode portion of the first end effector of the first mechanical arm, and the high voltage booster unit is electrically connected to the second electrode portion of the second end effector of the second mechanical arm; an electronic memory storage medium housed in the ground vehicle unit, the electronic memory storage medium comprising computer-executable instructions; one or more processors housed in the ground vehicle unit, the one or more processors in electronic communication with the electronic memory storage medium, the one or more processors configured to execute the computer-executable instructions stored in the electronic memory storage medium for implementing a plant species control management operation, the computer-executable instructions comprises: analyzing, by the one or more processors, the generated one or more images to identify a plant organism and surrounding soil; determining, by the one or more processors, a soil type of the surrounding soil and a plant species of the identified plant organism in the one or more images; comparing, by the one or more processors, the determined plant species type of the identified plant organism to a data store, the comparing performed to determine whether the plant organism is set for plant organism control; generating, by the one or more processors, based on determining that the identified plant organism is set for plant organism control, ground vehicle unit control instructions configured to advance the ground vehicle unit and/or the first mechanical arm to be within a threshold proximity of the identified plant organism; determining, by the one or more processors, a method of plant organism control for the identified plant organism based on the analysis of the identified plant organism and the surrounding soil in the one or more images generated by the camera, the method of plant organism control having options, the options comprising electrical control and mechanical control; generating, by the one or more processors, based on determining the method plant organism control is electrical control, mechanical arm control instructions for electrical control comprising: positioning the first electrode portion to be in contact with the identified plant organism; positioning the second electrode portion to be in contact with the soil or a second plant adjacent to the identified plant organism; activating the high voltage booster unit to generate electric current through the first electrode portion, the identified plant organism, and the second electrode portion; generating, by the one or more processors, based on determining the method plant organism control is mechanical control, mechanical arm control instructions for mechanical control comprising: positioning at least the first hoe portion to be in contact with soil distal to the identified plant organism; moving the first hoe portion through the soil to remove at least a portion of the identified plant organism; executing, by the one or more processors, the generated mechanical arm control instructions.

In some embodiments, the mechanical propulsion mechanism may comprise mechanical legs. In some embodiments, the ground vehicle unit further comprises one or more protrusions coupled to an external portion of the ground vehicle unit, the one or more protrusions configured to engage with the first hoe portion to remove debris material from the first hoe portion. In some embodiments, the autonomous ground vehicle further comprises an energy storage unit housed in the ground vehicle unit, the energy storage unit is electrically coupled to the high voltage booster unit. In some embodiments, the autonomous ground vehicle further comprises a solar panel unit electrically coupled to the energy storage unit, the solar panel unit is coupled to the ground vehicle unit, the solar panel unit is configured to electrically recharge the energy storage unit housed in the ground vehicle unit. In some embodiments, the activating the high voltage booster unit comprises activating with a switch relay. In some embodiments, determining, by the one or more processors, a plant species type of the identified plant organism comprises use of a computer vision algorithm. In some embodiments, determining, by the one or more processors, a plant species type of the identified plant organism comprises use of an artificial intelligence algorithm. In some embodiments, the second end effector of the second mechanical arm further comprises a second hoe portion. In some embodiments, the first hoe portion and the first electrode portion of the first end effector form a single unit.

According to some embodiments, a computer-implemented method for using an autonomous ground vehicle for agricultural plant and soil management and operations, the computer-implemented method comprising: analyze, by a computing system, one or more generated images to identify a plant organism and surrounding soil, the one or more generated images a camera unit coupled to a ground vehicle unit having two or more wheels or mechanical propulsion mechanisms; determining, by the computing system, a soil type of the surrounding soil and a plant species type of the identified plant organism in the one or more generated images; comparing, by the computing system, the determined plant species type of the identified plant organism to a data store, the comparing performed to determine whether the plant organism is set for plant organism control; generate, by the computing system, based on determining that the identified plant organism is set for plant organism control, ground vehicle unit control instructions configured to advance the ground vehicle unit and/or a first mechanical arm to be within a threshold proximity of the identified plant organism, the ground vehicle unit comprises the first mechanical arm coupled to a first undercarriage portion of the ground vehicle unit, the first mechanical arm having a first end effector comprising a first hoe portion and a first electrode portion and a second electrode portion, the ground vehicle unit houses a high voltage booster unit, the high voltage booster unit is electrically connected to the first electrode portion of the first end effector of the first mechanical arm, and the high voltage booster unit is electrically connected to the second electrode portion of the first end effector of the first mechanical arm, the first electrode portion configured to contact a first portion of the plant organism and the second electrode portion configured to contact the surrounding soil or a second portion of the plant organism; determine, by the computing system, a method of plant organism control for the identified plant organism based on the analysis of the identified plant organism and the surrounding soil in the one or more generated images by the camera, the method of plant organism control having options, the options comprising electrical control and mechanical control; generate, by the computing system, based on determining the method plant organism control is electrical control, mechanical arm control instructions for electrical control comprising: positioning the first electrode portion to be in contact with the first portion of the identified plant organism; positioning the second electrode portion to be in contact with the surrounding soil or the second portion of the identified plant organism or an adjacent plant organism to the identified plant organism; activating the high voltage booster unit to generate electric current through the first electrode portion, the identified plant organism, and the second electrode portion; generate, by the computing system, based on determining the method plant organism control is mechanical control, mechanical arm control instructions for mechanical control comprising: positioning at least the first hoe portion to be in contact with soil distal to the identified plant organism; moving the first hoe portion through the soil to remove at least a portion of the identified plant organism; executing, by the computing system, the generated mechanical arm control instructions; wherein the computing system comprises one or more hardware computer processors in communication with one or more computer readable data stores and configured to execute a plurality of computer executable instructions.

In some embodiments, the mechanical propulsion mechanism comprises mechanical legs. In some embodiments, the ground vehicle unit further comprises one or more protrusions coupled to an external portion of the ground vehicle unit, the one or more protrusions configured to engage with the first hoe portion to remove debris material from the first hoe portion. In some embodiments, the autonomous ground vehicle further comprises an energy storage unit housed in the ground vehicle unit, the energy storage unit is electrically coupled to the high voltage booster unit. In some embodiments, the autonomous ground vehicle further comprises a solar panel unit electrically coupled to the energy storage unit, the solar panel unit is coupled to the ground vehicle unit, the solar panel unit is configured to electrically recharge the energy storage unit housed in the ground vehicle unit. In some embodiments, the activating the high voltage booster unit comprises activating with a switch relay. In some embodiments, determining, by the one or more processors, a plant species type of the identified plant organism comprises use of a computer vision algorithm. In some embodiments, determining, by the one or more processors, a plant species type of the identified plant organism comprises use of an artificial intelligence algorithm. In some embodiments, the ground vehicle unit further comprises a second mechanical arm coupled to a second undercarriage portion of the ground vehicle unit, the second mechanical arm having a second end effector comprising a second electrode portion. In some embodiments, the first hoe portion and the first electrode portion of the first end effector form a single unit.

BRIEF DESCRIPTION OF THE DRAWINGS

Various embodiments will be described hereinafter with reference to the accompanying drawings. These embodiments are illustrated and described by example only and are not intended to limit the scope of the disclosure. In the drawings, similar elements have similar reference numerals.

FIG. 2A is a diagram of Collaborative Robot Network showing a drone and a ground robot performing an inspection, according to an embodiment.

FIG. 2B is a diagram of Collaborative Robot Network showing a drone acting as an antenna for a ground robot, according to an embodiment.

FIG. 4A is a diagram of a front view of ground robot showing a camera enabled weed control end effector, according to an embodiment.

FIG. 4B is a diagram of a person holding a manual weed control showing a camera enabled weed control end effector attached to a handheld unit, according to an embodiment.

FIG. 24A is a diagram of a Hybrid Electrical Mechanical Autonomous Ground Vehicle performing an inspection, according to an embodiment.

FIG. 24B is a diagram of a Hybrid Electrical Mechanical Autonomous Ground Vehicle taking advanced mechanical action on farmland, according to an embodiment of the disclosure.

FIG. 25A is a diagram of a Hybrid Electrical Mechanical Autonomous Ground Vehicle performing an inspection, according to an embodiment of the disclosure.

FIG. 25B is a diagram of a Hybrid Electrical Mechanical Autonomous Ground Vehicle taking advanced mechanical action on farmland, according to an embodiment of the disclosure.

FIG. 26A is a diagram of a Hybrid Electrical Mechanical Autonomous Ground Vehicle with a single hoe with integrated positive and negative electrodes, according to an embodiment of the disclosure.

FIG. 26B is a diagram of a Hybrid Electrical Mechanical Autonomous Ground Vehicle with a single hoe with integrated positive and negative electrodes, according to an embodiment of the disclosure.

FIG. 26C is a diagram of a Hybrid Electrical Mechanical Autonomous Ground Vehicle showing a cleaning mechanism, according to an embodiment of the disclosure.

FIG. 26D is a diagram of a Hybrid Electrical Mechanical Autonomous Ground Vehicle taking cleaning action, according to an embodiment of the disclosure

FIG. 28A is a diagram of a Hybrid Electrical Mechanical Autonomous Ground Vehicle showing three functional mechanical arm positions, according to an embodiment of the disclosure.

FIG. 28B is a diagram of a Hybrid Electrical Mechanical Autonomous Ground Vehicle showing a front view.

FIG. 37D is a diagram of a link drone latching onto the ground transferring data, according to an embodiment.

FIGS. 38A-38C are diagrams of a link drone on a powerline transferring data, according to an embodiment.

FIG. 39 is a diagram of solar charging on the ground, according to an embodiment.

FIG. 40 is a diagram of solar charging in flight, according to an embodiment.

FIG. 41 is a diagram of a link drone interchanging with a network drone, according to an embodiment.

FIG. 54A-54B is a diagram of Hybrid Electrical Mechanical Autonomous Ground Vehicle showing symmetric reverse turning, according to an embodiment.

DETAILED DESCRIPTION

Figure 1:
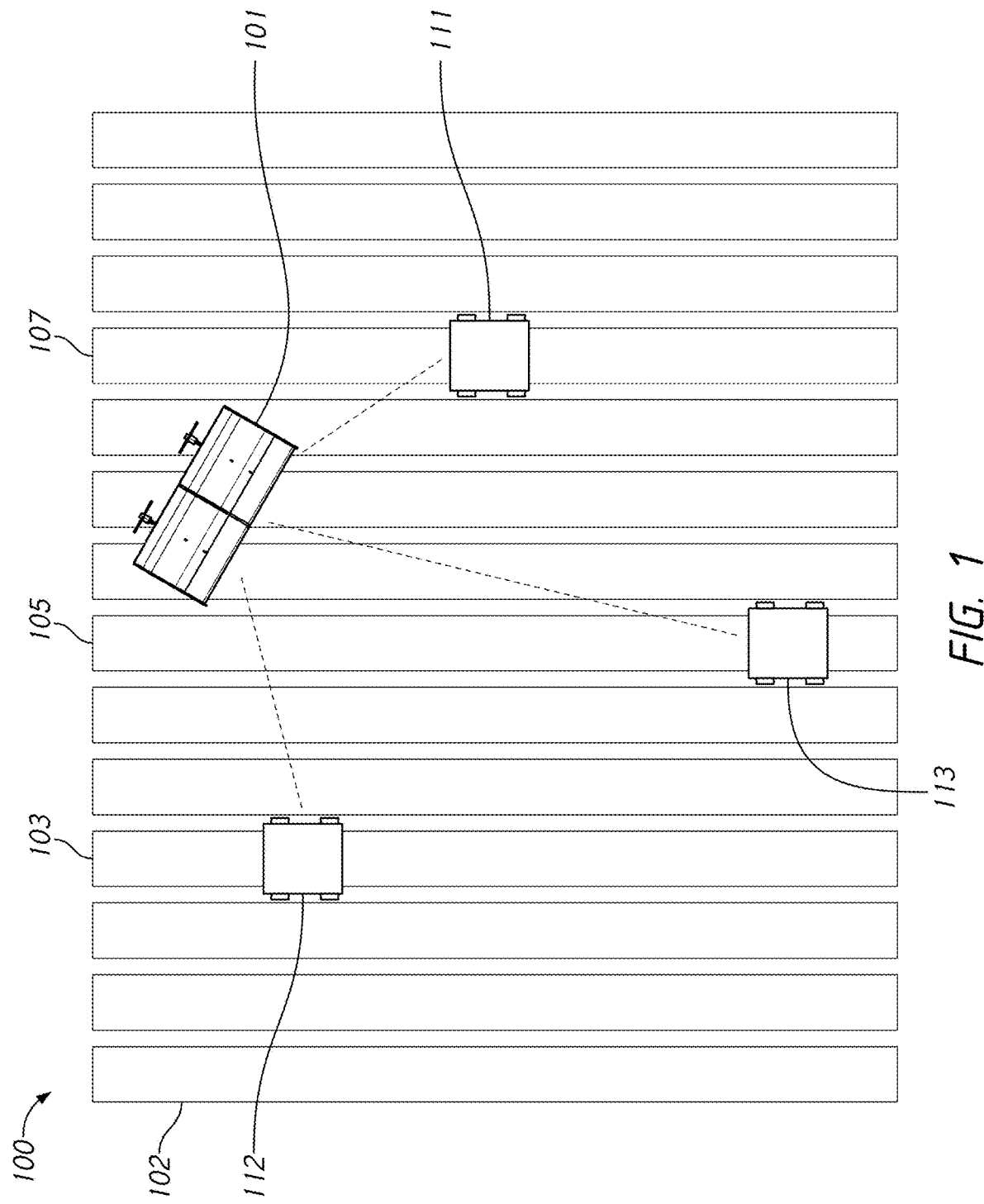
FIG. 1 is a diagram of Collaborative Robot Network performing an inspection and taking an advanced action on farmland, according to an embodiment of the disclosure.

Although embodiments, examples, and illustrations are disclosed below, the disclosure described herein extends beyond the specifically disclosed embodiments, examples, and illustrations and includes other uses of the disclosure and obvious modifications and equivalents thereof. Embodiments of the disclosure are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the disclosure. In addition, embodiments of the disclosure can comprise several novel features, and no single feature is solely responsible for its desirable attributes or is essential to practicing the disclosures herein described.

By 2050, the global population will increase from 7.8 billion to 9.7 billion people, and food demand will increase by 70%. During this time, the amount of farmland will be relatively unchanged. As a result, farmers will be challenged to find more efficient, sustainable methods of farming. It is clear that farmers do not have access to the data, analysis, and guidance needed to manage their crops to meet the elevated demands.

Furthermore, a high percentage of farmers cannot use current technology because it is not scalable or affordable. Farmers and agriculture professionals need technology that not only gathers data but also takes immediate action, since agriculture is largely based on weather and timing. Specifically, farmers only take action when it is too late. By the time farmers find the problems on their farmland, they have spread. Also, satellites don't provide the resolution needed even for the most basic analysis.

To combat these issues, various concepts are disclosed herein to provide solutions for more efficient and sustainable farming. In some embodiments of the disclosure, autonomous ground vehicles perform various weed control operations using mechanical, electrical, and/or both mechanical and electrical means to eliminate weeds. In some embodiments, the autonomous ground vehicles disclosed herein can comprise one or more mechanical arms coupled to the autonomous ground vehicles. In some embodiments, the autonomous ground vehicles disclosed herein can comprise one or more electrode portions coupled to the one or more mechanical arms, wherein the one or more electrode portions are configured to make contact with one or more plants or plant portions and/or ground areas in order to damage the plant by sending an electric current through the plant and/or the roots of the plant. In some embodiments, the autonomous ground vehicles disclosed herein can comprise one or more hoe portions coupled to the one or more mechanical arms. In some embodiments, the one or more hoe portions are configured to mechanically remove a plant from the soil or remove a portion of a plant. In some embodiments, the autonomous ground vehicles disclosed herein can comprise one or more cameras configured to capture one or more image(s) and/or video of areas around the autonomous ground vehicle, including but not limited to a forward path of the autonomous ground vehicle. In some embodiments, the one or more image(s) and/or video are analyzed by a computing system either housed in the autonomous ground vehicle or in a cloud server connected to the autonomous ground vehicle through a communications network, wherein the computing system is configured to identify plant types in the one or more image(s) and/or video and determine whether the identified plant should be terminated or allowed to continue to grow. In some embodiments, the computing system can be configured to determine whether the identified plant should be terminated by using the one or more hoe portions and/or the one or more electrode portions. In some embodiments, the computing system can be configured to determine the method of plant termination, for example, by mechanical damage through using the one or more hoe portions or by electrical current damage through using the one or more electrode portions, based on analyzing the one or more image(s) and/or video. In some embodiments, the computing system is configured to analyze plant types and compare the identified plant type to determine whether the plant is a desirable plant type, and/or is conducive or detrimental to the desired crop and/or soil by comparing the plant type to a database, data store, lookup table, configuration file, or the like. In some embodiments, the computing system is configured to analyze soil conditions and/or soil type and/or soil moisture and/or soil composition and/or the like to determine the method of plant termination. In some embodiments, if the computing system determines that the soil is hard, then the system can be configured to not use the one or more hoe portions to remove the plant because the one or more hoes may not be able to dig into the soil, and the system can be configured to use the one or more electrode portions to terminate the plant. In some embodiments, autonomous ground vehicles perform ground terraforming operations (for example, ground soil management operations and/or the like) to restore arid environment ground soil conditions and degraded farmland. In some embodiments, the autonomous ground vehicle disclosed herein is configured to use the one or more hoe portions in conjunction with the one or more cameras to create openings and/or hills and/or crescent shaped mounds and/or sloped areas and/or other land features configured to capture water and/or wind and/or soil and/or seeds and/or other items in order to restore the ground soil conditions. In some embodiments, autonomous ground vehicles perform livestock herd and ground soil management by monitoring which plant life is consumed and the quantity consumed by livestock and the ground and vegetation condition to prevent detrimental overgrazing of the land. In some embodiments, the autonomous ground vehicles disclosed herein can be configured to use the one or more mechanical arms to produce waving motions or sliding motions or gyrating motions or oscillating motions or other types of motions in order to scare the livestock or herd the livestock towards a particular grazing area and away from a grazing area that has been determined by the autonomous ground vehicle and/or computing system to be overgrazed and/or to prevent damage to the area. In some embodiments, the one or more mechanical arms may comprise one or more mirrors or flags or other items that are configured to capture the attention of the livestock in order to scare or herd the livestock in a particular direction. In some embodiment, the autonomous ground vehicle can be configured to be a ground vehicle that can be used for multiple purpose, for example, weed management, ground soil management, and/or livestock herding management such that a user of the autonomous ground vehicle need only one machine to perform one or more forgoing tasks. In some embodiments, the autonomous ground vehicle can comprise the necessary software to perform one or more of the weed management, ground soil management, and/or livestock herding management operations. In some embodiments, the autonomous ground vehicle can comprise one or more instruments necessary for performing weed management, ground soil management, and/or livestock herding management operations.

In some embodiments, the mechanical arm includes a yaw motor, a pitch motor and a hoe arm with an end effector comprising a hoe portion, a shovel portion, and an electrode, or any combination thereof. In some embodiments, the hoe arm is coupled to the autonomous ground vehicle structure, for example, to the undercarriage portion of the ground vehicle unit's frame. In some embodiments, the pitch motor is connected to the vehicle structure, with the output shaft of the pitch motor being oriented in a vertical direction such that the output shaft rotates about a vertical rotation axis. In some embodiments, a bracket is coupled to the output shaft of the pitch motor. In some embodiments, the yaw motor is coupled to the bracket and positioned on the bracket such that an output shaft of the yaw motor is oriented in a horizontal direction, such that the output shaft rotates about a horizontally oriented rotation axis. In some embodiments, the output shaft of the yaw motor is coupled to a proximal end of the hoe arm. With such an arrangement, the hoe arm can be caused to rotate about two separate axes of rotation, namely a vertical axis defined by the output shaft of the pitch motor and a horizontal axis defined by the output shaft of the yaw motor. Other embodiments may include more or less drive motors and/or axes of rotation, other embodiments may position the multiple axes of rotation in different orientations, and/or the like. Further, in some embodiments, the two motors are actually motor assemblies that each include a motor and gearbox. In such a configuration, the output shafts are actually an output shaft of a gearbox that is coupled to the motor. Such a configuration can be desirable, for example, to provide a mechanical advantage, to change an orientation of the rotation axis, and/or the like. In some embodiments, the motors desirably comprise brushless DC motors, which can operate relatively efficiently. Some embodiments may, however, use different types of electric motors, hydraulic and/or pneumatic motors, linear actuators, rack and pinon systems, hydraulic and/or pneumatic cylinders or actuators, and/or the like.

Some embodiments comprise an autonomous network of robots and/or drones wherein at least one drone inspects an area for a specific agriculture asset and at least one ground robot performs an action based on the drone inspection. In some embodiments, drones perform an inspection of an area of farmland, the inspection data is analyzed via AI to identify areas with high concentrations of weeds, and ground robots travel to identified areas and perform weed control.

Some embodiments relate to an autonomous network of drones that transfer data between each other and are linked to the other networks through a link drone capable of ground and aerial mobility, and in some embodiments, the drones are powered by solar charging and align themselves to the sun. In some embodiments, the drones can affix to the ground at night and during extreme weather.

Current robotic systems have struggled to meet farmers' and agriculture professionals' needs because these systems have not successfully integrated drones, robots, and software analytics. Instead, each individual technology has been used in and of itself and generally relies on human interaction and infrastructure. Companies have specialized in designing, building, and in some cases operating drones. Other companies have specialized in software analytics for crops. Other companies have specialized in creating ground robots to perform actions on a farm such as weed control or seeding. However, in order for farmers to truly benefit, it can be desirable to combine all three of these technologies, or at least two of these technologies. Each technology has significant shortcomings when used by itself, although it is also possible to use them by themselves.

In some embodiments, it can be disadvantageous to have ground robots without drones because ground robots have limited scouting capability due to their speed. The addition of drones to the system reduces the number of ground robots required to perform weed control. It can be beneficial to use ground robots without drones, however, because the use of drones increases the level of sophistication for the system. For some applications, such as livestock management and terraforming, drones may not be necessary to achieve the full benefit of the ground robots.

Weeds compete with crops for nutrients and water, and the presence of weeds will reduce a farmer's crop yield. Currently, farmers are spraying large amounts of herbicides over entire fields, even for isolated problems, with spraying equipment attached to tractors or airplanes. These methods are expensive and are becoming ineffective as weeds are becoming resistant to herbicides. Over 250 herbicide resistant species of weeds exist in the United States of America. Additionally, herbicides are known carcinogens and harmful to farmers and farmland.

While mechanical and electrical weed control robots have been used previously, these robots are very expensive, and struggle to catch issues after weeds spread seeds. Current robots also struggle to effectively remove weeds. Removing weeds before they spread seeds decreases the probability of recurring weeds in the next growing season. Because farmers are heavily invested in pesticide application equipment and infrastructure, farmers need an efficient, low-cost method of removing weeds. Traditional mechanical weed control robots undergo high levels of wear that force the robots to be large and complex and require the farmer to perform frequent in-field service. In addition, the current robots are heavy and cause damage to the farmland due to soil compaction. Many electrical weed control robots have a high voltage system which runs continuously, resulting in an unsafe environment for people or animals near the robot. Additionally, running continuously results in large amounts of energy consumption.

In addition, the industry has struggled to develop ground robots that can perform weed control in close proximity to the crops and without damaging the crops without pesticide use.

One of the major issues with current drones is that they are not optimized for solar charging both in flight and on the ground. As a result, nearly all drones on the market have to charge at a centrally located charging infrastructure. Due to current drones' dependency on charging infrastructure, the technology is not scalable for agricultural applications because their battery life last about 30 minutes before new batteries or a charging is required. This limitation directly impacts the current technology's ability to provide meaningful use to farmers in remote areas.

Furthermore, current drones have to transfer data over the internet or cellular connection to a cloud-based analytics platform or directly onto a secure digital (SD) card for a farmer or agriculture professional to transfer a computer. This process is time consuming and does not offer the farmer immediate analysis and guidance as to how to take action in his field. Furthermore, this data is not mapped directly onto a robot or machine to address any areas of concern identified in the analysis in a timely manner.

Therefore, it is desirable to provide a network of autonomous, self-charging robots wherein drones collect data and transfer the data directly to a farmer or machine to take immediate action. In some cases, the drones can use onboard artificial intelligence (AI) processers to analyze the data in real time and either send a report directly to a farmer's device or send points of concern to ground robots where ground robots take immediate action. In other cases, a drone sends inspection data to the ground robot for analysis, and after the ground robot performs AI analysis, then ground robot takes action on areas of concern.

In some cases, the autonomous, self-charging drones can affix themselves directly to ground robots for protection in extreme weather.

Additionally, there is a need for a network of drones and ground robots that perform actions such as weed control. With the overuse of herbicides in modern farming practices and rise of organic farming, farmers need improved methods of weed control without harmful chemicals. Current agriculture robots are expensive, complex, large, and cannot perform weed control in close proximity to the crops after germination. Furthermore, the current technology requires a major capital investment and infrastructure investment for the farmer. As a result, the proposed robots in this disclosure create a dynamic and decentralized network with limited or no infrastructure, wherein the drones are continuously inspecting the fields to determine the location of weeds and the ground robots are performing weed control in areas identified by AI analysis of the drone data. To date, this problem in the industry has not been solved because drones are tied to infrastructure and their range is extremely limited.

Remote Network Connectivity

While connectivity has improved in highly urban areas, connectivity is poor to nonexistent in remote areas because there is no budget to invest in cellular bonding or satellite. Poor connectivity is a big issue in developing countries, such as Southeast Asia, Africa, and South America. In addition, poor connectivity is limiting telecommunication as well as data transfer of critical information for both individuals and entities.

Furthermore, poor connectivity is holding back many industries, such as agriculture and utility inspection, from growing and fully utilizing technology in other fields, such as Internet of Things (IOT), automated equipment, and cloud-based Artificial Intelligence (AI) analysis tools. Even in the United States, a pioneer country in connectivity, only about one-quarter of farms currently use any connected equipment or devices to access data, and that technology isn't typically state-of-the-art, running on 2G or 3G networks that telecommunication companies plan to dismantle or on very low-band IoT networks that are complicated and expensive to set up. In either case, those networks can support only a limited number of devices and lack the performance for real-time data transfer, which is essential to unlock the value of more advanced and complex use cases.

For the agriculture industry to advance and meet the increased food demands of the 21st century, it faces one major obstacle: many regions lack the necessary connectivity infrastructure, making development of it paramount to integrate advanced crop monitoring, livestock monitoring, building and equipment management, drone farming, and autonomous farming machinery. These advancements contribute to higher yields, lower costs, and greater resilience and sustainability for farmers and agriculture professionals allowing them to meet the 21st century food demand. In regions that already have a connectivity infrastructure, farms have been slow to deploy digital tools because their impact has not been sufficiently proven. The global farming industry is highly fragmented, with most labor done by individual farm owners. Particularly in Asia and Africa, few farms employ outside workers. On such farms, the adoption of connectivity solutions should free significant time for farmers, which they can use to farm additional land for pay or to pursue work outside the industry.

Since rural areas do not have access to high-speed cellular networks or satellite communications, small aircrafts, specifically drones, are an alternative; however, the current infrastructure requirements and limited flight for drones have limited their use in the telecommunication applications.

One of the major issues with current VTOL aircrafts, specifically drones, is that they are not optimized for solar charging both in flight and on the ground. As a result, all or most of all of the drones on the market have to charge at a centrally located charging infrastructure. Due to current drone's dependency on charging infrastructure, the technology is not scalable for remote networking solutions as their battery life is about 30 minutes before having to swap out batteries or charge. This limitation directly impacts the current technology to provide networking solutions in remote areas.

In addition, another one of the major issues with current VTOL aircrafts, and UAVs in general, is drones struggle to fly in light to moderate wind and/or rain. During moderate to extreme weather, most drones cannot fly and require being stored in a hanger or place of shelter from the elements. This limitation directly impacts the current technology to provide networking solutions in remote areas.

Surveillance and inspection drones, specifically traditional tail sitter drone designs, are susceptible to tipping over during landing in areas with moderate wind. As a result, aforesaid drones struggle to operate and perform mission in extreme weather conditions.

Another one of the major issues with current VTOL aircrafts, specifically drones, is the drones are relatively immobile while on the ground. Most drones have wheels, skis, or skids, which limit mobility unless the land is completely even. These characteristics limit the aircraft's ability to land in remote areas, affix itself to the ground, and charge on the ground.

Therefore, it is desirable to provide a network of autonomous, self-charging VTOL aircrafts that is optimized for collecting and transferring data to and from rural areas. The autonomous, self-charging VTOL aircraft desirably has the ability to efficiently maneuver on the ground on any terrain in order to optimize charging on the ground and latch to the ground for shelter during extreme weather.

Additionally, there is a need for a network of VTOL aircrafts that charge both in flight and on the ground to eliminate the need for charging infrastructure, where drones are staged in a field, hillside, park lot, or even the top of a building prior to performing inspection. As a result, the network of drones is creating dynamic and decentralized networks with limited or no infrastructure that are flexible enough to support any area or industry. To date, this problem in the industry has not been solved as individuals and businesses, specifically rural farms, do not have access to the networks they need to transfer data and take advantage of technology dependent on network connectivity. In a number of the embodiments described herein, the drones will act as a network node to gather and transfer data and will make use of the aircraft itself to charge the battery packs supporting the powertrains necessary to transfer data and make temporary shelter by affixing itself to its environment.

Most VTOL aircraft designs do not have the capability to effectively maneuver on the ground, especially when the terrain is not flat. Also, VTOL aircrafts do not have the ability to attach themselves to the ground for protection from the environment. Furthermore, most designs are not optimized to maximize charging on both the ground and the air. Additionally, the current VTOL aircraft require infrastructure that is not feasible in remote areas.

Reference will now be made in detail to the preferred embodiments of the disclosure, examples of which are illustrated in the accompanying drawings. While the disclosure will be described in conjunction with the preferred embodiments, it will be understood that they are not intended to limit the disclosure to these embodiments. On the contrary, the disclosure is intended to cover alternatives, modifications, and equivalents that may be included within the spirit and scope of the disclosure. Furthermore, in the following detailed description of the present disclosure, numerous specific details are set forth in order to provide a thorough understanding of the present disclosure. However, it will readily be apparent to one skilled in the art that the present disclosure may be practiced without these specific details.

In other instances, well-known methods, procedures, and components have not been described in detail so as not to unnecessarily obscure aspects of the present disclosure. These conventions are intended to make this document more easily understood by those practicing or improving on the inventions, and it should be appreciated that the level of detail provided should not be interpreted as an indication as to whether such instances, methods, procedures, or components are known in the art, novel, or obvious.

Definitions

Artificial Intelligence is the theory and development of computer systems able to perform tasks that normally require human intelligence, such as visual perception, speech recognition, decision-making, and translation between languages. In addition, artificial intelligence may be used to teach the aircraft how to maneuver on the ground or align to the sun.

Gantry is interchangeable with "robot arm" and is the movable structure that is attached frame of the robot wherein the end effector is at the terminating action end. In some cases, the gantry may be attached to a track system capable of moving in multiple direction.

End effector is a device or tool attached to or integrally formed at the terminating end of a robot arm or gantry. In some embodiments, the end effector is a weed control application unit, such as an electrical probe and/or mechanical weed device. In some embodiments, the end effector is a weed control application unit such as an electrical probe, mechanical tool, or combination thereof. In some embodiments, the end effector comprises a hoe unit, a shovel unit, and an electrode or any combination thereof.

Linear actuator converts energy into linear push or pull movements, and some examples include hydraulic cylinder, pneumatic cylinder, electromechanical cylinder, ball screw, lead screw, and/or the like.

Wi-Fi is a wireless networking technology that allows devices to interface with the Internet and interface with one another, creating a network.

Wi-Fi Router is wireless routers offer a convenient way to connect a small number of wired and any number of wireless devices to each other for access to the Internet.

Mobile Hotspot is a common feature on smartphones with both tethered and untethered connections. When you turn on your phone's mobile hotspot, you share your wireless network connection with other devices that can then access the Internet.

Wi-Fi Hotspot is a mobile hotspot obtained through a cell phone carrier. It's a small device that uses cellular towers that broadcast high-speed 3G or 4G broadband signals. Multiple devices, like tablets, phones, and laptops, can then connect wirelessly to the device.

LTE is short for "Long-Term Evolution" and broadcasts signals over cellular towers. LTE download speeds from 5 Mbps to 100 Mbps.

Satellite is a machine that is launched into space and moves around Earth or another body in space. At a minimum, a satellite comprises an antenna and power source, such as a battery or solar panel.

Solar Energy is radiant light and heat generated from the sun that can be harnessed using a range of ever-evolving technologies, such as solar heating or solar charging.

Biomimicry is a practice that learns from and mimics the strategies found in nature to solve human design challenges. The robotic system seeks to use artificial intelligence to mimic nature and evolve to continuously adapt to the robotic system's environment.

Multi-modal VTOL Robot is capable of attaching itself to the ground or object, moving on the ground, or aerial movement and may be referred to as a weather resistant VTOL robotic system, aircraft, drone, or an aircraft in various embodiments through the disclosure.

Herbicide is a chemical substance toxic to plants.

Central Processing Unit (CPU) performs basic arithmetic, logic, controlling, and input/output (I/O) operations specified by the instructions in the program. In some embodiments, the CPU may include a GPU and/or a TPU.

Accelerator is the use of computer hardware specially made to perform some functions more efficiently than is possible in software running on a general-purpose central processing unit (CPU).

Graphics Processing Unit (GPU) is a specialized, electronic circuit designed to rapidly manipulate and alter memory to accelerate the creation of images in a frame buffer intended for output to a display device.

Tensor Processing Unit (TPU) is a highly optimized for large batches and convolutional neural networks and has the highest training throughput.

Transformer is a device that transfers electricity from one circuit to another with changing voltage level but no frequency change.

RGB is an additive color model in which red, green, and blue light are added together in various ways to reproduce a broad array of colors.

Vertical Take Off and Landing (VTOL) refers to aircraft that can depart, hover, and land vertically, including fixed-wing aircraft with the ability to take off and touch down vertically.

Thrust Propeller produces lift, but in a forward direction—a force we refer to as thrust. Its rotary motion through the air creates a difference in air pressure between the front and back surfaces of its blades.

Aileron is a movable control surface, which on traditional airplanes is located on the trailing edge of an airplane wing and is used for imparting a rolling of the aircraft structure relative to its longitudinal axis and adjusting the pitch of the aircraft. For traditional airplanes, the aileron is very important for banking turns.

Rudder is a flight control surface which controls rotation about the vertical axis of an aircraft. This movement is referred to as yaw.

Elevator is a flight control surface that control the aircraft's pitch, which is critical for controlling the angle of attack and the lift of the wing.

Landing Gear is the part of an aircraft that supports weight of the aircraft when the aircraft is in contact with the land or water.

Vertical Stabilizer is a flight control surface that prevents side slippage.

Exemplary Embodiments

Collaborative Robot Network with Optimized Weed Control Methods

It should be noted that the disclosed embodiments of a Collaborative Robot Network with Optimized Weed Control Methods may be combined with any embodiments disclosed herein, and individual features of the Collaborative Robot Network with Optimized Weed Control Methods may be combined with individual features of any other embodiment. Any other embodiments may also be combined with the disclosed Collaborative Robot Network with Optimized Weed Control Methods, and individual features of any embodiment may be combined with individual features of the disclosed Collaborative Robot Network with Optimized Weed Control Methods.

A ground robot or autonomous ground vehicle, as the terms are used herein, are broad terms that can include, but are not limited to, ground-based robot, ground vehicle, ground-based vehicle, autonomous ground vehicle, autonomous ground-based vehicle, unmanned vehicle, unmanned robot, autonomous robot, autonomous vehicle, autonomous robotic vehicle, land robot, land-based robot, land vehicle, land-based vehicle and/or the like. Drone, as the term is used herein, is a broad term that can include, but is not limited to, aircraft, flying vehicle, plane, solar plane, UAVs (Unmanned Aerial Vehicles), RPAS (Remotely Piloted Aerial Systems), AAVs (Autonomous Aerial Vehicles), and/or the like. Robotic arm, as the term is used herein, is a broad term that can include, but is not limited to, robot arm, mechanical arm, probe, hoe arm, and/or the like. A weed, as the term is used herein, is a broad term that can include, but is not limited to, a plant, agricultural plant, shrub, greenery, vegetation, undergrowth, plant species, plant organism, herb, flower, vegetable, flora, and/or the like.

As shown in FIG. 1, an embodiment of Collaborative Robot Network 100 comprises at least one inspection drone 101, at least one ground robot 111-113, agriculture asset 102, and sun (not shown). Inspection drone 101 may fly or move on the ground to collect data with sensors or cameras. Sun beams (not shown) emitted from sun (not shown) hit the solar panel of inspection drone 101 and ground robot 111-113 to provide power for flight, ground movement, data collection, and data transmission. Inspection drone 101 analyzes inspection data with on-board AI processor and transfers points of action to ground robots 111-113. Ground robots 111-113 move on the ground to the point of action. After reaching the point of action, ground robots 111-113 will perform an action, such as weed control (mechanical, chemical, electrical, and/or a combination thereof), soil samples, moisture level sampling, nitrogen sampling, or more detailed imaging. Inspection drone 101 and ground-based robots 111-113 are operated autonomously via AI. In some embodiments, inspection drone 101 and ground-based robots 111-113 may be remotely operated by at least one pilot. In some embodiments, ground robots 111-113 weigh no more than, for example 150 pounds, which allows a single robot to be shipped over standard freight and reduces soil compaction and damage to the farmland without using a complex track system to distribute the ground robot's weight. In some embodiments, ground robots 111-113 weigh no more than 75 pounds, 100 pounds, 125 pounds, 175 pounds, 200 pounds, 250 pounds, 300 pounds, 350 pounds, 400 pounds, and/or the like.

In some embodiments, inspection drone 101 flies over agriculture asset 102 that is a field of crops, such as corn. Inspection drone 101 takes pictures of crop rows 103, 105, and 107. Inspection drone compiles imagery including RGB, RGB and near infrared, or hyperspectral, and analyzes imagery to identify areas of action, which may include areas with weeds, areas with irrigation issues, areas with high crop stress, or the like. The areas of action are transferred to ground robots 111-113. Ground robots 111-113 travel to the point of action and begin taking action, such as weed control (see FIGS. 4-5). In some cases, ground robots can perform mechanical, electrical, chemical, or hot oil weed control. In some cases, a farmer may receive a notification to take ground robot to a specific place in the field, and farmer will transport the ground robot manually. In some embodiments, ground robots weigh less than 150 pounds which allows them to be easily transport from one filed to another via a truck or tractor.

In some embodiments, inspection drone 101 will inspect after ground-based robots 111-113 take action. In the case of weed control actions, inspection drone 101 will inspect to see if all of the weeds are removed and to see if any crops have been damaged by comparing images before weed control and after weed control. In some embodiments, re-inspection takes place days after the weed control is performed, for example, 2-3 days later, because it may take time for the weed to weaken, biodegrade, or otherwise be eliminated.

In some embodiments, inspection drone 101 will inspect consecutive days or multiple times a day to determine the accuracy of the imagery. Inspection drone 101 may capture imagery multiple times when performing crop count of, for example rows 103, 105, 107, and/or the like. In some embodiments, ground robots 111-113 will capture further images near the crop or on the ground to provide more data for analysis via AI.

In some embodiments, inspection drone 101 and ground-based robots 111-113 have at least one solar panel. Sun beams (not shown) emitted from sun (not shown) hit solar panel of inspection drone and ground-based robots to provide power for flight, ground movement, data collection, and data transmission. In other embodiments, inspection drone 101 has batteries (for example, like battery 503 in FIG. 5A). In another embodiment, inspection drone 101 and ground-based robots 111-113 have solar panels (for example, like solar panel 415 in FIG. 5A) and batteries.

In some embodiments, inspection drone 101 transmits inspection data to ground-based robots 111-113, and ground-based robots 111-113 transmit inspection data to cloud computing and storage via satellite. In some embodiments, inspection drone 101 transmits data to ground-based robots 111-113, and ground-based robots 111-113 transmit inspection data to cloud computing and storage via Wi-Fi networks. In some embodiments, inspection drone 101 transmits inspection data to ground-based robots 111-113, and ground-based robots 111-113 transmit inspection data to cloud computing and storage via cellular networks. In some embodiments, inspection drone transmits inspection data to ground-based robots 111-113, and ground-based robots 111-113 utilize on-board AI processors to process inspection data. In some embodiments, inspection drone 101 can fly and perform an inspection task, such as taking pictures of agriculture asset 102 and transfer the picture to cloud computing network via LTE network. In some embodiments, agriculture asset 102 is field of row crops, such as corn or sugar beets. In some embodiments, agriculture asset 102 is field of field crops, such as soybeans or rice. In some embodiments, agriculture asset 102 is group of livestock, such as cattle.

As shown in FIGS. 2A & B, an embodiment of Collaborative Robot Network 200. Drone 201 can fly above ground robot 211 and act as an antenna for ground robot 211. In some embodiments, ground robot 211 uses wheels 213 to move on ground 202 along agricultural asset 203. Ground robot 211 transfer data to drone 201, and then drone 201 transfers data to a cellular network (not shown). In some embodiments, ground robot 211 transfer data to drone 201, and then drone 201 transfers data to a satellite (for example, like satellite 3103 in FIG. 31). In some embodiments, ground robot 211 transfer data to drone 201, and then drone 201 transfers data to a Wi-fi network (not shown). The ground robot may have issues with data transfer because of ground effects and signal distortion. Therefore, it may be advantageous for drone 201 to transfer data. One advantageous configuration is for drone 201 to be elevated above ground-based robot 211 to eliminate ground effects and signal distortion by greater than 5 wave lengths of communication signal from the ground. In some embodiments, the number of wave lengths is approximately 10. In addition, drone 201 is able to transfer data to satellite, cellular tower, or an individual with less obstructions than if ground-based robot 211 was trying to transmit data. In some embodiments, ground robot 211 has solar panel 215 coupled to it.

Some Differences Between Collaborative Robot Network with Optimized Weed Control Methods and the Prior Art Farmers are struggling to catch issues on the farmland early. Current farming methods and practices find issues after significant damage to crops, such an irrigation leak or plant disease. Therefore, it is advantageous to have a drone that can continuously inspect a parcel of land and have means to quickly analyze the data and either take immediate action or provide an actionable report to the farmer.

One area of interest is weed control. Weeds compete with crops for nutrients, and the presence of weeds will reduce a farmer's crop yield. Currently, farmers are spraying large amounts of herbicides over entire fields even for isolated problems with spraying equipment attached to tractors or airplanes. These methods are expensive and becoming ineffective as weeds are becoming resistant to herbicides. Over 250 herbicide resistant species of weeds exist in the United States of America. Additionally, herbicides are known carcinogens and harmful to farmers and farmland.

While mechanical and electrical weed control robots have been used previously, these robots are very expensive, and struggle catch issues after weeds spread seeds and struggle to effectively remove weeds. By removing weeds before they spread seeds, seeds will need to transfer from another field, which will decrease the probability of recurring weeds in the next growing season. Since farmers are heavily invested in pesticide application equipment and infrastructure, farmers need an efficient, low-cost method of removing weeds. Traditional mechanical weed control robots undergo high levels of wear that force the robots to be large and complex and require the farmer to perform frequent in field service. In addition, the current robots are heavy and cause damage to the farmland due to soil compaction. Also, a number of the electrical weed control robots have the high voltage system run continuously which results in an unsafe environment for people or animals near the robot and this creates large amounts of energy consumption. Therefore, it is advantageous to have robots that can detect weeds before they spread and quickly remove the weeds, which decreases the wear on the robots and size of the robots.

Drone and Ground Robot Perch System

Figure 3A:
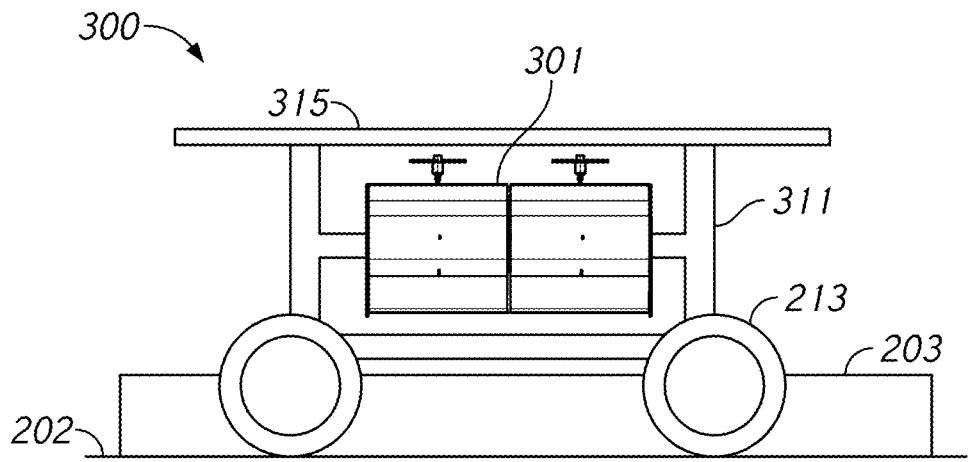
FIG. 3A is a diagram of Collaborative Robot Network showing a side view of a drone attached to a ground robot, according to an embodiment.
Figure 3B:
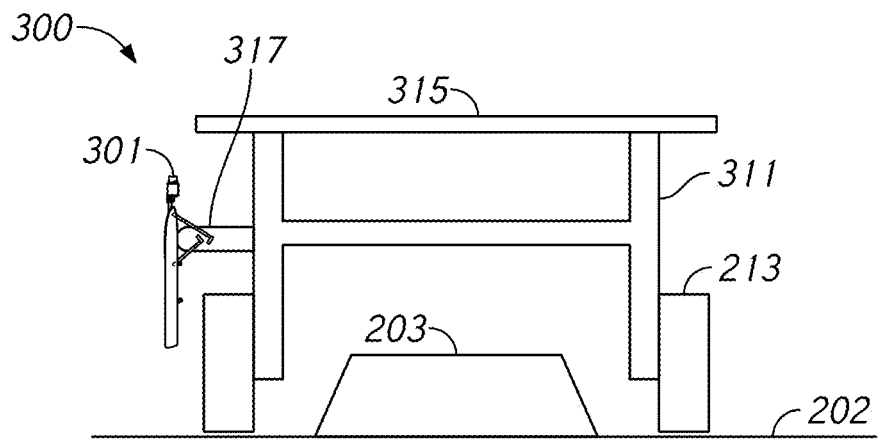
FIG. 3B is a diagram of Collaborative Robot Network showing a front view of a drone attached to a ground robot, according to an embodiment.
Figure 3C:
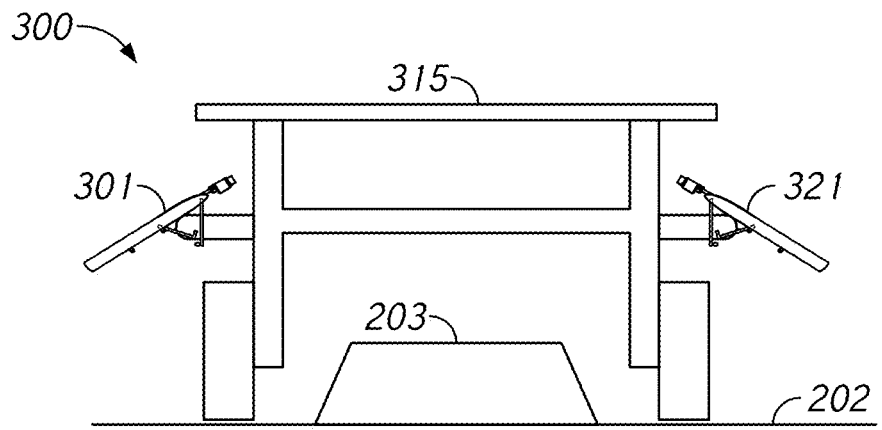
FIG. 3C is a diagram of Collaborative Robot Network showing a front view of multiple drones attached to a ground robot, according to an embodiment.

FIGS. 3A-C shows an embodiment of drone and ground robot perch system 300, drone 301 attached with latching legs to perch bar 317 of ground-based robot 311. Drone 301 can take off and land on ground-based robot 311. Drone 301 can angle towards the sun and charge while affixed to perch bar 317 as shown in FIG. 3C. In some embodiments, drone 301 rotates with propellers to under solar panel 315 for shelter. In some embodiments, perch bar 317 can be replaced by a box, an enclosure, or a substantially similar feature located under the solar panel of the ground robot where the drone can land and take off from. In this case, the drone does not need latching legs. In some embodiments, several drones, such as drones 301 and 321, can affix to a single ground robot.

Precision Weeding with Camera and CPU.

As shown in FIG. 4A, an embodiment of a precision weeding system 400A, ground robot 411 uses wheels 414 to travel on ground 402 along crop row 403 to find weeds.

Motor and gearboxes 419 are coupled to ground robot 411. In some embodiments, ground robot 411 uses camera 420 to detect weed 430 in crop row 403. When camera 420 takes an image, records a video, and/or the like, and CPU (for example, like CPU 507 in FIG. 5A) determines the existence and location of weed 430, high voltage circuit (for example, like HV Booster 511 in FIG. 5A) is enabled and the gantry end effector assembly containing probes 417 controlled by the CPU moves towards weed 430. In some embodiments, each end effector is comprised of at least one probe, and the end effector is attached to a gantry that can move on a track system 416 powered by motors that allow the gantry and end effector assembly to move in 2 or 3 dimensions. In some embodiments, ground robot is powered by solar panel 415. In some embodiments, ground robot 411 is powered by batteries (for example, like battery 503 in FIG. 5A). In some embodiments, ground robot 411 is powered by solar panels 415 and batteries, wherein solar panels 415 charge batteries.

As shown in FIG. 4B, an embodiment of a weed control system 400B, person 440 using handheld weed control unit 442 to eliminate weed 430. Handheld weed control unit 442 uses camera 444 to take an image, record a video, and/or the like, of the farmland and CPU (for example, like CPU 507 in FIG. 5A) determines the existence and location of weed 430. If weed 430 is identified, high voltage circuit (for example, like HV Booster 511 in FIG. 5A) is enabled and probes 446 move towards the weed 430. In some cases, probe 446 comprises a negative terminal at the tip of 446 and positive terminal along the shaft of probe 446 where an insulator is adjacent to the negative terminal and positive terminal in order to separate the two elements. Probe 446 extends into the ground where the tip makes contact with the ground and the shaft makes contact with the weed, creating a circuit through the ground.

Figure 4C:
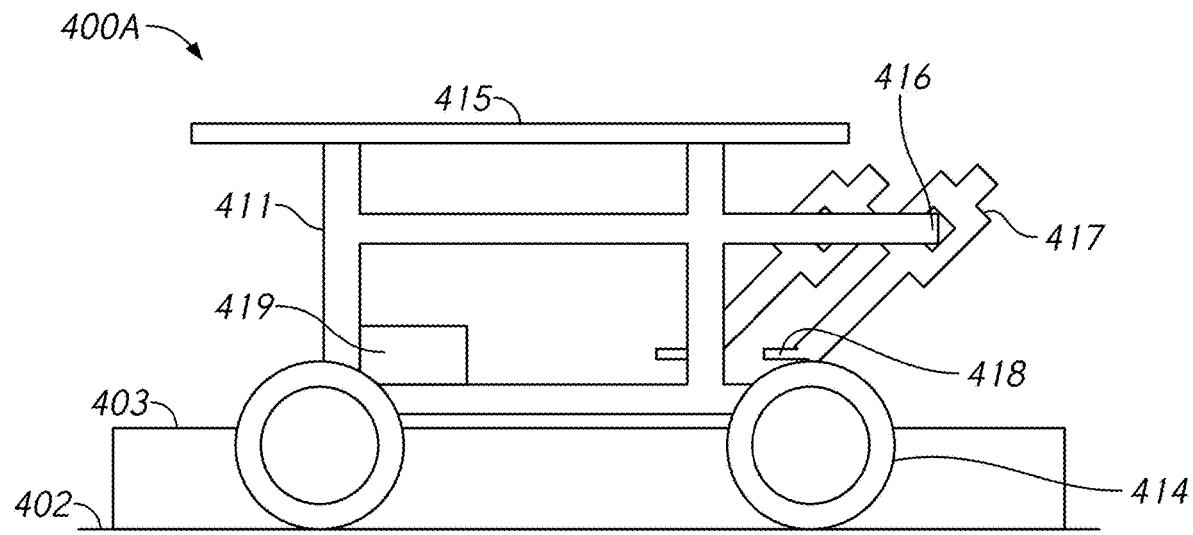
FIG. 4C is a diagram of a side view of a ground robot showing a plant management end effector with two moving probes, according to an embodiment.
Figure 4D:
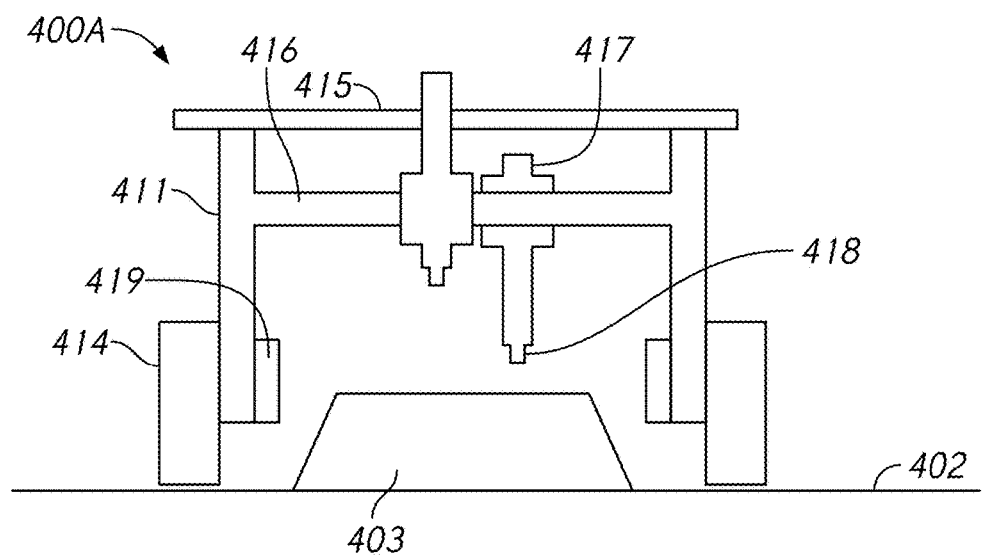
FIG. 4D is a diagram of a front view of the ground robots showing a plant management end effector with two moving probes, according to an embodiment.

As shown in FIGS. 4C & D, ground robot 411 uses angled gantry end effector containing probes 417 to move towards weeds. One angled probe 417 will move towards the weed identified by the CPU (for example, like CPU 507 in FIG. 5A) and camera (for example, such as camera 420 in FIG. 4A), and the other angled probe 417 will move towards the ground to create a circuit through the ground. In some embodiments, one angled probe 417 will move towards the weed identified by the CPU and camera, and the other angled probe 417 will move towards another weed identified by the CPU and camera, creating a circuit through the ground to both weeds. In some embodiments, probes 417 may contain tip, distal end, and/or the like 418. The tip 418 may include an electrode in any embodiments disclosed herein.

Figure 4E:
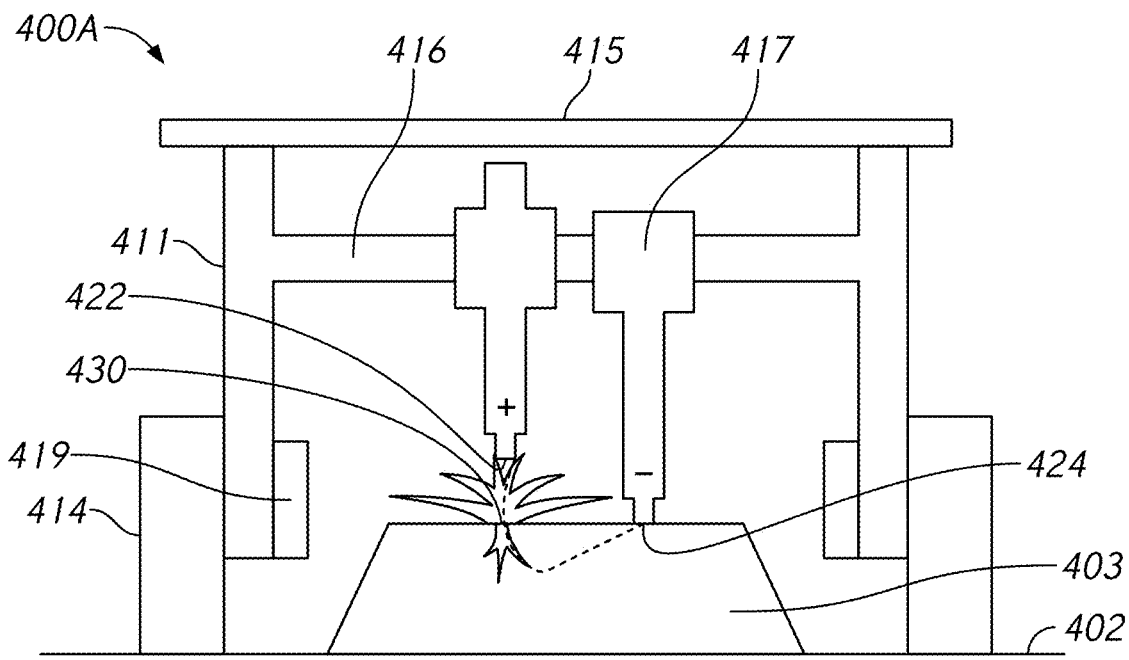
FIG. 4E is a diagram of a front view of a ground robot showing weed control circuit for eliminating weeds through the ground, according to an embodiment.
Figure 4F:
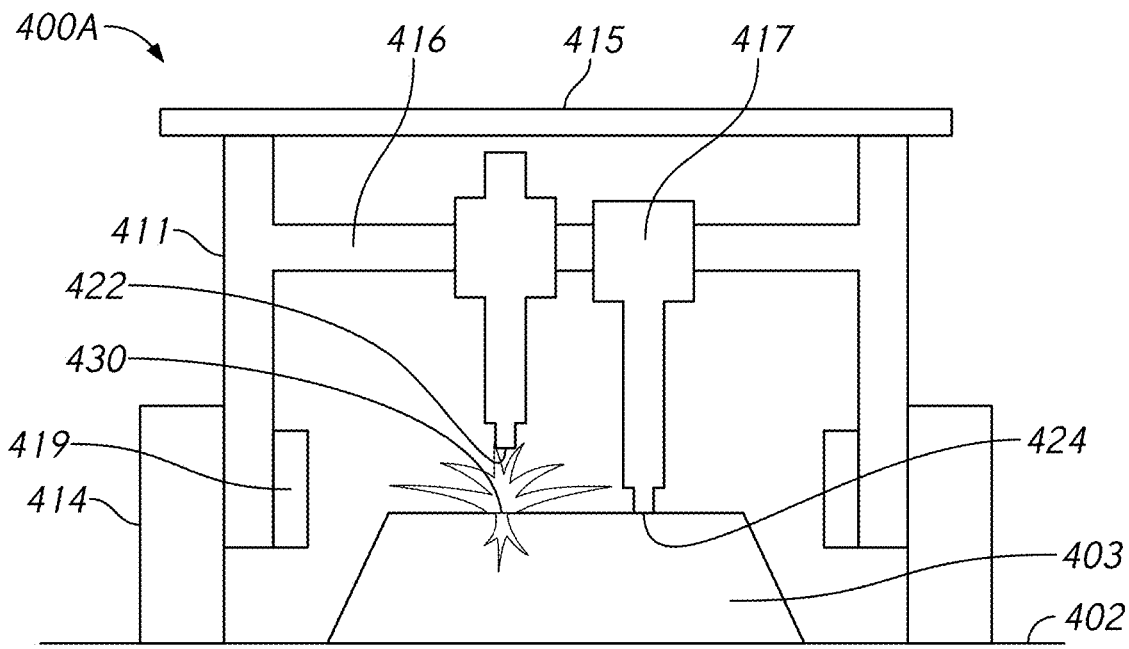
FIG. 4F is a diagram of a front view of a ground robot showing a weed control circuit for eliminating weeds through the ground after high voltage circuit is activated, according to an embodiment.

FIGS. 4E & F show the circuit for eliminating weeds wherein positive probe 422 makes contact with weed 430, negative probe 424 makes contact with ground, the ground and weed are resistors, and the power source is the solar panel. In some embodiments, the negative probe makes contact with another weed. In some embodiments, positive probe 422 and negative probe 424 are made of metal, such as nickel, steel, or aluminum. In some embodiments, positive probe 422 and negative probe 424 are coated with a metallic plating, such as nickel, zinc, or a combination thereof. In some embodiments, negative probe 424 is sharp in order to pierce the ground 403.

Figure 4G:
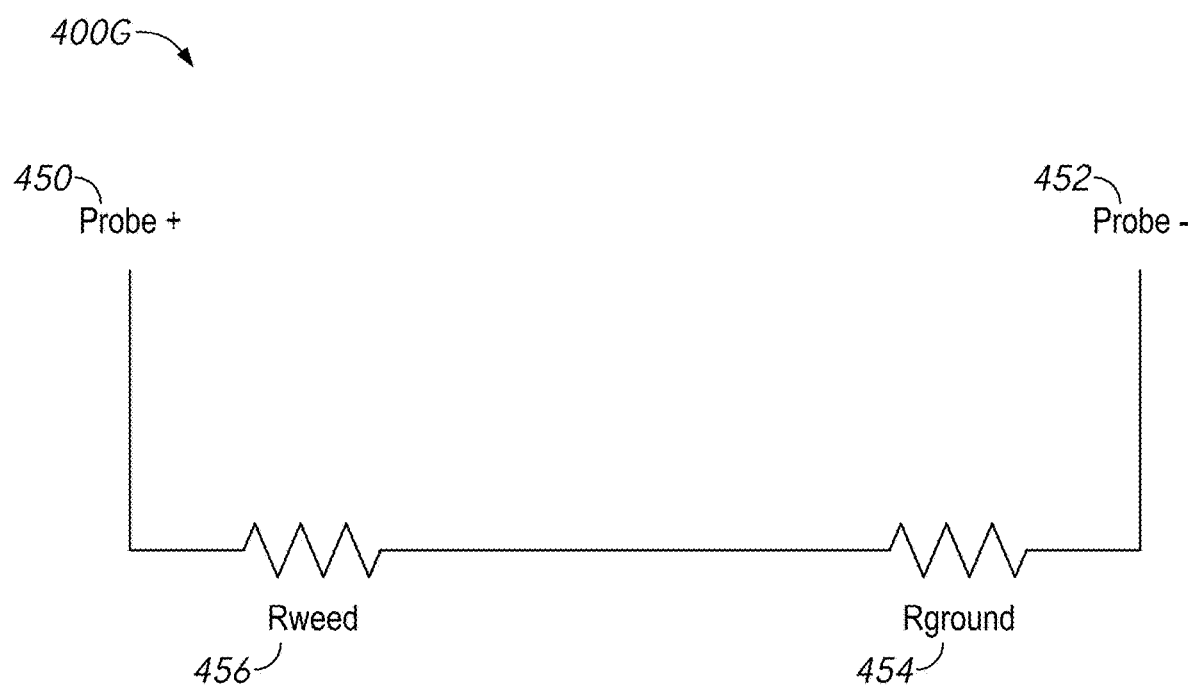
FIG. 4G is an electrical schematic showing the circuit between the positive probe and negative probe to eliminate weeds, according to an embodiment.

FIG. 4G shows a circuit 400G for eliminating or weakening weeds through their roots wherein there is a current path from positive probe 450 to negative probe 452 through the resistance for weed 456 and resistance of ground 454. In some embodiments, two or more weeds may be added to the circuit in series, where all weeds would be eliminated or weakened. In some embodiments, positive probe 450 and negative probe 452 are controlled by a CPU connected to a camera wherein the probes are moved to locations of weeds determined by the CPU and the circuit is activated only when the probes have reached the locations determined by the CPU.

Figure 4H:
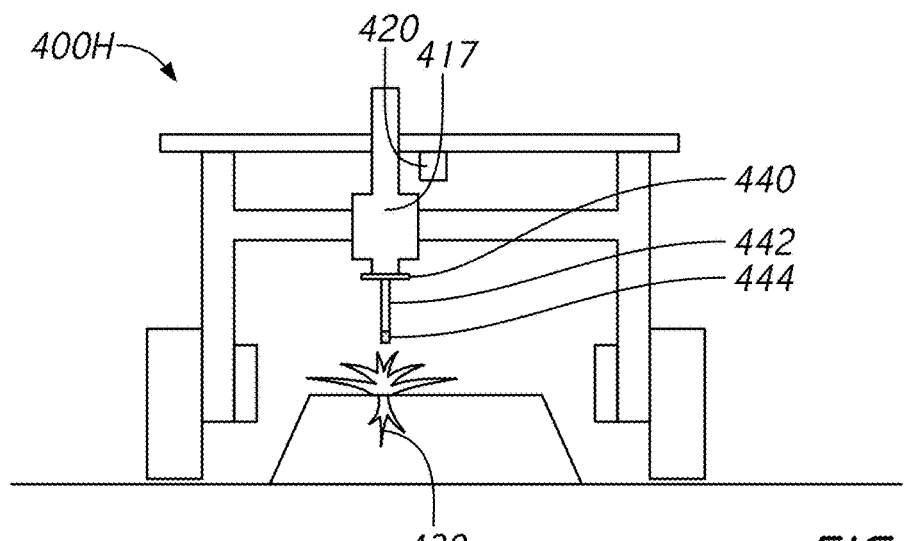
FIG. 4H is a diagram of a front view of a ground robot with an end effector with a single probe for eliminating weeds where the gantry is in a retracted position, according to an embodiment.
Figure 4I:
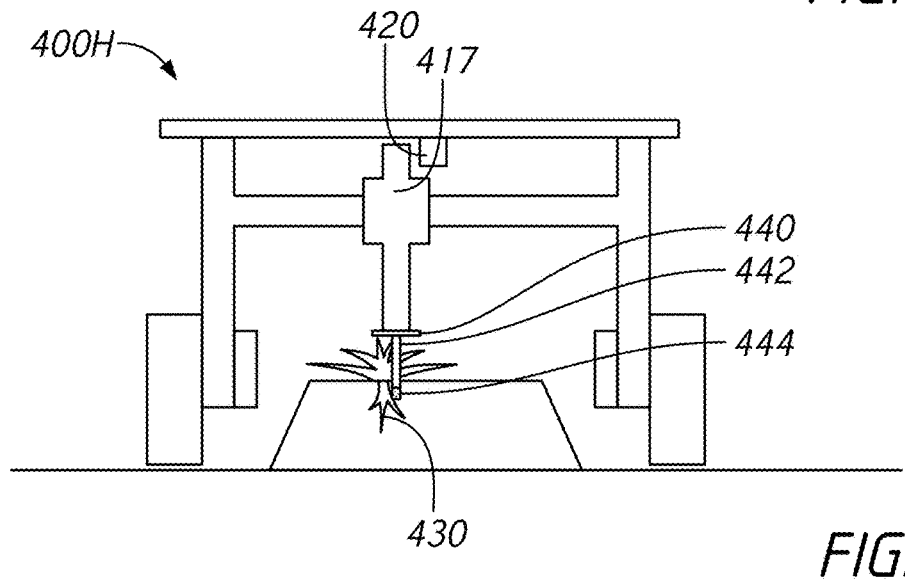
FIG. 4I is a diagram of a front view of a ground robot with an end effector with a single probe for eliminating weeds where the gantry is in an extended position and the probe is making contact with a weed, according to an embodiment.
Figure 4J:
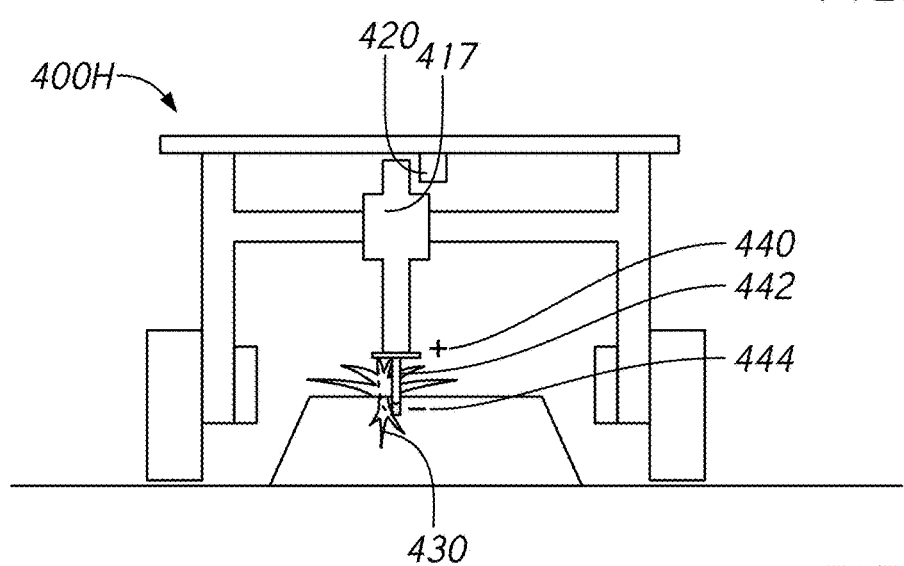
FIG. 4J is a diagram of a front view of a ground robot with an end effector with a single probe showing the electrical circuit when the high voltage system is activated, according to an embodiment.

FIG. 4H-J shows an embodiment where ground robot 411 has a single probe 442 comprised of a negative region 444 near the terminating end of probe 442 and a positive region 440 along the body or at the base of probe 442. In some embodiments, negative region 444 is a sharp or rounded tip, positive region 440 is a collar, and the region between negative region 444 and positive region 440 is an insulator. As shown in FIG. 4I, camera 420 takes an image, records a video, and/or the like, and the CPU analyzes the image to locate the weed; the CPU then communicates with the motors of controlling the position of the gantry and end effector assembly 417 to move the probe to the approximate position of the weed and extend probe 442 towards the weed. Once negative region 444 of probe 442 makes contact with the ground and positive region 440 makes contact with the weed, a switch flips to activate the high voltage circuit and the weed is electrocuted. In some embodiments, the switch is turned on based on the camera determining when probe 442 makes contact with the ground and the weed. After the weed is eliminated, the switch is turned off and probe 442 retracts. In some embodiments, the switch is turned on to activate the circuit for a predetermined amount of time (t). In some embodiments, the predetermined amount of time is between 1-5 seconds. In some embodiments, the predetermined amount of time for the high voltage circuit to be switched on is based on any combination of weather, size of the weed, moisture level (humidity), and weed type. CPU receives inputs for parameters that determines the amount of time need to weaken and eliminate weeds. In some embodiments, the model for predicting predetermined amount of time is adjusted based on feedback from aerial inspection data after weed control that determines efficiency of the model. Predetermined times will be adjusted accordingly. In some embodiments, the model for predicting predetermined amount of time is adjusted based on feedback from ground robot inspection data after weed control that determines efficiency of the model. Predetermined times will be adjusted accordingly.

In some embodiments, the camera could be used in combination with at least one sensor that could be capable of measuring voltage or resistance such as a comparator or ADC, ultra-sonic sensors, force feedback sensors, or the like. In some embodiments, a camera could be replaced by at least one sensor capable of measuring voltage or resistance such as a comparator or ADC, ultra-sonic sensors, force feedback sensors, or the like.

FIG. 23A-D shows alternatives of ground robot designs and configurations. In some embodiments, the ground robots can perform electrical weed control described herein without a drone.

Figure 5A:
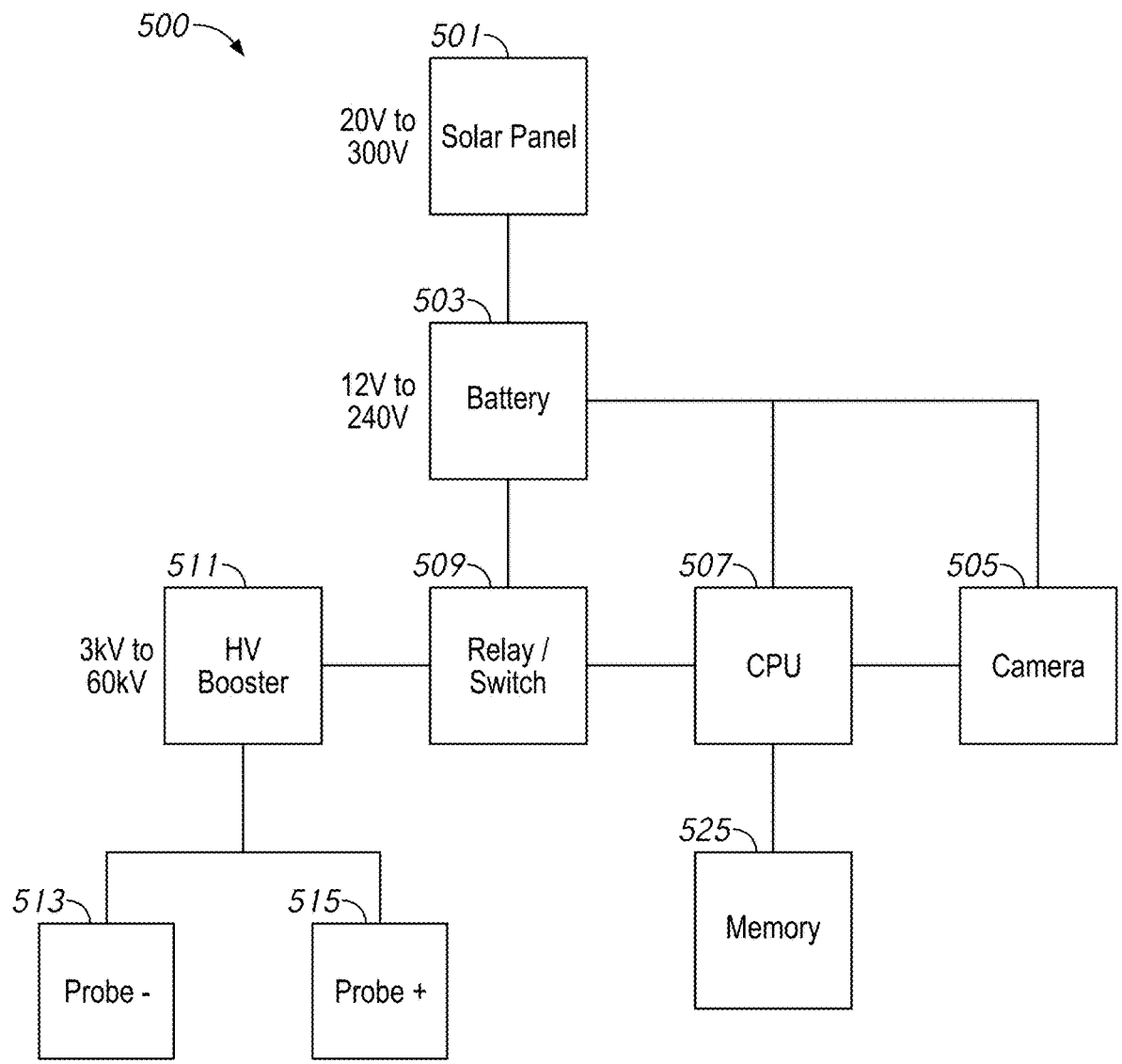
FIG. 5A is a diagram of a weed control circuit used in robots to electrocute a weed through the roots of said weed, according to an embodiment.

As shown in FIG. 5A, ground robot 500 comprises at least one solar panel 501, at least one energy storage device 503, high voltage booster 511, switch 509, CPU 507, camera 505, negative probe 513, and positive probe 515 to weaken and eliminate weeds. Robot 500 moves on a farmland and camera 505 takes imagery, records a video, and/or the like. CPU continuously analyzes the imagery being taken, and when the CPU identifies a weed, switch 509 connected to energy storage device 503 and high voltage booster 511 are activated, where high voltage booster 511 is connected to positive probe 515 and negative probe 513. In some embodiments, the voltage of solar panel 501 is between 20 volts and 300 volts; the voltage of energy storage device 503 is between 12 volts and 240 volts; and the voltage of high voltage booster 511 is between 3,000 volts and 60,000 volts. In some embodiments, solar panel 501 generates 100 watts of power. In some embodiments, high voltage booster 511 is a pulsed circuit transformer. In other embodiments, high voltage booster 511 is a current source or negative ion generator. After positive probe 515 and negative probe 513 create a circuit through the weed and ground for a predetermined amount of time, the switch 509 disconnects energy storage device 503 and high voltage booster 511. In some embodiments, there is no energy storage device 503 and the switch 509 connects high voltage 511 and solar panel 501 where solar panel 501 provides power for CPU 507 and camera 505. In this case, positive probe 515 and negative probe 513 are stationary. In some embodiments, the circuit for eliminating weeds of robot 500 is a direct current (DC) circuit. In some embodiments, the energy storage device is a battery.

In some embodiments, robot 500 comprises at least one solar panel 501, high voltage booster 511, switch 509, CPU 507, camera 505, negative probe 513, and positive probe 515 to eliminate weeds. In some embodiments, switch 509 is a relay. In some embodiments, positive probe 515 and negative probe 513 are combined into a single probe that moves to the location of a single weed. In some embodiments, the voltage of energy storage device 503 is between 12 volts and 240 volts. In some embodiments, the voltage of energy storage device 503 is between 24 volts and 240 volts and/or the like. In some embodiments, there is a super-capacitor bank with the energy storage device on the low voltage side. In some embodiments, the system comprises one or more capacitors on the high voltage side. In some embodiments, the one or more capacitors may comprise one or more super-capacitors. In some embodiments, robot 500 includes memory 525. In some embodiments, memory 525 is connected to CPU 507.

Figure 5B:
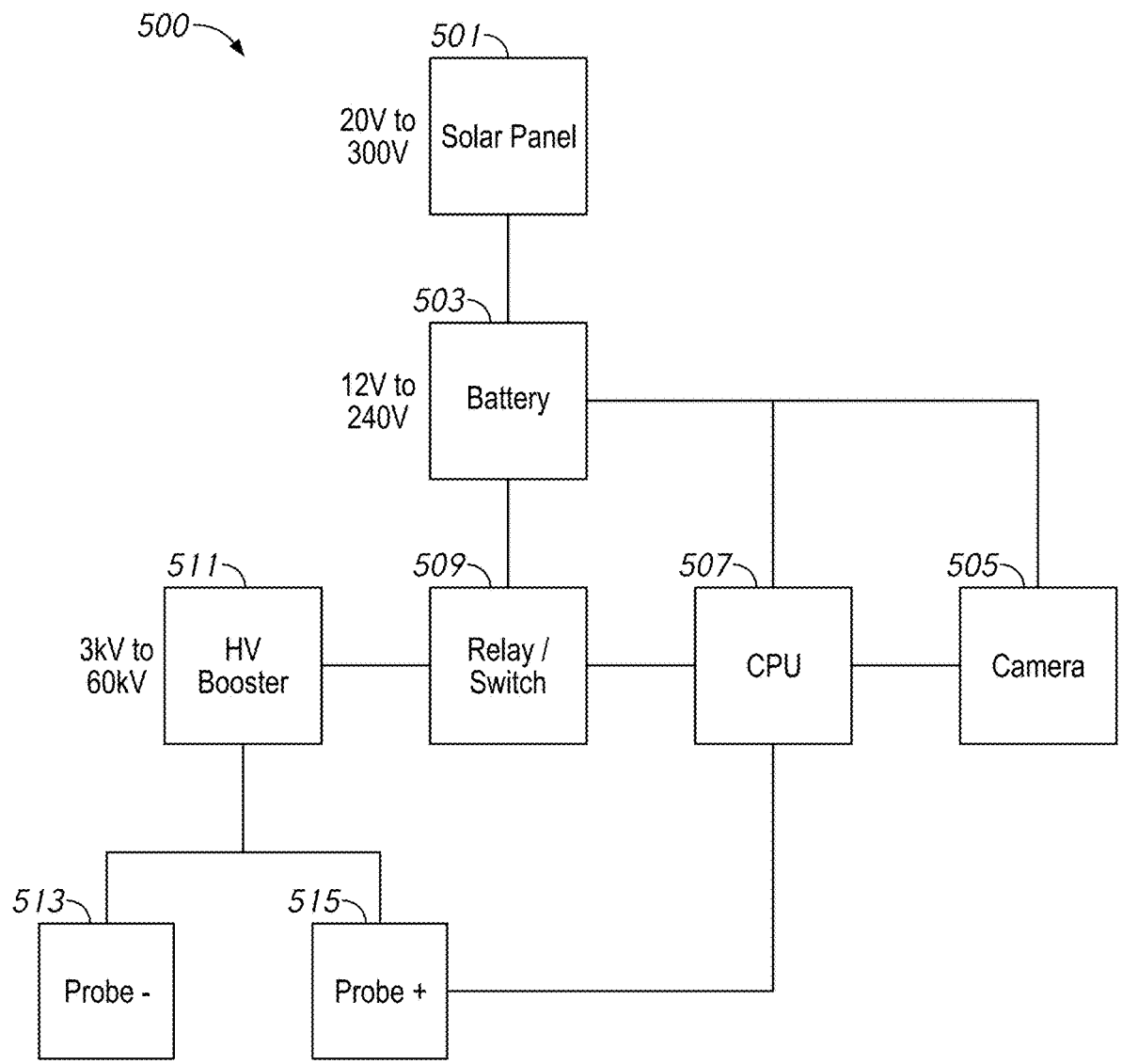
FIG. 5B is a diagram of a weed control circuit used in robots to electrocute a weed through the roots of said weed in FIG. 5A, where the position of the probes is controlled by a CPU, according to an embodiment.

As shown in FIG. 5B, another embodiment of ground robot 500 wherein positive probe 515 and negative probe 513 are components of an end effector that is attached to a gantry, where the gantry is controlled by the CPU and moves on a track system with motors or other methods to a specific position determined by CPU 507. In some embodiments, the end effector is configured such that the probe tip is oriented at angle to the ground (see FIG. 21). In some embodiments, the angle is between 20-75 degrees. In some cases, positive probe 515 moves to a position of a weed determined by CPU 507 analysis of image taken by camera 505 and negative probe 513 moves to a position of ground determined by CPU 507 analysis of image, video, and/or the like taken by camera 505. Once the probes are in the position and camera verifies the position, the switch is turned on and the high voltage circuit is activated to eliminate the weeds. This process creates a safety mechanism since the camera verifies that a human or animal is not present in the circuit prior to the high voltage circuit being activated. In some embodiments, the positive probe and negative probe are a single probe as described in FIGS. 4H-J. FIG. 22 shows a software diagram where the image is processed by the CPU, and the CPU identifies the weed, controls the gantry and end effector assembly, and controls the switch to turn on the high voltage circuit to weaken or eliminate weeds. In some embodiments, image processing is performed by the GPU, TPU, or accelerator onboard the ground robot.

In some embodiments, the latching legs of the drone are made of a conductive materials and act as electrodes to create a circuit between the ground, weed, and a conductive surface on the underside of the drone. The drone would have similar components to the ground robot as described in FIGS. 5A & B to weaken and eliminate weeds.

High Speed Precision Weeding with Camera and GPU.

Figure 6A:
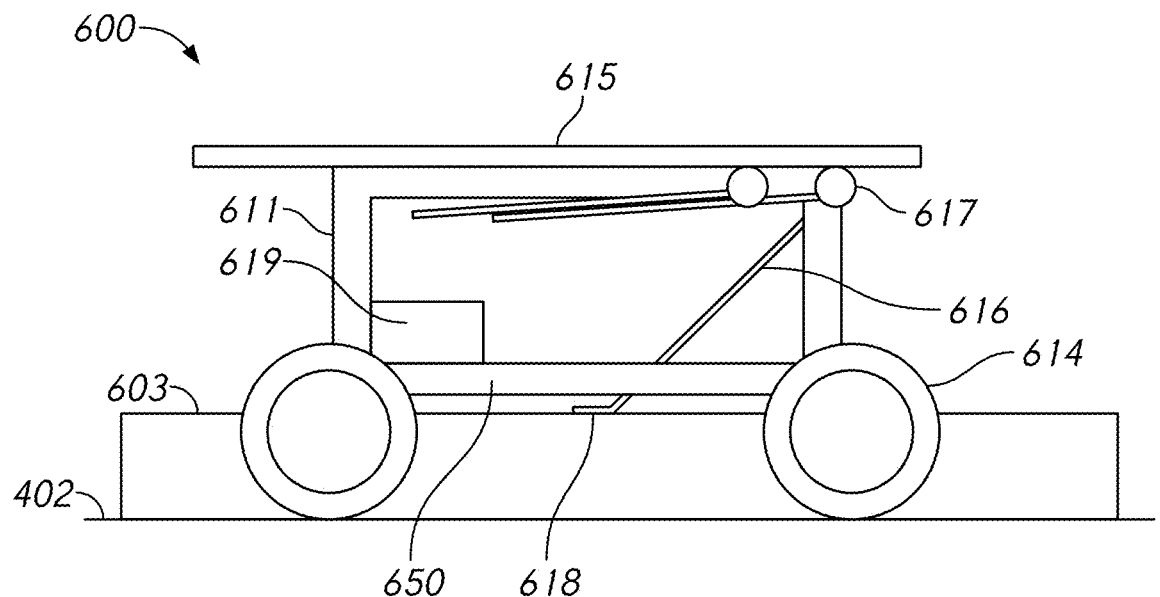
FIG. 6A is a side view showing a ground robot with a high volume weed control end effector used to eliminate multiple weeds at the same time, according to an embodiment.
Figure 23A:
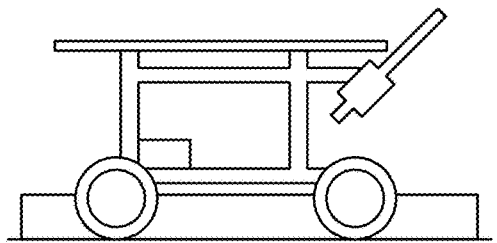
FIGS. 23A-23F show alternative designs for weed control robots with end effectors and probes in various positions to perform weed control, according to an embodiment.
Figure 23B:
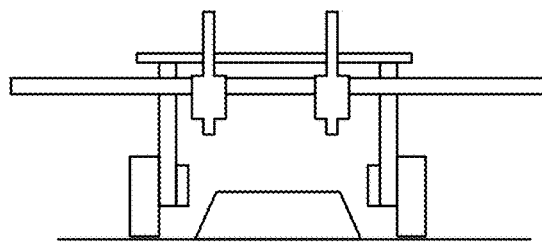
Figure 23C:
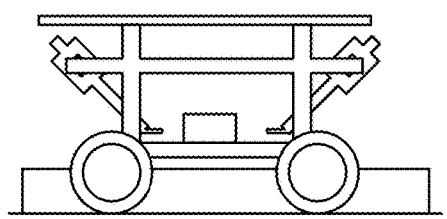
Figure 23D:
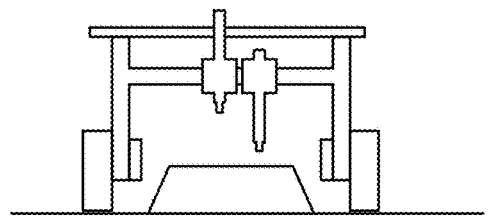
Figure 23E:
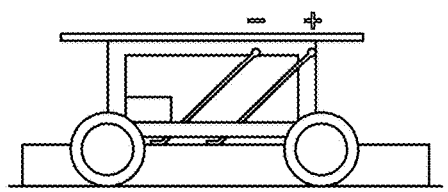
Figure 23F:
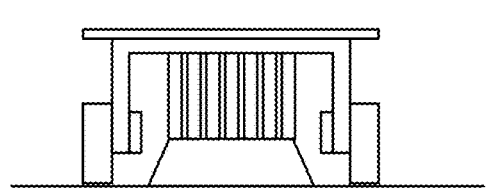

As shown in FIGS. 6A & B, an embodiment of high-speed precision weeding system 600, ground robot 611 includes a frame 650 which comprises, among other elements, an undercarriage portion 652, and may be coupled to wheels 614 to travel along crop row 603 to find weeds. In some embodiments, motor and gearboxes 619 are coupled to ground robot 611. In some embodiments, ground robot 611 uses camera (for example, such as camera 420 in FIG. 4A) to detect weed 630 in crop row 603. When camera takes an image, records a video, and/or the like, and CPU (for example, like CPU 507 in FIG. 5A) determines the existence and location of weed 630, high voltage circuit (for example, like HV Booster 511 in FIG. 5A) is enabled and the closest finger 616 moves towards the weed. Each finger is controlled by a motor 617. In some embodiments, fingers 616 have contain a tip 618 at the distal end of 616. In some embodiments, ground robot is powered by solar panel 615. In some embodiments, multiple fingers can move to eliminate more than one weed at a time. In some embodiments, one finger moves to the weed and another finger moves towards the ground. In some embodiments, the wheels are made of metal or have metal studs to act as the negative probe to connect the circuit to the ground. In some embodiments, ground robot 611 is powered by batteries (for example, like battery 503 in FIG. 5A). In some embodiments, ground robot 611 is powered by solar panels 615 and batteries wherein solar panels 615 charge batteries. In some embodiments, the fingers are stationary and drag across the ground as shown in FIGS. 23E &F wherein the camera and CPU identify the streamer to activate the high voltage switch to eliminate the weed closest to the weed of interest. In some embodiments, the ground robots can perform electrical weed control described herein without a drone. In some embodiments, image processing is performed by the GPU, TPU, or accelerator onboard the ground robot.

Method for Precision Weeding with Camera and CPU.

Figure 7:
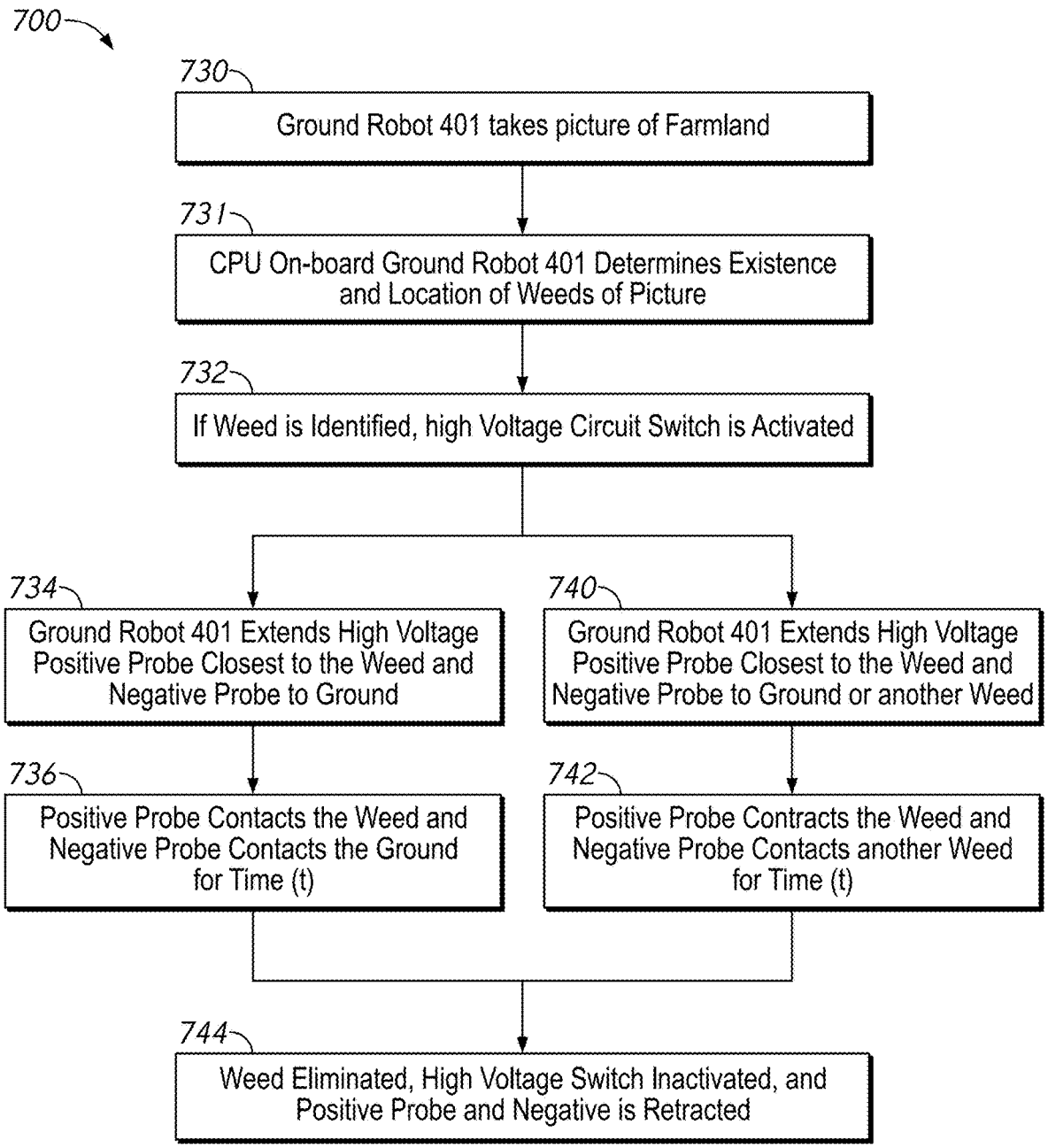
FIG. 7 is a method for identifying and eliminating a weed with a ground robot, according to an embodiment.

FIG. 7 shows an embodiment of a process flow diagram 700 illustrating an example of precision weed control with ground robot 401 (where ground robot 401 can be any ground robot disclosed herein, such as ground robot 411, 611, and/or the like). The process flow illustrated in FIG. 7 may be performed by a ground robot while in operation at, for example, a farmland while performing a crop inspection.

At block 730, the process begins when ground robot uses a camera to take an image, records a video, and/or the like, of the farmland. At block 731, the CPU on-board the ground robot identifies the existence and location of a weed. In some embodiments, image processing is performed by the GPU, TPU, or accelerator onboard the ground robot.

At block 732, if a weed was identified in block 731 the high voltage circuit switch is activated.

The process flow then varies depending on whether it would be better, more efficient, and/or the like to move the negative probe to the ground or to another weed. For example, if multiple weeds are within reach of the probe, the AI system may choose to move the negative probe to another weed to complete the circuit. If the AI system decides it would be better to move the negative probe to the ground, the process flow proceeds to block 734. If the AI system decides it would be better to move the negative probe to another weed, the process flow proceeds to block 740.

At block 734, the ground robot extends the high voltage positive probe that is closest to the weed to the weed and the negative probe to the ground. At block 736, the positive probe contacts the weed and the negative probe contacts ground, connecting the weed and the ground to the high voltage circuit for a substantial amount of time (t) to eliminate the weed. The time to eliminate the weed is dependent on the size of the high voltage booster (pulsed transformer circuit), voltage, and the size of the power source. As the voltage increases, the size of the transformer increases, or the size of the power source increases, the time to eliminate weeds when the probes are making contact with the weed and ground decreases.

At block 744, when the weed is eliminated or weaken, the high voltage switch is inactivated, and the positive probe and negative probe are retracted.

At block 740, the ground robot extends the high voltage positive probe to one weed and the negative probe to the other weed. At block 742, the positive probe contacts one weed and the negative probe contacts another weed, connecting the two weeds to the high voltage circuit for a substantial amount of time (t) to eliminate the weed. At block 744, when the weeds are eliminated or weaken, the low voltage switch is inactivated, and the positive probe and negative probe are retracted.

Solar Optimization.

Solar power can be important to sustain passive power requirements that could be used to power data transfer, electrical weed control, data compression, low voltage power systems, or communication systems. Power consumption for transferring data to satellites is approximately 25 watts. Power consumption for transferring data to cellular networks is approximately 2.5 watts. Power consumption for transferring data to Wi-Fi is approximately 1.5 watts.

With traditional drone and ground robots, the current robots would run out of battery very quickly when transferring data and have to perform a large number of battery swaps. However, with the ability to charge while moving on the ground and in the air, the ground robots and private network drones in this embodiment are able to transfer data throughout the day when the sun is out and do not require centralized charging. The systems disclosed herein enable the entire network to be in remote and rural areas since there is no infrastructure or human involvement needed.

This technology eliminates the need for a large infrastructure of charging stations and creates sustainable surveillance and inspection methods. By enabling the robots to charge on the ground or in flight, the robots essentially have unlimited range while using clean energy.

Figure 8:
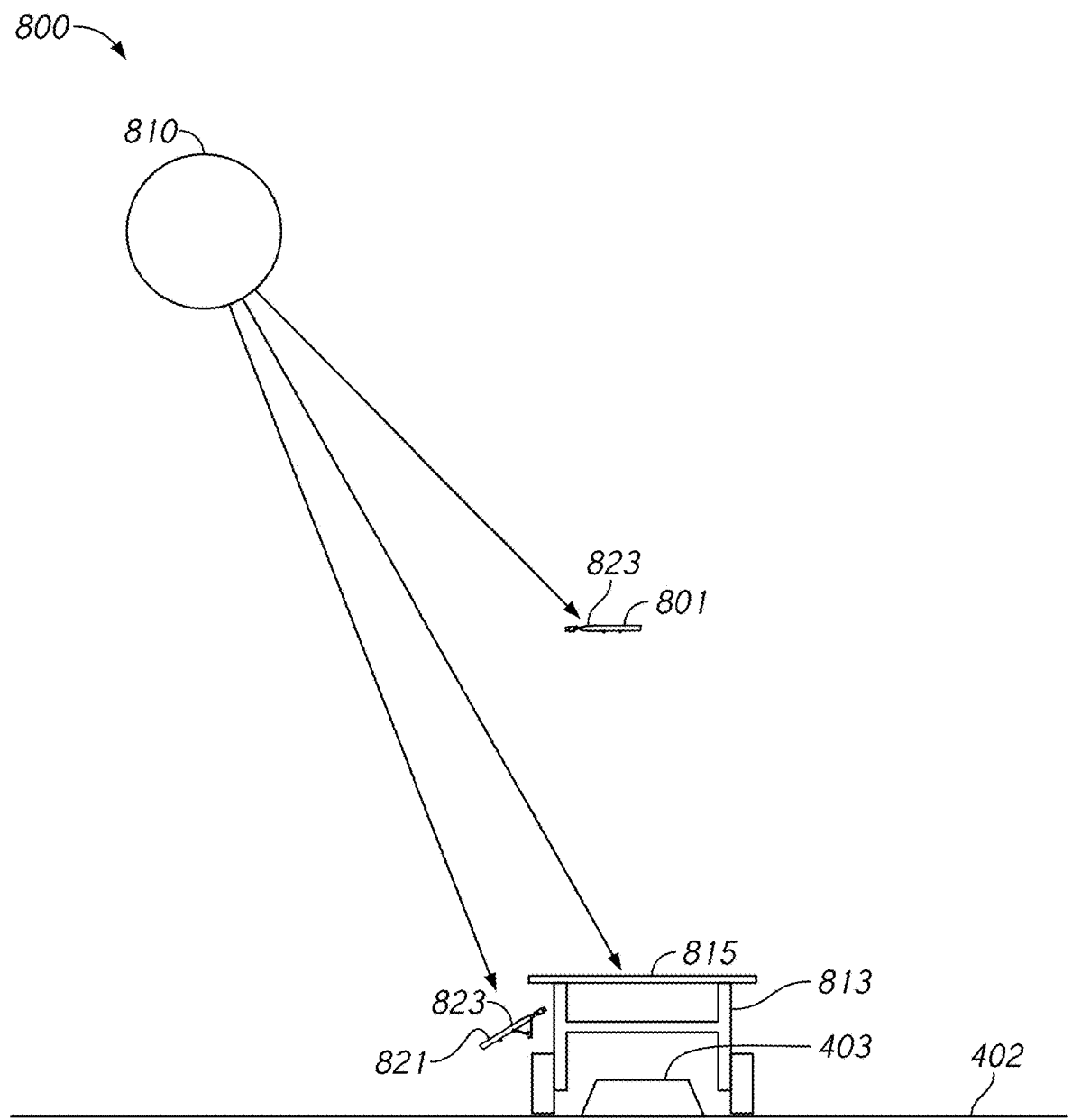
FIG. 8 is a diagram of solar charging ground robots and drones in Collaborative Robot Network, according to an embodiment.

FIG. 8 shows an embodiment of solar optimization system 800. FIG. 8 illustrates the path of the solar rays emitted from the sun 810 to solar panels 823 of the drones and the solar panels 815 of the ground robots. While drone 821 is attached to ground robot 813, drone 821 rotates by using its propellers to find the optimal orientation to the sun in order to maximize the surface area of the aircraft facing the sun. FIG. 8 illustrates the path of the solar rays emitted from the sun 810 to drone 801 during flight. The drone 801 also has the ability to charge in horizontal flight or when the drone is hovering as shown in FIG. 8. In some embodiments, the drone 801 will hover in the sky and rotate until it finds the sun's location of the sky; after finding the sun's location, the aircraft can charge while hovering or land on the ground to charge. FIG. 8 also illustrates the path of the solar rays emitted from sun 810 to solar panel 815 of ground robot. Most tractors and farm machines require gas for power; however, in some embodiments ground robot 813 uses solar energy to move up and down the fields and take actions, such as eliminating weeds.

In some embodiments, drones 801 and 821 have solar panels. In other embodiments, drones 801 and 821 have batteries (for example, like battery 503 in FIG. 5A) and are charged by ground robot 813 which is powered by the sun. In yet another embodiment, drones 801 and 821 have solar panels and batteries. By having both solar panels and batteries, the drones and ground robots are able to transfer data and perform actions via solar power during the day and batteries during the night. The batteries can be fully charged when the sun goes down.

Inspection Drone Interface with Tractors and Other Farming Machines.

Figure 9:
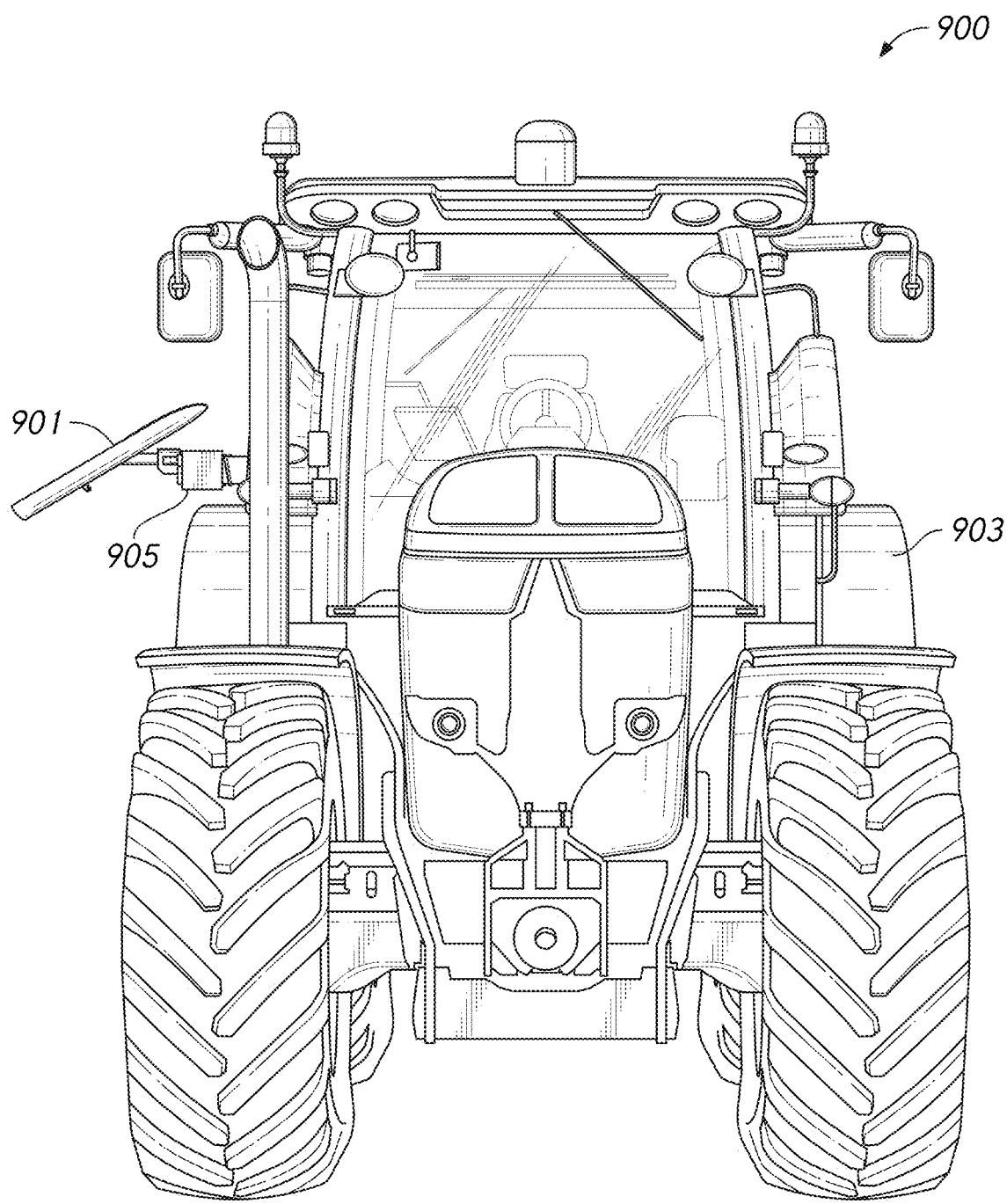
FIG. 9 is a front view of a drone attached to a tractor, according to an embodiment.

As shown in FIG. 9, an embodiment of inspection drone interface with farming machines 900. Drone 901 attaches to perch bar 905 of tractor 903. In this embodiment, drone 901 inspects farmland and identifies areas of interest for tractor 903 to take action on. In some embodiments, drone 901 takes pictures of farmland and analyzes data with on-board AI processor to identify areas on the farmland with weeds. Drone 901 transfers data regarding areas with weeds to tractor 903, and tractor 903 sprays identified areas of concern with pesticides. This practice reduces wear on the tractor and soil compaction that will help preserve the farming equipment and reduce crop yield loss. In some embodiments, drone 901 can identify where standing water or high moisture content exists on the field and transfer these areas back to the tractor to avoid the areas to prevent damage to the tractor and the field itself.

In some embodiments, drone 901 can attach to combines, fruit pickers, harvesters, and/or the like. In some embodiments, drone 901 can provide a Wi-Fi connectivity signal to tractor 903 in order to transfer data and interface with other machines or sensors. In some embodiments, drone 901 can fly into the air and act as an antenna for tractor 903 to enable transfer of data, such as crop yield or loss to farmer or agriculture professional.

Wi-Fi Network and Robot Network Interface.

Figure 10:
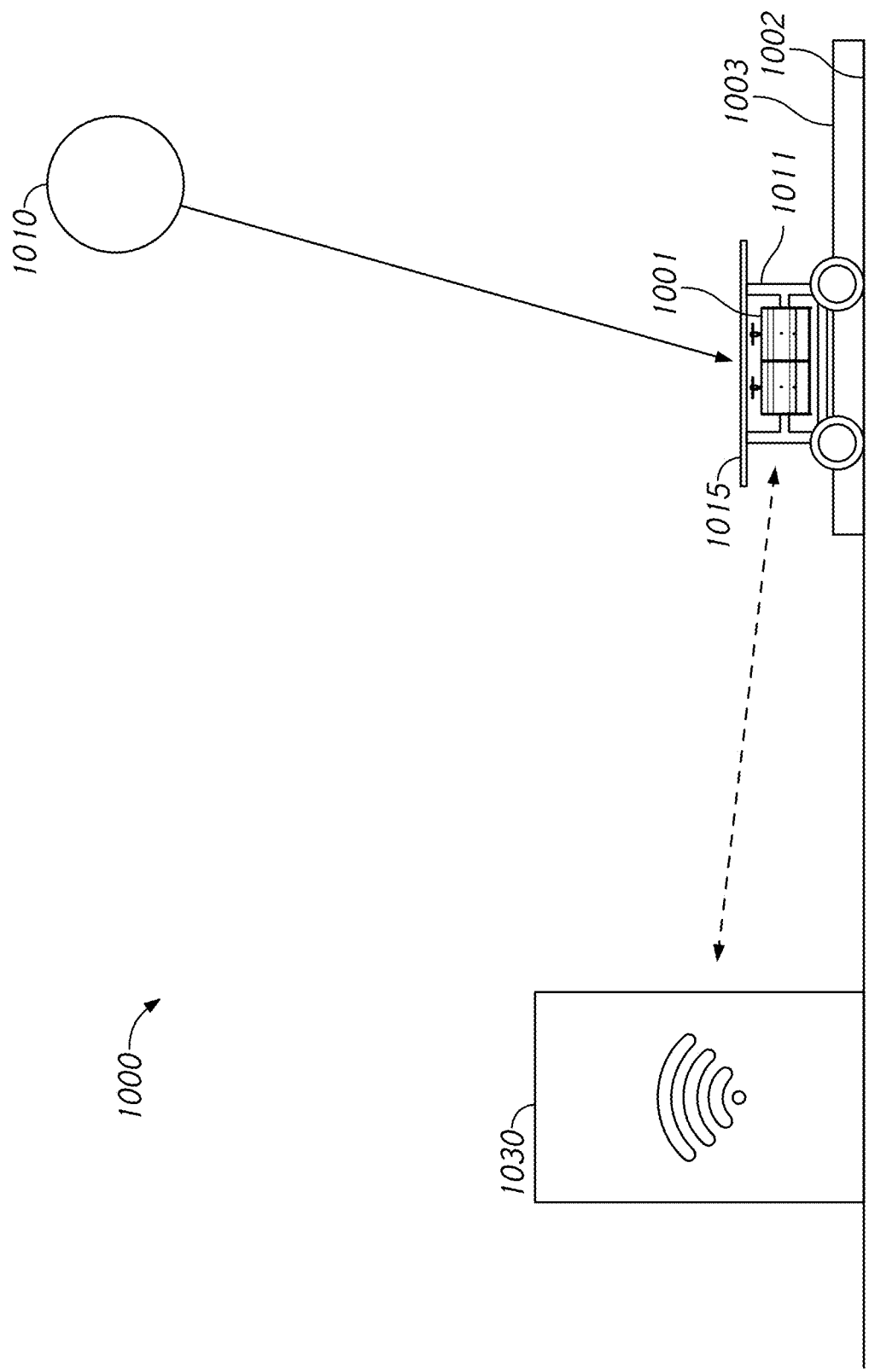
FIG. 10 is a diagram of Collaborative Robot Network wherein a ground robot is connected to a Wi-Fi network and a plurality of drones, according to an embodiment.

As shown in FIG. 10, an embodiment of Collaborative Robot Network 1000 generally comprises at least one autonomous drone 1001, at least one Wi-Fi Network 1030, ground robot 1011, and sun 1010 wherein autonomous drone 1001 could be an inspection drone or an action drone. Autonomous drone 1001 may fly or move on the ground 1002 to collect data with sensors or cameras. Ground robot 1011 has the ability to move on farmland 1003 and perform actions, such as take imagery or perform weed control. In some embodiments, autonomous drone 1001 attaches to ground robot 1011 to charge and seek protection during extreme weather events. In some embodiments, autonomous drone 1001 transfers imagery to ground robot to perform analysis of data with on-board AI processer of ground robot 1011.

In some embodiments, sun beams emitted from sun 1010 hit solar panel 1015 of ground robot 1011 to provide power for ground movement, data collection, and data transmission to Wi-Fi connection 1030. In order to transmit data over, ground robot must be within 500 feet of the connection. Autonomous drone 1001 can transfer imagery data over private LTE network to ground robot, and ground robot can transfer data via Wi-Fi to cloud analytics software provider. In some embodiments, Wi-Fi connection could be in a building or at a farm. In some embodiments, ground robot 1011 is positioned within 500 feet of potential user, such as a home, business, building, or person. Ground robot 1011 transfers Wi-Fi with the nearest autonomous drone 1011 that remotes Wi-Fi connection ground robot through a network of drones linked to a network in another area.

Private User and Robot Network Interface

Figure 11:
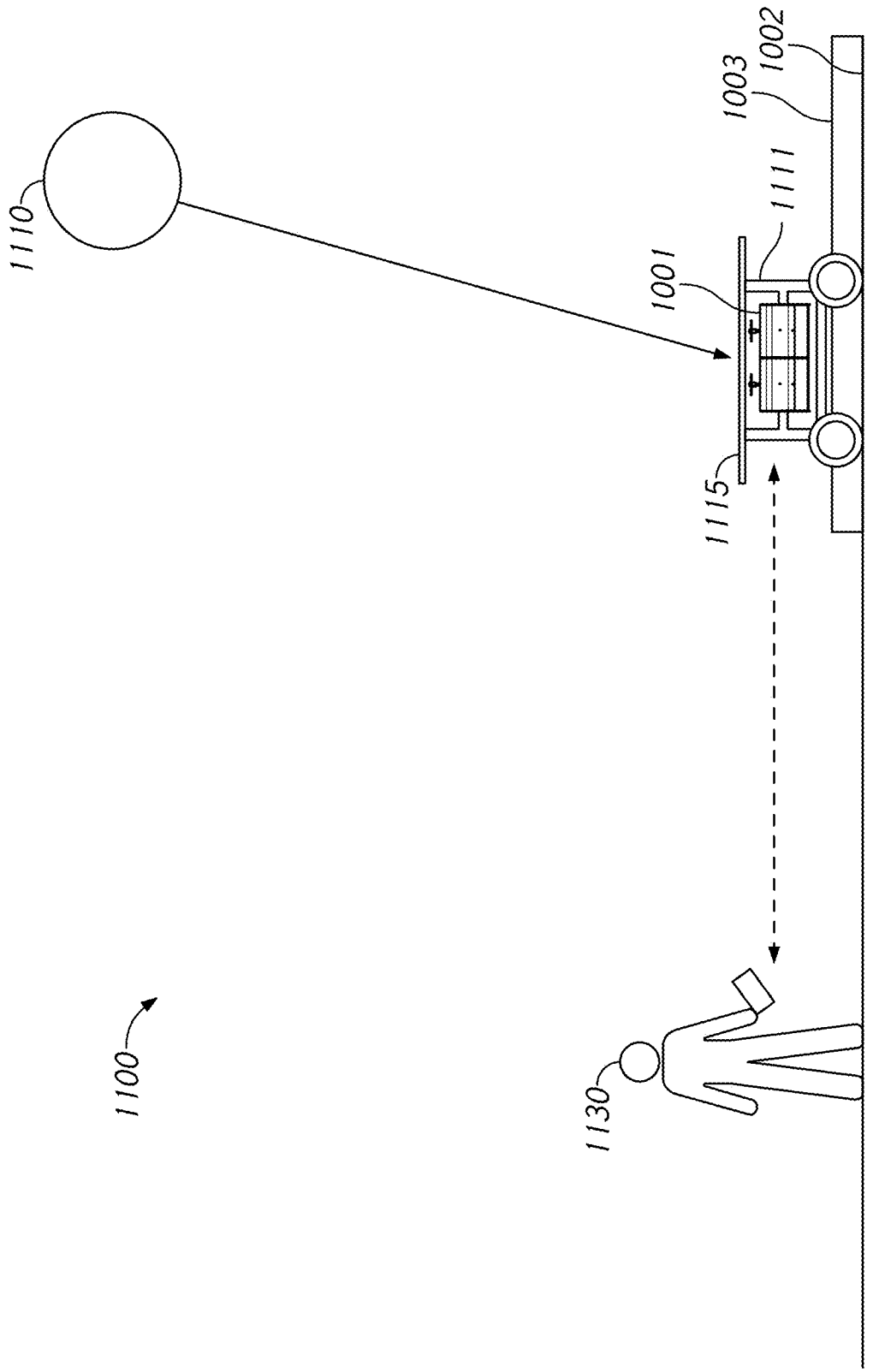
FIG. 11 is a diagram of Collaborative Robot Network wherein ground robot is transmitting data from a person to a plurality of drones, according to an embodiment.

FIG. 11 shows ground robot 1111 transferring data from user 1130. In some embodiments, data may be cell phone calls, text messages, emails, pictures, or videos. The user will have a chip in his device that specifies a frequency allowing the user to access the private drone network. Once the data is transferred onto the ground robot, the data is transferred back to Collaborative Robot Network 1100 comprised of drones and ground robots. The closest robot to the cell tower transfers data directly to the cellular tower. In 1100 dynamic telecommunication network, users will access the nearest robot to transfer data. In some embodiments, the user must be within 30 miles the nearest network robots. Private network robots can move on the ground or fly to where users have requested data. If service subscriptions are cancelled, the private network robot can be repositioned easily. In some embodiments, sun beams emitted from sun 1110 hit solar panel 1115 of ground robot 1111 to provide power for ground movement, data collection, and data transmission to user 1130

Method for Inspection and Immediate Action by Drones and Ground Robots.

Figure 12:
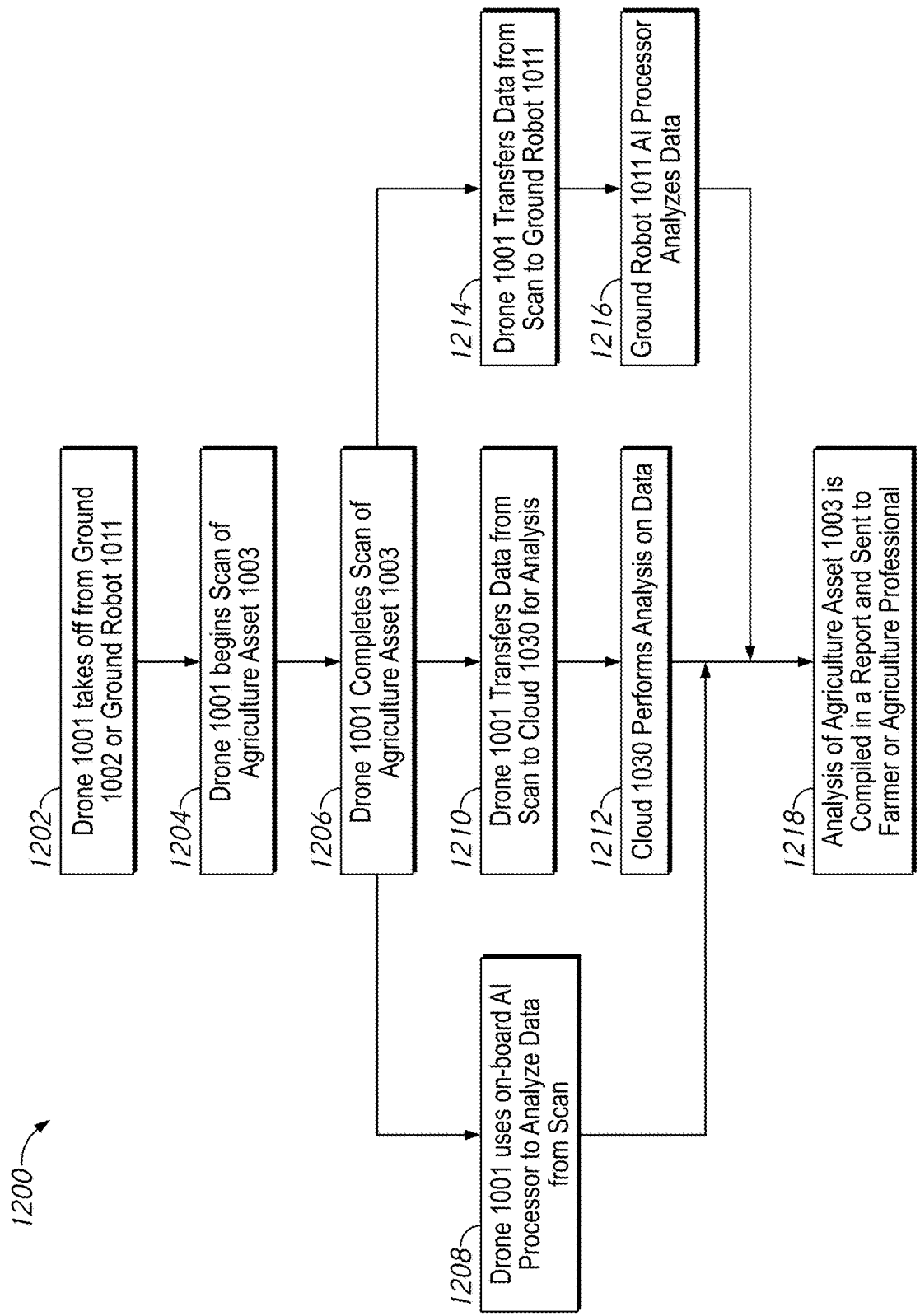
FIG. 12 is a process flow diagram showing a method for Collaborative Robot Network to inspect an agriculture asset and perform analysis that is provided to a farmer, according to an embodiment.

FIG. 12 shows an embodiment of a process flow diagram 1200 illustrating an example of a method of drone 1001 performing an inspection of an agriculture asset and various forms of analyzing the data and transferring the data to farmer. In some embodiments, the agriculture asset is a group of crops, such as sugar beets, corn, and/or the like. In some embodiments, the agriculture asset is a group of livestock, such as cattle, sheep, and/or the like.

At block 1202, the process begins when drone 1001 takes off from the ground 1002 or takes off from ground robot 1011. At block 1204, drone 1001 begins to scan the agricultural asset 1003. At block 1206, drone 1001 completes the scan of the agricultural asset. For example, a completed scan may be scanning a certain number or crop rows, a certain number of livestock, a certain number of fields and/or the like. Depending on the embodiment, the drone may use different methods to analyze the data from the scan.

Block 1208 illustrates one embodiment, where drone 1001 uses an on-board AI processor to analyze data from the scan. At block 1218, the analysis of the agricultural asset 1003 is compiled in a report and sent to farmer, agricultural professional, and/or the like.

Block 1210 illustrates another embodiment, where drone 1001 transfers data from the scan to cloud 1030 for analysis. At block 1212, cloud 1030 performs analysis on the data. At block 1218, the analysis of the agricultural asset 1003 is compiled in a report and sent to farmer, agricultural professional, and/or the like.

Block 1214 is yet another embodiment, where drone 1001 transfers data from scan to ground robot 1011. At block 1216, ground robot 1011 uses AI processor to analyze the data. At block 1218, the analysis of the agricultural asset 1003 is compiled in a report and sent to farmer, agricultural professional, and/or the like.

Figure 13:
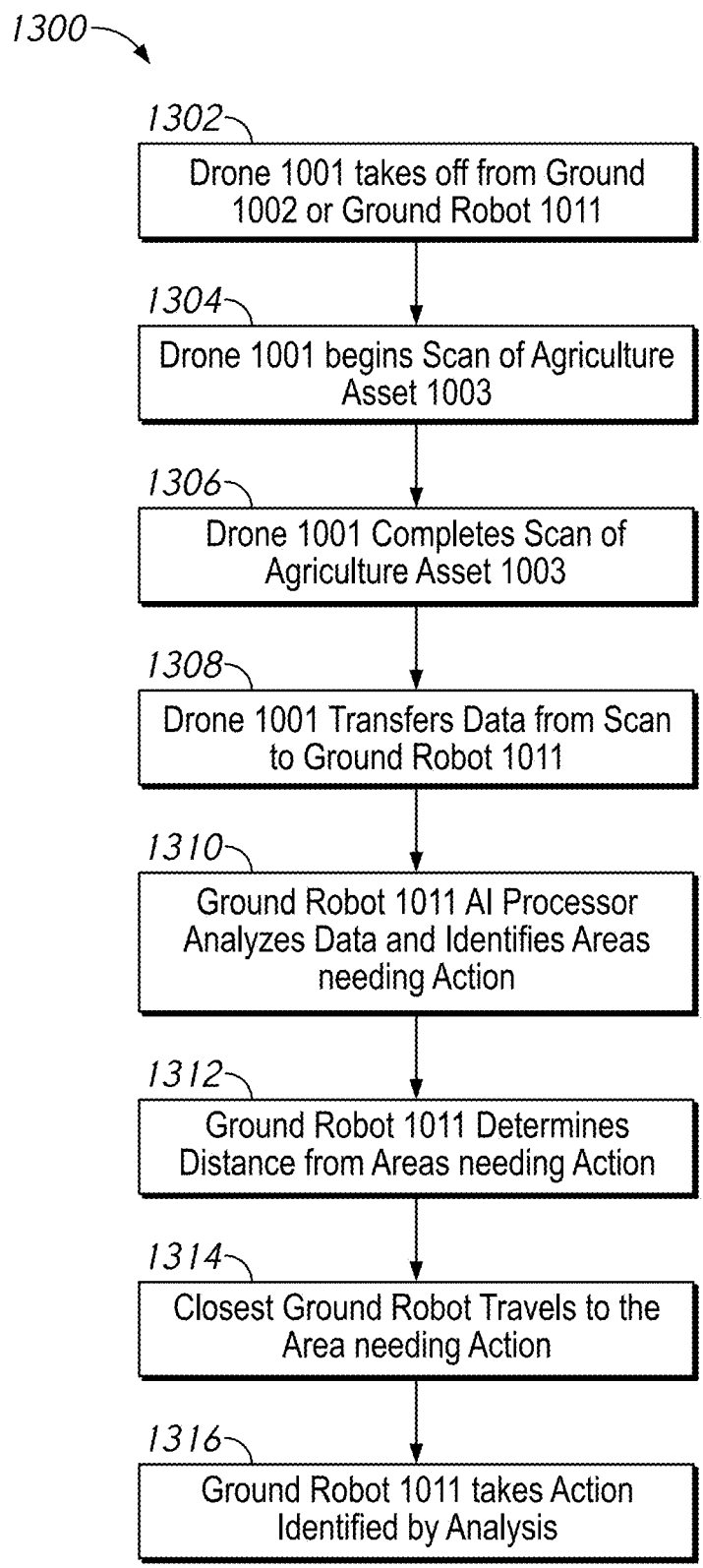
FIG. 13 is a process flow diagram showing a method for Collaborative Robot Network to inspect an agriculture asset, perform analysis, and take action based on the results of the analysis, according to an embodiment.

FIG. 13 shows an embodiment of a process flow diagram 1300 illustrating an example of a method for a drone to perform an inspection and then the ground robot to take an action based on the inspection data. In some embodiments, the drone identifies an area where it may appear to have an issue with a plant disease, and ground robot will analyze the data and travel to the area to capture more images. The images from the drone and the ground robot will be analyzed and compiled into a report with recommendations to the farmer on crop health and weed populations.

At block 1302, the process begins when drone 1001 takes off from the ground 1002 or takes off from ground robot 1011. At block 1304, drone 1001 begins to scan the agricultural asset 1003. At block 1306, drone 1001 completes the scan of the agricultural asset 1003. For example, a completed scan may be scanning a certain number or crop rows, a certain number of livestock, a certain number of fields and/or the like. At block 1308, drone 1001 transfers data from scan to ground robot 1011.

At block 1310, ground robot 1011 uses AI processor to analyze the data and identify areas that require action. At block 1312, the ground robot 1011 determines the distance from the areas that require action. At block 1314, the closest ground robot travels to the area that requires action. At block 1316, ground robot 1011 takes action identified by analysis. For example, the action may be herding livestock, removing weeds, performing a crop inspection, digging holes and/or the like.

In some embodiments, at block 1314, the ground robots communicate with each other to determine which ground robot should travel to the area that requires action. For example, some robots might be presently occupied with a task and will continue completing the tasks even if they are the closes robot. Some robots may have special equipment for completing the required action.

Figure 14:
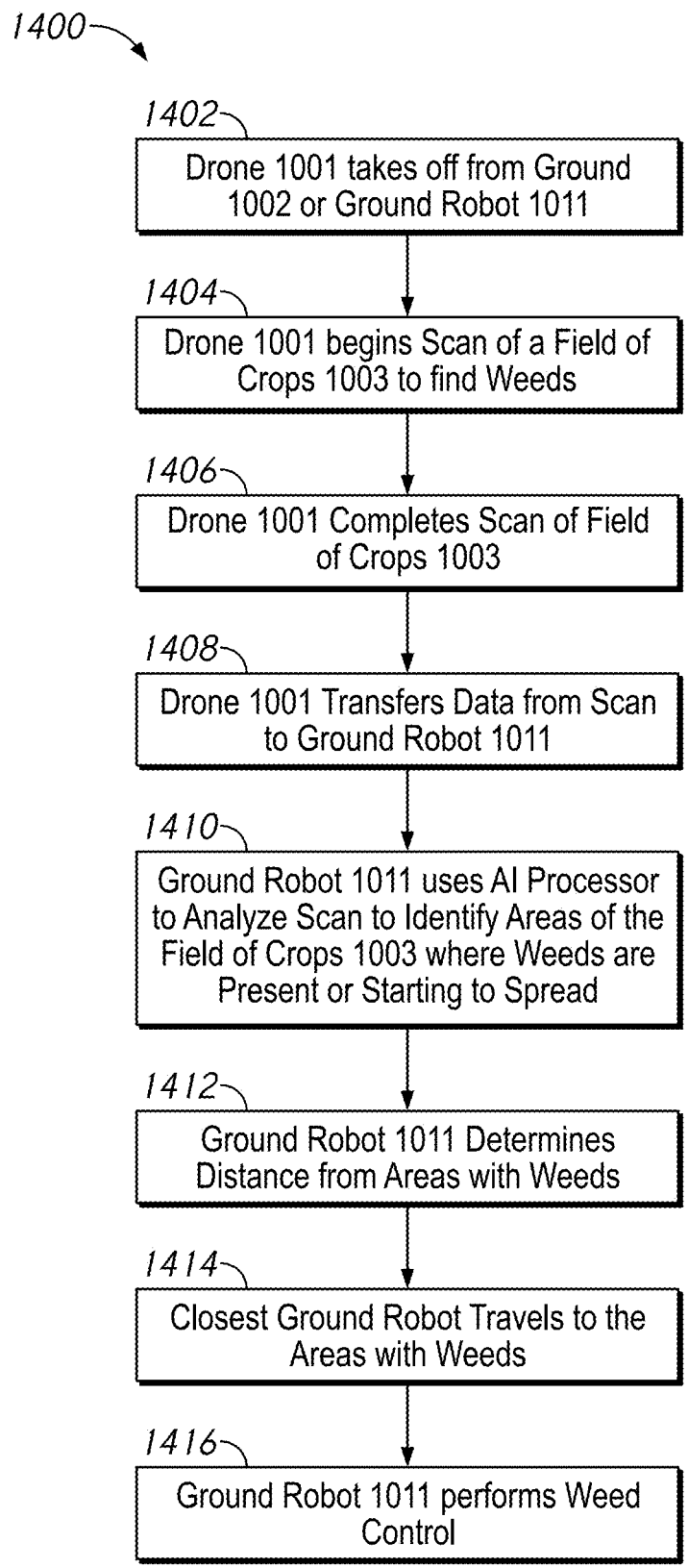
FIG. 14 is a process flow diagram showing a method for Collaborative Robot Network to inspect a field, perform analysis to determine areas with high concentrations of weeds, and perform weed control based on the results of the analysis, according to an embodiment.

FIG. 14 shows an embodiment of a process flow diagram 1400 illustrating an example of a method for a drone to perform an inspection of a parcel farmland and then the ground robot to analyze the data to identify areas of high weed concentration where actions need to be taken.

At block 1402, the process begins when drone 1001 takes off from the ground 1002 or takes off from ground robot 1011. At block 1404, drone 1001 begins to scan a field of crops 1003 to find weeds. At block 1406, drone 1001 completes the scan of the field of crops 1003. At block 1408, drone 1001 transfers data from scan to ground robot 1011.

At block 1410, ground robot 1011 uses AI processor to analyze the data and identify areas of the field of crops 1003 where weeds are present or starting to spread. At block 1412, the ground robot 1011 determines the distance from the areas with weeds. At block 1414, the closest ground robot travels to the area that requires action. In some embodiments, there may be more than one ground robot on the farm and the ground robot will communicate with other ground robots to determine which robot is closest to the area with weeds and the closest robot will travel to the area and perform weed control. At block 1416, ground robot 1011 performs weed control. In some embodiments, the weed control may be with chemical, mechanical, machine, or electrical means or any combination thereof.

Figure 15:
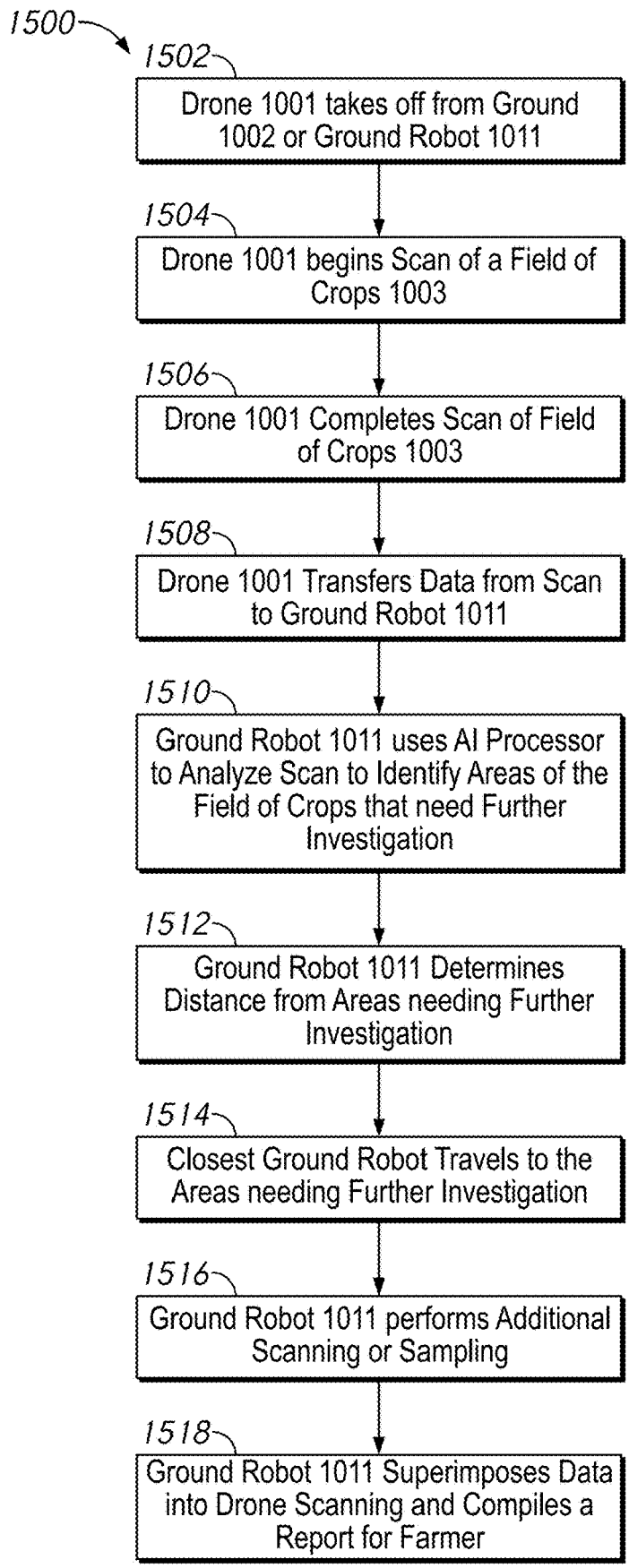
FIG. 15 is a process flow diagram showing a method for Collaborative Robot Network where a drone reinspects the field after weed control shown in FIG. 14, according to an embodiment.

FIG. 15 shows an embodiment of a process flow diagram 1500 illustrating an example of a method for a drone to perform re-inspection of a plot of land after ground robot performs weed control. The drone will take images, records a video, and/or the like of crops and weeds prior to weed control and after weed control to determine weed elimination efficiency and if there is damage to crops during the process.

At block 1502, the process begins when drone 1001 takes off from the ground 1002 or takes off from ground robot 1011. At block 1504, drone 1001 begins to scan a field of crops 1003. At block 1506, drone 1001 completes the scan of the field of crops 1003. At block 1508, drone 1001 transfers data from scan to ground robot 1011.

At block 1510, ground robot 1011 uses AI processor to analyze the data and identify areas of the field of crops 1003 that need further inspection. At block 1512, the ground robot 1011 determines the distance from the areas that require inspection. At block 1514, the closest ground robot travels to the areas that that need further inspection. In some embodiments, there may be more than one ground robot on the farm and the ground robot will communicate with other ground robots to determine which robots are closest to the areas that require further inspection, and the closest robots will travel to the areas.

At block 1516, ground robot 1011 performs additional inspection. In some embodiments the additional inspection could be additional scanning, sampling, and/or the like. At block 1518, ground robot superimposes data into drone scanning and compiles a report for farmer. In some embodiments, the ground robot will compile a report based on the imagery to show the metrics to the farmer.

Moveable Solar Panel on Ground Robot for More Effective Solar Charging and Protection of Drone.

Figure 16A:
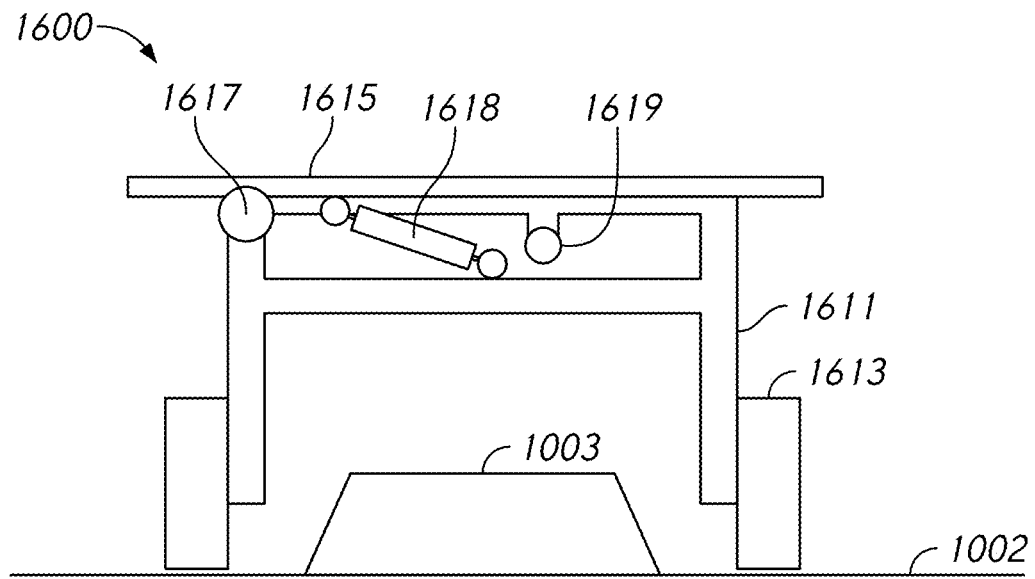
FIG. 16A is a diagram of Collaborative Robot Network showing a side view of a ground robot with a movable solar panel, according to an embodiment.

As shown in FIG. 16A, an embodiment Collaborative Robot Network 1600. Ground robot 1611 comprises moveable solar panel 1615, pivot 1617, linear actuator 1618, robot frame, perch bar 1619, and at least two wheels 1613. FIG. 16A shows linear actuator 1618 in a fully retracted position. In some embodiments, linear actuator 1618 is a pneumatic linear actuator. In some embodiments, linear actuator 1618 is a hydraulic linear actuator. Linear actuator 1618 can extend to angle solar panel 1615 towards the sun, which can result in up to, for example 35% more efficiency in solar charging. In some embodiments, the increase in solar charging efficiency can be 5%, 10%, 15%, 20%, 25%, 30%, 35%, 40%, and/or the like. As linear actuator 1618 extends or retracts, moveable solar panel 1615 pivots about pivot 1617. Pivot 1617 could be on either side of the robot. In some embodiments, pivot 1617 is a hinge mechanism capable of at least 60 degrees of rotation. In some embodiments, wheels 1613 may be a track system for ground movement. In some embodiments, perch bar 1617 can be replaced by a box, an enclosure, or a substantially similar feature located under the solar panel of the ground robot where the drone can land and take off from. In this case, the drone does not need latching legs.

Figure 16B:
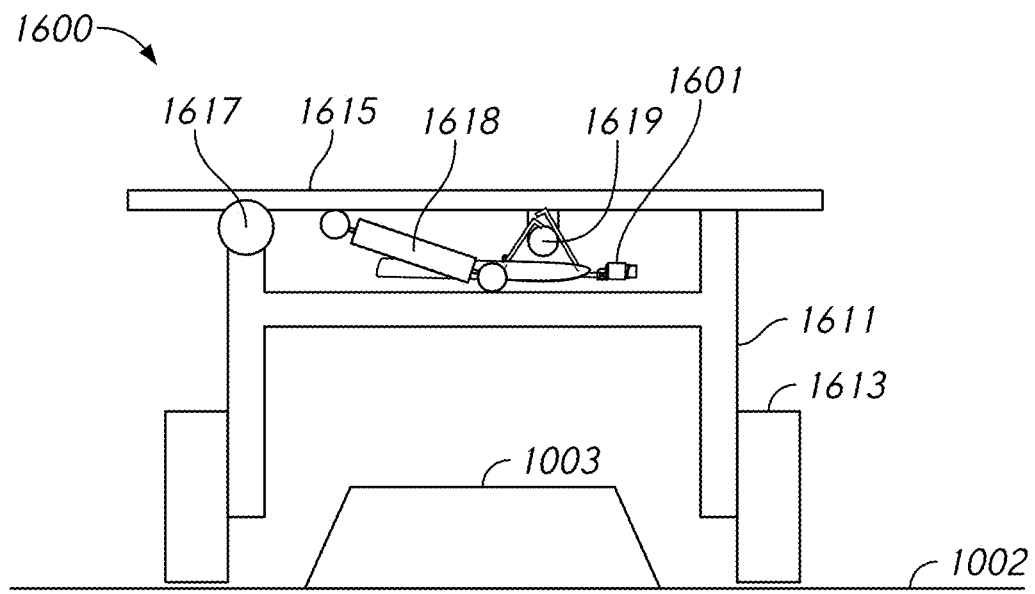
FIG. 16B is a diagram of Collaborative Robot Network showing a side view of a drone attached to a ground robot with a movable solar panel, according to an embodiment.

As shown in FIG. 16B, drone 1601 is attached to perch bar 1619 of ground robot 1611 wherein the legs of drone 1601 are fully retracted to attach to perch bar 1619. In this embodiment, drone 1601 is shielded from severe weather such as heavy wind, rain, hail and/or the like. In some embodiments, the drone is able to charge as shown in FIG. 18.

Figure 17A:
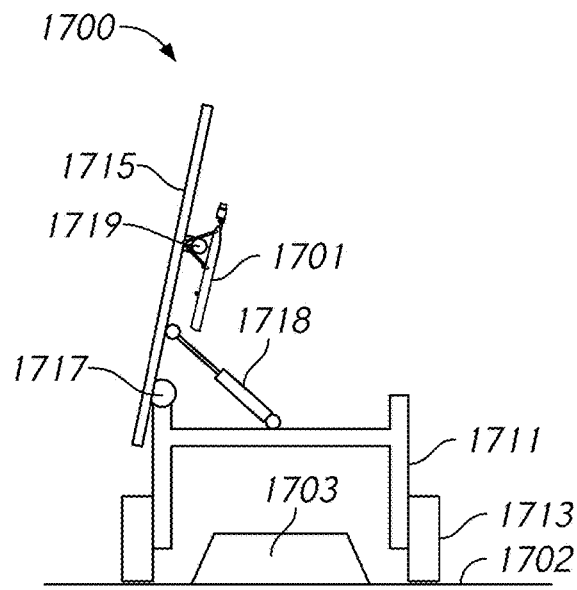
FIG. 17A is a diagram of Collaborative Robot Network showing a front view of a drone attached to a ground robot while a movable solar panel extends for said drone to take off, according to an embodiment.
Figure 17B:
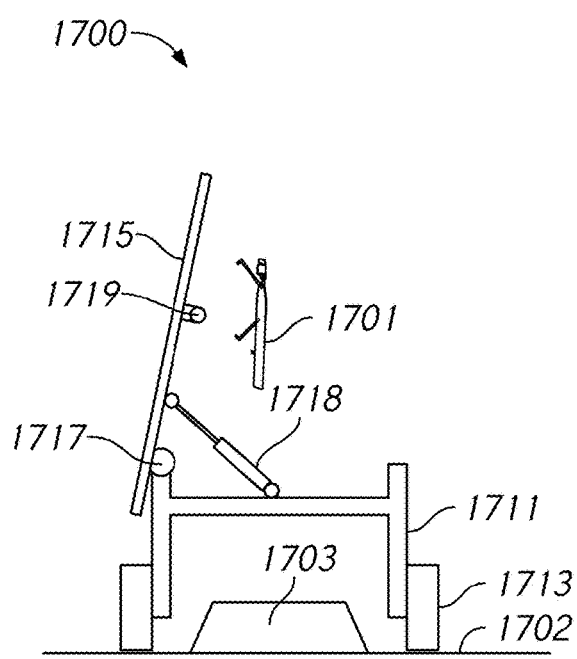
FIG. 17B is a diagram of Collaborative Robot Network showing a front view of a drone detaching from a ground robot while a movable solar panel is fully extended as said drone hovers, according to an embodiment.
Figure 17C:
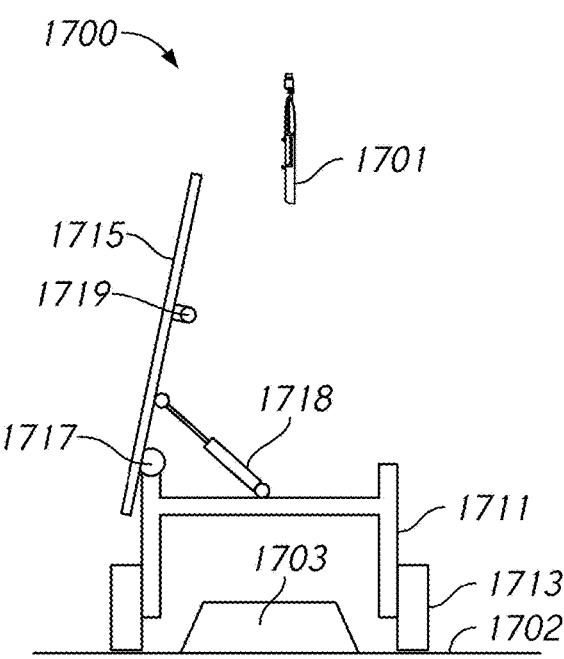
FIG. 17C is a diagram of Collaborative Robot Network showing a front view of a ground robot with a movable solar panel that is fully extended as said drone enters vertical flight, according to an embodiment.

FIGS. 17A-C show an embodiment of Collaborative Robot Network 1700. Linear actuator 1718 of ground robot 1711 in a fully extended position where drone 1701 can attach or detach from perch bar 1719 of ground robot 1711. FIG. 17B shows drone 1701 extending the latching legs while the propellers of 1701 are allowing the drone to hover, and FIG. 17C shows drone 1701 entering vertical flight mode. Once drone 1701 takes off, linear actuator of 1718 of ground robot 1711 retracts in order for ground robot 1711 to perform actions on agriculture asset 1703 while traveling wheels 1713 on ground 1702. In some embodiments, the actions include inspection and weed control. In this case, drones can be fixed wing, even without VTOL capabilities. Ground robot 1711 can launch a drone not specifically designed for VTOL with the mechanism outlined herein. In some embodiments, as linear actuator 1718 extends or retracts, moveable solar panel 1715 pivots about pivot 1717. Pivot 1717 could be on either side of the robot. In some embodiments, pivot 1717 is a hinge mechanism capable of at least 60 degrees of rotation.

Figure 18:
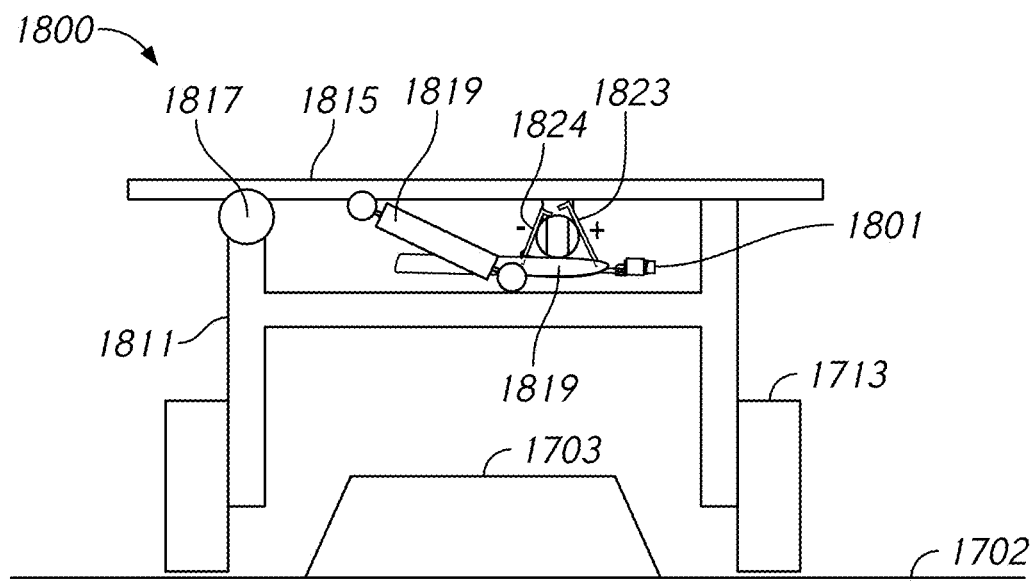
FIG. 18 is a diagram of Collaborative Robot Network showing a front view of a drone attached and charging on a ground robot, according to an embodiment.
Figure 19:
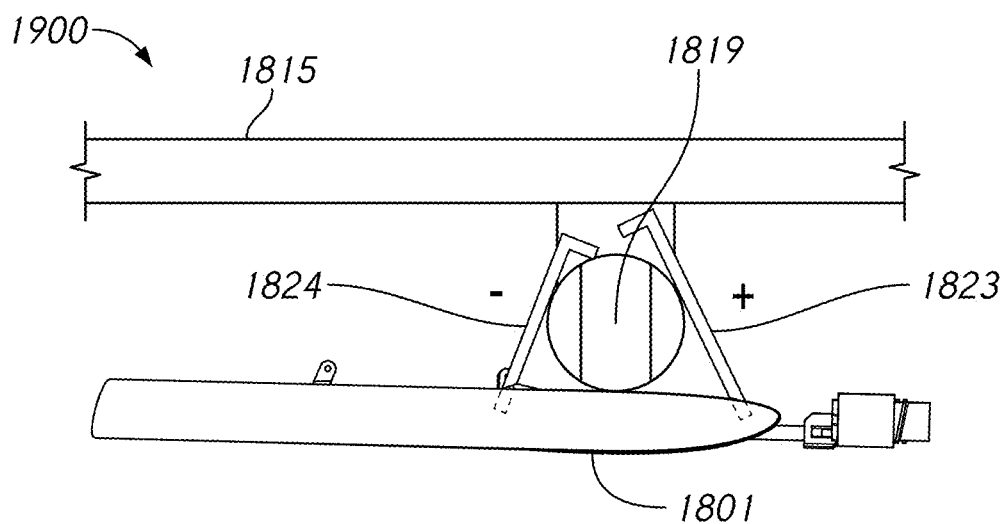
FIG. 19 is a diagram of Collaborative Robot Network showing a detailed view of the circuit of FIG. 18 for a drone charging while attached to a ground robot, according to an embodiment.

As shown in FIGS. 18 & 19, embodiments Collaborative Robot Network 1800 and 1900. Drone 1801 is attached to ground robot 1811 and in this position, ground robot 1811 is capable of charging drone 1801. In some embodiments, ground robot 1811 charges drone 1801 with solar power. In some embodiments, ground robot 1811 charges drone with battery power. In some embodiments, latching leg 1823 of drone 1801 is a positive terminal and latching leg 1824 of drone 1801 is a negative terminal. In some embodiments, perch bar 1819 of ground robot 1811 has a positive region and a negative region as shown in FIG. 19. When drone 1801 attaches to perch bar 1819 of ground robot 1811, latching leg 1823 of drone 1801 makes contact with the positive region of perch bar 1819 and latching leg 1824 of drone 1801 makes contact with the negative region of perch bar 1819; when both legs are in contact, then a circuit is created to charge the battery of the drone with a current path through the latching legs of the drone to the battery (for example, like battery 503 in FIG. 5A) of drone 1801. In some embodiments, a solar panel 1815 is coupled to ground robot 1811. In some embodiments, a linear actuator (for example, linear actuator 1618 in FIG. 16) extends or retracts and solar panel 1815 is movable such that solar panel 1815 pivots about pivot 1817. Pivot 1817 could be on either side of the robot. In some embodiments, pivot 1817 is a hinge mechanism capable of at least 60 degrees of rotation.

Figure 20:
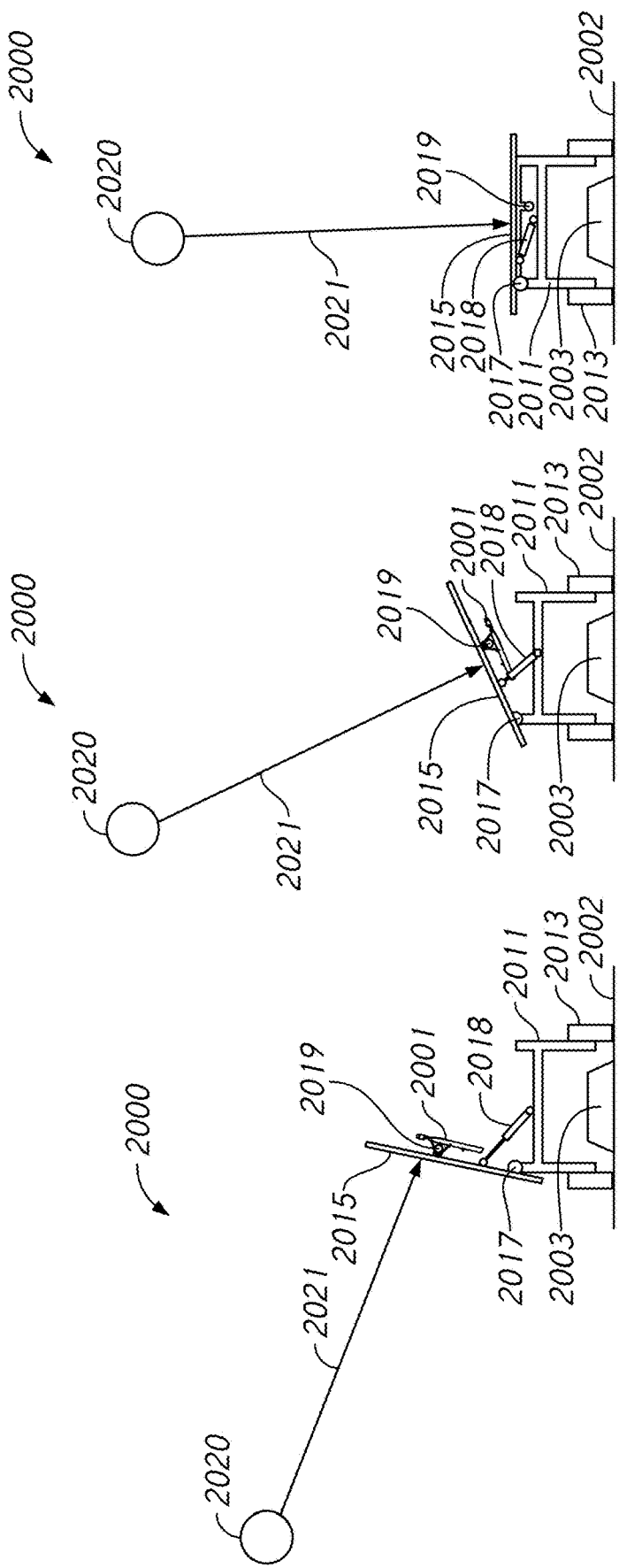
FIG. 20A is a diagram of Collaborative Robot Network showing a front view of a ground robot with a movable solar panel aligned to the sun for solar charging, according to an embodiment.
FIG. 20B is a diagram of Collaborative Robot Network showing a front view of a ground robot with a movable solar panel aligned to the sun at yet another position for solar charging, according to an embodiment.
FIG. 20C is a diagram of Collaborative Robot Network showing a front view of a ground robot with a movable solar panel aligned to the sun at the highest point in the sky for solar charging, according to an embodiment.

FIGS. 20A-20C show an embodiment Collaborative Robot Network 2000. FIGS. 20A-20C illustrate the placement of moveable solar panel 2015 of ground robot 2011. By identifying the location of sun 2020 with a camera and controlling linear actuator 2018 to orient solar panel 2015 to the sun 2020 for an optimal angle for sun beam 2021, ground robot 2015 is able to increase its charging rate in up to, for example 35%. In some embodiments, the increase in charging rate can be 5%, 10%, 15%, 20%, 25%, 30%, 35%, 40%, and/or the like. As sun 2020 moves in the sky, the CPU will control linear actuator 2018 to angle solar panel 2015 towards sun 2020. In some embodiments, ground robot 2011 travels on wheels 2013 on ground 2002 down crop row 2003 in order for sun 2020 to be on the same side as hinge 2017. In order to do this, ground robot 2011 travels down one crop row, and at the end of the crop row, ground robot drives forward at a slight angle and then reverse the motors to travel down the next row. Ground robot 2011 will continue to use this method to keep the solar panel oriented towards the sun. In some embodiments, drone 2001 is may attach to perch bar 2019 of ground robot 2011 wherein the legs of drone 2001 are fully retracted to attach to perch bar 2019.

Ground Robot with Integrated Camera Angled Weed Control End Effectors.

Figure 21:
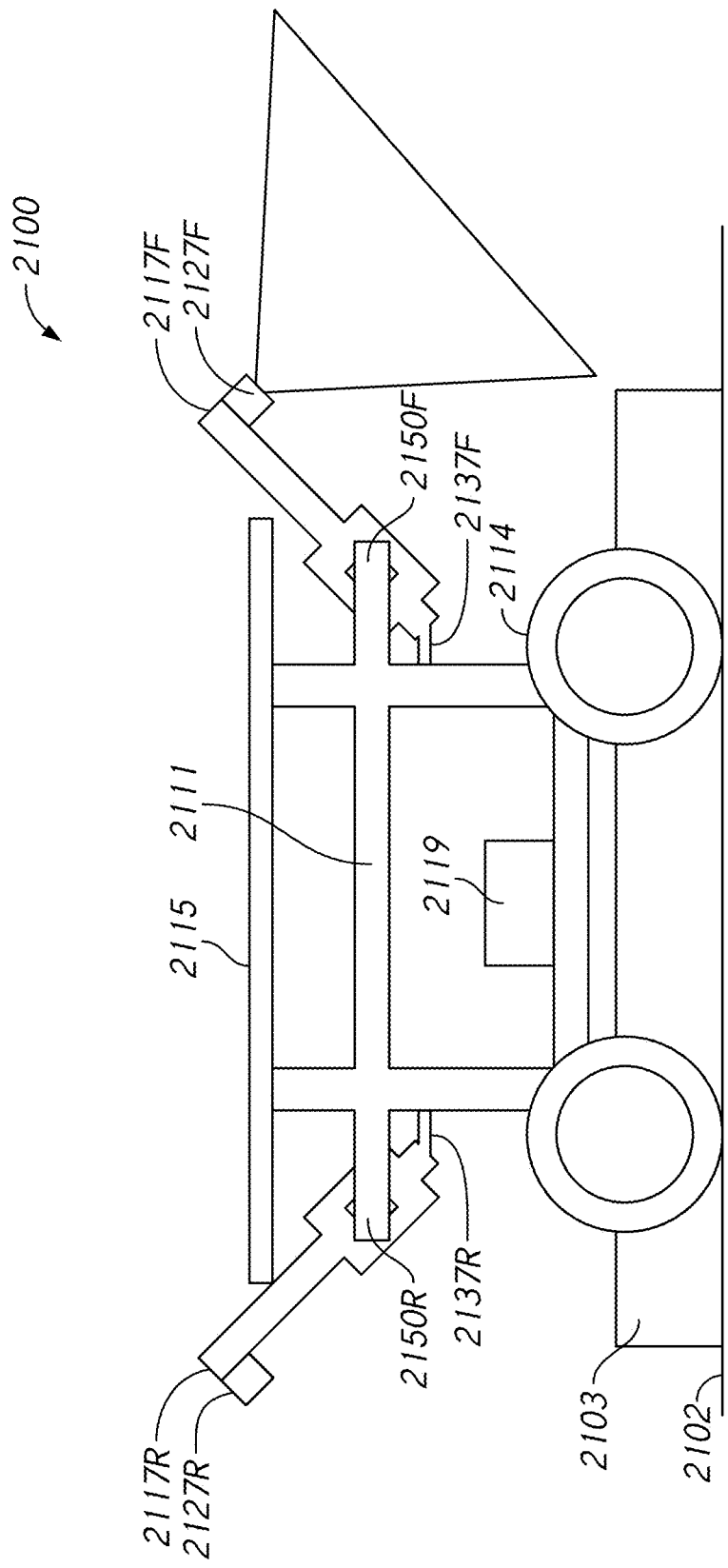
FIG. 21 is a diagram of a side view of a ground robot showing a rear end effector and forward end effector, where each gantry contains at least one camera, according to an embodiment.
Figure 22:
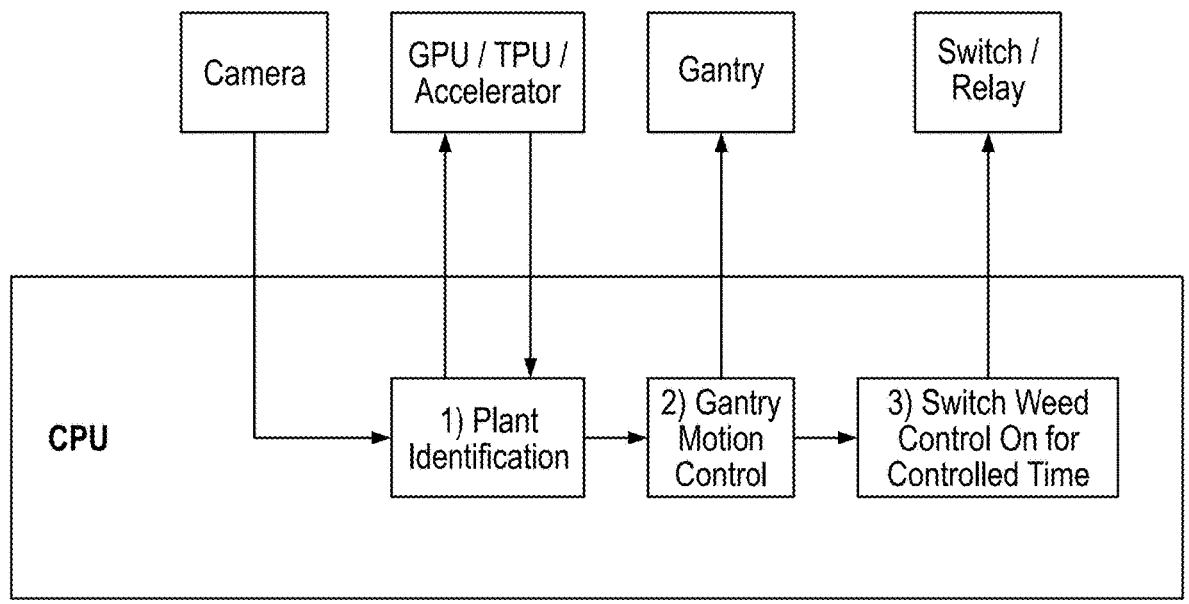
FIG. 22 is a schematic of a software control flow for a ground robot for identification of weeds, movement of end effector, and activation of high voltage circuit, according to an embodiment.

As shown in FIG. 21, an embodiment Collaborative Robot Network 2100. Ground robot 2111 comprises at least one solar panel 2115, at least one rear gantry 2117R, at least one forward gantry 2117F, a frame, at least two wheels 2114, and at least one battery 2119. Each rear gantry 2117R comprises an end effector containing at least one probe 2137R, and each forward gantry comprises an end effector containing at least one probe 2137F. In some embodiments, each rear gantry 2117R comprises camera 2127R and end effector containing at least one probe 2137R, and each forward gantry comprises camera 2127F and end effector containing at least one probe 2117F. In some embodiments, rear gantry 2117R is coupled and/or connected to ground robot 2111 at 2150R. In some embodiment, 2150R may be a motor system to allow rotation in one or more plants of motion of rear gantry 2117R. In some embodiments, forward gantry 2117F is coupled and/or connected to ground robot 2111 at 2150F. In some embodiment, 2150F may be a motor system to allow rotation in one or more plants of motion of forward gantry 2117F. In some embodiments, the gantries are angled between 20-70 degrees and the end effectors are attached to a gantry that can move on a track system in up to 3 directions. This configuration is advantageous as it allows ground robot 2111 to move either in the forward or reverse direction since there are rearward and forward-facing cameras. Furthermore, if the probe of the forward end effector cannot contact a weed, then the probe of the rear end effector can contact the weed to weaken or eliminate the weed. This is important so that the ground robot does not have to travel back down the row if it misses a weed. In some embodiments, ground robot 2111 uses wheels 2114 to travel on ground 2102 along crop row 2103.

Some Disclosed Embodiments May Include One or More of the Following Benefits and Advantages The Collaborative Robot Networks disclosed herein may have at least one or more of the following advantages over traditional agriculture robotics and methods of weed control:
1. Early detection of weeds and long-term mitigation. By inspecting with the drone and taking immediate action with ground robots, farmers are able to catch weeds early and remove them before seeding. Ground robots can perform mechanical, electrical, chemical, or hot oil weed control on the areas identified to eliminate the weeds prior to seeding. This will eliminate transfer of weed seeds in a specific field to the next year since in some cases weed seeds can stay in the ground for up to 5 years. Farmers will be able to stop future weeds from sprouting and spreading, decreasing the amount of weed controlled need in the future.
2. Flexible, continuous weed control. By continuously inspecting the fields, this system is able to perform effective weed control when environmental factors change to ensure weeds are removed at or before they reach a critical size prior to seeding.
3. Weed control without herbicides. In some embodiments, the ground robot described herein kills weeds by electrical means. Farmers are able to reduce the herbicides, water, and gasoline used in traditional weed control by using electricity to eliminate weeds.
4. Improved safety over other electrical weed control methods. Since the camera and CPU work together to identify a weed in order to activate the high voltage circuit, the risk of hurting a human or animal is greatly reduced compared to other electrical weeding methods. Furthermore, since the high voltage circuit is shut off after the weed control for each weed, a person servicing the robot is relatively safe. Also, the proposed circuit uses DC power instead of AC power. AC power stimulates sweating and causes muscular contractions in mammals, which makes it 4-5 times more dangerous for humans or animals in close proximity to the robots.
5. Compared to the traditional electrical weed control methods, this system saves power because the circuit is activated for a small amount of time only during weed control for an individual weed. Traditional electrical weed control has the electrical high voltage circuit continuously running in order to eliminate weeds, which requires large amounts of power that would make solar powered weeding difficult, if not impossible. Instead, large batteries are needed that increase the weight and complexity of the robots.
6. Compared to traditional weed control systems, the ground robot has the ability to take precise action on a specific weed which allows it to perform weed control very close to the crops. In row crops, this is critical because the farmer needs to remove the weeds closest to the crops because they compete with the crops for nutrients and water.
7. Compared to traditional systems, coupling the ground robot with a drone allows the ground robot to be more efficient and address issues in a specific location based on the drone's inspection data. This reduces the number of ground robots needed to monitor a parcel of land, especially when it comes to performing weed control. The drone acts as a force multiplier for each robot improving the efficiency of the robot by at least 3 times compared to ground robots only.
8. Compared to traditional weed control systems, both the drone and ground robot have electrical methods and mechanisms to eliminate weeds and eliminate pesticide use. By using a camera-controlled switch to enable the high voltage system, the proposed electric method of weed control ensures that people and animals will not be harmed by the robots since the circuit will not activate unless a weed is identified. Also, a single probe design further reduces the weight and complexity of the hardware required to build an end effector to facilitate electric weed control to eliminate or weaken weeds.
9. By using a moveable solar panel, the ground robot is able increase its charging efficiency by up to 35% by aligning the solar panel to the sun. In addition, the drone can use the ground robot as shelter during extreme weather and charge when attached to the ground robot. This enables the collaborative network of robots to function with little to no infrastructure for farmers.
10. Compared to traditional inspection systems, collaboration between the ground robot and the drone enables the system to gain higher resolution and more useful data because the drone can identify areas that need to be inspected close up by the ground robot. By superimposing this data, the farmer will have access to better data to take action. Also, in some cases, by having AI processors on board the ground robot, the collaborative robot network will be able to perform edge AI analysis that saves time and cost of transferring to the cloud for analysis.
11. Compared to traditional systems, the drones can act as an antenna for the ground robot to minimize ground effect and facilitate data transfer between farms and cloud analysis software, which will enable next generation analytics at farms to increase yield and reduce waste. In some cases, a network of drones could be connected to a ground robot and transfer data such as phone calls, text messages, and pictures in remote areas.
12. Edge AI with ground robots. Traditional drones have to transfer data back to a cloud platform in order to perform AI analysis on the farmland. With the ground robot, the drone can transfer data directly to the ground robot which will have an accelerator, GPU, or TPU to analyze the data and transfer reports directly to the farmer. In some cases, the ground robot will transfer a point of interest to other ground robots or a drone to take an action, such as weed control. This saves time and money since large images do not have to be upload to the cloud.

Hybrid Electrical Mechanical Autonomous Ground Vehicle

It should be noted that the disclosed embodiments of a Hybrid Electrical Mechanical Autonomous Ground Vehicle may be combined with any embodiments disclosed herein, and individual features of the Hybrid Electrical Mechanical Autonomous Ground Vehicle may be combined with individual features of any other embodiment. Any other embodiments may also be combined with the disclosed Hybrid Electrical Mechanical Autonomous Ground Vehicle, and individual features of any embodiment may be combined with individual features of the disclosed Hybrid Electrical Mechanical Autonomous Ground Vehicle. For example, the hybrid electrical mechanical autonomous ground vehicle embodiments can comprise one or more hoe portions and one or more electrode portions coupled to a distal end of the one or more mechanical arms that are proximately coupled to the ground vehicle in such a way that the one or more mechanical arms can be positioned and/or rotated to use any of the one or more hoe portions, shovel portions, and/or electrode portions.

The ground robots described in Hybrid Electrical Mechanical Autonomous Ground Vehicle share many similarities to the ground robots describe in Collaborative Robot Network with Optimized Weed Control Methods, and the same or similar reference numbers are used to refer to the same or similar elements.

Figure 6B:
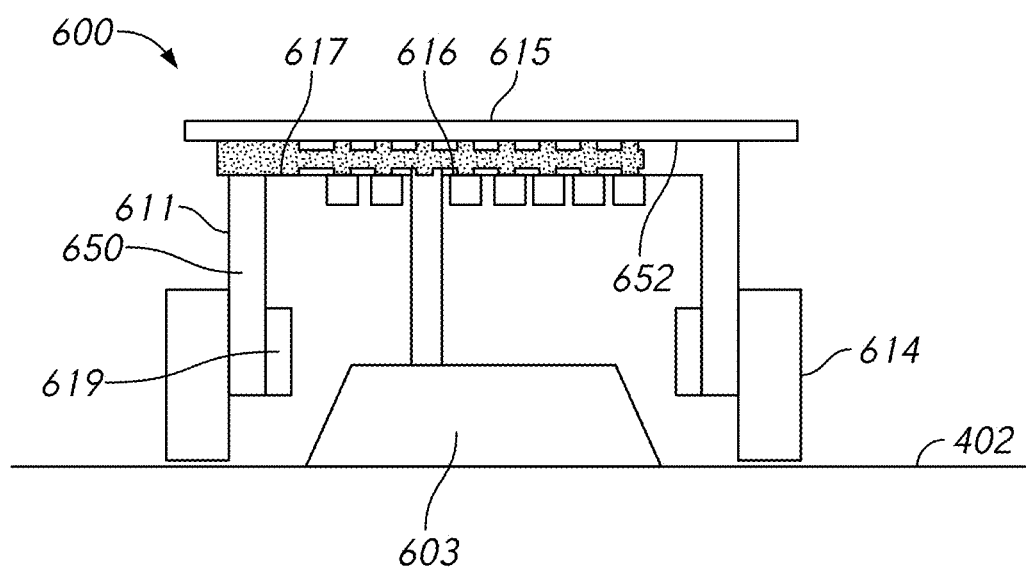
FIG. 6B is a front view showing a ground robot with a high volume weed control end effector used to eliminate multiple weeds at the same time, according to an embodiment.

As shown in FIGS. 24A-24D, an embodiment of Hybrid Electrical Mechanical Autonomous Ground Vehicle 2400. Ground robot 2411 generally comprises at least two wheels 2414 (such as two, three, four, or more wheels), solar panel 2415, camera 2420, computer 2490, robotic arm 2440 (e.g., robotic arm, mechanical arm, and/or the like), robotic arm 2450 (e.g., robotic arm, mechanical arm, and/or the like). In this embodiment, the robot 2411 desirably comprises four wheels 2414 (with two shown in the side views of FIGS. 24A and 24B, and a similar set of two wheels on the other side, as can be seen in the end views of FIGS. 24C and 24D). Other embodiments may include more or fewer wheels and/or may use a different type of propulsion system, such as tracks. The robotic arm 2440 includes a hybrid mechanical electrical end-effector with a positive electrode 2442 and a hoe 2444. The robotic arm 2450 includes a hybrid mechanical electrical end-effector with a negative electrode 2452 and a hoe 2454. For clarity, these figures (and FIGS. 25A-25F, 26A-26D, 28A-28B, 54A-54B discussed below) do not show the full frame of the ground vehicle unit that connects the other elements of the Autonomous Ground Vehicle (such as the wheels 2414, the solar panel 2415, the camera 2420, robotic arms 2440 and 2450, and/or the like) to each other and to the ground vehicle unit, in order to show more detail of other features of the robot 2411. A frame similar to frame 650 including the undercarriage 652 as used in robots 611 described above with reference to FIGS. 6A-6B may be included in robot 2411.

In some embodiments, the hoe can comprise a warren hoe. A warren hoe is a hoe that comprises a generally heart or triangular-shaped blade set at a generally right angle to the handle (e.g., to the mechanical arm which would be equivalent to the handle in this use case). Such a warren hoe has been found to be desirable in the present use cases. Some embodiments may use different hoe shapes and/or different blades that may not necessarily be considered a hoe. For example, in some of the embodiments disclosed herein, the systems can comprise a draw hoe, a warren hoe, a hula hoe, a scuffle hoe, a collinear hoe, a wheel hoe, a fork hoe, a cultivator, a plough hoe, a sharp hoe, a dull hoe, a rounded hoe, a plant and/or soil disturbance tool that can come in various shapes and sizes, and/or the like. Further, some embodiments may position the hoe blade at an angle other than a right angle to the mechanical arm, such as approximately, no greater than, or no less than, 30, 45, 50, 60, 70, 80, or 90 degrees.

A shovel is a tool that comprises a generally broad flat blade with upturned sides set at generally a 45-degree angle to the handle (e.g., to the mechanical arm which would be equivalent to the handle in this use case). Such a shovel has been found to be desirable in the present use cases. Some embodiments may use different shovel shapes and/or different blades that may not necessarily be considered a shovel. For example, some embodiments may utilize a trench shovel, a flat shovel, an edging shovel, a square digging shovel, a pointed digging shovel, a round digging shovel, a scoop shovel, and/or the like. Further, some embodiments may position the shovel blade at an angle other than a 45-degree angle to the mechanical arm, such as approximately, no greater than, or no less than, 0, 10, 20, 30, 40, 45, 50, 60, 70, 80, or 90 degrees. In some embodiments, the shovel does not have upturned sides.

The positive electrode 2442 of robotic arm 2440 is coupled to hoe 2444 such that when a switch (for example, like switch 509 in FIG. 5A) is activated, the hoe 2444 becomes positively charged. The negative electrode 2452 of robotic arm 2450 is coupled to hoe 2454 such that when a switch is activated, the hoe 2454 becomes negatively charged. As describe below, the switches (which may comprise one or more switches, relays, transistors, and/or the like) may desirably be automatically activatable by the robot's control system, without requiring manual activation by a user. In some embodiments the system can activate the high voltage booster unit using a switch relay such that the system need not continuously generate electrical current. In some embodiments, the high voltage booster unit can be configured to continuously generate electrical current. Robotic arm 2440 and robotic arm 2450 are coupled to Ground Robot 2411 and are powered by at least one motor (and desirably at least two motors, such as to control two separate degrees of motion and/or to control rotation of the arm about two separate rotational axes). Robotic arm 2440 and robotic arm 2450 can rotate around a central axis 2465 and move up and down. In this embodiment, the central axis is a pitch axis that is parallel to the wheel rotation axis. In other embodiments, the central axis may be a yaw axis or a roll axis. In some embodiments robotic arm 2440 and robotic arm 2450 can use the structures of FIGS. 27A-27C. Further details of example rotation axis orientations are provided below with reference to FIGS. 27A-27C.

In operation, ground robot 2411 uses wheels 2414 to travel on ground 2402 along crop row 2403 to find weeds. Ground robot 2411 uses camera 2420 to detect weed 2430 in crop row 2403. When camera 2420 takes an image, records a video, and/or the like, and CPU (for example, like CPU 507 in FIG. 5A) determines the existence and location of weed 2430, Ground Robot 2411 uses an AI system (such as the AI systems discussed below) to determine whether to remove weed 2430 with either hoes 2444 or 2454, or by electrical means. This determination desirably considers several factors which can include the type of soil, the condition of the soil, the type of crop, the type of weed, and/or the like. Although some embodiments desirably use an AI system, other types of systems such as machine learning, machine vision, coded image processing systems and/or the like, could be implemented in other embodiments.

As shown in FIG. 24B, if mechanical means are found optimal based on the AI determination, ground robot 2411 uses wheels 2414 to position itself above weed, uses camera 2420 and CPU (for example, like CPU 507 in FIG. 5A) to determine the location of weed 2430, and then uses either robot arm 2440 or 2450 to hoe the weed out of the ground. In some embodiments, only a portion of the weed is removed from the remaining plant matter, such as removing the stem from the roots and/or the like.

Figure 24C:
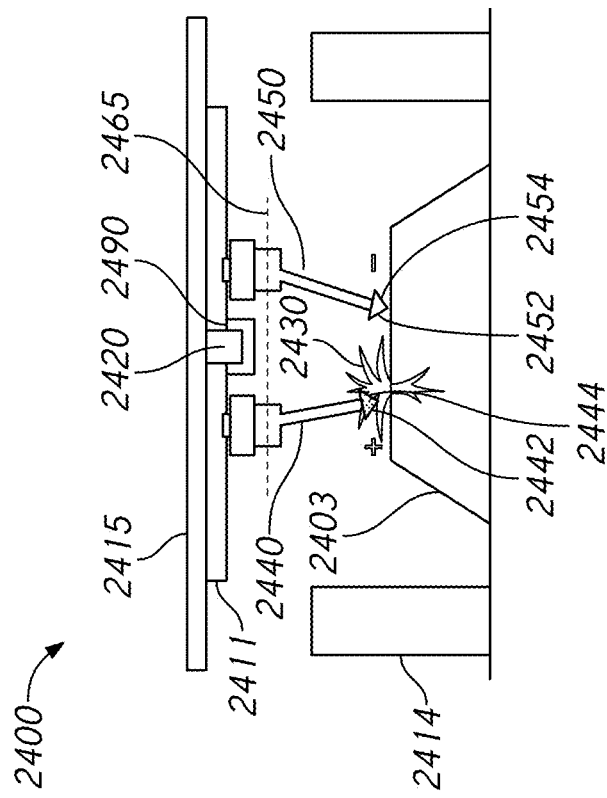
FIG. 24C is a front view of a Hybrid Electrical Mechanical Autonomous Ground Vehicle, according to an embodiment of the disclosure.
Figure 24D:
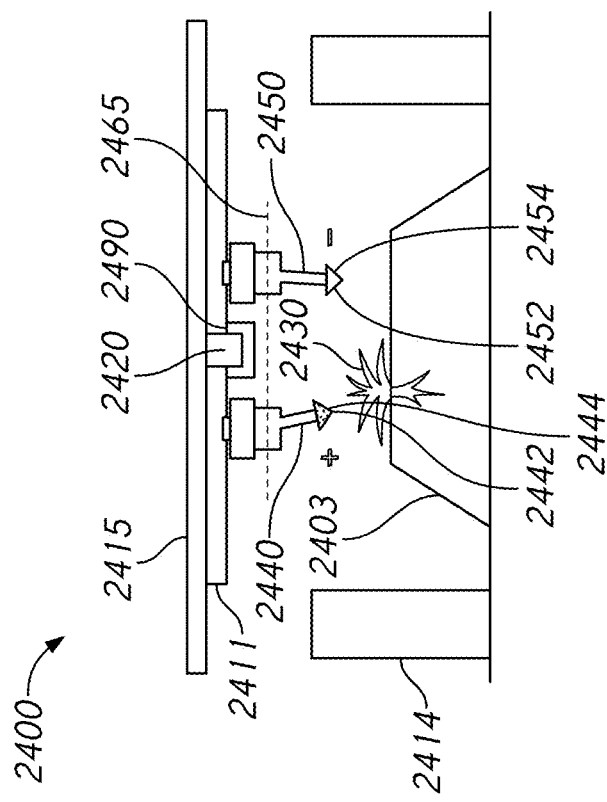
FIG. 24D is a diagram of a Hybrid Electrical Mechanical Autonomous Ground Vehicle taking advanced electrical action on farmland, according to an embodiment of the disclosure.

As shown in FIG. 24D, if electrical means are found optimal based on the AI determination, ground robot 2411 uses wheels 2414 to position itself above weed 2430, ground robot high voltage circuit (for example, like HV Booster 511 in FIG. 5A) is enabled, robotic arm 2440 moves to make contact with the weed 2430, while robotic arm 2450 makes contact with the ground, creating a circuit to electrocute the weed. In some embodiments, robotic arm 2440 makes contact with one weed, while robotic arm 2450 makes contact with another weed. When the high voltage circuit is enabled, a circuit is created between the two weeds and both weeds are electrocuted.

In some embodiments, the wheels (and/or other propulsion system, such as tracks) are made of metal or have metal studs or some other conductive component to act as the negative probe to connect the circuit to the ground. In some embodiments, ground robot 2411 is powered by batteries (for example, like battery 503 in FIG. 5A). In some embodiments, ground robot 2411 is powered by solar panels 2415 and batteries, wherein solar panels 2415 charge the batteries. In some embodiments, image, video, and/or the like, processing is performed by the GPU, TPU, or an accelerator onboard the ground robot.

In some embodiments, ground robot 2411 can have more than one camera. In some embodiments, ground robot 2411 can have more than two robotic arms (or only one robotic arm, which could, for example, be desirable if something other than a second robotic arm is used as a negative electrode). In some embodiments, robotic arms 2440 and 2450 are coupled to a hybrid mechanical electrical end-effector that includes any combination of a shovel, a hoe, and an electrode, or all three as shown in FIGS. 28A-28B. In some embodiments, a cleaning mechanism (such as cleaning mechanism 2660 shown in FIGS. 26C-26D and discussed in more detail below) can be coupled to ground robot 2411. In some embodiments, the robotic arm is a two-axis robotic arm.

In some embodiments, ground robot 2411 houses an electronic memory storage medium, such as memory 525 shown in FIG. 5A, comprising computer-executable instructions. In some embodiments, the electronic memory storage medium may be external to computer 2490. In some embodiments, the ground robot 2411 houses one or more processors (such as CPU 507 shown in FIG. 5A) that are in electronic communication with the electronic memory storage medium and are configured to execute the computer-executable instructions stored in the electronic memory storage medium for implementing a plant species control management operation. In some embodiment, a high voltage booster (for example, high voltage booster 511 in FIG. 5A) is electrically connected to the end-effector of robotic arm 2440. A high voltage booster can comprise, for example, an electrical circuit that takes electrical current at a first voltage level as an input, and outputs electrical current at a second, higher voltage level. For example, the voltage booster may receive electrical current from a solar array and/or battery at a level in a range of 1 kV-10 kV, and output electrical current at a higher voltage level, such as in a range of 20 kV-200 kV. Such an output range can be desirable, for example, as a level of voltage that is sufficient to eliminate weeds. In some embodiments, the high voltage booster is electrically coupled to the end effector of robotic arm 2450. In some embodiments, the high voltage booster is or comprises a transformer. In some embodiments, the high voltage booster is or comprises a pulse transformer circuit. In some embodiments, the camera 2420 generates one or more images. In some embodiments, the camera generates one or more images of the agricultural ground soil and plant organisms in the forward path of the vehicle. In some embodiments, an additional camera is coupled to the undercarriage of ground robot 2411 to generate additional images. In some embodiments, the generated one or more images are used to determine whether a detected plant organism is set for a plant species control management operation, such as mechanical removal, electrocution, and/or the like, by determining the plant species type and/or analysis of the agricultural ground soil. In some embodiments, the plant species type is determined by one or more processors comparing the generated image of the plant to a data store, catalogue, list, look up table, and/or the like of other plant species. In some embodiments, the one or more processors generate ground robot control instructions configured to advance the ground robot and mechanical arm to be within a threshold proximity of the identified plant organism. In some embodiments, when the method of plant organism control is electrical control, the one or more processors generate and execute mechanical arm control instruction to: position the end-effector of robotic arm 2440 to be in contact with the identified plant organism, position the end effector of robotic arm 2450 to be in contact with the soil or a second plant organism adjacent to the identified plant organism, and activate the high voltage booster to generate electric current through the end-effector of robotic arm 2440, the identified plant organism, and the end effector of robotic arm 2450. In some embodiments, when the method of plant organism control is mechanical control, the one or more processors generate and execute mechanical arm control instruction to: position the hoe portion 2454 of robotic arm 2440 to be in contact with soil distal to the identified plant organism and move the hoe portion 2454 through the soil to remove at least a portion of the identified plant organism.

In some embodiments, an energy storage unit (which may include, for example, a battery, supercapacitor, and/or the like) is housed in ground robot 2411 and the energy storage unit is electrically coupled to a high voltage booster unit. In some embodiments, solar panel 2415 is electrically coupled to the energy storage unit and is configured to recharge the energy storage unit. In some embodiments, solar panel 2415 is coupled to ground robot 2411. In some embodiments, the one or more processors are in electronic communication through an electronic network with a central server system. In some embodiments, activating the high voltage booster unit comprises activating with a switch relay. In some embodiments, the plant species type is determined by use of a computer vision algorithm. In some embodiments, the plant species type is determined by use of an artificial intelligence algorithm.

In some embodiments, the AI system determines if the weed should be mechanically or electrically eliminated based on the energy required for the removal. The AI system makes this determination based on the one or more images of the agricultural ground soil and plant organisms in the path of the ground robot. There are some cases where electrical removal will use less energy, and some cases where mechanical will use less energy. For example, sometimes electrical removal will be more efficient when removing large weeds or weeds in hard, compact, and/or the like soil conditions. Further, sometimes mechanical removal will be more efficient when removing weeds from soft, non-compact, and/or the like soil conditions. In some embodiments, being able to mechanically remove a weed can be used a safety feature when the AI system in conjunction with the cameras disclosed herein (such as cameras 2420, 2520, 420, and/or the like) determine that electrical removal may be unsafe because of external conditions such as a person or animal nearby. In some embodiments, the AI system may determine that electrical weeding is desirable so that the soil is not disturbed. In some embodiments, the AI system may determine that mechanical weeding is desirable to till the soil. In some embodiments, the AI system uses a predictive algorithm to determine where the plant organism that is set for plant organism control is, based on the one or more images generated by the one or more cameras. Based on the analysis of the one or more images, the AI systems predicts a movement to be within a threshold distance. This method allows the plant organism control operations to occur in real time while the ground robot moves in a continuous forward path without stopping.

In some embodiments, the robotic arms disclosed herein (such as robotic arms 2440, 2640, 2840, and/or the like) are coupled to the undercarriage portion of the ground vehicles disclosed herein (such as undercarriage portion 652 of ground robot 611 and/or the like). In some embodiments, the robotic arms can move in two axes such as the pitch axis and the yaw axis (for example, by use of a pitch and yaw motor like robotic arm 2740 in FIG. 27A, discussed in more detail below) and/or the like. In some embodiments the robotic arms can move in more than two axes. In some embodiments the robotic arms can move in three axes such as the pitch axis, yaw axis, and roll axis or any combination thereof. In some embodiments, the robotic arms can move in two degrees of motion. In some embodiments, the robotic arms can move in more than two degrees of motion. In some embodiments, the robotic arms can move in three degrees of motion. In some embodiments, the multiple degrees of motion involve only rotational motion. In some embodiments, the multiple degrees of motion involve a combination of rotational motion and translational motion (such as, for example, sliding along a track coupled to the robot frame, the arm including a telescopic portion, and/or the like). In some embodiments, the robotic arm has a hybrid mechanical electrical end-effector comprising a hoe portion and an electrode portion that form one unit such that the hoe portion can be electrically charged. In some embodiments, the robotic arm has a hybrid mechanical electrical end-effector comprising a hoe unit and a shovel unit that are electrically charged. In some embodiments, the robotic arm has a hybrid mechanical electrical end-effector comprising a separate hoe unit and a separate electrode. In some embodiments, the robotic arm has a hybrid mechanical electrical end-effector comprising a separate hoe unit, a separate shovel unit, and a separate electrode. In some embodiments, the robotic arm has a hybrid mechanical electrical end-effector that is separated from the primary rod of the robotic arm by an insulator. In some embodiments, the primary rod of the robotic arm is a conductor. In some embodiments, the primary rod of the robotic arm is not a conductor. In some embodiments, the hoe and/or shovel unit are fixedly coupled (or integrally formed) to an end portion of the robotic arm. In some embodiments, the hoe and/or shovel unit are able to move with respect to the end portion of the robotic arm (such as by rotating, translating, and/or the like, under the power of a motor, hydraulic cylinder, pneumatic cylinder, and/or the like).

In some embodiments, the ground robot can use the end effectors of the robotic arms disclosed herein (such as robotic arms 2440, 2640, 2840, and/or the like) to peel back layers of soil and take images with the cameras disclosed herein (such as cameras 2420, 2520, 420, and/or the like) of the root structure and soil color of each layer to estimate the amount of carbon stored in the ground. In some embodiments, peeling back layers of soil may include positioning a portion of the mechanical arm (for example, a hoe portion, shovel portion and/or the like) to be in contact with the ground and then using the propulsion units (for example, the wheels) to drag the mechanical portion arm along the ground to remove a layer of soil. In some embodiments, the motors in the mechanical arm are used to drag the mechanical portion arm along the ground to remove a layer of soil. In some embodiments, this analysis is conducted by use of the AI system. This feature is advantageous because it enables the ground robot to measure carbon sequestration. In some embodiments, the ground robots use the shovel portion of the hybrid electrical mechanical end effectors disclosed herein to peel back the layers of soil. In some embodiments, the ground robots use the hoe portion of the hybrid electrical mechanical end effectors, also known as a multi-use end-effector, disclosed herein to peel back the layers of soil.

In some embodiments, ground robots as described herein may use an AI system to process images recorded by the one or more cameras, where image processing generally refers to a method of manipulating an image to enhance and/or extract information from the image. The AI system performs digital images processing where the digital images are manipulating using computer algorithms. In some embodiments, the image processing is used to measure, characterize, classify and/or the like objects in the image. In some embodiments, the image processing follows some and/or all the following steps. First, image acquisition can be performed, where one or more images are captured using one or more cameras, other sensors and/or the like, and converted into a manageable entity. In some embodiments, the manageable entity is for example, a digital image file and/or the like. In some embodiment, the image acquisition method is scraping. Next, image enhancement can be performed, where the quality of the image is improved in order to extract information from the image for further process. Next, image restoration can be performed to improve the image quality. In some embodiment, the image restoration comprises removal of noise (for example, senor noise, motion blue, and/or the like) from the images. In some embodiments, the noise can be removed by using filters (for example, low-pass filter, median filters, and/or the like). In some embodiments, the AI system analyses the image data by using a model of the local image structure and controls filtering based on local information. In some embodiments, image restoration removes other corruptions from the image such as blue, missing pixels, camera misfocus, and/or the like by using models such as probabilistic and mathematical and/or the like. In some embodiments, the AI system uses edge detection methods for data extraction and image segmentation. Next, color imaging processing can be performed, where one or more images are undergo different processing, for example, pseudocolor, RGB and/or the like processing. Next, image compression and/or decompression can be performed, where compression can be used to reduce the size and/or resolution or the images and decompression can be used to restore the image to the original size and/or resolution. In some embodiments, image compression and/or decompression can be used during an image augmentation process to extend the data set with augmented images. Next, morphological processing can be performed to describe and/or define the shapes and structures of the objects in the one or more images. In some embodiments, the morphological processing can be used to create data sets for training AI models (for example, to train the AI model to detect and/or recognize certain objects in the images such as plants, weeds, soil, humans, animals, and/or the like). Next, image recognition can be performed, where certain features of individual objects in the one or more images can be identified. In some embodiments, various techniques are used for image recognition, such as object detection, objection recognition, segmentation, and/or the like. Use of object detection can be beneficial to identify and/or detect semantic objects of particular classes (for example, such as plants, weeds, soil types, humans, animals, and/or the like) in the images. In some embodiments, the AI system undergoes a process of deep learning development that may include cycles of the previously described image processing method to further develop the AI model. Finally, representation and description may be performed, where the processed data may be visualized and described. In some embodiments, the visualization tools are used to turn AI model outputs into readable image that may be used to perform additional analysis.

In some embodiments, ground robots as described herein may use an AI system to make decisions that can be used for operation of the ground robot vehicle and/or to perform one or more of the weed management, ground soil management, and/or livestock herding management operations. In some embodiments, the decision making can utilize the image processing described above to make decisions. For example, based on the results of the image processing in a weed management operation, the AI system may choose to perform either and/or both a mechanical weed management operation and an electrical weed management operation. In some embodiments, the AI system determines if the weed should be mechanically or electrically eliminated based on the energy required for the removal. The AI system makes this determination based on one or more images of the agricultural ground soil and plant organisms in the path of the ground robot. There are some cases where electrical removal will use less energy, and some cases where mechanical will use less energy. For example, the AI system may determine that electrical removal will be more efficient when the image processing is used to determine that a weed set for elimination is large, the soil is hard or compact, and/or the like. Sometimes, the AI system may determine that mechanical removal will be more efficient when the image processing is used to determine that a weed set for elimination is small, the soil is soft or not compact, and/or the like. As shown in FIGS. 25A-25F, an embodiment of Hybrid Electrical Mechanical Autonomous Ground Vehicle 2500. Ground robot 2511 generally comprises at least two wheels 2514 (and/or other propulsion systems, as discussed above), solar panel 2515, camera 2520, computer 2490, robotic arm 2540, robotic arm 2550. The robotic arm 2540 includes a hybrid mechanical electrical end-effector with a positive electrode 2542 and a hoe 2544. The robotic arm 2550 includes a hybrid mechanical electrical end-effector with a negative electrode 2552 and a hoe 2554.

In some embodiments, the hoe may comprise a hula hoe. A hula hoe is a hoe that comprises a square or stirrup-shaped blade set at a generally right angle to the handle (e.g., to the mechanical arm which would be equivalent to the handle in this use case). Such a hula hoe has been found to be desirable in the present use cases. Some embodiments may use different hoe shapes and/or different blades that may not necessarily be considered a hoe. For example, some embodiments may utilize a draw hoe, a hoe, a scuffle hoe, a collinear hoe, a wheel hoe, a fork hoe, a cultivator, a plough hoe, a stirrup hoe, and/or the like. In some embodiments, the hula hoe may be a pendulum-type hoe that allows it to move in a back and forward motion with respect to the handle. The back and forward motion may be achieved by including a pivot in the connection between the hoe and the handle, which allows the blade to change angle with respect to the handle. This pendulum action may be advantageous to allow for the blade to cut at the correct angle on both backwards and forwards cuts. Some embodiments may position the hoe blade at an angle other than a right angle to the mechanical arm, such as approximately, no greater than, or no less than, 30, 45, 50, 60, 70, 80, or 90 degrees.

The positive electrode 2542 of robotic arm 2540 is coupled to hoe 2544 such that when a switch (for example, like switch 509 in FIG. 5A) is activated, the hoe 2544 becomes positively charged. The negative electrode 2552 of robotic arm 2550 is coupled to hoe 2554 such that when a switch is activated, the hoe 2554 becomes negatively charged. As describe below, the switches (which may comprise one or more switches, relays, transistors, and/or the like) may desirably be automatically activatable by the robot's control system, without requiring manual activation by a user. Robotic arm 2540 and robotic arm 2550 are coupled to Ground Robot 2511 and are powered by at least one motor (and desirably at least two motors, such as to control two separate degrees of motion and/or to control rotation of the arm about two separate rotational axes). Robotic arm 2540 and robotic arm 2550 can rotate around a central axis 2565 and move up and down. In this embodiment, the central axis is a pitch axis that is parallel to the wheel rotation axis. In other embodiments, the central axis may be a yaw axis or a roll axis. In some embodiments, robotic arm 2540 and robotic arm 2550 can use the structures of FIGS. 27A-27C. Further details of example rotation axis orientations are provided below with reference to FIGS. 27A-27C.

In operation, ground robot 2511 uses wheels 2514 to travel on ground 2502 along crop row 2503 to find weeds. Ground robot 2511 uses camera 2520 to detect weed 2530 in crop row 2503. When camera 2520 takes an image, records a video, and/or the like, and CPU (for example, like CPU 507 in FIG. 5A) determines the existence and location of weed 2530, Ground Robot 2511 uses an AI system to determine whether to remove weed 2530 with either hoes 2544 or 2554, or by electrical means. This determination considers a number of factors which can include the type of soil, the condition of the soil, the type of crop, and the type of weed.

As shown in FIG. 25B, if mechanical means are found optimal based on the AI determination, ground robot 2511 uses wheels 2514 to position itself above weed, uses camera 2520 and CPU (for example, like CPU 507 in FIG. 5A) to determine location of weed 2530, then uses either robot arm 2540 or 2550 to hoe the weed out of the ground.

Figure 25D:
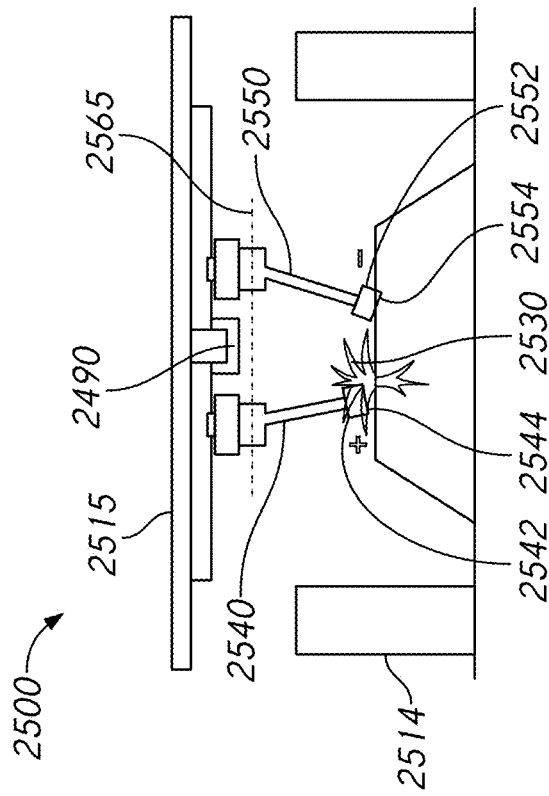
FIG. 25D is a diagram of a Hybrid Electrical Mechanical Autonomous Ground Vehicle taking advanced electrical action on farmland, according to an embodiment of the disclosure.
Figure 25C:
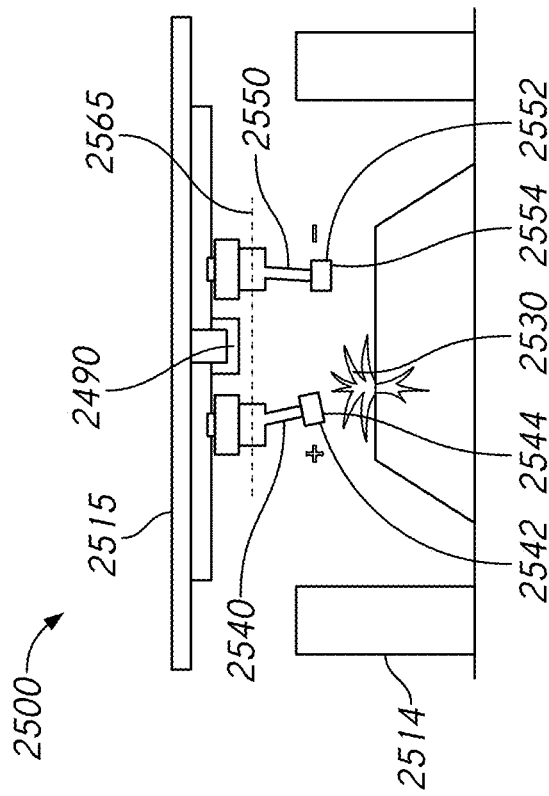
FIG. 25C is a front view of a Hybrid Electrical Mechanical Autonomous Ground Vehicle, according to an embodiment of the disclosure.
Figure 25E:
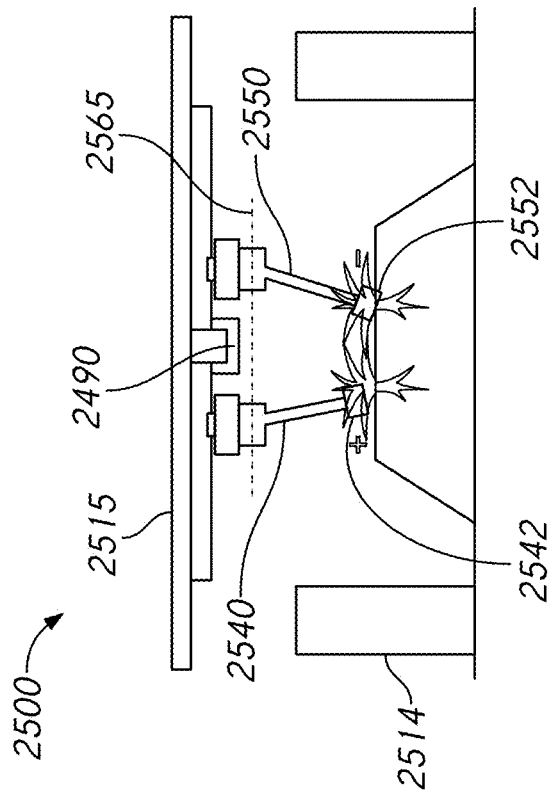
FIG. 25E is a front view of a Hybrid Electrical Mechanical Autonomous Ground Vehicle, according to an embodiment of the disclosure.
Figure 25F:
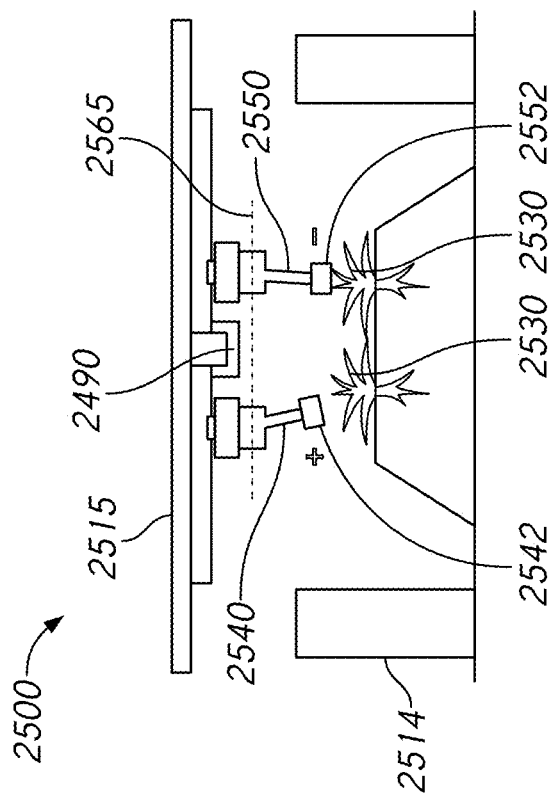
FIG. 25F is a diagram of a Hybrid Electrical Mechanical Autonomous Ground Vehicle taking advanced electrical action on multiple weeds on farmland, according to an embodiment of the disclosure.

As shown in FIG. 25D, if electrical means are found optimal based on the AI determination, ground robot 2511 uses wheels 2514 to position itself above weed 2530, ground robot high voltage circuit (for example, like HV Booster 511 in FIG. 5A) is enabled, robotic arm 2540 moves to make contact with the weed 2530 while robotic arm 2550 makes contact with the ground, creating a circuit to electrocute the weed. In some embodiments, robotic arm 2540 makes contact with one weed, while robotic arm 2550 makes contact with another weed. When the high voltage circuit is enabled, a circuit is created between the two weeds and both weeds are electrocuted. In some embodiments, ground robot 2511 positions itself above weed 2530 while in continuous motion, such that the plant management operation occurs while the ground robot 2511 continues to travel in a forward or backwards path. In some embodiments, this process can be accomplished by use of an AI system that uses a predictive algorithm to determine where the plant organism that is set for plant organism control is, based on the one or more images generated by the one or more cameras. Based on the analysis of the one or more images, the AI systems predicts a movement to be within a threshold distance. This method allows the plant organism control operations to occur in real time while the ground robot moves continuously without stopping. In some embodiments, the wheels (and/or other propulsion system, such as tracks) are made of metal or have metal studs to act as the negative probe to connect the circuit to the ground. In some embodiments, ground robot 2511 is powered by batteries (for example, like battery 503 in FIG. 5A). In some embodiments, ground robot 2511 is powered by solar panels 2515 and batteries wherein solar panels 2515 charge the batteries. In some embodiments, image, video, and/or the like, processing is performed by the GPU, TPU, or an accelerator onboard the ground robot.

In some embodiments, ground robot 2511 can have more than one camera. In some embodiments, ground robot 2511 can have more than two robotic arms. In some embodiments, robotic arms 2540 and 2550 are coupled to a hybrid mechanical electrical end-effector that includes any combination of a shovel, a hoe, and an electrode, or all three as shown in FIG. 28. In some embodiments a cleaning mechanism as shown in FIG. 26C-D can be coupled to ground robot 2511. In some embodiments, the robotic arm is a two-axis robotic arm.

As shown in FIGS. 26A-26D, an embodiment of Hybrid Electrical Mechanical Autonomous Ground Vehicle 2600. FIGS. 26A-26B show an embodiment of a ground robot 2611 generally comprises at least two wheels 2614 (and/or other propulsion systems, as discussed above), solar panel 2615, camera (for example, like camera 2520 in FIG. 25A), and robotic arm 2640. The robotic arm 2640 includes a hybrid mechanical electrical end-effector comprised of a hoe 2644. The hoe 2644 is comprised of a negative region 2646 near the terminating end of hoe 2644 and a positive region 2648 along the body or at the base of hoc 2644. In some embodiments, negative region 2646 is a sharp or rounded tip, positive region 2648 is a collar, and the region between negative region 2646 and positive region 2648 is an insulator. In some embodiments, when a switch (for example, like switch 509 in FIG. 5A) is activated, the hoe becomes charged. As describe below, the switches (which may comprise one or more switches, relays, transistors, and/or the like) may desirably be automatically activatable by the robot's control system, without requiring manual activation by a user. Robotic arm 2640 is coupled to Ground Robot 2611 and is powered by at least one motor (and desirably at least two motors, such as to control two separate degrees of motion and/or to control rotation of the arm about two separate rotational axes). Robotic arm 2640 can rotate around a central axis 2665 and move up and down. In this embodiment, the central axis is a pitch axis that is parallel to the wheel rotation axis. In other embodiments, the central axis may be a yaw axis or a roll axis. In some embodiments, robotic arm 2640 can use the structures of FIGS. 27A-27C. Further details of example rotation axis orientations are provided below with reference to FIGS. 27A-27C.

In operation, ground robot 2611 uses wheels 2614 to travel on ground 2602 along crop row 2603 to find weeds. Ground robot 2611 uses camera to detect weed 2630 in crop row 2603. When camera takes an image, records a video, and/or the like, and CPU (for example, like CPU 507 in FIG. 5A) determines the existence and location of weed 2630, Ground Robot 2611 uses AI system to determine whether to remove weed 2630 with either hoe 2644, or by electrical means. This determination considers a number of factors which can include the type of soil, the condition of the soil, the type of crop, the type of weed, and/or the like.

As shown in FIG. 26B, if mechanical means are found optimal based on the AI determination, ground robot 2611 uses wheels 2614 to position itself above weed, uses camera and CPU (for example, like CPU 507 in FIG. 5A) to determine location of weed 2630, then uses robotic arm 2640 to hoe the weed out of the ground.

As shown in FIG. 26A, if electrical means are found optimal based on the AI determination, ground robot 2611 uses wheels 2614 to position itself above weed, the ground robot high voltage circuit (for example, like HV Booster 511 in FIG. 5A) is enabled, robotic arm 2640 moves to make contact with the weed. Once hybrid electrical mechanical end effector makes contact with the weed, a switch flips to activate the high voltage circuit and the weed is electrocuted. Electricity travel directly through the stem of the weed. In some embodiments, the switch is activated and the weed is electrocuted when the hybrid electrical mechanical end effector makes contact with the weed and the ground. In some embodiments, the switch is activated and the weed is electrocuted when the hybrid electrical mechanical end effector makes contact with the weed and an adjacent weed, the adjacent weed also being electrocuted.

In some embodiments, the wheels (and/or other propulsion system, such as tracks) are made of metal or have metal studs to act as the negative probe to connect the circuit to the ground. In some embodiments, ground robot 2611 is powered by batteries (for example, like battery 503 in FIG. 5A). In some embodiments, ground robot 2611 is powered by solar panels 2615 and batteries wherein solar panels 2615 charge the batteries. In some embodiments, image, video, and/or the like, processing is performed by the GPU. TPU, or an accelerator onboard the ground robot.

In some embodiments, ground robot 2611 can have more than one camera. In some embodiments, robotic arm 2640 are coupled to a hybrid mechanical electrical end-effector that includes any combination of a shovel, a hoe, and an electrode, or all three as shown in FIG. 28. In some embodiments the hoe 2644 is a warren hoe, a hula hoe, and/or the like. In some embodiments, the robotic arm is a 2-axis robotic arm.

As shown in FIG. 26C-26D, in some embodiments a cleaning mechanism 2660 can be coupled to ground robot 2611. In some embodiments, the cleaning mechanism comprises one or more protrusions, one or more brushes, one or more integrated brushes, one or more finger elements, and/or the like. Once the ground robot has removed a weed as previously described, the robotic arm 2640 can move the end effector 2644 to the cleaning mechanism 2660 to remove debris such as dirt, soil, plant matter, rocks, sand, dust, water, sticks and/or the like. A cleaning mechanism is advantageous for optimal weed removal as well as to prevent the end effector from short circuiting.

In some embodiments, the robotic arm 2640 moves the end effector 2644 through the cleaning mechanism in different planes of motion to remove the debris. In some embodiments, the ground robot 2611 uses camera and an AI system to ensure the debris has been removed. In some embodiments, the end effector 2644 is cleaned after every weed is removed. In some embodiments, the end effector 2624 is cleaned after a certain number of weeds are removed, or a duration of time has passed. In some embodiments, the end effector 2644 is cleaned when the AI system determined a cleaning is necessary, for example, such as when the AI system detects a specific quantity of debris or issues with the circuit, and/or the like. In some embodiments, the cleaning mechanism comprises one or more protrusions coupled to an external portion of the ground vehicles disclosed herein (such as ground robot 2811, 2611, 2411 and/or the like). In some embodiments, the cleaning mechanism can be used to clean a robotic arm, an end effector, an electrode, a hoe portion, a shovel portion, and/or the like (including any of the robotic arms, end effectors, electrodes, hoe portions, and shovel portions disclosed herein).

In some embodiments, the cleaning mechanism 2660 contains a sharpener, hone, grinder and/or the like that can be used to sharpen tools on the end effector 2644 such a shovel, a hoc, and/or the like. In some embodiments the robotic arm 2640 moves the end effector 2644 through the sharpener to sharpen the tools.

Figure 27A:
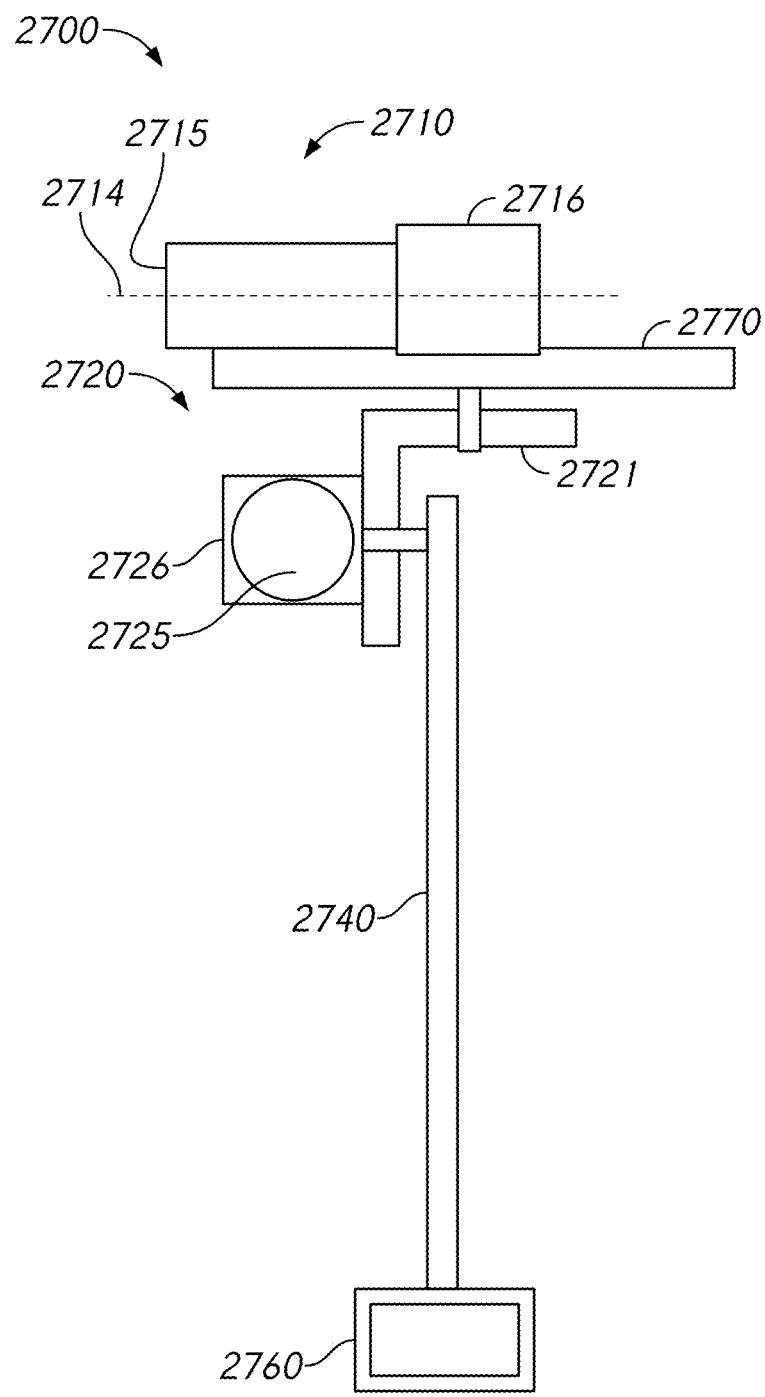
FIG. 27A is a diagram of a front view of a mechanical arm, according to an embodiment of the disclosure.
Figure 27B:
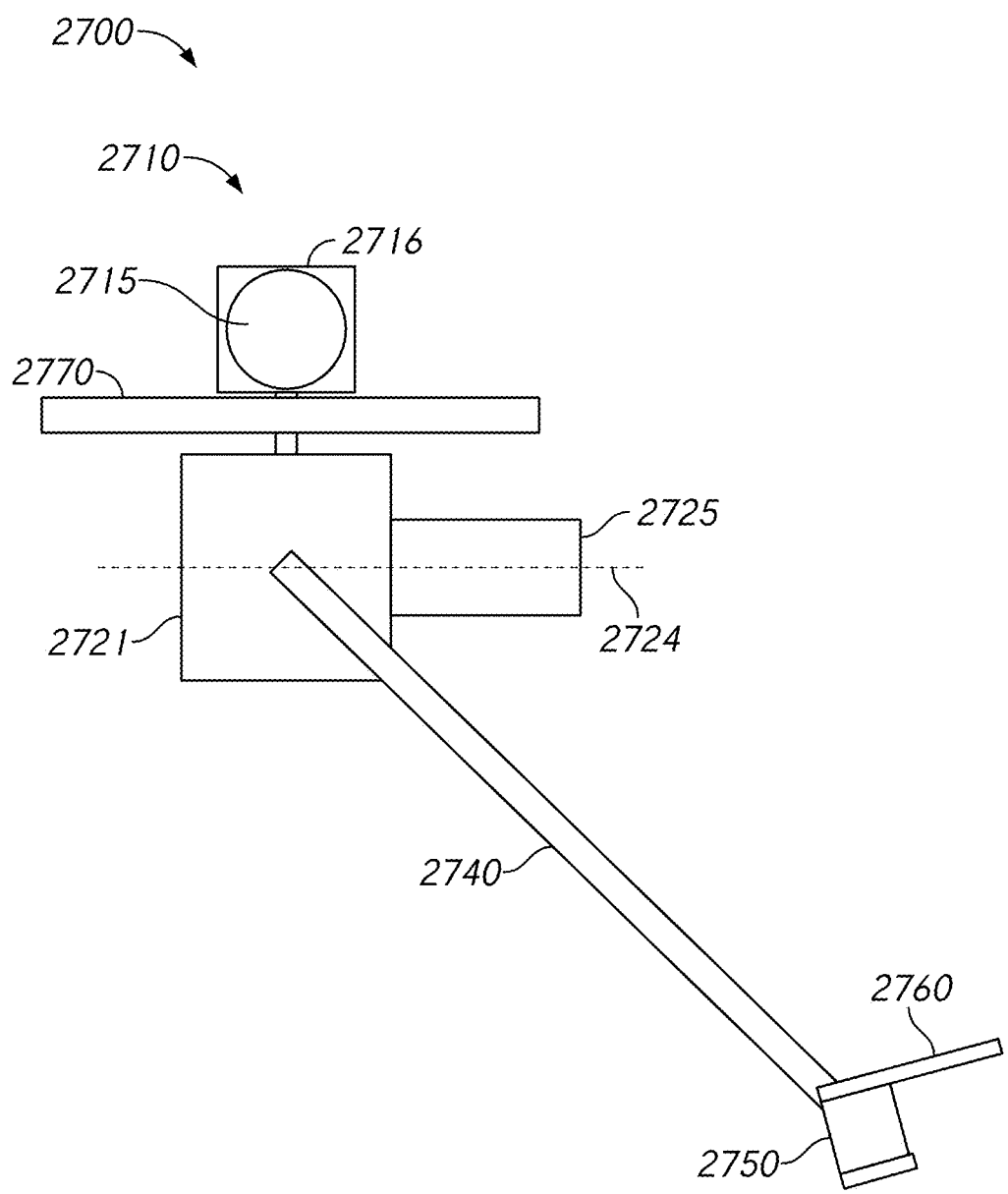
FIG. 27B is a diagram of a side view of a mechanical arm, according to an embodiment of the disclosure.
Figure 27C:
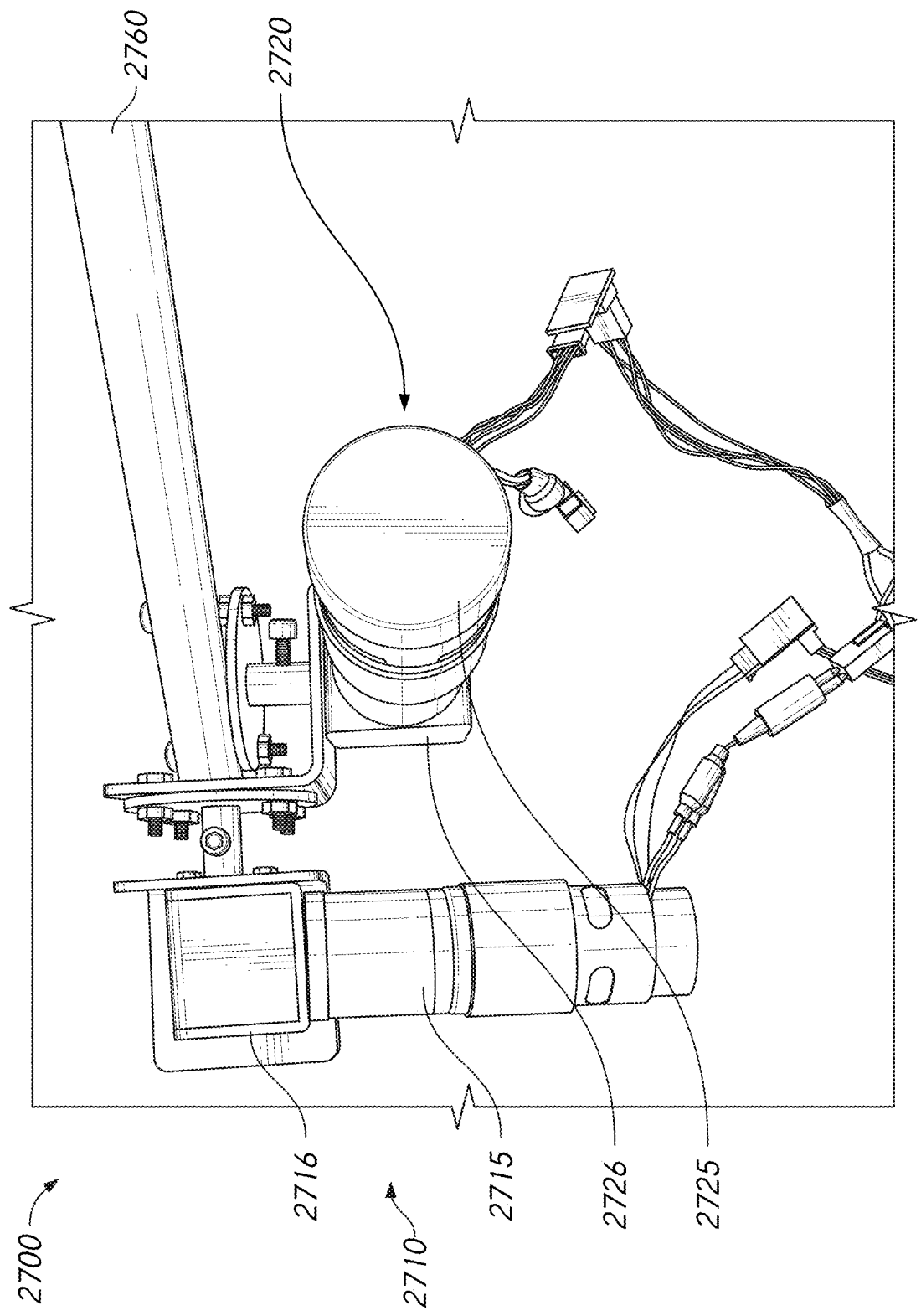
FIG. 27C is a diagram of a mechanical arm, according to an embodiment of the disclosure.

FIG. 27A-27C illustrate an embodiment of a robotic arm 2700 (which may be used as, for example, any of the robotic arms disclosed herein). The robotic arm 2700 includes a yaw motor 2710 (e.g., a first motor), a pitch motor 2720 (e.g., a second motor), a hoe arm 2740 (e.g., a mechanical arm and/or the like), a hoe 2750, and shovel 2760. Hoe arm 2740 is coupled to the ground robotic vehicle structure 2770 (which may be, for example, the undercarriage 652 of frame 650 disclosed herein). The hoe 2750 is coupled to the hoe arm 2740. The shovel 2760 is coupled to the hoe arm 2740. In some embodiments, the hoe is a warren hoe, a hula hoe, and/or the like.

In this embodiment, the pitch motor 2720 is connected to the vehicle structure 2770, with an output shaft 2725 of the pitch motor 2720 being oriented in a vertical direction such that the output shaft rotates about a vertical rotation axis 2724. A bracket 2721 is coupled to the output shaft of the pitch motor 2720, and the yaw motor 2710 is coupled to the bracket 2721. The yaw motor 2710 is positioned on the bracket 2721 such that an output shaft 2715 of the yaw motor 2710 is oriented in a horizontal direction, such that the output shaft rotates about a horizontally oriented rotation axis 2714. The output shaft 2715 of the yaw motor 2710 is coupled to a proximal end of the hoe arm 2740. With such an arrangement, the hoe arm 2740 can be caused to rotate about two separate axes of rotation, namely a vertical axis 2724 defined by the output shaft 2725 of the pitch motor 2720 and a horizontal axis 2714 defined by the output shaft 2715 of the yaw motor 2710. Other embodiments may include more or less drive motors and/or axes of rotation, other embodiments may position the multiple axes of rotation in different orientations, and/or the like. Further, in some embodiments, including the embodiment shown in FIG. 27A, the two motors are actually motor assemblies that each include a motor and gearbox (for example, gearbox 2726 for the pitch motor 2720 and gearbox 2716 for the yaw motor 2710. In such a configuration, the output shafts 2725 and 2715 are actually an output shaft of a gearbox that is coupled to the motor. Such a configuration can be desirable, for example, to provide a mechanical advantage, to change an orientation of the rotation axis, and/or the like.

In this embodiment, the motors 2710, 2720 desirably comprise brushless DC motors, which can operate relatively efficiently. Some embodiments may, however, use different types of electric motors, hydraulic and/or pneumatic motors, linear actuators, rack and pinon systems, hydraulic and/or pneumatic cylinders or actuators, and/or the like.

As shown in FIG. 28A, an embodiment of Hybrid Electrical Mechanical Autonomous Ground Vehicle 2800. Ground robot 2811 includes at least two wheels 2814 (and/or other propulsion systems, as discussed above), robotic arm 2840, hoe 2850, shovel 2860, and ground robot vehicle structure 2870. Robotic arm 2840 is coupled to the ground robotic vehicle structure 2870 and is powered by at least one motor (and desirably at least two motors, such as to control two separate degrees of motion and/or to control rotation of the arm about two separate rotational axes). Robotic arm 2840 can rotate around a central axis 2865 and move up and down. In this embodiment, the central axis is a pitch axis that is parallel to the wheel rotation axis. In other embodiments, the central axis may be a yaw axis or a roll axis. In some embodiments, robotic arm 2840 can use the structures of FIGS. 27A-27C. Further details of example rotation axis orientations are provided above with reference to FIGS. 27A-27C. The hoe 2850 is coupled to the robotic arm 2840. The shovel 2860 is coupled to the robotic arm 2840. FIG. 28B, shows a front view of an embodiment of ground robot 2811.

FIG. 28A shows robotic arm 2840 in three functional positions. Position one is shown by robotic arm 2840A, hoe 2850A, and shovel 2860A. Position two is shown by robotic arm 2840B, hoc 2850B, and shovel 2860B. Position three is shown by robotic arm 2840C, hoc 2850C, and shovel 2860C. Position one is shown by robotic arm 2840A, where it can be used for plant management by mechanical or electrical means where robotic arm 2840 can hoe weeds and/or electrocute weeds as previously described.

FIG. 28A shows robotic arm 2840 in a second position at 2840B, where shovel 2860B can be used to dig holes in the ground 2802 and perform terraforming operations. Shovel 2860B can be used to dig holes when ground robot 2811 moves on wheels 2814 forwards and backwards or side to side while the robotic arm 2840B moves in one or more planes of motion using motors (for example, like motors 2710 and 2720 in FIG. 27A).

This method of digging holes is advantageous for creating pockets in the ground that can retain water and seeds. In one application, ground robot 2811 can use robot arm 2840 in position 2840B to dig crescent pockets shown in FIG. 29. When rainwater falls and seeds blow in the wind, the pockets collect the water and seeds to promote regrowth of vegetation. This application is advantageous to restore vegetation to land in previously arid environments and degraded farmland. In other embodiments, the pockets created can be half-circle, half-square or any other shaped hole that promotes water and/or seed retention.

Figure 29:
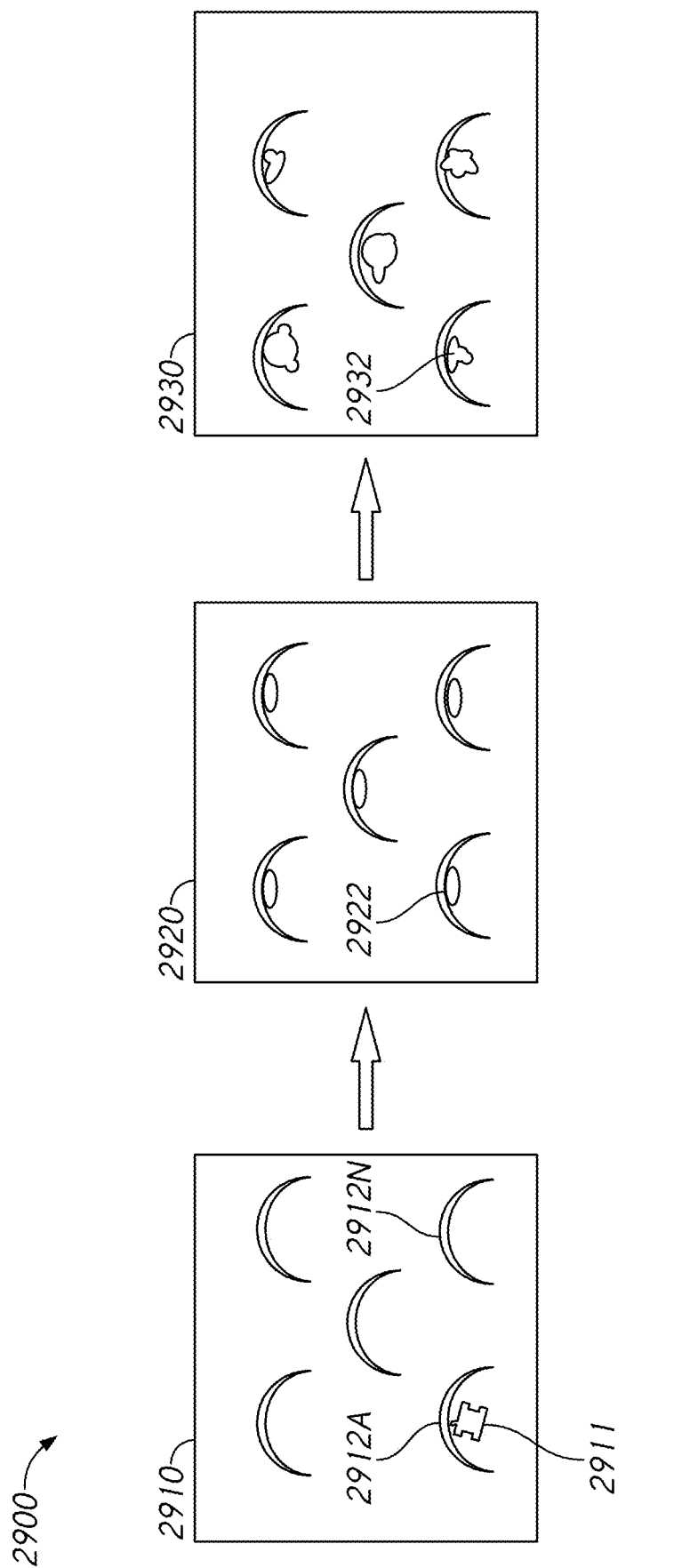
FIG. 29 is a diagram showing land improvement over time.

As shown in FIG. 29, an embodiment of a flow diagram 2900. At step 2910, an embodiment of ground robot 2911 creates crescent shaped pockets 2912A-2912N in the ground. At step 2920, seeds and water 2922 collect in the pockets 2912A-2912N through natural means such as rain and wind. At step 2930, after a certain amount of time, vegetation such as plants, trees, crops, and/or the like 2932, whose seeds land in the pockets grow in the pockets.

Figure 30:
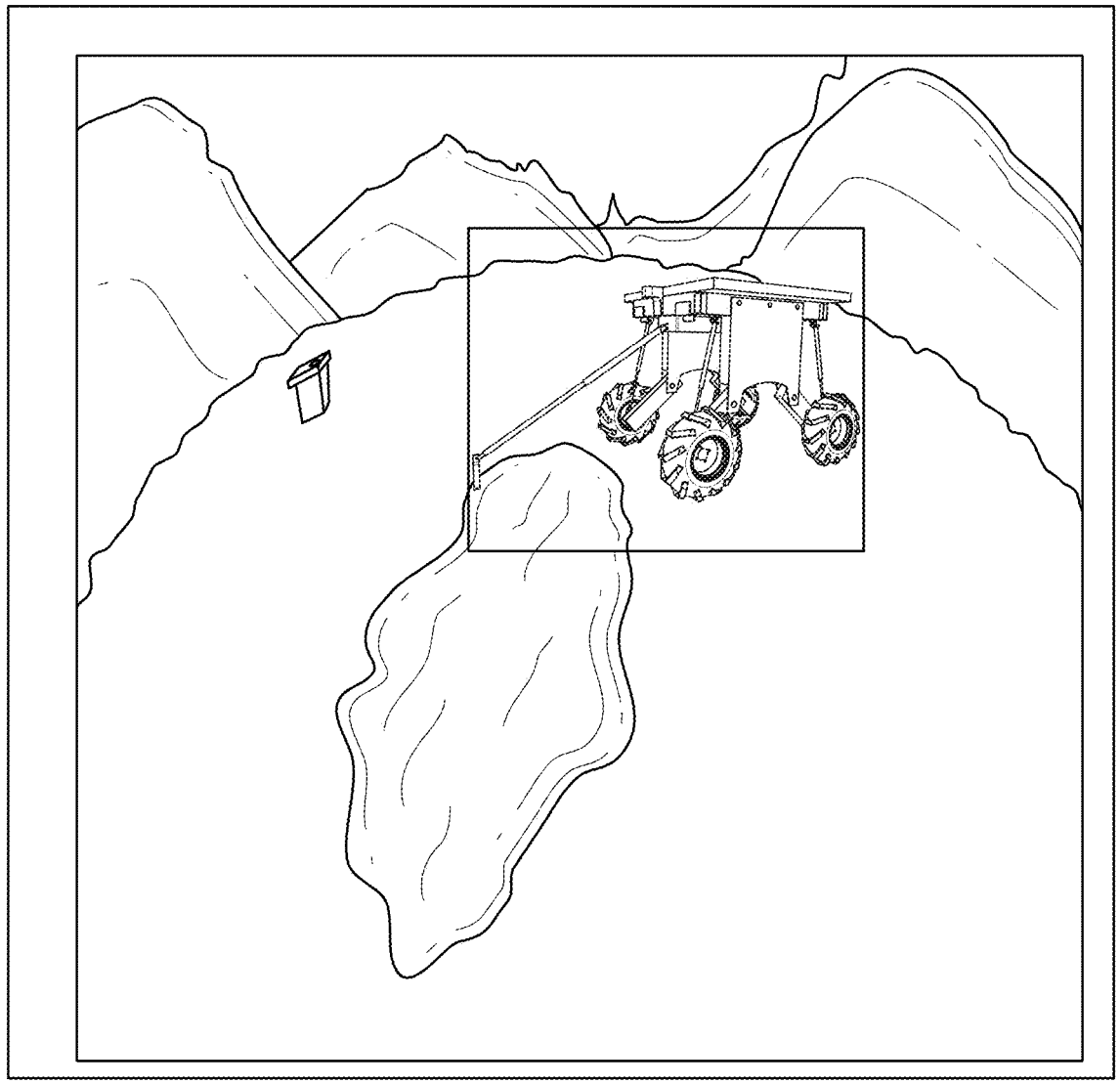
FIG. 30 is an image of a Hybrid Electrical Mechanical Autonomous Ground Vehicle creating soil water retention pockets, according to an embodiment of the disclosure.

FIG. 30 shows an embodiment of Hybrid Electrical Mechanical Autonomous Ground Vehicle using a shovel to create a soil water retention pocket. In some embodiments, a soil water retention pocket may be referred to as a ground pocket.

FIG. 28A shows robotic arm 2840 in a third position at 2840C. When robotic arm 2840C is moved in a plane or planes of motions, for example, from side to side or up and down or in a combination thereof by motors (for example, like motors 2710 and 2720 in FIG. 27A), ground robot 2811 can be used to herd livestock 2880. Livestock can be any animal such as cattle, sheep, and/or the like. In some embodiments, herding livestock can be moving different livestock from one area to another while the livestock graze.

Use of ground robot 2811 to move livestock can be advantageous because in some embodiments, ground robot 2811 can use cameras (for example, such as camera 2420 in FIG. 24A) and an AI system to analyze the plant life the livestock are eating. By monitoring which plant life is consumed and the quantity consumed by livestock, ground robot 2811 can prevent detrimental overgrazing of the land. In some embodiments, ground robot 2811 uses AI system to determine the value of the plants prior to moving the livestock to a specific area. In some embodiments, ground robot 2811 uses AI system to determine the value of the plants while herding the livestock to a specific area. In some embodiments, the AI system determines the value of plants by comparing the generated image of the plant to a data store, catalogue, list, look up table, and/or the like of other plants. In some embodiments, plants traditionally seen as a weed can be value adding, because the weeds can be used to store carbon in the ground or add nutrients to the soil. In some embodiments, the catalogue, list, look up table and/or the like is stored on a cloud server. In some embodiments, ground robot 2811 uses camera and CPU (for example, like CPU 507 in FIG. 5A) to map the land for analysis. In some embodiments, robotic arm 2840C has reflector, lights, a method of producing sounds, ribbons, strings, wires, and/or the like coupled to the end effector. In some embodiments, robotic arm 2840C may use the electrodes on the end effector, for example, similar to a taser, for moving livestock.

Use of ground robots disclosed herein (such as ground robot 2811, 2611, 2411 and/or the like), to dig soil water retention pockets is advantageous to prevent soil compression which is common when standard construction vehicles are used to dig holes in the ground. In some embodiments, a ground robot weighs no more than, for example 150 pounds, which allows a single robot to be shipped over standard freight and reduces soil compaction and damage to the land. In some embodiments, ground robot weights no more than 75 pounds, 100 pounds, 125 pounds, 175 pounds, 200 pounds, and/or the like. In some embodiments, ground robot's light weight is achieved by using large solar panel size instead of larger batteries. Further, in some embodiments, the light weight of ground robot is achieved by allowing the solar panel to pivot to improve solar efficiency by up to, for example 35%. In some embodiments, the increase in solar efficiency can be 5%, 10%, 15%, 20%, 25%, 30%, 35%, 40%, and/or the like. In some embodiments, ground robot's weight is reduced because it does not have any onboard fuel inputs, gas engines, heavy tools such as lasers and/or the like. In some embodiments, ground robot has two or more cameras. In some embodiments, ground vehicle unit is constructed with aluminum extrusions, thin steel, and/or the like. In some embodiments, ground robot applies a pressure of for example, approximately 6 PSI (pounds per square inch) on the ground. In some embodiments, ground robot applies a pressure on the ground of less than 4 PSI, 5 PSI, 6 PSI, 7 PSI, 8 PSI, 9 PSI, 10 PSI, 11 PSI, 12 PSI, 13 PSI, 14 PSI, 15 PSI, and/or the like. In some embodiments ground robot 2811 applies a pressure of less than 15 PSI on the soil to prevent soil compression. In some embodiments ground robot is symmetrical. In some embodiments, ground robot can operate the same way whether moving forwards or backwards. In some embodiments, ground robot has a mechanical propulsion mechanism that comprises mechanical legs. In some embodiments, ground robot has a mechanical propulsion mechanism that comprises four wheels. In some embodiments, the software in ground robot can be changed to complete any of the operations disclosed herein.

As shown in FIGS. 54A-54B, another embodiment of a ground robot 5411 generally comprises at least two wheels 5414, solar panel 5415, two cameras 5420, computer 5490, and robotic arm 2640. The robotic arm 2640 includes a hybrid mechanical electrical end-effector 5444.

In some embodiments ground robot 5411 is symmetrical. Symmetrical means that ground robot 5411 may have the same or similar components on each side (for example, a camera and/or the like) such that ground robot 5411 can perform agricultural plant and soil management operations whether moving forwards or in reverse. Being symmetrical and able to move and perform operations while moving forwards or in reverse is beneficial because it enables ground robot to move up and down crop rows without having to turn. FIG. 54A shows ground robot 5411 moving in a forward direction. FIG. 54B shows ground robot 5411 moving in a reverse direction.

Figure 54C:
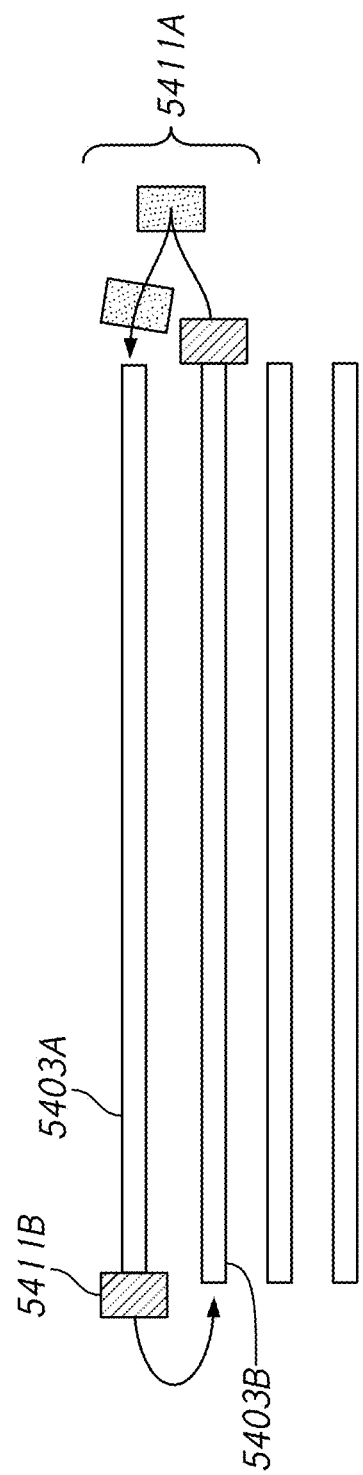
FIG. 54C is a diagram showing symmetric multiple crop row turning methods.
Figure 54D:
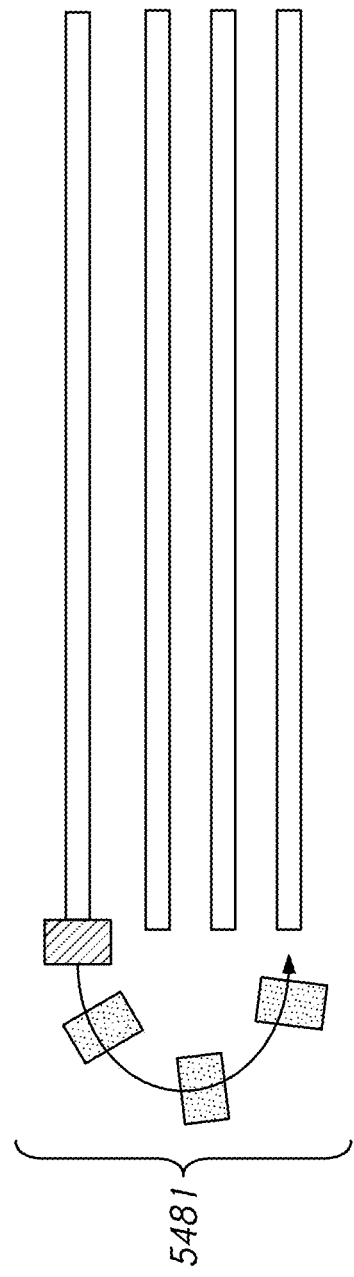
FIG. 54D is a diagram showing normal robotic crop row turning.

As shown in FIG. 54C, ground robot 5411A can symmetrically reverse which enables ground robot to progressively move down crop row 5403B in a forward direction and perform agricultural plant and soil management operations, then move down crop row 5403A in a reverse direction and perform agricultural plant and soil management operations without skipping a row. In some embodiments, ground robot 5451B has additional motors to rotate each wheel to provide for a tight turning radius. As shown in FIG. 54D, a ground robot 5481 without symmetrical turning or additional motors in each wheel may have to skip rows due to a large turning radius.

Dynamic, Infrastructure Free Robotic Network

It should be noted that the disclosed embodiments of a Dynamic, Infrastructure free Robotic Network may be combined with any embodiments disclosed herein, and individual features of the Dynamic, Infrastructure free Robotic Network may be combined with individual features of any other embodiment. Any other embodiments may also be combined with the disclosed Dynamic, Infrastructure free Robotic Network, and individual features of any embodiment may be combined with individual features of the disclosed Dynamic, Infrastructure free Robotic Network.

Figure 31:
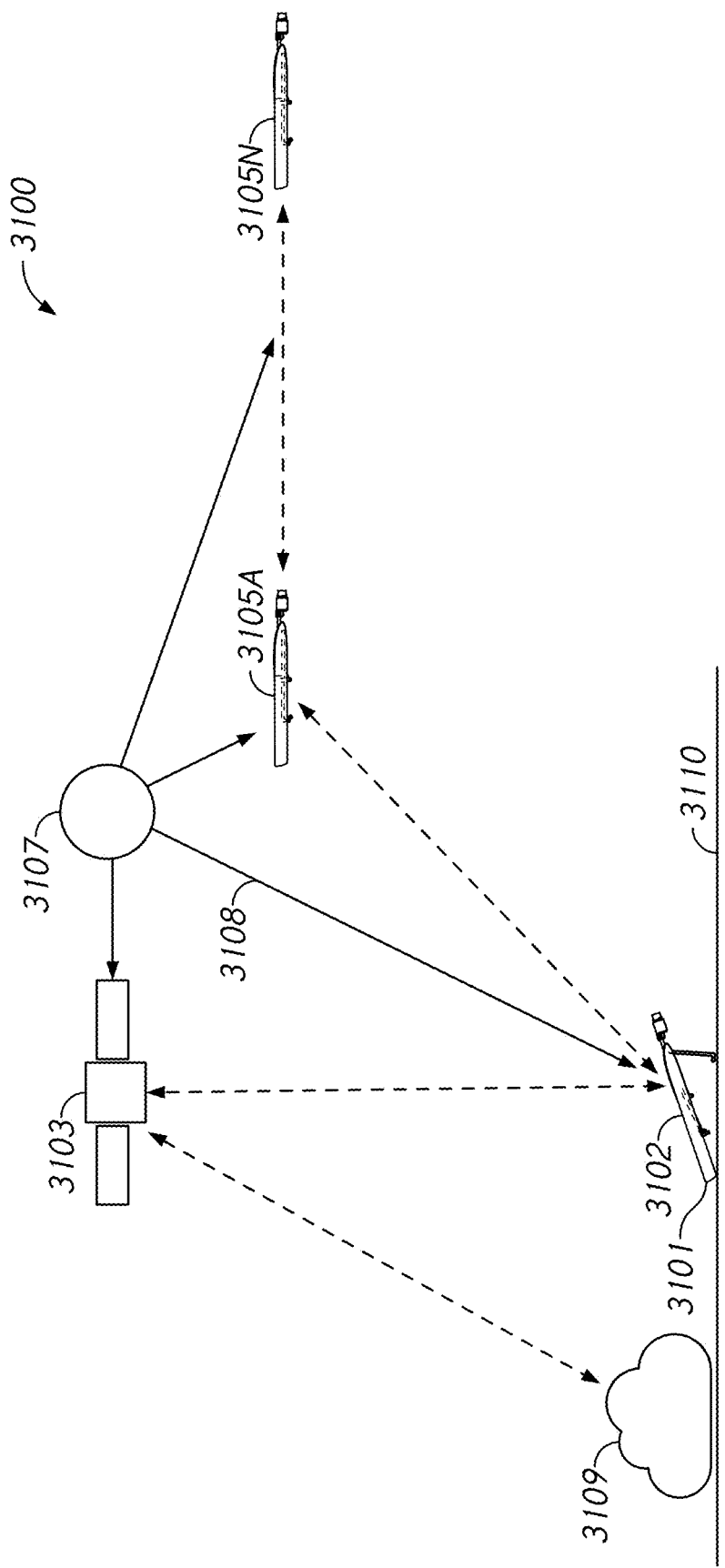
FIG. 31 is a diagram of a Multi-modal, Weather Resistant Robot Network and Methods of Data Transfer connected to a satellite, according to an embodiment.

As shown in FIG. 31, an embodiment of a Dynamic, Infrastructure free Robotic Network 3100 generally comprises at least one link drone 3101, at least one satellite 3103, and sun 3107. Link drone 3101 may fly or move on the ground 3110 to collect data with sensors or cameras. Sun beams 3108 emitted from sun 3107 hit solar panel 3102 of link drone 3101 to provide power for flight, ground movement, data collection, and data transmission to satellite 3103. In some embodiments, link drone 3101 has solar panel 3102. In other embodiments, link drone has batteries (for example, like battery 503 in FIG. 5A). In yet another embodiment, link drone has solar panel 3102 and batteries.

In some embodiments, link drone 3101 transmits data to cloud computing and storage 3109 via satellite 3103. In some embodiments, link drone is controlled via on-board AI processor. In some embodiments, a remote operator (not shown) can control link drone 3101 through satellite 3103. In some embodiments, link drone 3101 communicates with a private network of drones shown as network drone 3105A and network drone 3105N. The private network of drones is at least one drone. In some embodiments, network Drone 3105A can fly and perform an inspection task, such as taking pictures of a plot of land and transfer the picture to link drone 3101 via LTE network. After the picture is received by link drone 3101, link drone 3101 can transmit the picture to cloud computing and analysis 3109 through satellite 3103. In some embodiments, all of the networking, private LTE, WI-FI, and/or the like can be done between all of the robots themselves.

Figure 32A:
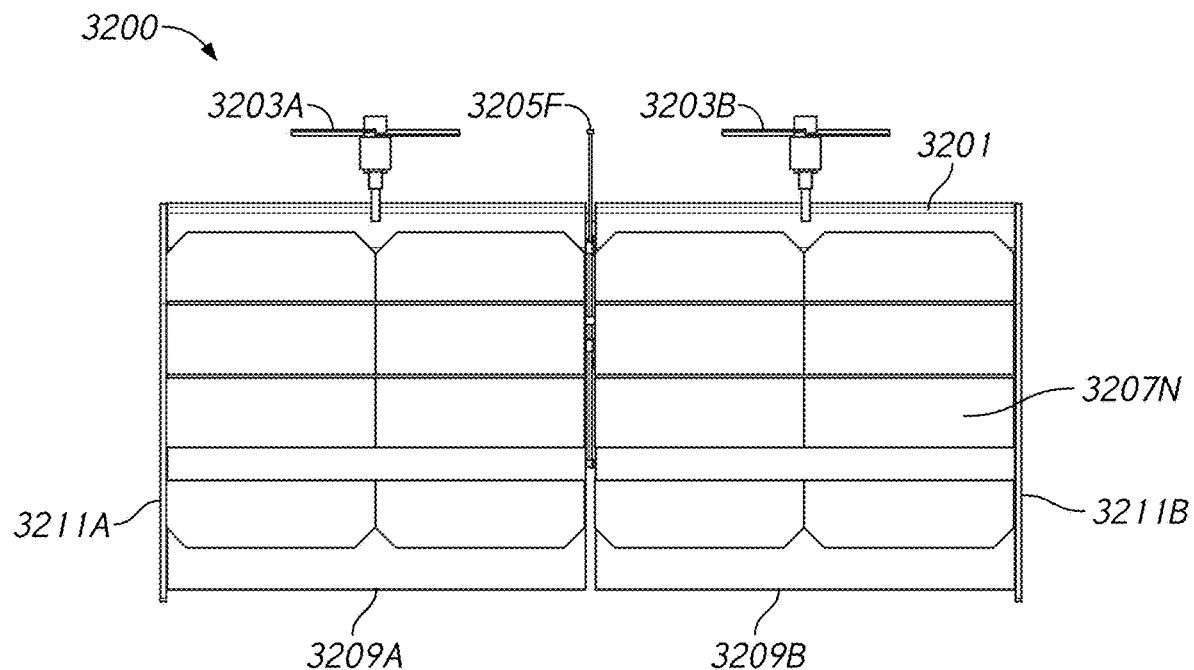
FIG. 32A is a top view showing the position of the latching legs on the ground, according to an embodiment.
Figure 32B:
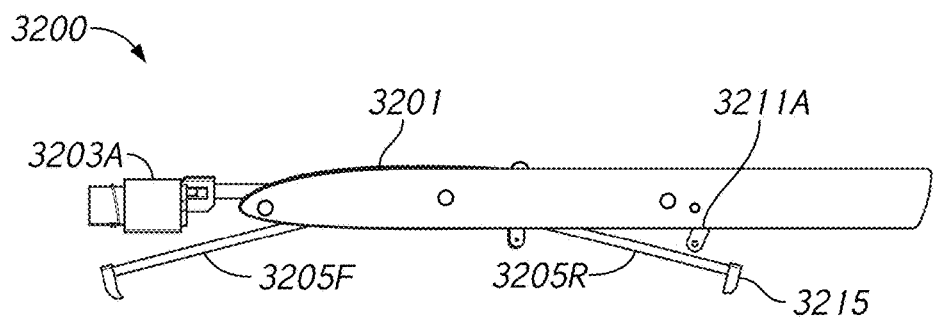
FIG. 32B is a side view showing the position of the latching legs of FIG. 32A on the ground, according to an embodiment.

FIGS. 32A-D, therein is shown an example of drone 3201 that may act as one or both of a link drone or a network drone. In some embodiments, the drone is called a Weather Resistant VTOL Robotic System with Biomimicry Capabilities 3200 compromising wing 3201, two thrust propellers 3203A & B, two ailerons 3209A & B, two multi-functional stabilizers 3211A & B, and two latching legs 3205F & R. As shown in FIG. 32B, while on the ground, the latching legs 3205F & R and the multi-functional stabilizers 3211A & B make contact with the ground. Servomotors (not shown) may control the movement of the latching legs 3205F & R to extend and retract the legs. Battery cells (for example, like battery 503 in FIG. 5A) power the propellers 3203A & B during takeoff, landing, and long-range flight. Battery cells may be housed in the wing 3201, and the top surface of wing 3201 and ailerons 3209A & B may be covered with solar panels 3207N for charging during flight and on the ground.

FIGS. 32A & B show the position of the latching legs 3205F & R while on the ground, according to an embodiment. While on the ground, the aircraft's control system will control the position of the latching legs 3205F & R in order to align the aircraft to the sun for solar charging as well as to "walk" and "latch" to the ground or an object. During these activities, multi-functional stabilizers 3211A & 3211B contact the ground.

Figure 32C:
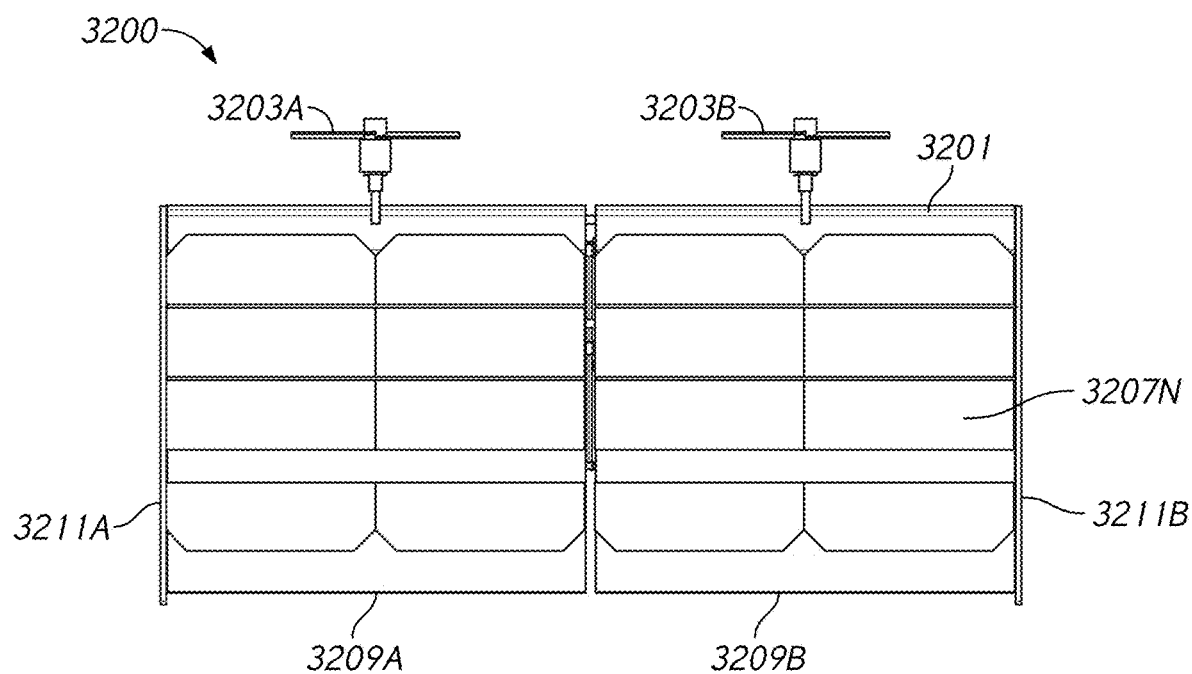
FIG. 32C is a top view showing the position of the latching legs of FIG. 32A in flight, according to an embodiment.
Figure 32D:
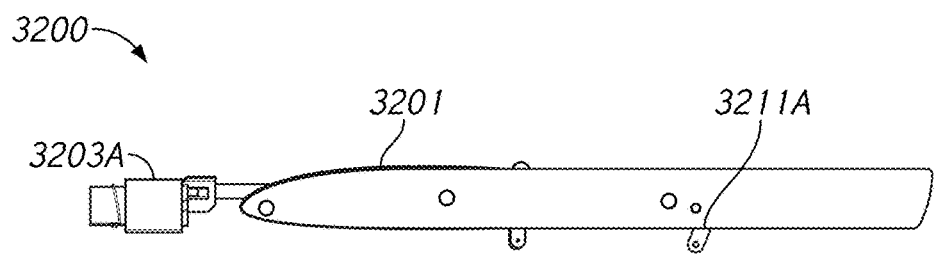
FIG. 32D is a side view showing the position of the latching legs of FIG. 32A in flight, according to an embodiment.

FIGS. 32C & 32D show the position of the latching legs 3205F & R while in flight. During long range flight, the aircraft's control system will retract the latching legs 3205 inside the wing or in line with the airstream to reduce drag.

Figure 33:
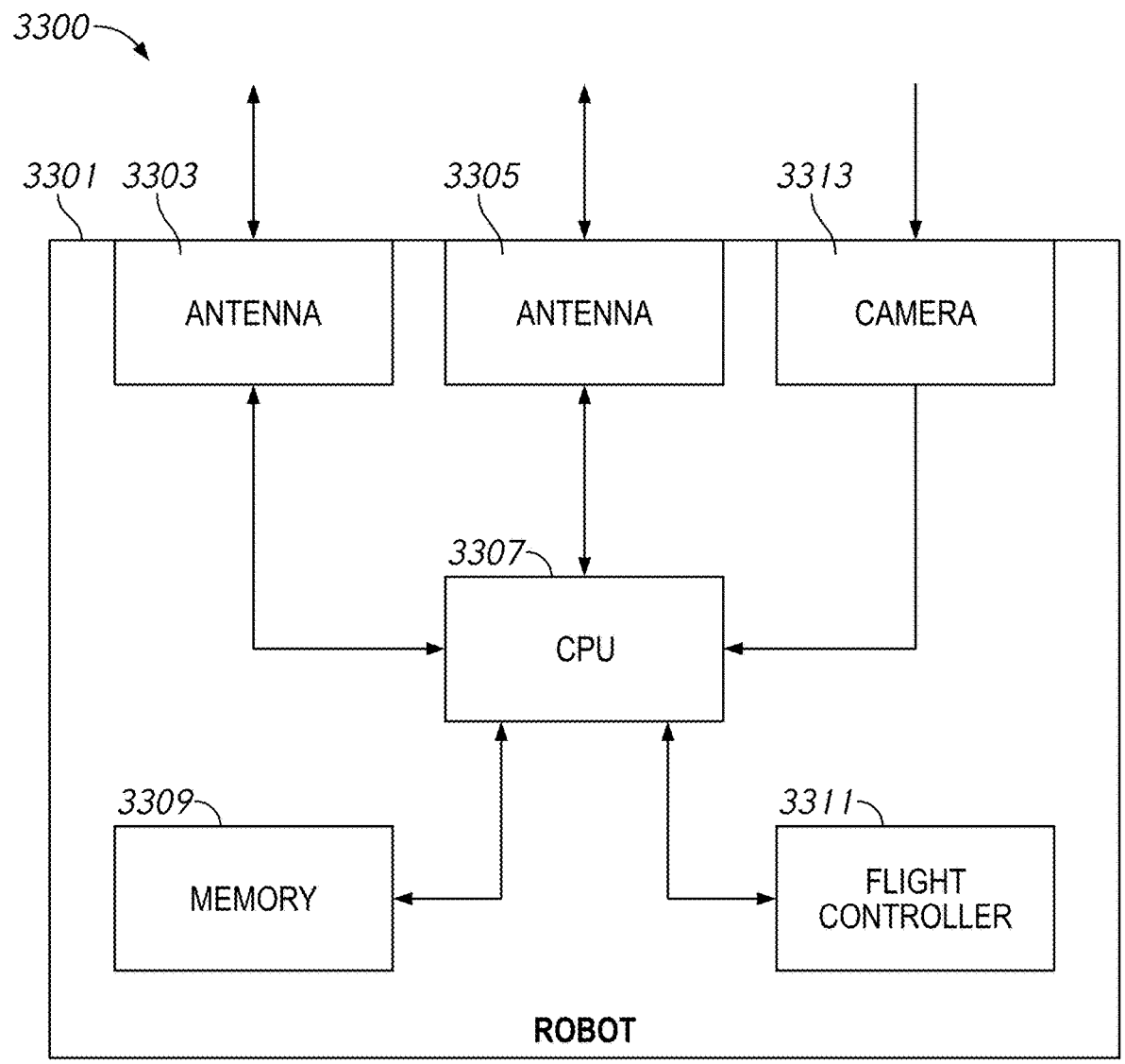
FIG. 33 is a diagram showing the components of a robot of FIG. 32A, according to an embodiment.

FIG. 33 shows electric diagram 3300 for robot 3301 representing link drones and private network drones. Robot 3301 generally comprises antenna 3303, antenna 3305, camera 3313, CPU 3307, memory 3309, and flight controller 3311. Antenna 3303 transfers data over Wi-Fi, satellite, or cellular networks; whereas antenna 3305 transfers data over private LTE networks at predetermined frequencies. In some embodiments, antenna 3305 transfers data over 900 Megahertz (MHz) private network between other network drones and link drones. By having two antennas, robot 3301 is capable of transferring data over Wi-Fi, satellite, or a cellular network at the same time that data is transferring to the private LTE network.

In some embodiments, antenna 3303 and antenna 3305 can be combined into a single antenna. In some embodiments, more than two antennas may be used, including Multi-Input Multi-Output (MIMO) antennas. In some embodiments, solar cells on the top of the wing of the drone can be used as an antenna. All the solar cells may be used as a single antenna or the solar cells may be grouped into smaller antennas.

Camera 3313 provides visual capability to the drone during flight and on the ground to locate obstructions and potential threats. In addition, camera 3313 can take pictures of objects of interests, such as crops on a farm. CPU 3307 performs most of the processing inside the robot. In some embodiments, CPU 3307 compresses image and data files prior to transfer. Memory 3309 is used for storing data during flight and on the ground. Flight controller 3311 controls robot 3301 during flight for auto stabilization. In some embodiments, robot 3301 may have a single CPU processor and may or may not include a GPU processor.

Figure 34:
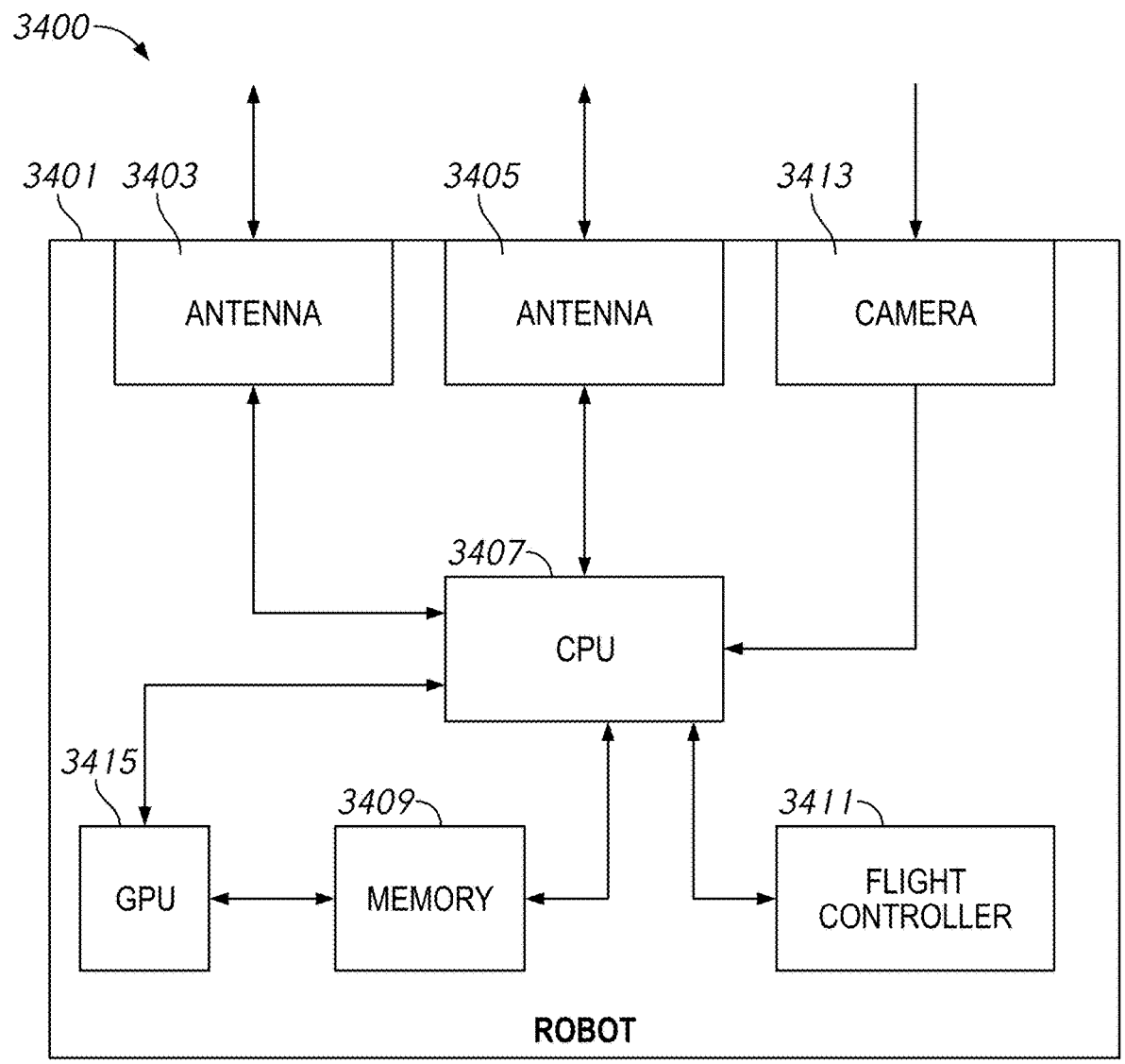
FIG. 34 is a diagram showing the components of a robot with a GPU of FIG. 32A, according to an embodiment.

FIG. 34 shows electric diagram 3400 for robot 3401 representing link drones and private network drones. Robot 3400 generally comprises antenna 3403, antenna 3405, camera 3413, CPU 407, memory 3409, flight controller 3411, and GPU 3415. By having GPU 3415, robot 3401 has the ability to compress bigger images and perform more advanced obstacle avoidance during flight. In some embodiments, image compression could be completed only by CPU 3407, for example, if the drones are only transferring data for telecommunications purposes, then GPU 415 may not be necessary. Antenna 3403 transfers data over Wi-Fi, satellite, or cellular networks; whereas antenna 3405 transfers data over private LTE networks at predetermined frequencies. In some embodiments, antenna 3405 transfers data over 900 Megahertz (MHz) private network between other network drones and link drones. By having two antennas, robot 3401 is capable of transferring data over Wi-Fi, satellite, or a cellular network at the same time that data is transferring to the private LTE network.

In some embodiments, antenna 3403 and antenna 3405 can be combined into a single antenna. In some embodiments, more than two antennas may be used, including Multi-Input Multi-Output (MIMO) antennas. In some embodiments, solar cells on the top of the wing of the drone can be used as an antenna. All the solar cells may be used as a single antenna or the solar cells may be grouped into smaller antennas.

Camera 3413 provides visual capability to the drone during flight and on the ground to locate obstructions and potential threats. In addition, camera 3413 can take pictures of objects of interests, such as crops on a farm. CPU 3407 performs most of the processing inside the robot. In some embodiments, CPU 3407 compresses image and data files prior to transfer. Memory 3409 is used for storing data during flight and on the ground. Flight controller 3411 controls robot 3401 during flight for auto stabilization.

In some embodiments, link drone may be elevated such as flying in the air, on a roof, in a tree, and/or the like, to reduce ground effects.

Figure 35:
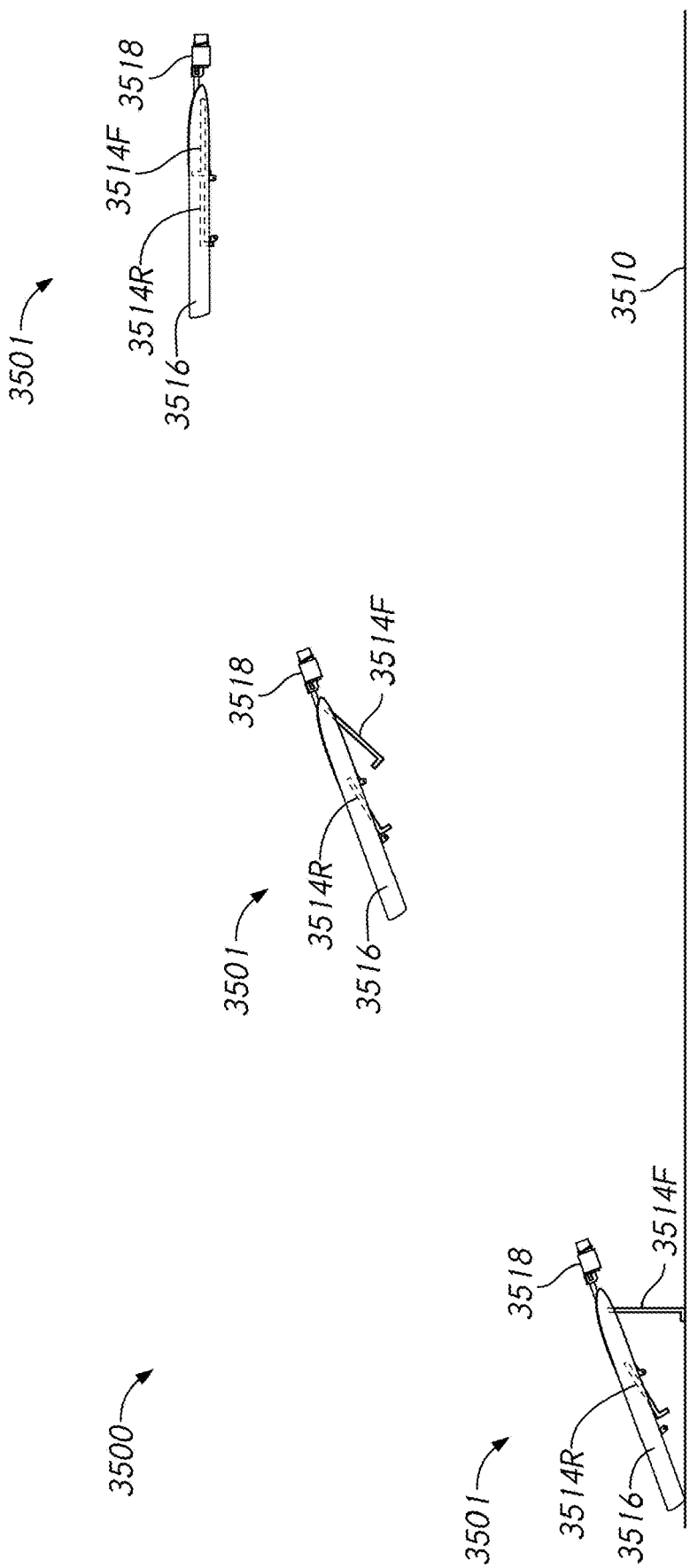
FIG. 35 is a side view showing the weather resistant VTOL robotic system's flight path for the take-off segment of flight, according to an embodiment.

FIG. 35 shows one possible method for efficient takeoff 3500 of aircraft 3501 from the ground 3510 as follows:
1. The aircraft's rear latching leg 3514R retracts to the minimum angle of rotation;
2. The front latching leg 3514F moves to a position to angle the aircraft for optimal flight trajectory depending on the environment;
3. The horizontal thrust propellers 3518 start to spin;
4. The ailerons (not shown) tilt upward as the propellers are spinning to allow the aircraft to lift;
5. Once the horizontal thrust propellers 3518 start spinning at full speed, the aircraft begins to lift;
6. Once the aircraft reaches a minimum altitude for horizontal flight, the front latching leg 3514F retracts to a minimum angle of rotation for long range flight to minimize drag; and
7. Sustained horizontal flight begins.

In some embodiments, the aircraft can takeoff vertically by angling the large ailerons for thrust vectoring, and once at a minimum flight altitude, the aircraft's leading edge of the wing will rotate until it is parallel to the ground. Other methods of takeoff will be satisfactory but may result in wasted power. In some embodiments, aircraft 3501 has multi-functional stabilizers 3516.

Figure 36:
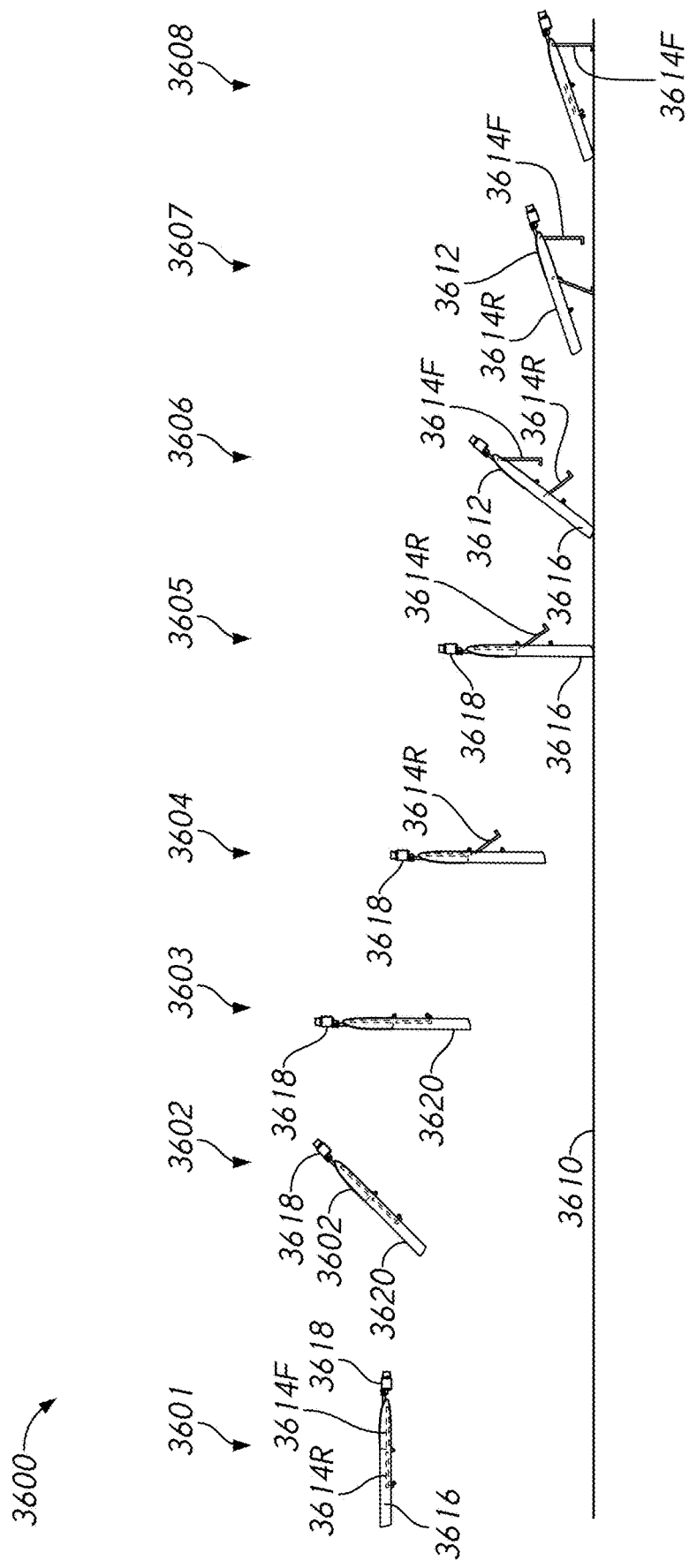
FIG. 36 is a side view showing the weather resistant VTOL robotic system's flight path for the landing segment of flight, according to an embodiment.

FIG. 36 shows one possible method for steps for landing as follows:

3601. The aircraft is in horizontal flight;

3602. The aircraft pulls back on the ailerons 3620 in order to bring the wing 3602 to be perpendicular to the ground;

3603. Once the aircraft wing 3602 is perpendicular to the ground, the aircraft decrease the thrust of the propellers 3618 in order to lower the aircraft towards the ground;

3604. As the aircraft approaches the ground 3610, the rear latching leg 3614R extends to a maximum angle of rotation;

3605. Once the multi-functional stabilizers 3616 make contact with the ground, the rear latching leg 3614R extends to shift the center of gravity forward and the ailerons 3620 are angled, resulting in the aircraft falling forward towards the ground;

3606. The rear latching leg 3614R makes contact with the ground;

3607. The thrust propellers 3618 turn off and the front latching leg 3614F extends until front latching leg 3614F makes contact with the ground;

3608. The rear latching leg 3614R retracts to a minimum angle of rotation.

Some Disclosed Embodiments May Include One or More of the Following Benefits and Advantages Current networking technology is too expensive and requires too much infrastructure to support remote and rural areas. For example, satellites require large investments into rockets to launch into space, and even technology such as Starlink™ require users to set up ground stations, which is not feasible in remote and rural areas. Furthermore, these ground stations require high power consumption on the order of 25 watts for data transfer, which is not feasible in developing countries where individuals are struggling to keep a light bulb lit.

Alternatively, low altitude solar planes cannot immediately land to establish a Wi-Fi signal for a user; these planes require large amounts of power to operate and are expensive; and furthermore, low altitude solar planes require infrastructure for landing and cannot immediately land to improve solar charging capability. Solar planes typically require a custom receiver, and the planes themselves are very expensive. Balloons like Google Loon and solar planes are subject to issues with weather, wind, and clouds which prevent them from providing constant uplink. Also, solar planes require large, heavy battery packs to fly at night.

While cellular towers are viable options in urban areas, cellular towers are too expensive for rural areas, especially ones that are in developing countries. Cellular towers are also immobile and infrastructure, such as roads, must be in place to access the cellular tower for maintenance and service. In addition, most cellular towers require power and hardline communications connections in order to function, which are both challenging to get in rural and developing areas.

Several companies have proposed their own VTOL aircraft designs; however, their proposed designs have efficiency issues during takeoff mode and long-range mode due to the large drag surfaces. In addition, most of the VTOL aircraft designs do not have the capability to effectively maneuver on the ground, especially when the terrain is not flat. This is important when the aircraft cannot land close to a Wi-Fi connection and has to walk inside of the 460-foot radius. Furthermore, most designs are not optimized to maximize charging both on the ground and in the air. As a result, an autonomous network of drones is not possible because of the current technologies dependency on charging and launching infrastructure and inability to survive in extreme weather.

Certain embodiments of the inventions solve the following issues (among others) with traditional quadcopter drone designs:

Quadcopter designs are not efficient in sustained horizontal flight because of high drag forces, low lift to drag ratios, and therefore, quadcopter designs have limited range.

Due to the placement of propellers, quadcopter designs struggle to integrate solar charging capability on the ground or in the flight, and furthermore, the design is not optimized for maximizing the charging surface area since propellers and other structure will block the sun's rays' path to the solar charging surface.

The majority of quadcopter designs do not have means to move on the ground, and if they happen to have wheels, movement is restricted to areas that are primarily paved or flat.

Embodiments of the Dynamic, Infrastructure Free Robotic Network Disclosed Herein have One or More of these Advantages or Benefits As shown in FIG. 32A-D, the latching legs 3205F and 3205R are mechanisms that can replace the need for traditional landing gears. Each of latching legs 3205F and 205R comprises a member, such as a carbon fiber tube, of length L, a fitting located at one end capable of attaching to the structure of the wing 3201, such as a hole in the side of the member, and a terminating fitting 3215 capable of affixing itself to the ground, such as a hook, at the opposite end. The latching legs 3205F and 3205R are attached to the structure members of the wing 3201 and are controlled by servo motors (not shown) and have the ability to retract and extend.

Method for Latching on the Ground or Objects for Link Drones

Figure 37A:
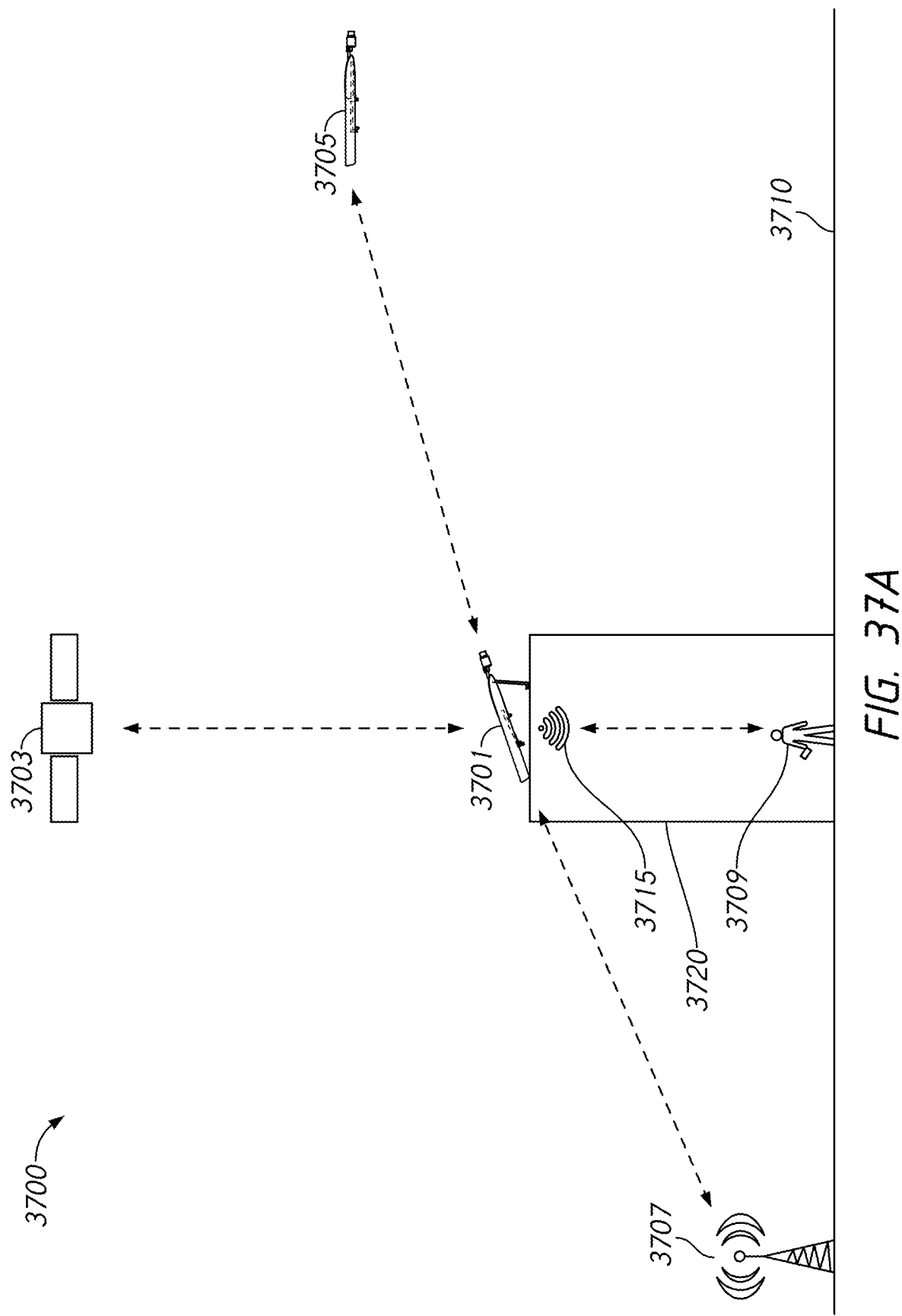
FIG. 37A is a diagram of a link drone on a building transferring data, according to an embodiment.
Figure 37B:
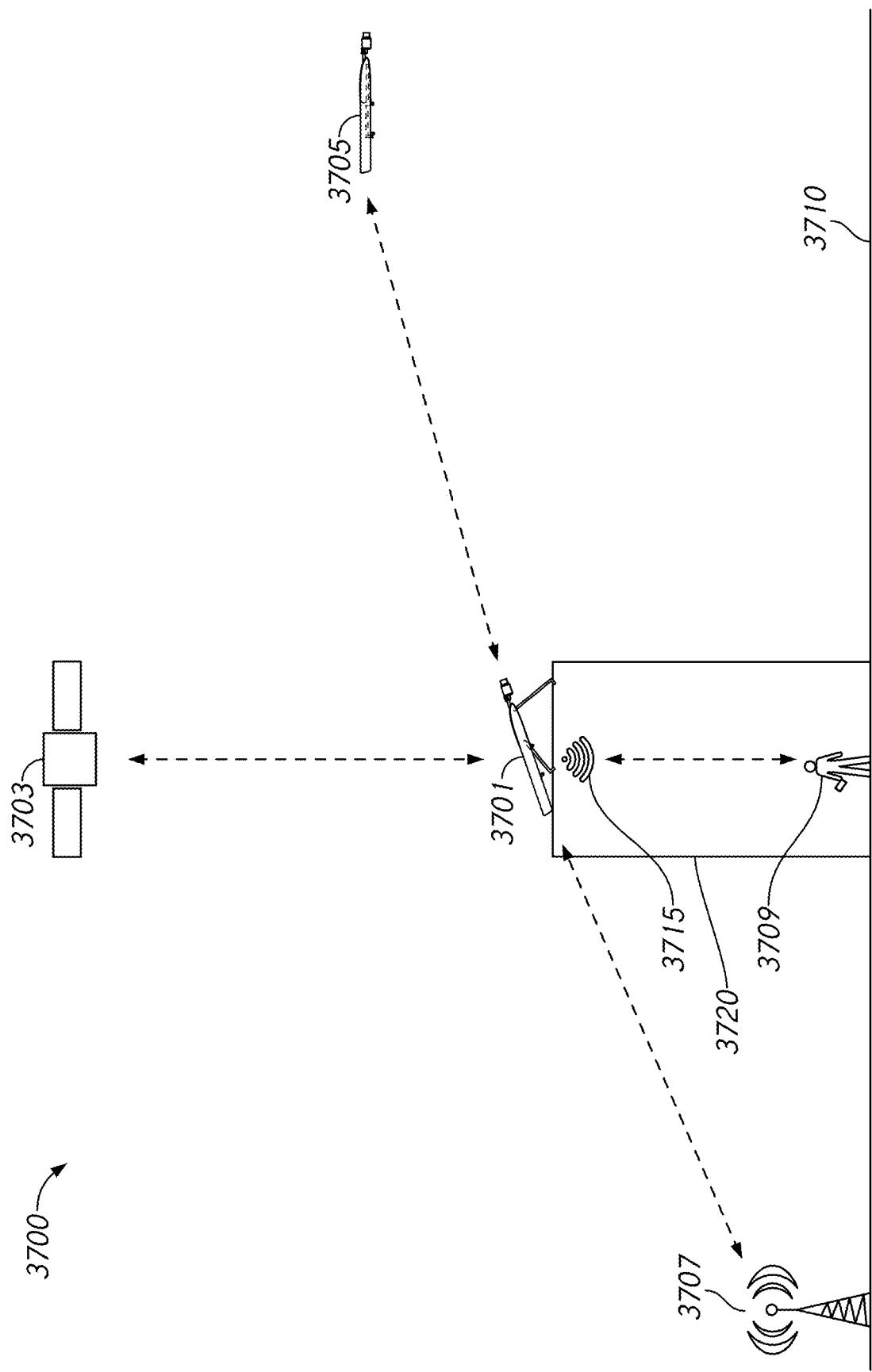
FIG. 37B is a diagram of a link drone latching onto a building transferring data, according to an embodiment.

As shown in FIGS. 37A & B, an embodiment of Dynamic, Infrastructure Free Robotic Network 3700. Link drone 3701 is on the top of building 3720 and link drone 3701 is transferring data to satellite 3703 and private drone network 3705 comprising at least one drone. In some embodiments, link drone 3701 transfers data between cellular tower 3707 and private drone network 3705 comprising at least one drone. In some embodiments, data includes cell phone calls, text messages, pictures, videos, and email. FIG. 37B shows link drone 3701 latching to the top of the building to avoid being blown away by the wind from the building.

Link drone 3701 has the ability to latch onto ground 3710 or objects, such as building 3720, using its legs. When link drone 3701 is transferring data, the ideal configuration is for link drone to be elevated above ground 3710 to eliminate ground effects and signal distortion by greater than 5 wave lengths of communication signal from the ground. In some embodiments, the number of wave lengths is approximately 10. In addition, by landing on building 3720, link drone 3701 is able to transfer data to satellite 3703, cellular tower 3707, private drone network 3705 or an individual 3709 with less obstructions than if link 3701 was latched on the ground, improving the data quality and transfer. By latching onto the ground or building, link drone 3701 can avoid being blown away by the wind, rain, or extreme weather conditions. Link drone 3701 is able to create a temporary Wi-Fi router 3715 allowing individual 3709 in building 3720 to transfer data from a device to the internet since link drone 3701 can connect to satellite 3703 or cellular tower 3707. In some embodiments, there could be more than on link drone to improve bandwidth of the private drone network 3705.

Figure 37C:
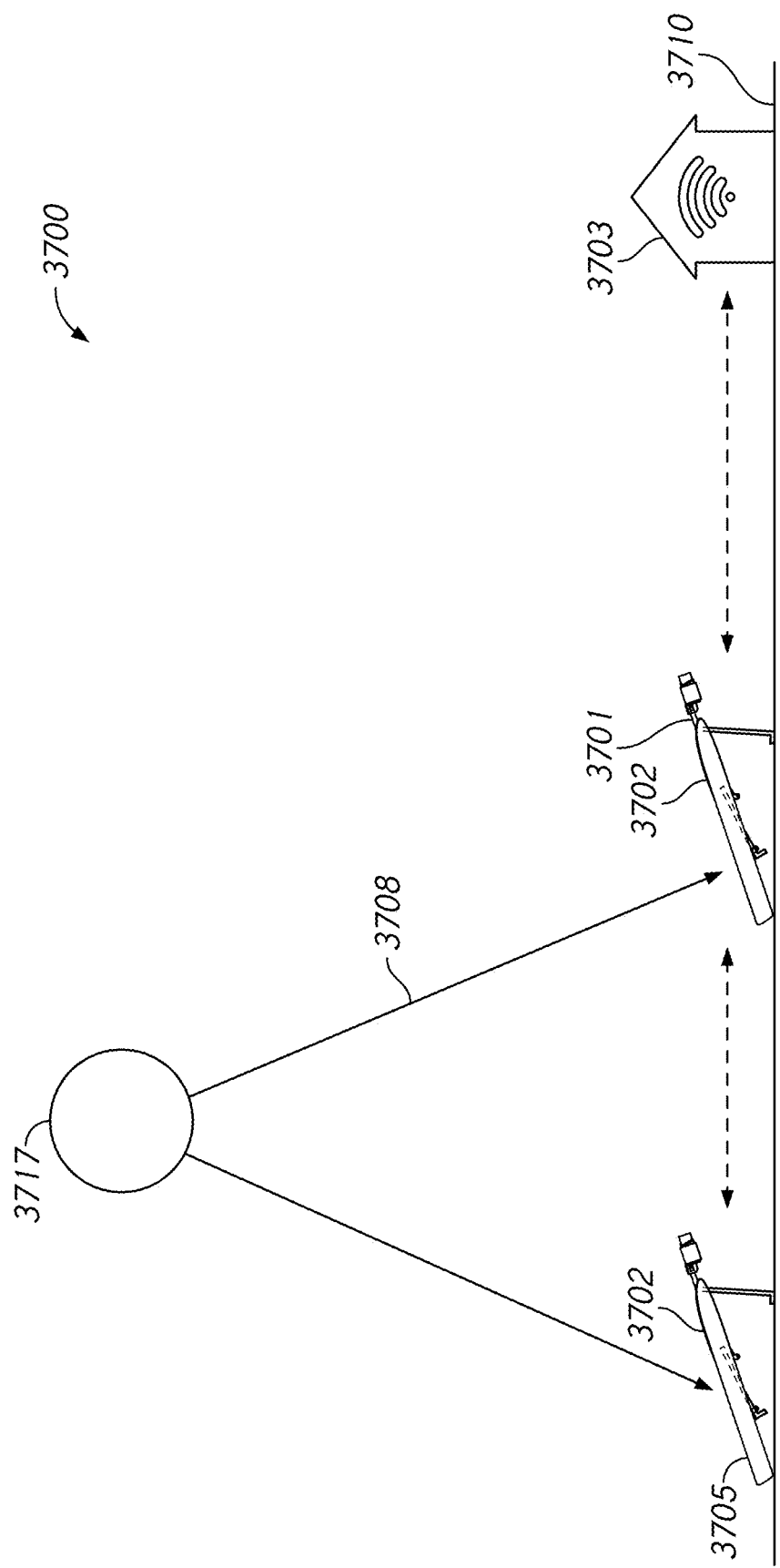
FIG. 37C is a diagram of a link drone on the ground transferring data, according to an embodiment.

As shown in FIGS. 37C & D, link drone 3701 is on the ground 3710 and link drone 3701 is transferring data to Wi-Fi Router 3713 and private drone network 3705 comprising at least one drone. Private network drone 3705 is also on ground 3710. In some embodiments, link drone 3701 transfers data between Wi-Fi Router 3713 and private drone network 3705 comprising at least one drone. In some embodiments, data includes cell phone calls, text messages, pictures, videos, and email. FIG. 37D shows link drone 3701 and private network drone 3705 latching to ground to avoid being blown away by the wind from the building.

Link drone 3701 and private network drone 3705 have the ability to latch onto ground 3710 or objects, such as building 3720, using its legs. By latching onto the ground or building, link drone 3701 and private network drone can avoid being blown away by the wind, rain, or extreme weather conditions. In some embodiments, there could be more than on link drone to improve bandwidth of the private drone network 3705.

The latching legs extend and retract, which allows the aircraft to "walk" on the ground. The aircraft can have two or more latching legs, and one desirable method is to have two latching legs to minimize the weight and complexity of the aircraft.

The latching legs position and geometry allow link drone 3701 to attach itself to the environment, which is essential in extreme weather. Furthermore, if there are high winds, the link drone 3701 can quickly land and latch to the environment to avoid damage to the aircraft. In some embodiments, the aircraft can latch to a tree, shrub, another object in nature, or manmade object.

A method for the aircraft latching on the ground, according to an embodiment is set forth below:
a. The link drone 3701 on the ground 3710 and the rear latching leg as well as the multi-functional stabilizers (for example, like multi-functional stabilizers 3211A & 3211B in FIG. 32A) make contact with the ground;
b. The front latching leg extends to the maximum angle;
c. Once the front latching leg reaches the maximum angle, the rear latching leg and the front latching leg latching attachment fixture (hook) make contact with the ground 3710;
d. The servomotors (not shown) apply torque to retract the front latching legs and extend the rear latching leg such that the latching attachment fixtures (hooks) dig into the ground;
e. At a specific predetermined force or duration of time, the front latching leg servomotor will stop extension, the rear latching leg servomotor will stop retraction, and link drone 3701 will be rooted to the ground 3710.

In some embodiments, sun beams 3708 emitted from sun 3717 hit solar panels 3702 of link drone 3701 and/or solar panels 3702 of private network drone 3705 to provide power for flight, ground movement, data collection, and data transmission to satellite 3703, Wi-Fi Router 3713, and/or the like. In some embodiments, link drone 3101 and/or private network drone 3705 have solar panel 3102. In other embodiments, link drone 3101 and/or private network drone 3705 has batteries (for example, like battery 503 in FIG. 5A). In yet another embodiment, link drone 3101 and/or private network drone 3705 have solar panel 3102 and batteries.

FIGS. 38A-38C show an embodiment of Dynamic, Infrastructure Free Robotic Network link 3800. Drone 3801 attached to power line 3812. The proposed design utilizes the latching legs of link drone to extend and retract, which allows the aircraft to "latch" onto powerline 3801. Link drone 3801 could have more than two latching legs. When link drone 3801 is transferring data, the ideal configuration is for link drone to be elevated above ground 3810 to eliminate ground effects and signal distortion by greater than 5 wave lengths of communication signal from the ground.

Solar Optimization on the Ground and in Flight

Based on the position of the propellers and that some embodiments do not contain a fuselage, the exterior surfaces of the wing and ailerons are optimized for accepting sun rays. This design strives to eliminate obstructions from blocking the sun rays' path to surface where solar panels can be attached. In this configuration, solar panels will be placed on the top of the wing and ailerons.

Solar power is beneficial to sustain passive power requirements that could be used to power data transfer, data compression, low voltage power systems, or communication systems. Power consumption for transferring data to satellites is approximately 25 watts. Power consumption for transferring data to 4G cellular networks is approximately 2 watts. Power consumption for transferring data to Wi-Fi is approximately 6 watts. With traditional drone technology, the drones would run out of battery very quickly when transferring data and have to perform a large number of batter swaps. However, with the ability to solar charge both on the ground and in flight, the link drones and private network drones in these embodiments are able to transfer data through-out the day when the sun is out and do not require centralized charging, which enables the entire network to be in remote and rural areas since there is no infrastructure or human involvement needed. This embodiment creates an aircraft that can charge both in flight and on the ground. When flying, solar charging can produce more than enough power to transfer data over private LTE network, and when landed and aligned to the sun, solar can produce 35 watts of power which is enough to transfer data over satellite, cellular tower, and Wi-Fi router connections. This technology eliminates the need for a large infrastructure of charging stations and create sustainable surveillance and inspection methods. By enabling the aircraft to charge on the ground or in flight, the aircraft essentially has unlimited range while using clean energy.

FIG. 39 illustrates the path of the solar rays emitted from the sun to the VTOL aircraft's, which is representative of both the link drone and drones in the private network, solar panels while the aircraft is on the ground. While the aircraft is on the ground, and as shown in FIG. 39, the aircraft rotates in order to find the optimal orientation to the sun in order to maximize the surface area of the aircraft facing the sun. FIG. 40 illustrates the path of the solar rays emitted from the sun to the VTOL aircraft's solar panels during flight. The aircraft also has the ability to charge in horizontal flight or when the drone is hovering as shown in FIG. 40. In some embodiments, the aircraft will hover in the sky and rotate until it finds the sun's location of the sky; after finding the sun's location, the aircraft can charge while hovering or land on the ground to charge.

FIGS. 39 & 40 show embodiments of Dynamic, Infrastructure Free Robotic Network 3900 and 4000. The various views of illustrate the placement of the solar panels 3913. By using the latching legs 3914R and 3914F to orient the largest surface area of the aircraft 3912 to the sun beams 3901 of sun 3902 while on the ground 3910, the aircraft 3912 is able to increase its charging rate by up to, for example 35%. In some embodiments, the increase in rate can be 5%, 10%, 15%, 20%, 25%, 30%, 35%, 40%, and/or the like. One desirable configuration is an aircraft with two latching legs and two multifunctional stabilizers that align to the sun as shown in FIG. 39. In some embodiments, a single latching leg will simplify the design and manufacturing of the aircraft. In the broadest configuration, the inventions do not have to use latching legs to align to the sun, but instead any component that makes contact with the ground and allows the aircraft to angle its largest surface towards the sun. This component could be a telescoping landing gear or poles that extend from the fuselage or wings. In this case, the latching legs are ideal since they are designed to extend and retract for maneuvering on the ground.

In some embodiments, link drone 3912 has solar panel 3913. In other embodiments, link drone has batteries (for example, like battery 503 in FIG. 5A). In yet another embodiment, link drone has solar panel 3913 and batteries. By having both solar panels and batteries, the drone is able to transfer data via solar power during the day and batteries during the night. The batteries will be fully charged when the sun goes down.

FIG. 41 show an embodiment of Dynamic, Infrastructure Free Robotic Network 4100. FIG. 41 illustrates that link drone 4101 can be replaced with network drone 4105A in private drone network. In some embodiments, the hardware of link drone 4101 and network drone 4105A may be substantially the same, which allows for interchangeability of link drones and private network drones. As a result, when private network drone 4105A is running low on battery, link drone 4101 and network drone 4105A can switch roles. When 4105A lands on ground 4110 and aligns with sun beams 4108 from sun 4107, the batteries of network drone 4105A will charge up to, for example 35% faster than when it was flying. In some embodiments, the increase in charging speed can be 5%, 10%, 15%, 20%, 25%, 30%, 35%, 40%, and/or the like. In some embodiments, more than one link drone is needed to transfer data from the private network. Drones may have ability to latch to ground 4110, maneuver on ground 4110, fly, and transfer data to both the private drone network as well as satellites, cell towers, and Wi-Fi networks, or any combination thereof.

Satellite Network and Private Drone Network Interface

Figure 42:
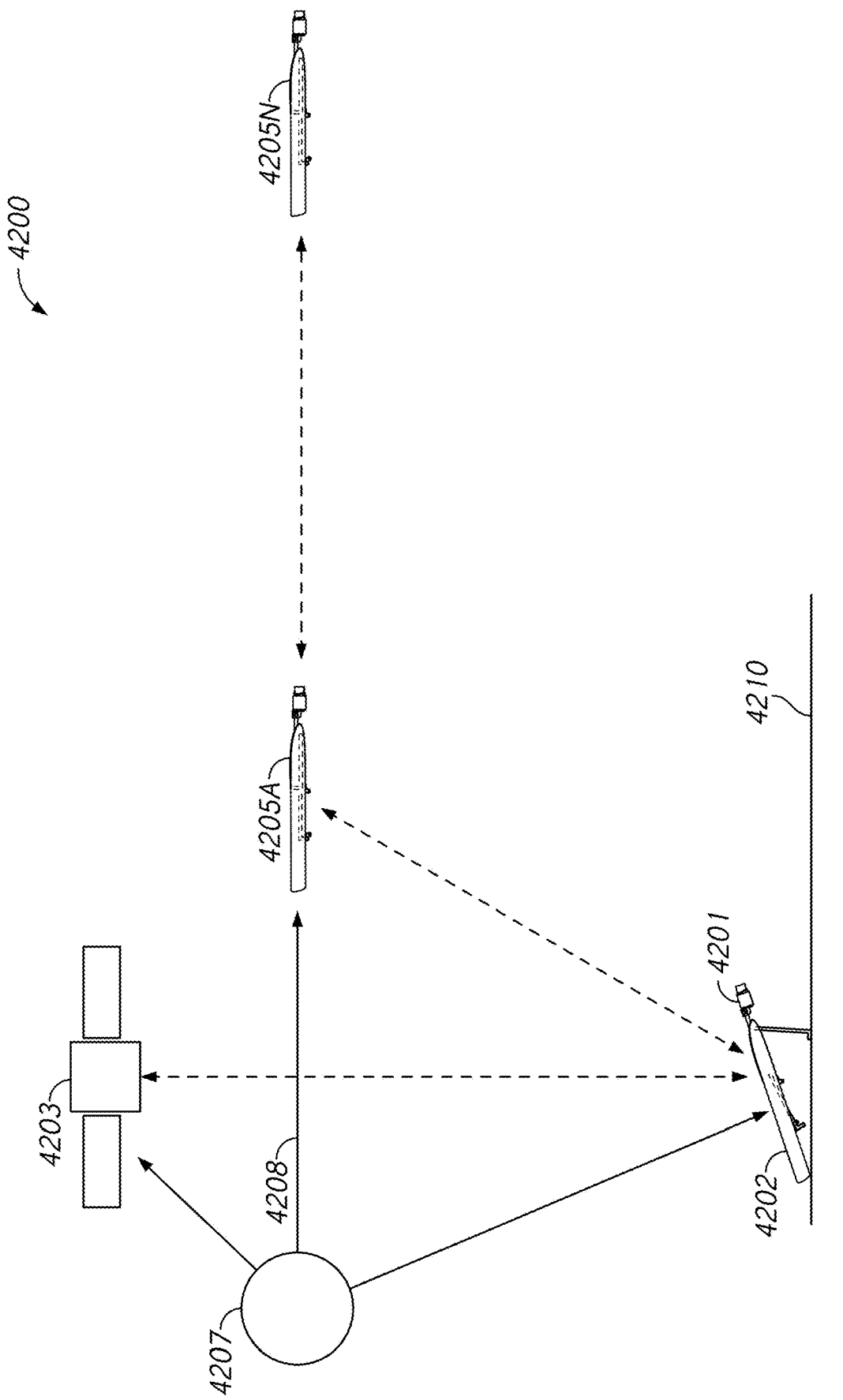
FIG. 42 is a diagram of a Multi-modal, Weather Resistant Robot Network and Methods of Data Transfer network data connected to a satellite, according to an embodiment.

As shown in FIG. 42, an embodiment of a Dynamic, Infrastructure Free Robotic Network 4200 generally comprises at least one link drone 4201, at least one satellite 4203, and sun 4207. Link drone 4201 may fly or move on the ground 4210 to collect data with sensors or cameras. Sun beams 4208 emitted from sun 4207 hit solar panel 4202 of link drone 4201 to provide power for flight, ground movement, data collection, and data transmission to satellite 4203. In some embodiments, link drone 4201 has solar panel 4202. In other embodiments, link drone has batteries (for example, like battery 503 in FIG. 5A). In yet another embodiment, link drone has solar panel 4202 and batteries. In some embodiments, there may be a plurality of link drones to transfer more data.

In some embodiments, link drone 4201 transmits data to cloud computing and storage 4209 via satellite 4203. In some embodiments, link drone is controlled via on-board AI processor. In some embodiments, a remote operator (not shown) can control link drone 4201 through satellite 4203.

In some embodiments, link drone 4201 communicates with a private network of drones shown as network drone 4205A and network drone 4205N. The private network of drones is at least one drone. In some embodiments, network Drone 4205A can fly and perform an inspection task, such as taking pictures of a plot of land and transferring the picture to link drone 4201 via LTE network. After the picture is received by link drone 4201, link drone 4201 can transmit the picture to cloud computing and analysis (for example, like cloud computing and analysis 3109 in FIG. 31) through satellite 4203.

Wi-Fi Network and Private Drone Network Interface

Figure 43A:
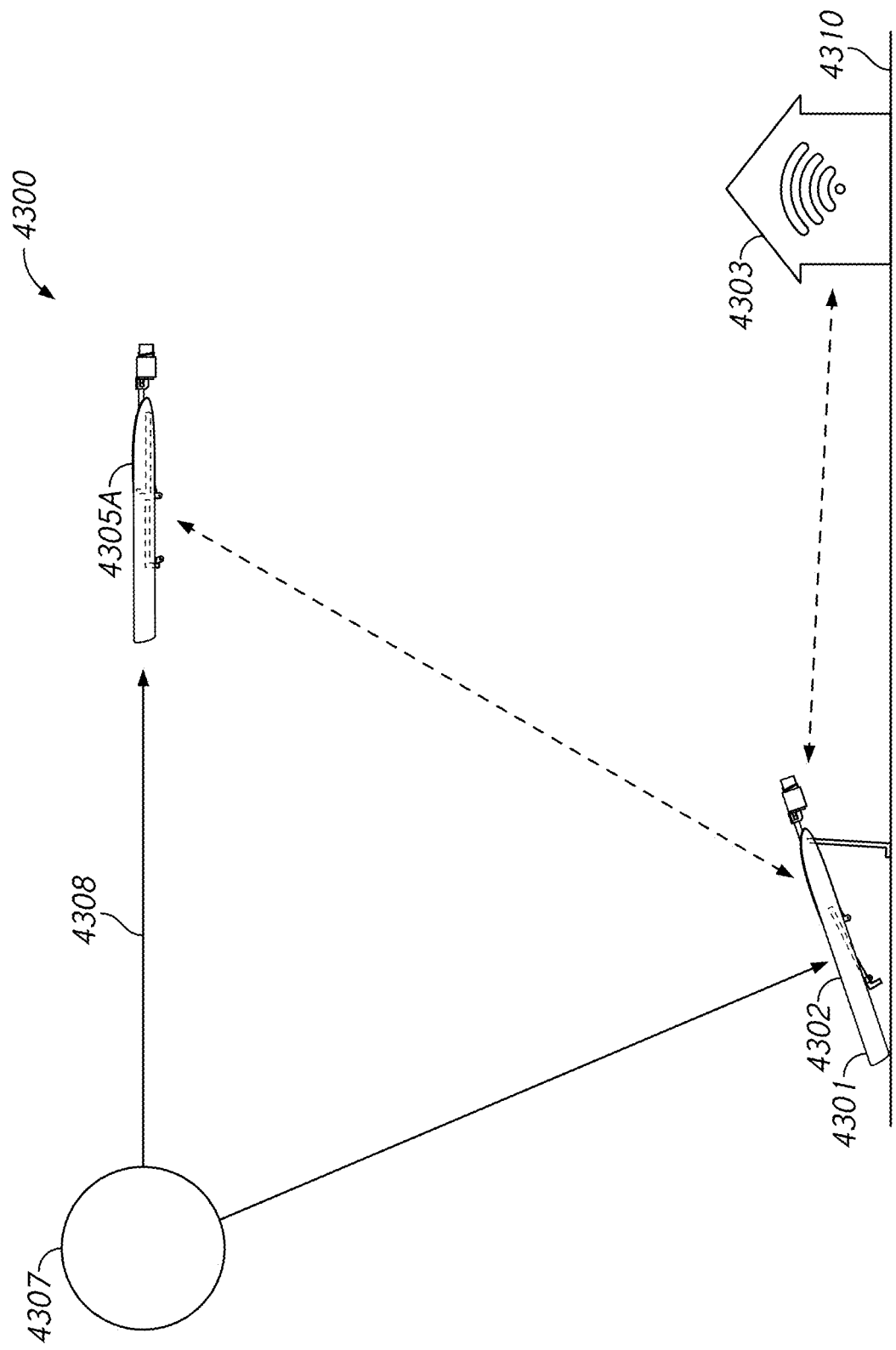
FIG. 43A is a diagram of Multi-modal, Weather Resistant Robot Network and Methods of Data Transfer network connected to Wi-Fi, according to an embodiment.
Figure 43B:
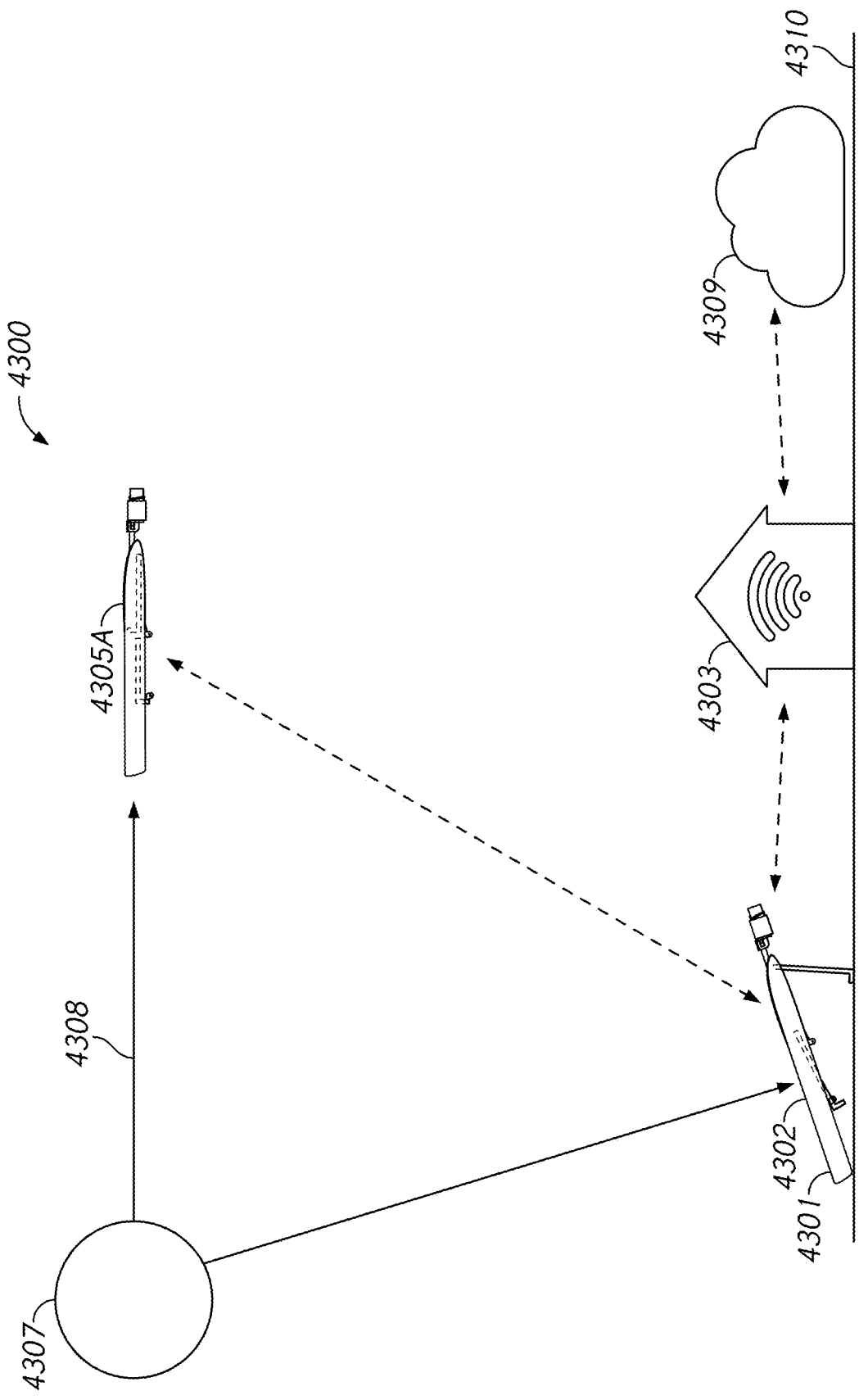
FIG. 43B is a diagram of Multi-modal, Weather Resistant Robot Network and Methods of Data Transfer network connected to Wi-Fi and a cloud storage and analysis platform, according to an embodiment.
Figure 43C:
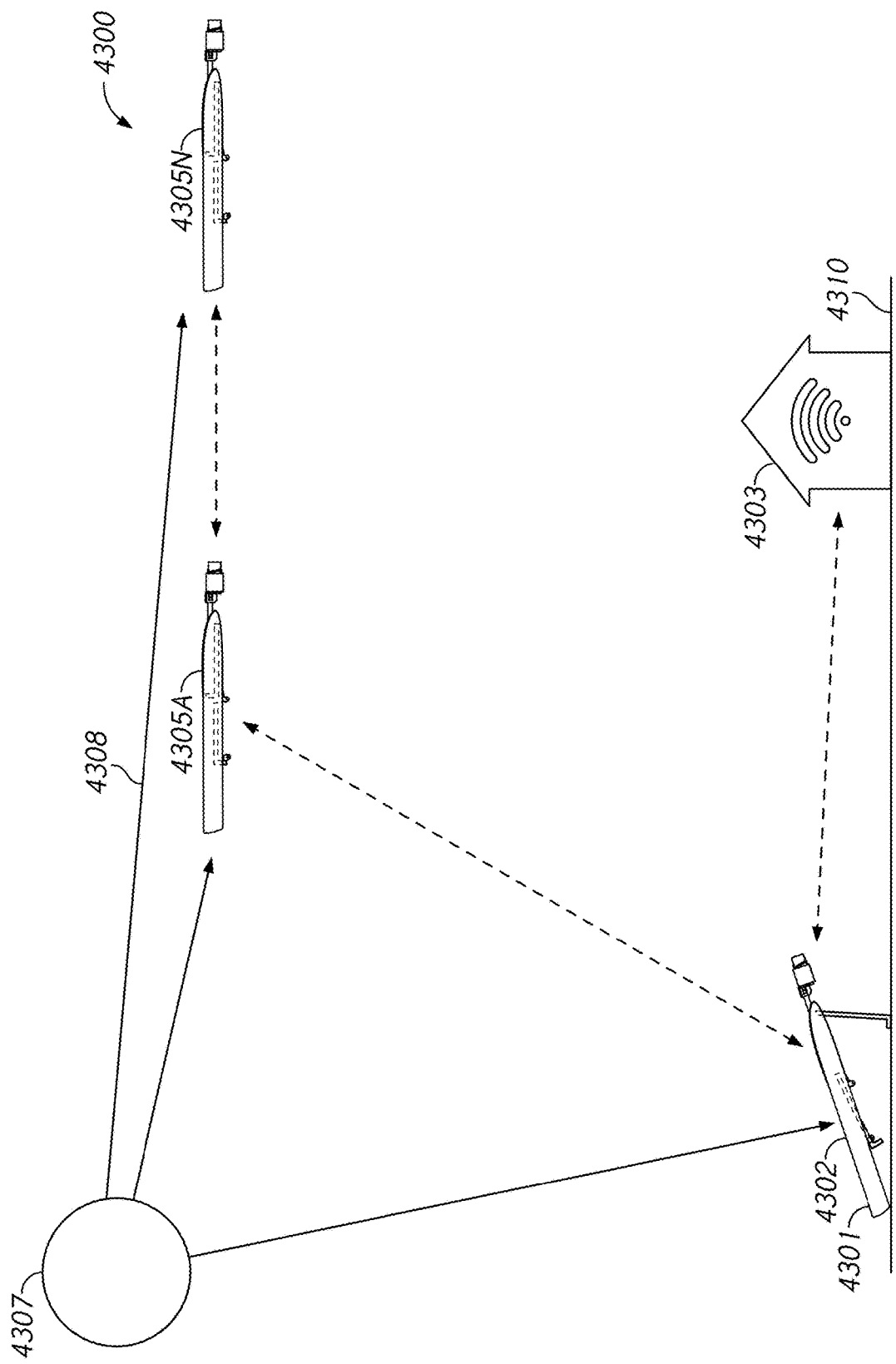
FIG. 43C is a diagram of Multi-modal, Weather Resistant Robot Network and Methods of Data Transfer network connected to Wi-Fi and a plurality of drones in a private drone network, according to an embodiment.

As shown in FIGS. 43A-C, an embodiment of a Dynamic, Infrastructure Free Robotic Network 4300 generally comprises at least one link drone 4301, at least one Wi-Fi Network 4303, and sun 4307. Link drone 4301 may fly or move on the ground 4310 to collect data with sensors or cameras. Sun beams 4308 emitted from sun 4307 hit solar panel 4302 of link drone 4301 to provide power for flight, ground movement, data collection, and data transmission to Wi-Fi connection 4303. In order to transmit data over, link drone 4301 may in some embodiments need to be within 460 feet of the connection, which makes aerial and ground mobility very beneficial. In some embodiments, link drone 4301 has solar panel 4302. In other embodiments, link drone has batteries (for example, like battery 503 in FIG. 5A). In yet another embodiment, link drone has solar panel 4302 and batteries. In some embodiments, there may be a plurality of link drones to transfer more data.

In some embodiments, link drone 4301 transmits data to cloud computing and storage 4309 via Wi-Fi connection 4303. In some embodiments, Wi-Fi connection could be in a building or at a farm. In some embodiments, link drone is controlled via on-board AI processor. In some embodiments, a remote operator (not shown) can control link drone 4301 through Wi-Fi connection 4303. In some embodiments, link drone 4301 communicates with a private network of drones shown as network drone 4305A and network drone 4305N. The private network of drones is at least one drone. In some embodiments, network drone 4305A can fly and perform an inspection task, such as taking pictures of a plot of land and transfer the picture to link drone 4301 via private LTE network. After the picture is received by link drone 4301, link drone 4301 can transmit the picture to cloud computing and analysis 4309 through Wi-Fi connection 4303.

Figure 44:
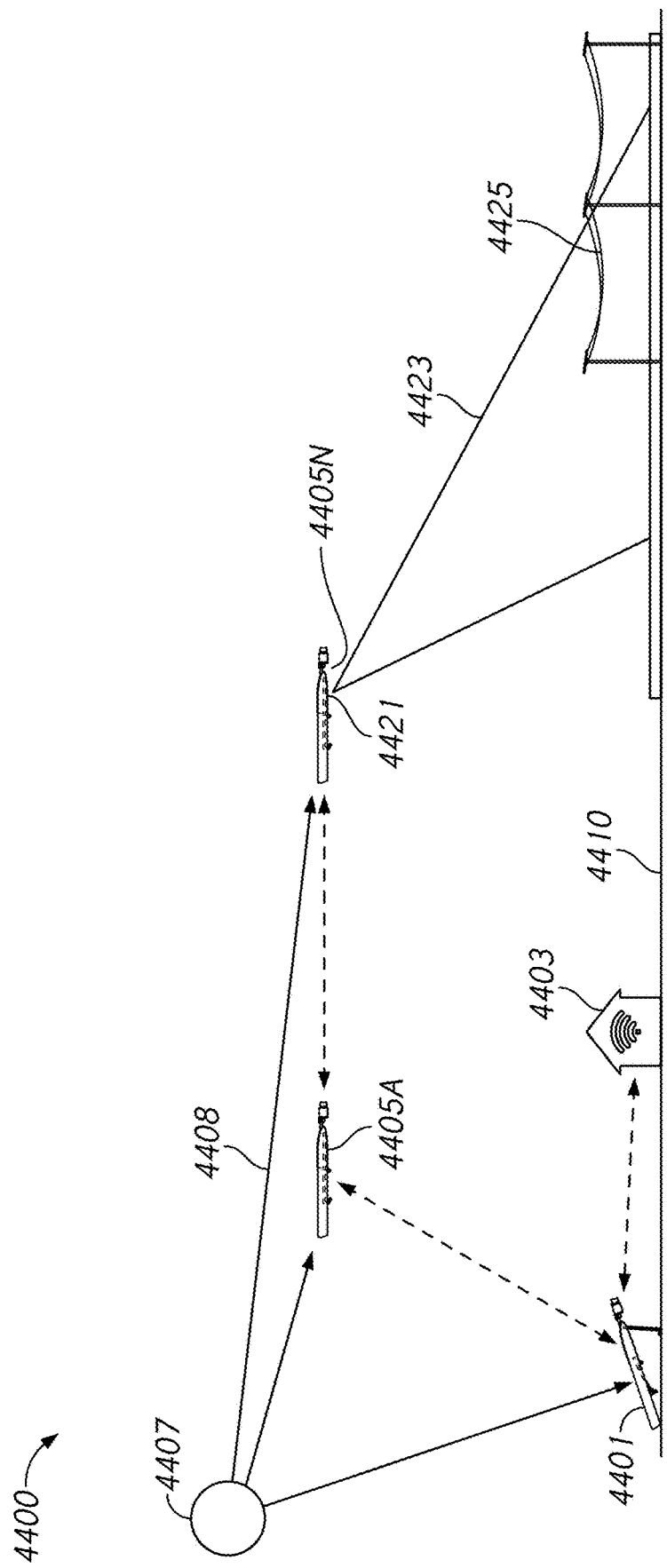
FIG. 44 is a diagram of Multi-modal, Weather Resistant Robot Network and Methods of Data Transfer network connected to Wi-Fi inspecting powerlines, according to an embodiment.

As shown in FIGS. 44, an embodiment of a Dynamic, Infrastructure Free Robotic Network 4400. FIG. 44 shows network drone 4405N using camera 4421 to take pictures, video, and/or the like 4423 of powerline 4425. After the picture is taken, the picture is transferred from network drone 4405N to link done 4401 on ground 4410. Link drone 4401 then transfers picture to cloud computing analysis tool through Wi-Fi network connection 4403. The analysis will be returned to someone who needs to take action, such as repair a fallen power line or transformer. The range between link drone and network drone 4405N is dependent on the number of drones in the network. The link drone communication radius to the next drone is 2-10 miles. In some embodiments, link drone 4401 communicates with a private network of drones shown as network drone 4405A and network drone 4405N. So, if there are two network drones, then the range could be 20 miles and scale proportionally as the number of drones increases. Range between the link drone 4401 and the Wi-Fi connection may in some embodiments be limited to 460 feet, so it is beneficial that the drone can either land near to the router or can walk to an area that is near the router. In some embodiments, the system also includes Wi-Fi connection 4403, In some embodiments, link drone 4401 may fly or move on the ground 4410 to collect data with sensors or cameras. In some embodiment, sun beams 4408 emitted from sun 4407 hit solar panel (for example, like solar panel 4302 in FIG. 43A) of link drone 4401 to provide power for flight, ground movement, data collection, and data transmission.

Cellular Network and Private Drone Network Interface.

Figure 45:
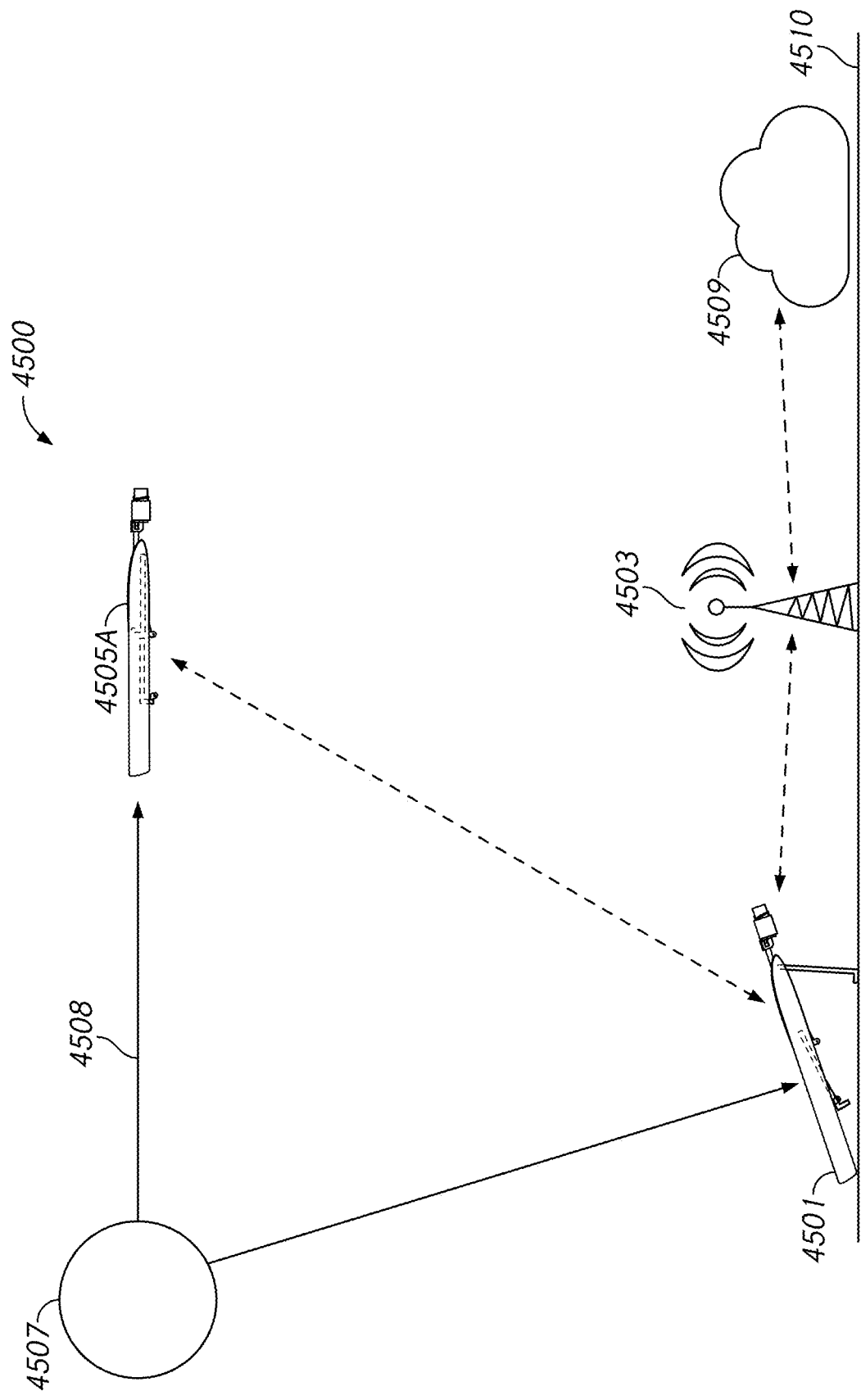
FIG. 45 is a diagram of Multi-modal, Weather Resistant Robot Network and Methods of Data Transfer network connected to a cellular network and a cloud storage and analysis platform, according to an embodiment.

As shown in FIG. 45, an embodiment of a Dynamic, Infrastructure free Robotic Network 4500 generally comprises at least one link drone 4501, at least one cellular tower connection 4503, at least one network drone 4505A and sun 4507. Link drone 4501 may fly or move on the ground 4510 to collect data with sensors or cameras. Sun beams 5508 emitted from sun 4507 hit solar panel 5502 of link drone 4501 to provide power for flight, ground movement, data collection, and data transmission to cellular connection 1503. In some embodiments, cellular tower network connection 4503 could be 2G, 3G, 4G, LTE, or 5G. In order to transmit data over, link drone 4501 may in some embodiments need to be within 30 miles of 3G cell tower, 10 miles of 4G cell tower, and 2.3 miles of 5G cell tower. In some embodiments, link drone 4501 have a solar panel. In other embodiments, link drone has batteries (for example, like battery 503 in FIG. 5A). In yet another embodiment, link drone has solar panel 1502 and batteries. In some embodiments, there may be a plurality of link drones to transfer more data.

In some embodiments, link drone 4501 transmits data to cloud computing and storage 4509 via cellular tower 4503. In some embodiments, link drone is controlled via on-board AI processor. In some embodiments, a remote operator (not shown) can control link drone 4501 through cellular tower connection 4503. In some embodiments, link drone 4501 communicates with a private network of drones shown as network drone 4505A and network drone 4505N (for example, like network drone 4405N in FIG. 44). The private network of drones is at least one drone. In some embodiments, network drone 4505A can fly and perform an inspection task, such as taking pictures of a plot of land and transfer the picture to link drone 4501 via private LTE network. After the picture is received by link drone 4501, link drone 4501 can transmit the picture to cloud computing and analysis 4509 through cellular tower connection 4503.

Figure 46:
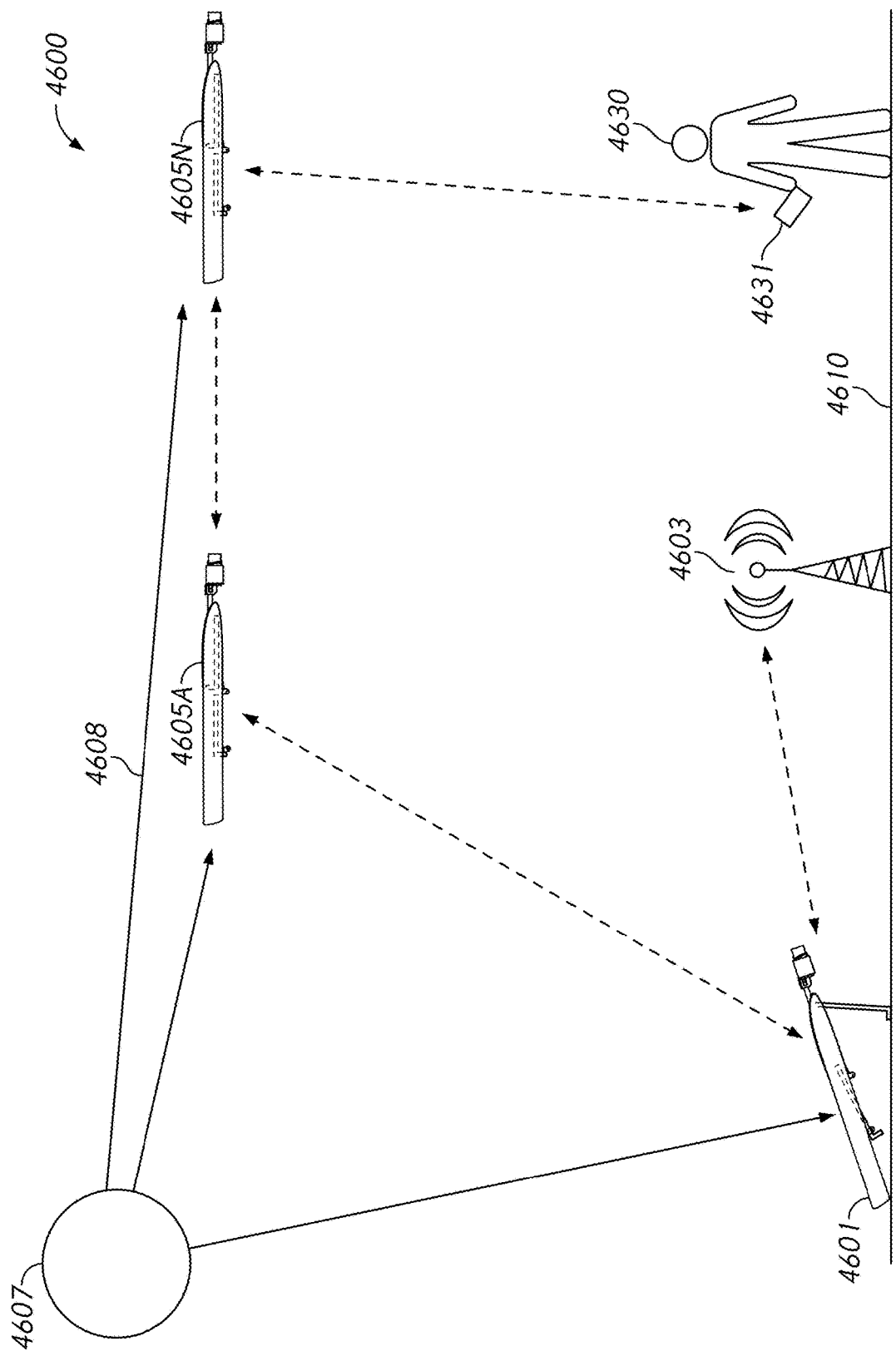
FIG. 46 is a diagram of Multi-modal, Weather Resistant Robot Network and Methods of Data Transfer network connected to a cellular network and transferring data to a user, according to an embodiment.

FIG. 46 shows an embodiment of a Dynamic, Infrastructure free Robotic Network 4600 generally comprising a sun 4607 which produces sun beams 4608, one or more link drones 4601, one or more network drones 4605A and 4605N, cellular tower 4603 on ground 4610, user 4630, and device 4631. FIG. 46 shows network drone 4605N transferring data from user 4630 by device 4631. In some embodiments, data may be cell phone calls, text messages, emails, pictures, or videos. The user will have a chip in his device that specifies a frequency allowing the user to access the private drone network. Once the data is transferred onto the private drone network, the data is transferred back to link drone 4601. Link drone then transfers data to cellular tower 4603. In 4600 dynamic telecommunication network, uses will access the nearest network drone to transfer data. In some embodiments, the user may need to be within 30 miles the nearest network drone. Private network drones can fly to where users have requested data, and if service subscriptions are cancelled, the private network drone can be repositioned easily.

Private Network Scalability and Flexibility

Figure 47:
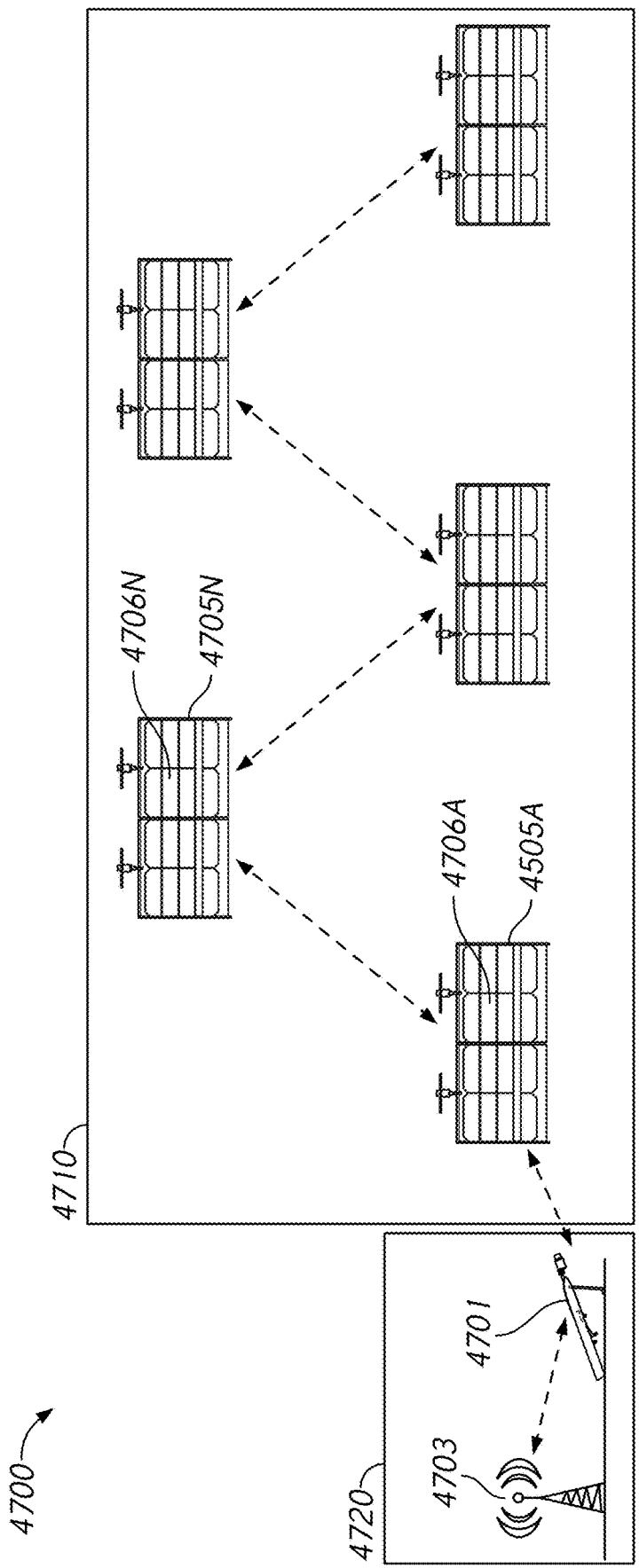
FIG. 47 is a diagram of Multi-modal, Weather Resistant Robot Network and Methods of Data Transfer network detailing the private network according to an embodiment.

As shown in FIG. 47, an embodiment of a Dynamic, Infrastructure free Robotic Network 4700 where private drone network 4710 comprises at least one drone 4705N or 5705A and can scale to meet the demand of users in some embodiments, drone 4705N has solar panel 4706N and drone 5705A has solar panel 4706A. This enables wireless networks and cellular networks to reach rural and remote areas when there are times of need, and if the need is temporary, then the network can be quickly dismantled or moved. Each drone in the private network can either fly, move on the ground, or latch to the ground to gather data or transfer data. At any point in time, any drone in the private network can become a link drone by connecting to a satellite, Wi-Fi connection, or cellular tower. Each drone has the ability to transfer data to one another, users, or other connection points. In some embodiments, drones in private network 4710 are controlled by a remote operator (not shown) communicated through cellular network 4720 including cellar tower 4703 and link drone 4701 to the private drone network 4710. In some embodiments, the drones are controlled by on-board AI processors.

On-Demand Remote Wi-Fi Routers

Figure 48:
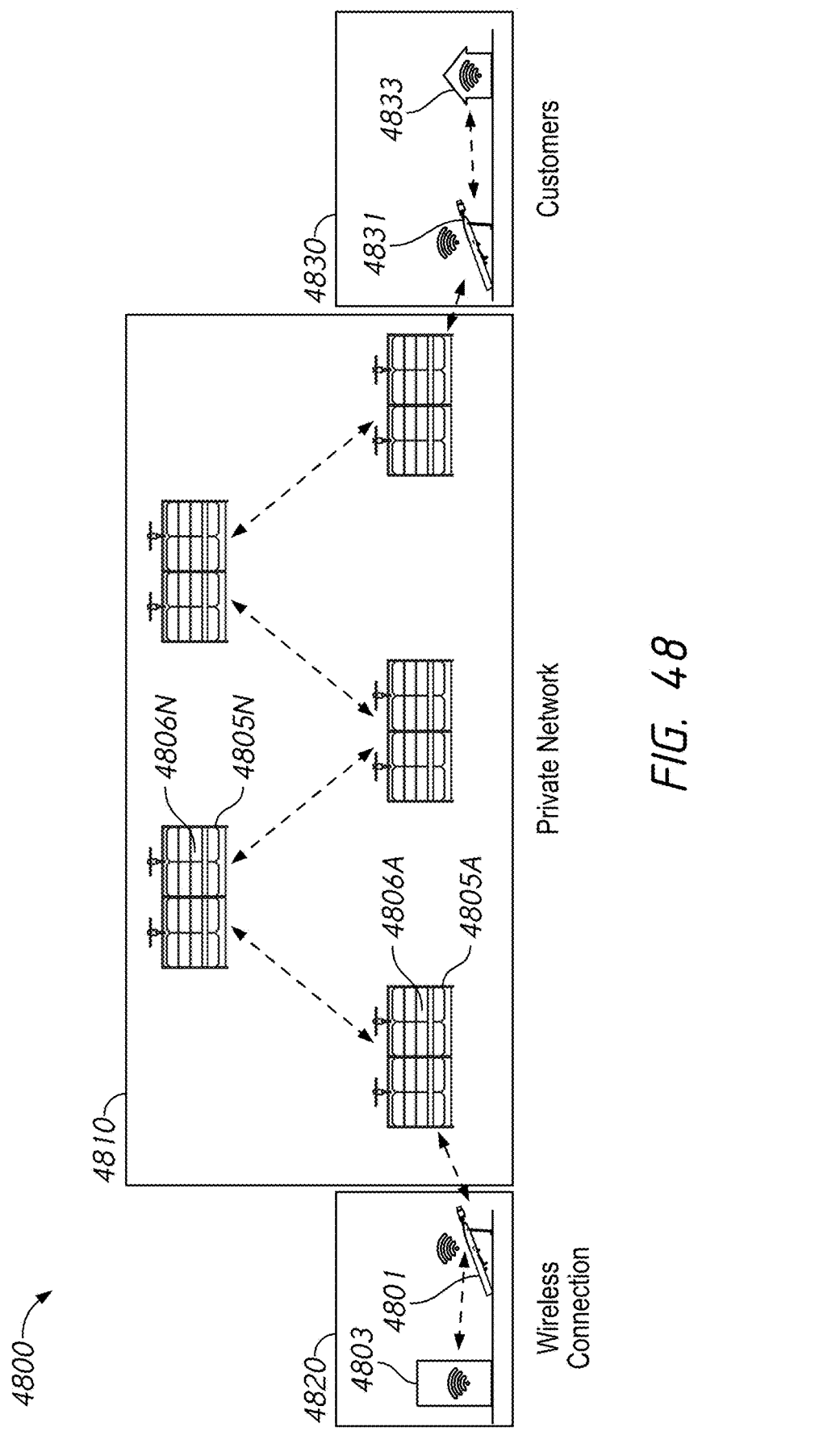
FIG. 48 is a diagram of an on-demand, dynamic Wi-Fi router, according to an embodiment.

As shown in FIG. 48, an embodiment of a Dynamic, Infrastructure Free Robotic Network 4800 generally comprises at least one link drone 4801 connected to at least one Wi-Fi connection 4803, private drone network 4810 where private network 4810 comprises at least one network drone 4805A or 4805N, and Wi-Fi customer link drone 4831. In some embodiments, system 4830 comprises Wi-Fi customer link drone 4831 and Wi-Fi consumer 4833. Link drone 4801 may fly or move on the ground and be within 460 feet of the Wi-Fi Connection 4803. Link drone 4801 communicates with private network of drones 4810 shown as plurality of drones. The private network of drones is at least one drone. In some embodiments, network drone 4805A can fly and perform an inspection task, such as taking pictures of a plot of land and transfer the picture to link drone 4801 via private LTE network. Link Wi-Fi drone 4831 is positioned within potential user 4833, such as a home, business, building, or person. Link Wi-Fi drone 4831 transfers with the nearest drone in private drone network 4810 that remotes Wi-Fi connection 4803 through link drone 4801 (in Wireless connection system 4820) to the private drone network 4810. Link Wi-Fi drones can fly away at any time form the user and join private drone network 4810. In some embodiments, all drones have solar panels and are powered by the sun. In some embodiments, drone 4805A has solar panel 4806A and/or drone 4805N has solar panel 4806N.

Furthermore, Dynamic, Infrastructure Free Robotic Network 4800 could deploy a drone directly to a remote farm and the drone acts as a Wi-Fi router that the farm could use. This connection could help the farm to gather and send data to companies to perform data analysis and give guidance back to the farmer to help the farmer to make informed decision to increase crop yield.

Certain Advantages of the Disclosed Embodiments of Dynamic, Infrastructure Free Robotic Networks FIG. 49 illustrates an embodiment of Dynamic, Infrastructure Free Robotic Network 4900 which comprises Wi-Fi connection 4903, ground 4910, cellular tower 4904, at least one link drone 4901 which may include solar panel 4902, sun 4907 which produces sun beams 4908, at least one network drone 4905A and/or 4905N, hill 4950, and Wi-Fi user 4931. In some embodiments, network drone 4905A has solar panel 4906A and network drone 4905N has solar panel

Figure 49A:
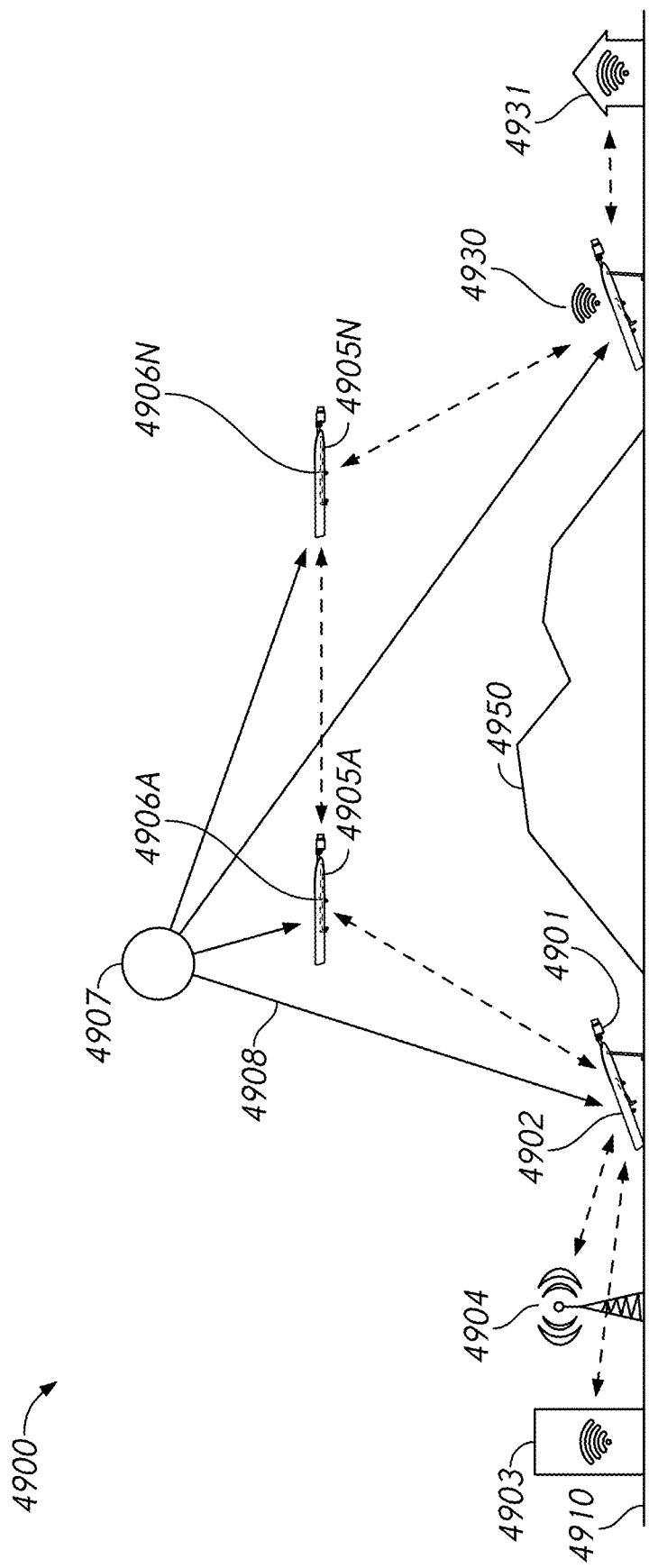
FIG. 49A is a diagram of Multi-modal, Weather Resistant Robot Network and Methods of Data Transfer network connected during the daytime, according to an embodiment.
Figure 49B:
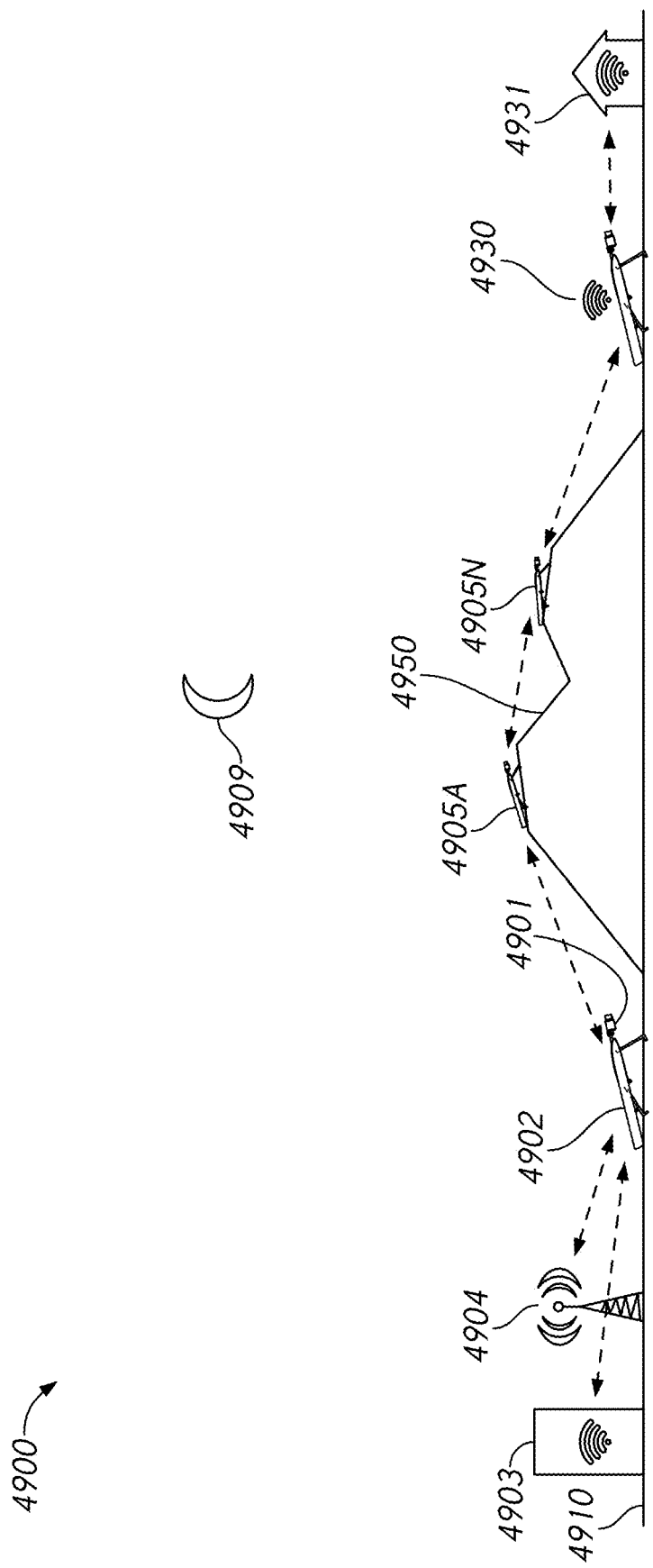
FIG. 49B is a diagram of Multi-modal, Weather Resistant Robot Network and Methods of Data Transfer network connected during the nighttime, according to an embodiment.

4906N. In some embodiments, the link drone 4930 provides Wi-Fi connects to remote Wi-Fi router 4931. In some embodiments, moon 4909 is out to illustrate the system at nighttime. Some embodiments of Dynamic, Infrastructure free Robotic Networks disclosed herein may have one or more of the following advantages or benefits over traditional VTOL aircrafts:

1. Ability to latch onto the ground. In extreme weather, the drones can quickly land and latch onto the ground. Other drones would simply be blown away and damaged. FIG. 49A shows the drones flying during the day and maneuvering on the ground and providing a remote Wi-Fi router to a user. FIG. 49B shows both the link drones and private network drones latched to the ground during the night and transferring data to the remote Wi-Fi router to a user. The drones need to latch to the ground at night for protection from the environment and to conserve energy.
2. Ability for link drone and private network drones to maneuver on uneven terrain. By using the latching legs, the aircraft can land and maneuver on any terrain. This drone can use its camera to detect if there is danger and maneuver on the side of a mountain or in someone's yard to avoid danger while transmitting data.
3. Ability for link drone and private network drones to charge both in flight and on the ground. This allows the aircraft to be fully autonomous and eliminates the need to go back to centralized charging locations. Furthermore, the ability to charge on the ground and in the flight will enable telecommunication and connectivity networks of drones to expanded quickly since the need for infrastructure development is no longer needed. In addition, all of the private network drones can land during the night to reduce power draw used for the powertrains and focus on using power to transfer data.
4. Ability to align to the sun when on the ground provides up to a 25% to 35% charging efficiency improvement and support high power draw for transferring data to satellites.
5. Ability to take off and land vertically in small areas or remote location. This allows the link drone to get close to Wi-Fi connections that a traditional solar plane could not. Also, the link drone can land on buildings, powerlines, trees, and other objects to reduce the electromagnetic effects from the ground and improve signal quality and data transfer.
6. Unlike traditional networks that are stationary in nature, this network can scale and change quickly based on user demands.
7. Unlike traditional networks that are stationary in nature, this network can extend the range of cellular towers and Wi-Fi providers into remote and rural areas that do not have access to connectivity.

Infrastructure Free Agriculture Connectivity Network

It should be noted that the disclosed embodiments of a Infrastructure Free Agriculture Connectivity Network may be combined with any embodiments disclosed herein, and individual features of the Infrastructure Free Agriculture Connectivity Network may be combined with individual features of any other embodiment. Any other embodiments may also be combined with the disclosed Infrastructure Free Agriculture Connectivity Network, and individual features of any embodiment may be combined with individual features of the disclosed Infrastructure Free Agriculture Connectivity Network.

Figure 50:
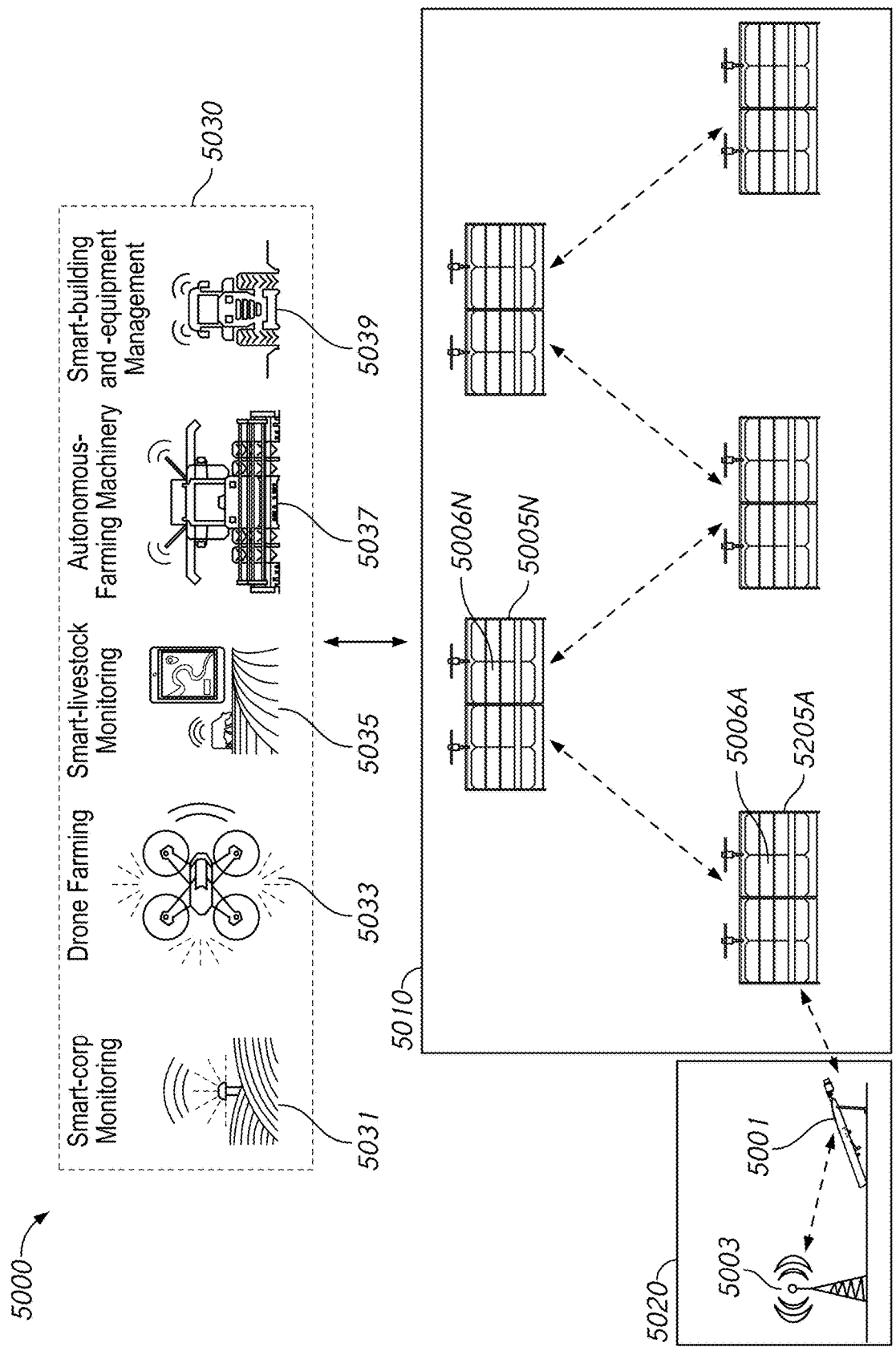
FIG. 50 is a diagram of an infrastructure-free agriculture connectivity network, according to an embodiment.

As shown in FIG. 50, an embodiment of an Infrastructure Free Agriculture Connectivity Network 5000 generally comprises at least one link drone 5001 connected to at least one Wi-Fi connection 5003, private drone network 5010 where private network 5010 comprises at least one network drone 5005, and farming technology devices 5030. Link drone 5001 may fly or move on the ground and be within 460 feet of the Wi-Fi Connection 5003. In some embodiments, link drone 5001 may be connected to a satellite or cellular tower. In some embodiments there may be more than one link drone.

Link drone 5001 communicates with private network of drones 5010 shown as plurality of drones. The private network of drones is at least one drone. In some embodiments, network drone 5005A can fly and perform an inspection task, such as taking pictures of a plot of land and transfer the picture to link drone 5001 via private LTE network. In some embodiments, link drone 5001 can communicate with cellular tower 5003. In some embodiments, private network of drones 5010 includes one or more drones 5005N and 5005A. In some embodiments private network drones have solar panels 5006N and 5006A. Any one of the drones in private drone network 5010 can communicate and transfer data with farming technology devices 5030. Farming technology 5030 includes sensors for smart-crop monitoring 5031, other farming drones 5033 such as pesticide spraying drones, sensors for live-stock monitoring 5035, autonomous farming machines 5037 such as tractors, and building and equipment 5039. In this situation, sensors on the farm can communicate to other equipment on the farm via the private drone network. The sensors and equipment will have an antenna matching the frequency of the private drone network 5010 network. For example, automated tractors can access GPS via this network and use data from drones to harvest crops at the optimal times.

Figure 51:
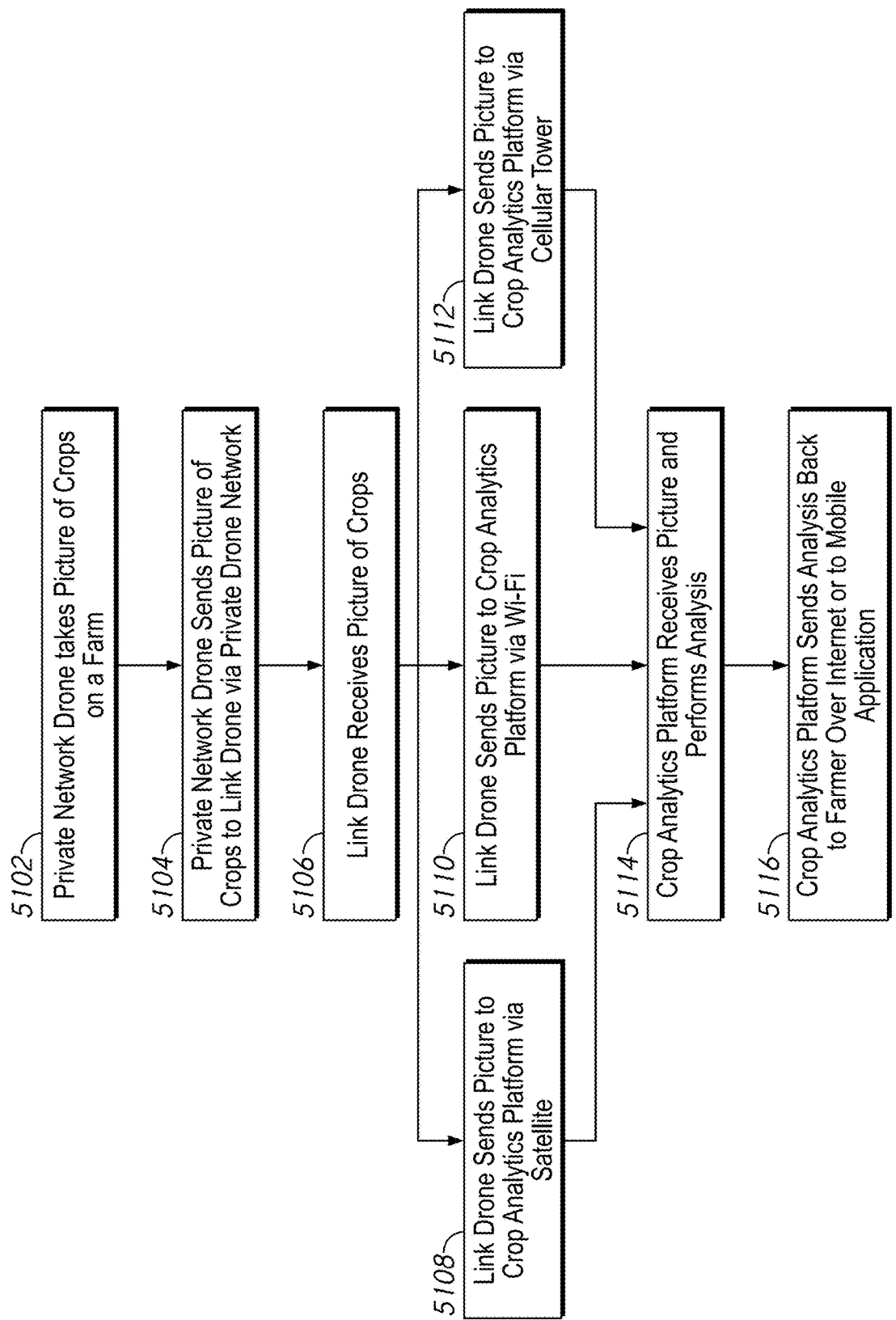
FIG. 51 is a process flow diagram showing a method of private network drone conducting an analysis on an agriculture asset, according to an embodiment.

FIG. 51 shows an embodiment of a process flow diagram illustrating an example of a method of private network drone conducting an analysis on an agriculture asset for crop analytics and analysis.

At block 5102, the process begins when private network drone takes a picture, records a video, and/or the like of crops on a farm. At block 5104, the network drone sends pictures, videos, and/or the like of crops to link drone via private drone network. At block 5106, link drone receives image of the crops. Depending on the embodiment, the drone may use different methods to send images. In some embodiments, the drone may use multiple combinations of the methods of sending images.

Block 5108 illustrates one embodiment, where link drone sends imagery to crop analytics platform via satellite. At block 5114, crop analytics platform receives imagery and performs analysis. At block 5116, crop analytics platform sends analysis back to farmer over internet. In some embodiments the analysis is sent to mobile application.

Block 5110 illustrates another embodiment, where link drone sends imagery to crop analytics platform via Wi-Fi. At block 5114, crop analytics platform receives imagery and performs analysis. At block 5116, crop analytics platform sends analysis back to farmer over internet. In some embodiments the analysis is sent to mobile application.

Block 5112 illustrates yet another embodiment, where link drone sends imagery to crop analytics platform via cellular tower. At block 5114, crop analytics platform receives imagery and performs analysis. At block 5116, crop analytics platform sends analysis back to farmer over internet. In some embodiments the analysis is sent to mobile application.

Figure 52:
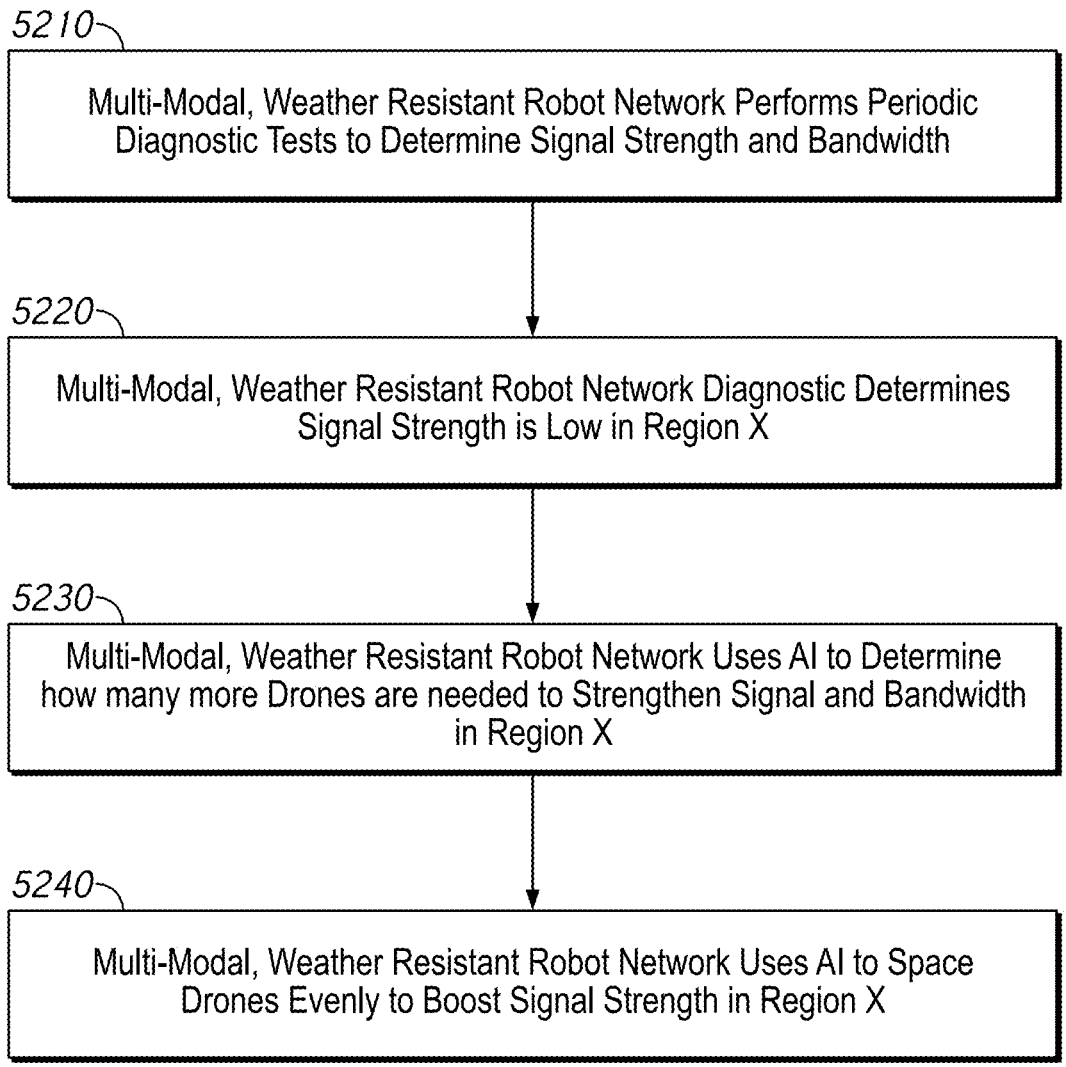
FIG. 52 is a process flow diagram showing a method of Multi-Modal, Weather Resistant Robot Network performing diagnostic tests to determine signal strength and bandwidth, according to an embodiment.

FIG. 52 shows an embodiment of a process flow diagram illustrating an example of a method of Multi-Modal, Weather Resistant Robot Network performing diagnostic tests to determine signal strength and bandwidth and implementing process to strengthen signal and bandwidth in regions that are found to be low.

At block 5210, the process begins when Multi-Modal, Weather Resistant Robot Network performs periodic diagnostic tests to determine signal strength and bandwidth. At block 5220, Multi-Modal, Weather Resistant Robot Network determines signal strength is low in region X. At block 5230, Multi-Modal, Weather Resistant Robot Network uses AI to determine how many more drones are needed to strengthen signal and bandwidth in region X. At block 5240, Multi-Modal, Weather Resistant Robot Network uses AI to space drones evenly to boost signal strength in region X.

Figure 53:
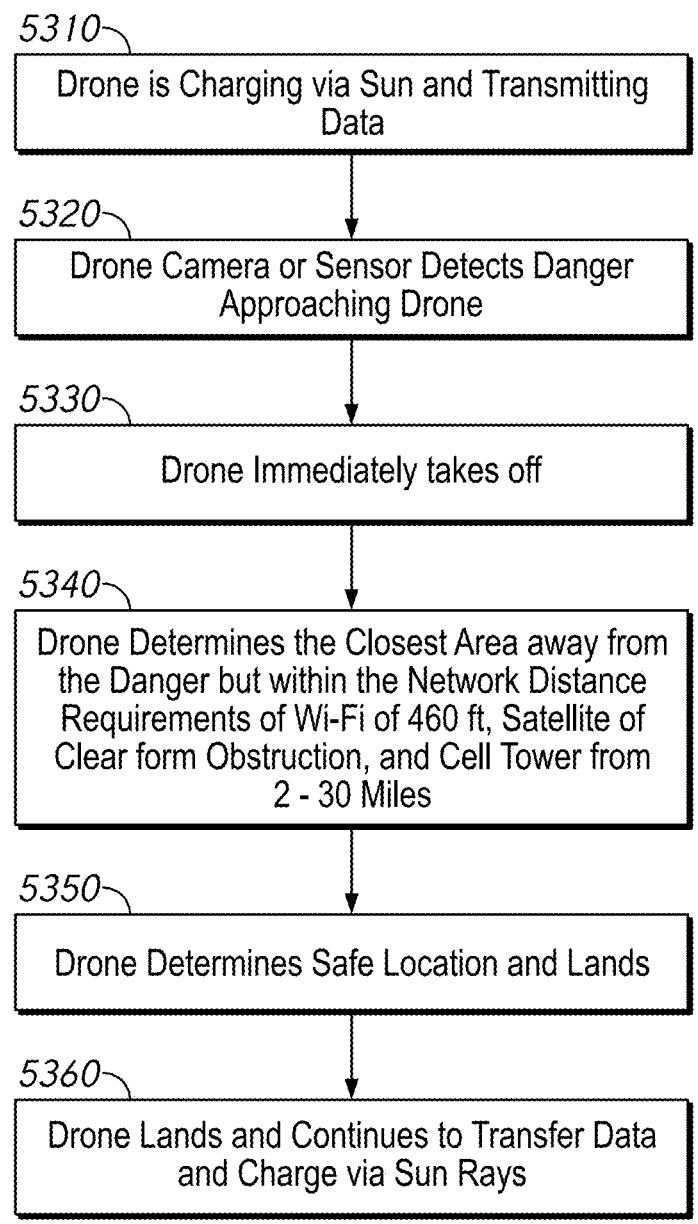
FIG. 53 is a process flow diagram showing a method for drones that are charging and/or transmitting data to detect danger and relocate, according to an embodiment.

FIG. 53 shows an embodiment of a process flow diagram illustrating an example of a method for drones that are charging and/or transmitting data to detect danger and relocate to a safe location to continue charging and/or transmitting data.

At block 5310, the process begins when drone is charging via sun and transmitting data. At block 5320, the drone camera and/or sensor detects danger approaching drone. In some embodiments, danger may be an extreme weather system, a group of animals approaching, and/or the like. At block 5330, drone immediately takes off.

At block 5340, drone determines the closest area away from the danger but within the network distance requirements of Wi-Fi of 460 ft, satellite of clear form obstruction, and/or cell tower from 2-30 miles. At block 5350, drone determines a safe location and lands. At block 5360, drone lands and continues to transfer data and/or charge via sun rays.

Some Disclosed Embodiments May Include One or More of the Following Benefits and Advantages Most farms do not have connectivity because they are located in remote areas and rural areas, especially ones in developing countries. Rural areas do not have the money to invest into cellular network towers and Wi-Fi has limited range from the router. Farms need a more flexible, low-cost solution for data transfer and telecommunications. Drones have been considered, but there are many dependencies that make a temporary, flexible farming network.

Current VTOL drones use standard infrastructure for charging the drone and taking shelter during extreme weather. However, these solutions require tethered power, and as a result, the solutions are static and cannot adapt to the environment or the mission. Some solutions also require human interaction and planning, which are not ideal when performing inspection and/or data transfer in remote areas or urban areas that do not have space for temporary infrastructure. Current drone surveillance systems also suffer from the same infrastructure problems that create a barrier for implementation of large-scale surveillance systems as it requires a significant investment into a charging station infrastructure. The disclosed technology aims to, among other things eliminate the need for additional infrastructure and promote flexible and sustainable inspection and data transfer networks.

Conventional thinking uses large solar panels attached to infrastructure to charge batteries; however, in our design, the drone itself will have the solar panels attached to it for charging on the ground shown in an embodiment, which eliminates the need for expensive, static infrastructure. In addition, conventional thinking also doesn't account for the importance of how spending the majority of time charging on the ground instead of in the air makes the solar panel charging practical. Also, the proposed design has features that allow the drone to mimic nature and affix itself to the environment.

Infrastructure Free Agriculture Connectivity Network.

Some embodiments of the Infrastructure Free Agriculture Connectivity Network may include one or more of the following advantages or benefits:
1. Compared to traditional transportation systems, the drones do not require human or robotic assistance to charge and take shelter.
2. Compared to traditional systems, the proposed system can connect link drones to multiple Wi-Fi connections and the private drone network can balance the data transfer between different networks to increase the speed.
3. Compared to traditional systems, the drones can facilitate communication between sensors and equipment on the farm, enabling advanced IoT at farms.
4. Compared to traditional systems, the drones can facilitate data transfer between farms and cloud analysis software, which will enable next generation analytics at farms to increase yield and reduce waste.

OTHER REMARKS

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the disclosures or claims.

Any ranges disclosed herein also encompass any and all overlap, sub-ranges, and combinations thereof. Language such as "up to," "at least," "greater than," "less than," "between," and the like includes the number recited. Numbers preceded by a term such as "approximately," "about," and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although the features that have been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present disclosure herein disclosed should not be limited by the particular disclosed embodiments described above.

What is claimed is:

1. An autonomous ground vehicle for agricultural plant and soil management operations, the autonomous ground vehicle comprising:
    a ground vehicle unit;
    a first camera unit coupled to the ground vehicle unit, the first camera unit configured to generate a first set of images of agricultural ground soil and plant organisms in a forward path of the ground vehicle unit;
    a first mechanical arm coupled to the ground vehicle unit, the first mechanical arm having a first end effector comprising a first hoe portion;
    an electronic memory storage medium housed in the ground vehicle unit, the electronic memory storage medium comprising computer-executable instructions;
    one or more processors housed in the ground vehicle unit, the one or more processors in electronic communication with the electronic memory storage medium, the one or more processors configured to execute the computer-executable instructions stored in the electronic memory storage medium to implement a plant species control management operation comprising:
        analyzing, by the one or more processors, the first set of images to identify a plant organism;
        using, by the one or more processors, an artificial intelligence algorithm to determine whether the identified plant organism is set for plant organism control, wherein the artificial intelligence algorithm is stored in the electronic memory storage medium;
        generating, by the one or more processors, based on the determination that the identified plant organism is set for plant organism control, ground vehicle unit control instructions configured to advance the ground vehicle unit and/or the first mechanical arm to be within a threshold proximity of the identified plant organism;
        determining, by the one or more processors, a mechanical control method of plant organism control for the identified plant organism;
        generating, by the one or more processors, based on the mechanical control method, mechanical arm control instructions for mechanical control comprising:
            positioning at least the first hoe portion to be in contact with soil distal to the identified plant organism;
            moving the first hoe portion through the soil to remove at least a portion of the identified plant organism;
        executing, by the one or more processors, the generated mechanical arm control instructions.

2. The autonomous ground vehicle of claim 1, wherein the ground vehicle unit comprises mechanical legs.

3. The autonomous ground vehicle of claim 1, wherein the ground vehicle unit comprises one or more protrusions coupled to an external portion of the ground vehicle unit, the one or more protrusions configured to engage with the first hoe portion to remove debris material from the first hoe portion.

4. The autonomous ground vehicle of claim 1, wherein the autonomous ground vehicle further comprises an energy storage unit housed in the ground vehicle unit.

5. The autonomous ground vehicle of claim 4, wherein the autonomous ground vehicle further comprises a solar panel unit electrically coupled to the energy storage unit, wherein the solar panel unit is configured to electrically recharge the energy storage unit housed in the ground vehicle unit.

6. The autonomous ground vehicle of claim 1, wherein the ground vehicle unit comprises two or more wheels.

7. The autonomous ground vehicle of claim 1, wherein analyzing, by the one or more processors, the first set of images to identify the plant organism comprises use of a computer vision algorithm.

8. The autonomous ground vehicle of claim 1, wherein the plant species control management operation further comprises: using, by the one or more processors, the artificial intelligence algorithm to determine a plant species type of the identified plant organism.

9. The autonomous ground vehicle of claim 1, wherein the first mechanical arm further comprises a first shovel portion.

10. The autonomous ground vehicle of claim 1, wherein the first hoe portion comprises a warren hoe.

11. A computer-implemented method for using an autonomous ground vehicle for agricultural plant and soil management and operations, the computer-implemented method comprising:
    analyzing, by a computing system, a first set of images to identify a plant organism, the first set of images generated by a first camera unit coupled to a ground vehicle unit of the autonomous ground vehicle;
    using, by the computing system, an artificial intelligence algorithm to determine whether the identified plant organism is set for plant organism control, wherein the artificial intelligence algorithm is stored in an electronic memory storage medium of the autonomous ground vehicle;
    generating, by the computing system, based on the determination that the identified plant organism is set for plant organism control, ground vehicle unit control instructions configured to advance the ground vehicle unit and/or a first mechanical arm to be within a threshold proximity of the identified plant organism, wherein the ground vehicle unit comprises the first mechanical arm coupled to the ground vehicle unit, the first mechanical arm having a first end effector comprising a first hoe portion;
    determining, by the computing system, a mechanical control method of plant organism control for the identified plant organism;
    generating, by the computing system, based on the mechanical control method, mechanical arm control instructions for mechanical control comprising:
        positioning at least the first hoe portion to be in contact with soil distal to the identified plant organism;
        moving the first hoe portion through the soil to remove at least a portion of the identified plant organism;
    executing, by the computing system, the generated mechanical arm control instructions;
    wherein the computing system comprises one or more hardware computer processors in communication with one or more computer readable data stores and configured to execute a plurality of computer executable instructions.

12. The computer-implemented method of claim 11, wherein the ground vehicle unit comprises mechanical legs.

13. The computer-implemented method of claim 11, wherein the ground vehicle unit comprises one or more protrusions coupled to an external portion of the ground vehicle unit, the one or more protrusions configured to engage with the first hoe portion to remove debris material from the first hoe portion.

14. The computer-implemented method of claim 11, wherein the autonomous ground vehicle further comprises an energy storage unit housed in the ground vehicle unit.

15. The computer-implemented method of claim 14, wherein the autonomous ground vehicle further comprises a solar panel unit electrically coupled to the energy storage unit, wherein the solar panel unit is configured to electrically recharge the energy storage unit housed in the ground vehicle unit.

16. The computer-implemented method of claim 11, wherein the ground vehicle unit comprises two or more wheels.

17. The computer-implemented method of claim 11, wherein analyzing, by the computing system, the first set of images to identify the plant organism comprises use of a computer vision algorithm.

18. The computer-implemented method of claim 11, wherein the method further comprises: using, by the computing system, the artificial intelligence algorithm to determine a plant species type of the identified plant organism.

19. The computer-implemented method of claim 11, wherein the first mechanical arm further comprises a first shovel portion.

20. The computer-implemented method of claim 11, wherein the first hoe portion comprises a warren hoe.

\* \* \* \* \*